US006495129B1

(12) United States Patent
Li et al.

(10) Patent No.: US 6,495,129 B1
(45) Date of Patent: Dec. 17, 2002

(54) METHODS OF INHIBITING HEMATOPOIETIC STEM CELLS USING HUMAN MYELOID PROGENITOR INHIBITORY FACTOR-1 (MPIF-1) (CKBETA-8/MIP-3)

(75) Inventors: Haodong Li, Gaithersburg, MD (US); Steven M. Ruben, Olney, MD (US)

(73) Assignee: Human Genome Sciences, Inc., Rockville, MD (US)

(*) Notice: Subject to any disclaimer, the term of this patent is extended or adjusted under 35 U.S.C. 154(b) by 5 days.

(21) Appl. No.: 09/689,693

(22) Filed: Oct. 13, 2000

Related U.S. Application Data

(63) Continuation of application No. 09/571,013, filed on May 15, 2000, and a continuation-in-part of application No. 09/334,951, filed on Jun. 17, 1999, said application No. 09/571,013, is a continuation of application No. 08/941,020, filed on Sep. 30, 1997, now abandoned, which is a continuation-in-part of application No. 08/722,723, filed on Sep. 30, 1996, now abandoned, and a continuation-in-part of application No. 08/722,719, filed on Sep. 30, 1996, now Pat. No. 6,001,606, said application No. 09/722,723, is a continuation-in-part of application No. 08/468,775, filed on Jun. 6, 1995, now abandoned, and a continuation-in-part of application No. 08/465,682, filed on Jun. 6, 1995, now abandoned, and a continuation-in-part of application No. 08/446,881, filed on May 5, 1995, now abandoned, said application No. 08/722,719, is a continuation-in-part of application No. 08/468,775, and a continuation-in-part of application No. 08/465,682, and a continuation-in-part of application No. 08/446,881, said application No. 08/468,775, is a continuation of application No. 08/446,881, and a continuation-in-part of application No. 08/208,339, filed on Mar. 8, 1994, now Pat. No. 5,504,003, said application No. 08/465,682, is a continuation of application No. 08/446,881, and a continuation-in-part of application No. 08/208,339, said application No. 08/446,881, is a continuation-in-part of application No. 08/208,339.

(60) Provisional application No. 60/212,658, filed on Jun. 19, 2000, provisional application No. 60/211,458, filed on Jun. 13, 2000, provisional application No. 60/199,142, filed on Apr. 24, 2000, provisional application No. 60/189,048, filed on Mar. 14, 2000, provisional application No. 60/172,063, filed on Dec. 23, 1999, provisional application No. 60/164,059, filed on Nov. 8, 1999, and provisional application No. 60/159,362, filed on Oct. 14, 1999.

(51) Int. Cl.[7] .............................................. A61K 38/19
(52) U.S. Cl. ........................ 424/85.1; 424/885; 514/2; 514/8; 514/12
(58) Field of Search ............... 424/85.1, 885; 514/2, 8, 12

(56) References Cited

U.S. PATENT DOCUMENTS

| 4,897,348 A | 1/1990 | Johnson et al. ............ 435/69.1 |
| 5,268,463 A | 12/1993 | Jefferson ................... 537/23.7 |
| 5,346,686 A | 9/1994 | Lyle et al. ................. 424/1.41 |
| 5,504,003 A | 4/1996 | Li et al. ................... 435/240.2 |
| 5,556,767 A | 9/1996 | Rosen et al. .............. 435/69.1 |
| 5,874,211 A | 2/1999 | Bandman et al. ............. 435/6 |
| 5,912,327 A | 6/1999 | Li et al. ................... 530/412 |
| 6,001,606 A | 12/1999 | Ruben et al. .............. 435/69.5 |
| 6,290,948 B1 | 9/2001 | White et al. .............. 424/85.1 |
| 6,406,688 B1 | 6/2002 | White et al. .............. 424/85.1 |
| 2002/0007047 A1 | 1/2002 | White et al. ................ 530/351 |
| 2002/0061551 A1 | 5/2002 | Ruben et al. .............. 435/69.1 |
| 2002/0076746 A1 | 6/2002 | Ruben et al. .............. 435/69.1 |

FOREIGN PATENT DOCUMENTS

| DE | 43 44 397 A1 | 7/1995 |
| DE | 44 27 395 A1 | 2/1996 |
| EP | 0 310 136 | 4/1989 |
| EP | 0 324 274 | 7/1989 |
| JP | 10-53533 | 2/1998 |
| JP | 2001-122801 | 5/2001 |
| WO | WO 90/02762 | 3/1990 |
| WO | WO 90/07009 | 6/1990 |
| WO | WO 91/04274 | 4/1991 |
| WO | WO 92/00326 | 1/1992 |
| WO | WO 92/00327 | 1/1992 |
| WO | WO 92/05198 | 4/1992 |
| WO | WO 92/13553 | 8/1992 |
| WO | WO 92/20372 | 11/1992 |
| WO | WO 93/09799 | 5/1993 |
| WO | WO 95/17092 | 6/1995 |
| WO | WO 95/18228 | 7/1995 |
| WO | WO 96/16979 | 6/1996 |
| WO | WO 96/22374 | 7/1996 |
| WO | WO 96/32481 | 10/1996 |
| WO | WO 96/34891 | 11/1996 |
| WO | WO 97/12041 | 4/1997 |
| WO | WO 97/15594 | 5/1997 |
| WO | 0 807 439 A2 | 11/1997 |
| WO | WO 98/14582 | 4/1998 |
| WO | WO 01/26676 A1 | 4/2001 |

OTHER PUBLICATIONS

Adema, G.J. et al., "A dendritic–cell–derived C–C chemokine that preferentially attracts naive T cells," *Nature* 387:713–717, Macmillan Publishers Ltd (Jun. 1997).

Arous, N. et al., "Structural study of hemoglobin Knossos, β27 (B9) Ala→Ser. A new abnormal hemoglobin present as a silent β–thalassemia," *FEBS Lett.* 147:247–250, Elsevier Biomedical Press (1982).

Bischoff, S. C., et al., "Monocyte Chemotactic Protein 1 Is a Potent Activator of Human Basophils," *J. Exp. Med.* 175:1271–1275, The Rockefeller University Press (1992).

(List continued on next page.)

Primary Examiner—Prema Mertz
(74) Attorney, Agent, or Firm—Sterne, Kessler, Goldstein & Fox, P.L.L.C.

(57) ABSTRACT

There are disclosed therapeutic compositions and methods using isolated nucleic acid molecules encoding a human myeloid progenitor inhibitory factor-1 (MPIF-1) polypeptide (previously termed MIP-3 and chemokine β8 (CKβ8 or ckb-8)), as well as MPIF-1 polypeptide itself, as are vectors, host cells and recombinant methods for producing the same.

16 Claims, 73 Drawing Sheets

OTHER PUBLICATIONS

Blum, S., et al., "Three Human Homologs of a Murine Gene Encoding an Inhibitor of Stem Cell Proliferation," *DNA and Cell Biology* 9(8):589–602, Mary Ann Liebert, Inc. (1990).

Bowie, J.U. et al., "Deciphering the Message in Protein Sequences: Tolerance to Amino Acid Substitutions," *Science* 247:1306–1310, American Association for the Advancement of Science (1990).

Chang, M., et al., "Cloning and Characterization of the Human Neutrophil–activating Peptide (ENA–78) Gene," *J. Biol. Chem.* 269(41):25277–25282, The American Society for Biochemistry and Molecular Biology, Inc. (Oct. 1994).

Clark–Lewis, I. et al., "Structural Requirements for Interleukin–8 Function Identified by Design of Analogs and CXC Chemokine Hybrids," *J. Biol. Chem.* 269:16075–16081, The American Society for Biochemistry and Molecular Biology, Inc. (Jun. 1994).

Clements, J.M., et al., "Biological and Structural Properties of MIP–1α Expressed in Yeast," *Cytokine* 4:76–82, Academic Press (1992).

Derynck, R., et al., "Recombinant Expression, Biochemical Characterization, and Biological Activities of the Human MGSA/gro Protein," *Biochem.* 29:10225–10233, American Chemical Society (1990).

Glover, D.M., "The Principles of Cloning DNA," in: *Gene Cloning: The Mechanics of DNA Manipulation*, Chapman and Hall, London, UK, pp. 1–20 (1984).

Graham, G. J. and Pragnell, I. B., "SCI/MIP–1α: A Potent Stem Cell Inhibitor with Potential Roles in Development," *Developmental Biol.* 151:377–381, Academic Press, Inc. (1992).

Guan, P. et al., "Genomic Organization and Biological Characterization of the Novel Human CC Chemokine DC–CK–1/PARC/MIP–4/SCYA18," *Genomics* 56:296–302, Academic Press (Mar. 1999).

Harlow, E. and Lane, D., from *"Antibodies, A Laboratory Manual,"* Cold Spring Harbor Laboratory, Cold Spring Harbor, NY, p. 6 (1988).

Hieshima, K. et al., "A Novel Human CC Chemokine PARC That Is Most Homologous to Macrophage–Inflammatory Protein–1α/LD78α and Chemotactic for T Lymphocytes, but Not for Monocytes," *J. Immunol.* 159:1140–1149, American Association of Immunologists (Aug. 1997).

Hutt, P.J. et al., "HB Cook [β132(H10)Lys→Thr] : A New Hemoglobin Variant in a Southeast Asian Family," *Hemoglobin* 20:371–376, Marcel Dekker, Inc. (Nov. 1996).

Johnson II, M. C., et al., "Cloning of two rabbit GRO homologues and their expression in alveolar macrophages," *Gene* 151:337–338, Elsevier Science B.V. (Dec. 1994).

Jose, P.J., et al., "Eotaxin: A Potent Eosinophil Chemoattractant Cytokine Detected in a Guinea Pig Model of Allergic Airways Inflammation," *J. Exp. Med.* 179:881–887, The Rockefeller University Press (Mar. 1994).

Kuna, P., et al., "Monocyte Chemotactic and Activating Factor Is a Potent Histamine–releasing Factor for Human Basophils," *J. Exp. Med.* 175:489–493, The Rockefeller University Press (1992).

Kwon, B.S., and Weissman, S.M., "cDNA Sequences of Two Inducible T–cell Genes," *Proc. Natl. Acad. Sci. USA* 86:1963–1967, National Academy of Sciences (1989).

Lerner, R.A., "Tapping the Immunological Repertoire to Produce Antibodies of Predetermined Specificity," *Nature* 299:592–596, Macmillan Journals Ltd. (1982).

Lukacs, N. W., et al., "The Role of Macrophage Inflammatory Protein 1α in *Schistosoma mansoni* Egg–induced Granulomatous Inflammation," *J. Exp. Med.* 177:1551–1559, The Rockefeller University Press (Jun. 1993).

Matsushima, K., et al., "Purification and Characterization of a Novel Monocyte Chemotactic and Activating Factor Produced by a Human Myelomoncytic Cell Line," *J. Exp. Med.* 169:1485–1490, The Rockefeller University Press (1989).

Mikayama, T., et al., "Molecular cloning and functional expression of a cDNA encoding glycosylation–inhibiting factor," *Proc. Natl. Acad. Sci. USA* 90:10056–10060, National Academy of Sciences (Nov. 1993).

Nakao, M., et al., "Structures of Human Genes Coding for Cytokine LD78 and Their Expression," *Molecular and Cellular Biology* 10(7):3646–3658, American Society for Microbiology (1990).

Nibbs, R.J.B. et al., "C–C Chemokine Receptor 3 Antagonism by the β–Chemokine Macrophage Inflammatory Protein 4, a Property Strongly Enhanced by an Amino–Terminal Alanine–Methionine Swap," *J. Immunol.* 164:1488–1497, American Association of Immunologists (Jan. 2000).

Obaru, K., et al., "A CDNA Clone Used to Study mRNA Inducible in Human Tonsillar Lymphocytes by a Tumor Promoter," *J. Biochem.* 99(3):885–894, The Japanese Biochemical Society (1986).

"PeproTech: Product Details," Peprotech online catalog, <<http://www.peprotech.com/store.taf?_function_prod=detail&catnumx 300–34&BA59773143D06854BEDB1EF0>>, Jun. 18, 2001.

*Physician's Desk Reference*, 54$^{th}$ Edition, pp. 519–524, Medical Economics Company, Inc., Montvale, NJ (2000).

Poltorak, A., et al., "Molecular Cloning of MIP–1$_γ$, A New Member of the Chemokine Family, through Differential Screening Based onb Extinction of Macrophage–Specific Genes," *Clinical Research* 42(2):306A XP000673113, American Federation For Clinical Research (Apr. 1994).

Poltorak, A. N., et al., "MIP–1$_γ$: Molecular Cloning, Expression, and Biological Activities of a Novel CC Chemokine That Is Constitutively Secreted In Vivo," *J. Inflam.* 45:207–219, Wiley–Liss, Inc. (Nov. 1995).

Power, C.A., et al., "Cloning of a full–length CDNA encoding the neutrophil–activating peptide ENA–78 from human platelets," *Gene* 151:333–334, Elsevier Science B.V. (Jan. 1994).

Proost, P., et al., "Purification, Sequence Analysis, and Biological Characterization of a Second Bovine Monocyte Chemotactic Protein–1 (Bo MCP–1B)," *Biochemistry* 33:13406–13412, American Chemical Society (Nov. 1994).

Ramachandran, M. et al., "A New Variant, HB Muscat [α$_2$β$_2$32(B14)Leu→Val] Observed in Association with HB S in an Arabian Family," *Hemoglobin* 16:259–266, Marcel Dekker, Inc. (1992).

Schall, T.J., "Biology of the RANTES/SIS Cytokine Family," *Cytokine* 3:165–183, W.B. Saunders Company (1991).

Sudo, K., et al., "2058 Expressed Sequence Tags (ESTs) from a Human Fetal Lung cDNA Library," *Genomics* 24:276–279, Academic Press, Inc. (Nov. 1994).

Voet, et al., "3. Chemical Evolution," in: *Biochemistry*, Voet, et al., eds., John Wiley & Sons, Inc., New York, New York, pp. 126–128 and 228–234, (1990).

Weber, M., et al., "Deletion of the NH$_2$–Terminal Residue Converts Monocyte Chemotactic Protein 1 from an Activator of Basophil Mediator Release to an Eosinophil Chemoattractant," *J. Exp. Med. 183*:681–685, The Rockefeller University Press (Feb. 1996).

Wells, T.N.C. and Peitsch, M.C., "The chemokine information source: identification and characterization of novel chemokines using the WorldWideWeb and expressed sequence tag databases," *Leukocyte Biol. 61*:545–550, the Society for Leukocyte Biology (May 1997).

Wolpe, S.D., and Cerami, A., "Macrophage Inflammatory Proteins 1 and 2: Members of a Novel Superfamily of Cytokines," *FASEB J. 3*:2565–2573, The Federation of American Societies for Experimental Biology (1989).

Yoshida, T., et al., "Molecular Cloning of a Novel C or γ Type Chemokine, SCM–1," *FEBS Letters 360*:155–159, Elsevier Science, Inc. (Feb. 1995).

Zhang, Y.J. et al., "Structure/Activity Analysis of Human Monocyte Chemoattractant Protein–1 (MCP–1) by Mutagenesis," *J. Biol. Chem. 269*:15918–15924, American Society for Biochemistry and Molecular Biology, Inc. (Jun. 1994).

Zipfel, P.F., et al., "Mitogenic Activation of Human T Cells Induces Two Closely Related Genes Which Share Structural Similarities with a New Family of Secreted Factors," *J. Immunol. 42*:1582–1590, The American Society of Immunologists (1989).

Diolog File 351, Accession No. 95–246393, Derwent WPI, English language abstract for WO 95/18228.

Dialog File 351, Accession No. 10339421, Derwent WPI English language abstract for DE 43 44 397 A1.

Dialog File 351, Accession No. 95–246393, Derwent WPI English language abstract for DE 44 27 395 A1.

Dialog File 351, Accession No. 11575719, Derwent WPI English language abstract for JP2001–122801.

Pending Non–Provisional U.S. patent application No. 09/334,951, Ruben et al., filed Jun. 17, 1999, Not Published.

Pending Non–Provisional U.S. patent application No. 09/567,225, White et al., filed May 9, 2000, Not Published.

Pending Non–Provisional U.S. patent application No. 09/571,013, Gentz et al., filed May 15, 2000, Not Published.

Pending Non–Provisional U.S. patent application No. 10/103,859, White et al., filed Mar. 25, 2002, Not Published.

Pending Non–Provisional U.S. patent application No. 10/105,285, White et al., filed Mar. 25, 2002, Not Published.

Pending Non–Provisional U.S. patent application No. 10/107,371, White et al., filed on Mar. 25, 2002, Not Published.

Pending Non–Provisional U.S. patent application No. 10/165,233, Ruben et al., filed Jun. 10, 2002, Not Published.

Brown, K.D., et al., "A Family of Small Inducible Proteins Secreted by Leukocytes are Members of a Superfamily that Includes Leukocyte and Fibroblast–Derived Inflammatory Agents, Growth Factors, and Indicators of Various Activation Processes," *J. Immunol. 142*:679–687, The American Association of Immunologists, (1989).

ATGAAGGTCTCCGTGGCTGCCCTCTCCTGCCTCATGCTTGTTACTGCCCTTGGATCCCAG    60
<u>M  K  V  S  V  A  A  L  S  C  L  M  L  V  T  A  L  G  S  Q</u>

GCCCGGGTCACAAAAGATGCAGAGACAGAGTTCATGATGTCAAAGCTTCCATTGGAAAAT   120
<u>A</u>  R  V  T  K  D  A  E  T  E  F  M  M  S  K  L  P  L  E  N

CCAGTACTTCTGGACAGATTCCATGCTACTAGTGCTGACTGCTGCATCTCCTACACCCCA   180
P  V  L  L  D  R  F  H  A  T  S  A  D  C  C  I  S  Y  T  P

CGAAGCATCCCGTGTTCACTCCTGGAGAGTTACTTTGAAACGAACAGCGAGTGCTCCAAG   240
R  S  I  P  C  S  L  L  E  S  Y  F  E  T  N  S  E  C  S  K

CCGGGTGTCATCTTCCTCACCAAGAAGGGGCGACGTTTCTGTGCCAACCCCAGTGATAAG   300
P  G  V  I  F  L  T  K  K  G  R  R  F  C  A  N  P  S  D  K

CAAGTTCAGGTTTGCATGAGAATGCTGAAGCTGGACACACGGATCAAGACCAGGAAGAAT   360
Q  V  Q  V  C  M  R  M  L  K  L  D  T  R  I  K  T  R  K  N

TGA    363
*

FIG.1

```
CKβ-8    MKVSVAALSCLMLVTALGSQARVTKDAETEFMMSKLPLENPVLLDRFHAT    50
         |.||.|||..|: . ||..| ... .|:                      |
MIP-1α   MQVSTAALAVLLCTMALCNQFSASLAAD.....................T    29

CKβ-8    SADCCISYTPRSIPCSLLESYFETNSECSKPGVIFLTKKGRRFCANPSDK   100
         ...||:|||.| || .::..||||.|:|||||||||||::|..||:||:.
MIP-1α   PTACCFSYTSRQIPQNFIADYFETSSQCSKPGVIFLTKRSRQVCADPSEE    79

CKβ-8    QVQVCMRMLKLDTRIKTRKN   120
         || ::. |.|..
MIP-1α   WVQKYVSDLELSA         92
```

FIG.2

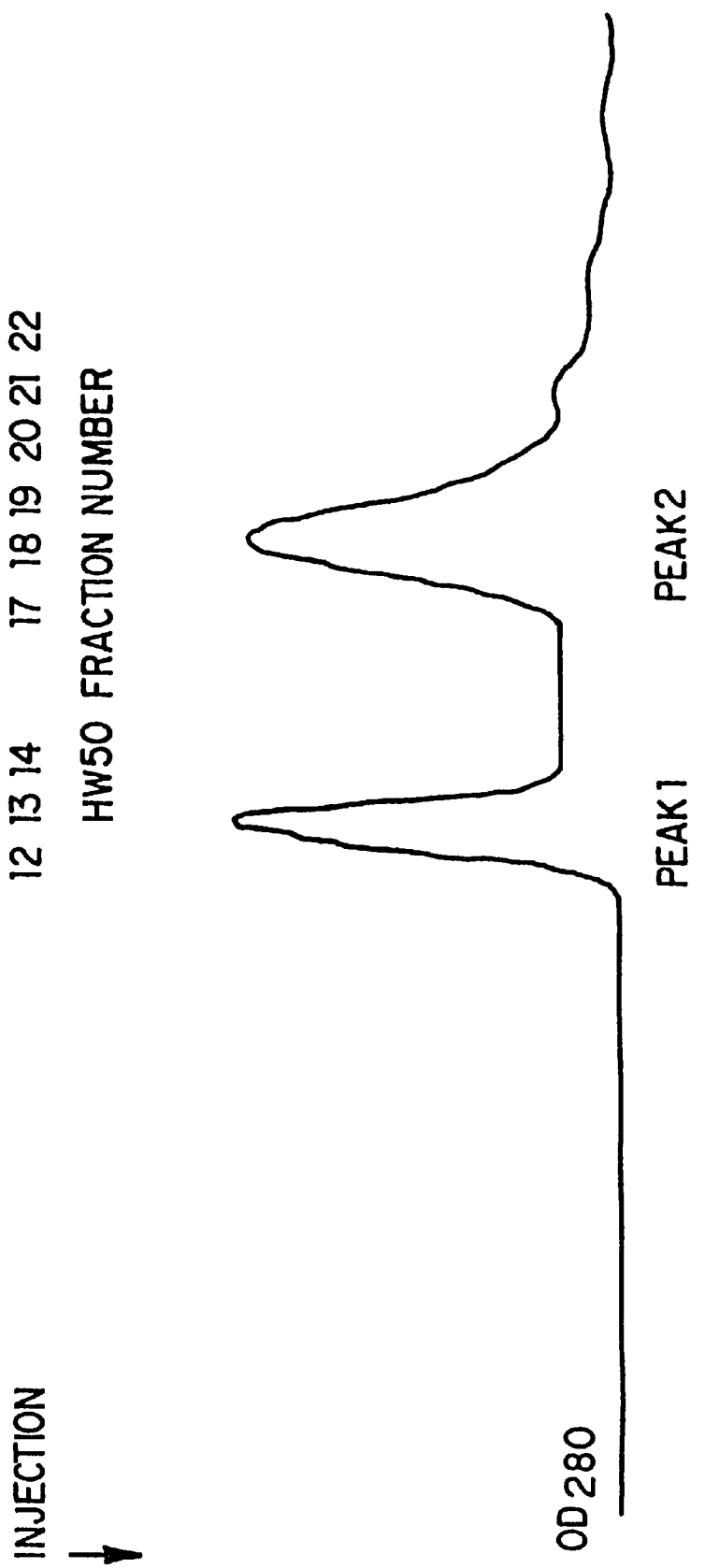

| TREATMENTS | NUMBERS OF CIRCULATING WBC PER MILLILITER OF BLOOD | | |
|---|---|---|---|
| | DAY 3 | DAY 6 | DAY 10 |
| Gr-1 (Saline) | $8.4 \times 10^6 \pm 3.0 \times 10^6$ | $10.2 \times 10^6 \pm 3.6 \times 10^6$ | $7.0 \times 10^6 \pm 9.9 \times 10^5$ |
| Gr-2, MPIF-1 ALONE | $7.8 \times 10^6 \pm 2.2 \times 10^6$ (100%) | $7.5 \times 10^6 \pm 6.5 \times 10^5$ (100%) | $10.6 \times 10^6$ (100%) |
| Gr-3, 5-Fu ALONE | $4.23 \times 10^6 \pm 2.8 \times 10^6$ (54) | $1.8 \times 10^6 \pm 1.4 \times 10^4$ (24) | $8.8 \times 10^6 \pm 4.9 \times 10^5$ (83) |
| Gr-4, MPIF-1 PLUS 5-Fu | $3.49 \times 10^6 \pm 6.5 \times 10^5$ (45) | $3.98 \times 10^6 \pm 4.3 \times 10^5$ (53) | $9.48 \times 10^6 \pm 9.4 \times 10^5$ (89) |

FIG.16

| GROUP | TREATMENTS | NUMBER OF COLONIES PER 2,000 CELLS | | | |
|---|---|---|---|---|---|
| | | DAY 6 | | DAY 9 | |
| | | HPP-CFC | LPP-CFC | HPP-CFC | LPP-CFC |
| 1 | SALINE<br>SALINE<br>SALINE | 10.5 ± 0.7<br>12 ± 0.7<br>14 ± 1.4 | 60 ± 9.8<br>92 ± 11<br>84 ± 1.4 | 15 ± 2<br>13 ± 1<br>11 ± 2 | 78 ± 3.5<br>80 ± 14<br>82 ± 0 |
| 2 | 5-Fu<br>5-Fu<br>5-Fu | 4.5 ± 3.5<br>12 ± 2<br>4 ± 2.8 | 3.5 ± 0.7<br>37 ± 16<br>6 ± 3 | 7 ± 2<br>6 ± 2<br>DEAD | 5 ± 0<br>2 ± 0<br>DEAD |
| 3 | 5-Fu PLUS MPIF-1<br>"   "    "    "<br>"   "    "    " | 0<br>0<br>0 | 6.5 ± 3.5<br>105 ± 10<br>120 ± 1.4 | 16 ± 1.4<br>12 ± 2.8<br>16 ± 0 | 75 ± 1.4<br>46 ± 12<br>95 ± 2.8 |

FIG.18

MPIF-1 Variants

```
         1          10         20         30         40         50         60         70         80
         MKVSVAALSC LMLVTALGSQ ARVTKDAETE FMMSKLPLEN PVLLDRFHAT SADCCISYTP RSIPCSLLES YFETNSECSK

1) Wild type:                  RVTKDAE.. .......... .......... .......... .......... ..........
2) Mutant-1(+1):              MRVTKDAE.. .......... .......... .......... .......... ..........
3) Mutant-2(-δ 24):                                            RFHAT..... .......... ..........
4) Mutant-3(-δ 23):                                            DRFHAT.... .......... ..........
5) Mutant-4(-δ 26):                                       HAT SAD....... .......... ..........
6) Mutant-5(-δ 27):                                        AT SAD....... .......... ..........
7) Mutant-6(-δ 24):                                            MRFHAT... .......... ..........
8) Mutant-7(-δ 17):                              EN PVLLD..... .......... .......... ..........
9) Mutant-8(-δ 22):                                           LDRFHAT... .......... ..........
10)Mutant-9(-δ 25):                                           HAAGFHAT.. .......... ..........
```

FIG. 19

```
gtcctcggccagccctgcctgcccaccaggaggatgaaggtctccgtggctgccctctcctgcctcatgctt
                                  M  K  V  S  V  A  A  L  S  C  L  M  L gttactgcccttggatcccaggcccgggtcacaaaagatgcagagacagagttcatgatgtcaaagcttcca
V  T  A  L  G  S  Q  A  R  V  T  K  D  A  E  T  E  F  M  M  S  K  L  P ttggaaaatccagtacttctggacatgctctggaggagaaagattggtcctcagatgacctttctcatgcc
L  E  N  P  V  L  L  D  M  L  W  R  R  K  I  G  P  Q  M  T  L  S  H  A gcaggattccatgctactagtgctgactgctgcatctcctacaccccacgaagcatcccgtgttcactcctg
A  G  F  H  A  T  S  A  D  C  C  I  S  Y  T  P  R  S  I  P  C  S  L  L gagagttactttgaaacgaacagcgagtgctccaagccgggtgtcatcttcctcaccaagaaggggcgacgt
E  S  Y  F  E  T  N  S  E  C  S  K  P  G  V  I  F  L  T  K  K  G  R  R ttctgtgccaacccccagtgataagcaagttcaggtttgcatgagaatgctgaagctggacacacggatcaag
F  C  A  N  P  S  D  K  Q  V  Q  V  C  M  R  M  L  K  L  D  T  R  I  K accaggaagaattgaacttgtcaaggtgaagggacacaagttgccagccaccaactttcttgcctcaactaa
T  R  K  N  * cttcctgaattattttttttaagaagcatttattcttgtgttctggatttagagcaattcatctttttctcacc
tttaaaaaaaaaaaaaaaaaa
```

FIG.20A

```
  1  MKVSVAALSCLMLVTALGSQARVTKDAETEFMMSKLPLENPVLLDMLWRR   50   MPIF-1 variant
     ||||||||||||||||||||||||||||||||||||||||||||||
  1  MKVSVAALSCLMLVTALGSQARVTKDAETEFMMSKLPLENPVLLDR....   46   MPIF-1

51  KIGPQMTLSHAAGFHATSADCCISYTPRSIPCSLLESYFETNSECSKPGV   100
                  |||||||||||||||||||||||||||||||||||||
 47  .............FHATSADCCISYTPRSIPCSLLESYFETNSECSKPGV   83

101  IFLTKKGRRFCANPSDKQVQVCMRMLKLDTRIKTRKN   137
     ||||||||||||||||||||||||||||||||||||
 84  IFLTKKGRRFCANPSDKQVQVCMRMLKLDTRIKTRKN   120
```

FIG.20B

| MPIF-1 MUTANTS | CONCENTRATION (ng/ml) |
|---|---|
| WILD TYPE | 100 |
| PREPARATION K0871 | 10 |
| MUTANT-1 | 50 |
| MUTANT-6 | 100 |
| HG00300-B7 | 10 |
| MUTANT-9 | 10 |

FIG.21

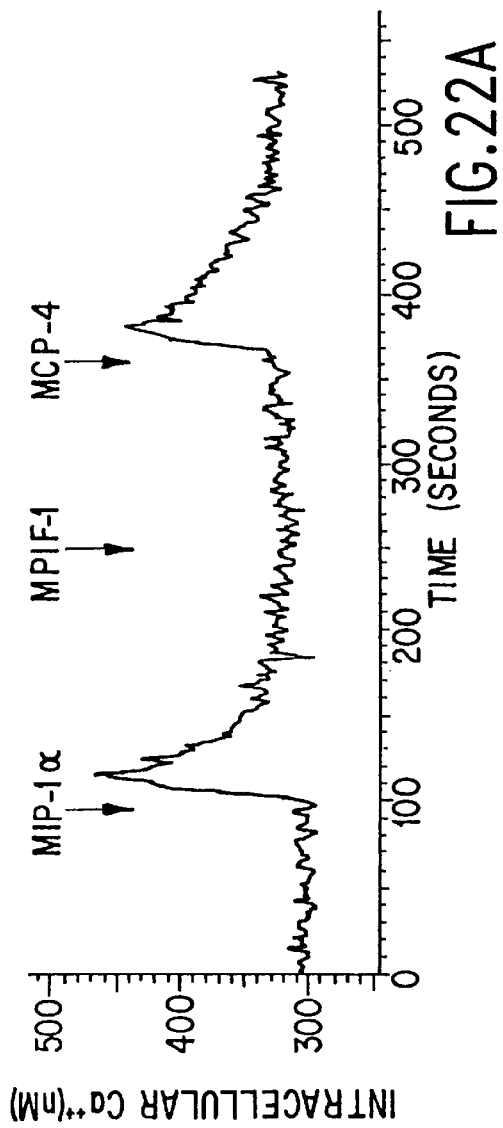
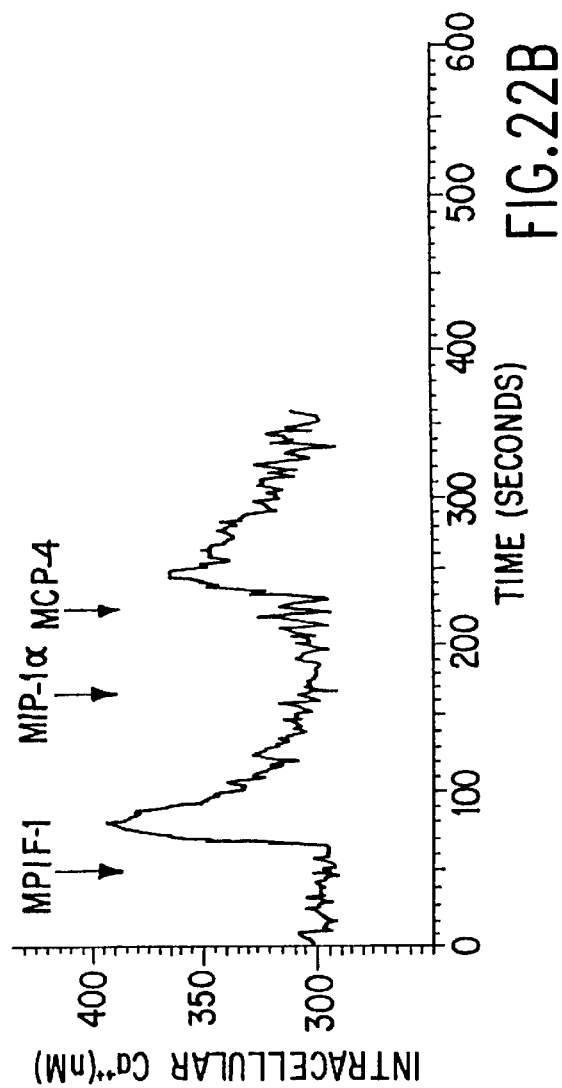

| ADDITIONS | CALCIUM MOBILIZATION RESPONSE |
|---|---|
| MIP-1a ALONE | + |
| MPIF-1 ALONE | + |
| MIP-1a FOLLOWED BY MPIF-1 | − |
| MPIF-1 FOLLOWED BY MIP-1a | − |
| | |
| MIP-1a FOLLOWED BY: | |
| PREPARATION K0871 | − |
| HG00300-B7 | − |
| MUTANT-6 | − |
| MUTANT-1 | − |
| MUTANT-9 | − |
| | |
| PREPARATION K0871 | + |
| K0871 FOLLOWED BY MIP-1a | − |
| HG00300-B7 | + |
| HG00300-B7 FOLLOWED BY MIP-1a | − |
| MUTANT-6 | + |
| MUTANT-6 FOLLOWED BY MIP-1a | − |
| MUTANT-1 | + |
| MUTANT-1 FOLLOWED BY MIP-1a | − |
| MUTANT-9 | + |
| MUTANT-9 FOLLOWED BY MIP-1a | − |

FIG.23

| PROTEINS | CHEMOTAXIS * |
|---|---|
| WILD TYPE | 50-100 ng/ml (3-4X) |
| PREPARATION K0871 | 10-30 ng/ml (6-7X) |
| MUTANT-1 | 50-100 ng/ml (3-4X) |
| MUTANT-6 | 50-100 ng/ml (5-7X) |
| HG00300-B7 | 10-30 ng/ml (4-5X) |

FIG.24

| ADDITIONS | CONCENTRATION REQUIRED FOR 50% OF MAXIMAL LPP-CFC INHIBITION (ng/ml) |
|---|---|
| MPIF-1, WILD TYPE | 10-20 |
| MUTANT-1 | 15-25 |
| MUTANT-6 | 1-10 |
| PREPARATION K0871 | 0.1-1.0 |
| HG00300-B7 | 0.1-1.0 |

STEM CELL MOBILIZATION IN RESPONSE TO ADMINISTERING MPIF-1 TO NORMAL MICE

| EXPERIMENT | TREATMENTS | WBC/ml BLOOD (× 10⁶) | PHENOTYPE OF CELLS | |
|---|---|---|---|---|
| | | | Gr.1 | CD34⁺Sca-1⁺ |
| 1. | SALINE | 4.7 ± 0.36 | 10 | 0.20 |
| | MPIF-1 | 7.1 ± 0.63 | 39 | 8 |

FIG.26

```
                                              -35           Operator 1
1  AAGCTT AAAAAACTGCAAAAAATAGT TTGACT TGTGAGCGGATAACAAT -10              Operator 2
50 TAAGAT GTACCCA ATTGTGAGCGGATAACAAT TTCACACATTAA

S/D
94 AGAGGAG AAATTA CATATG
```

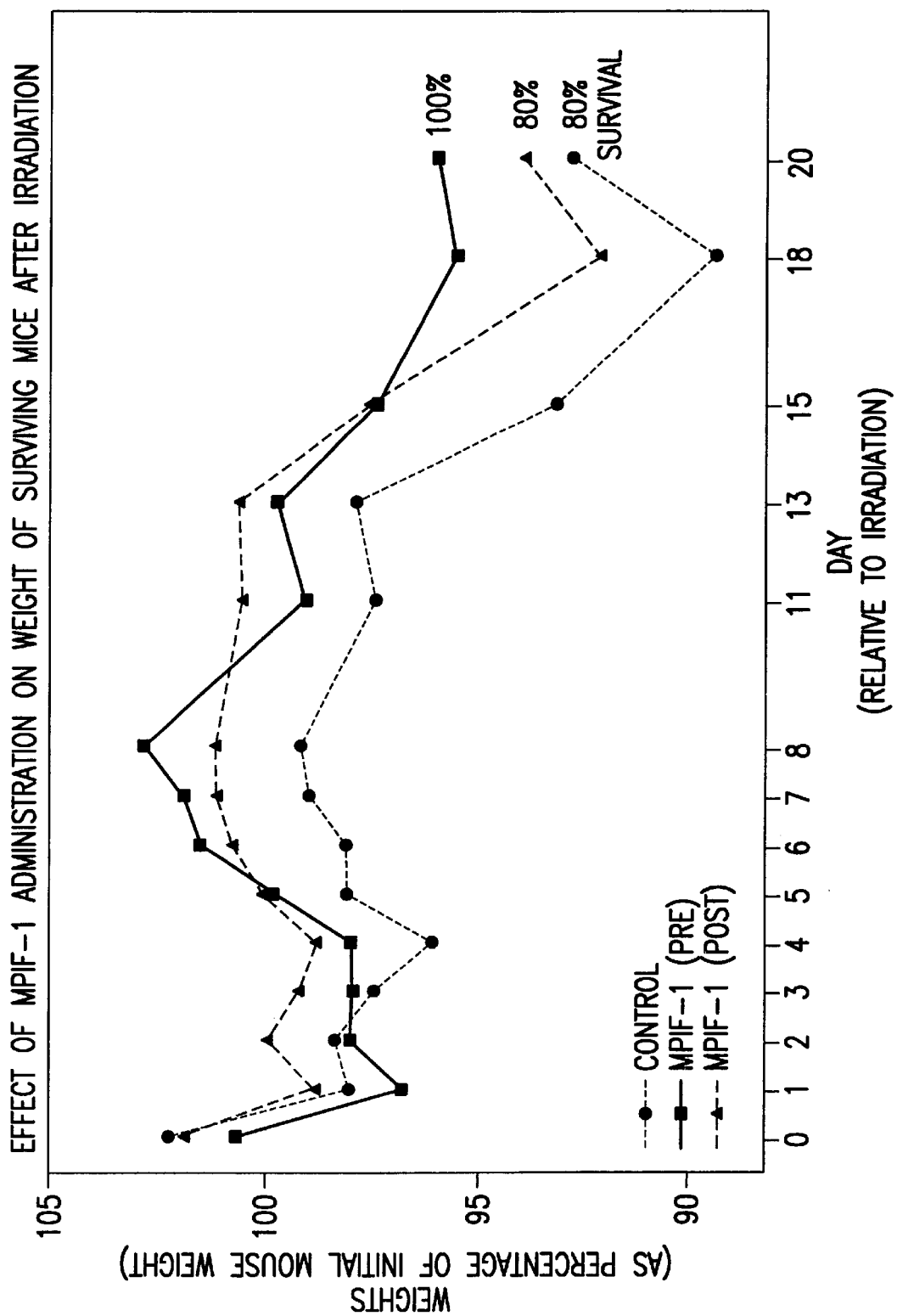

GENERAL SUMMARY OF MULTIPLE DOSE TOXICITY STUDIES

| SPECIES | STRAIN | INITIAL GROUP SIZE | ROUTE OF ADMINISTRATION | DURATION (DAYS) | TEST ARTICLE | DOSE RANGE | LAB/TESTING FACILITY | STUDY NUMBER |
|---|---|---|---|---|---|---|---|---|
| MOUSE | CD-1 | 5 MALES 5 FEMALES | INTRAVENOUS | 7 | MPIF | 0, 0.2, 2, AND 20 mg/kg | QUINTILES SCOTLAND | VRI 00201 |
| MOUSE | CD-1 | 15 MALES, 15 FEMALES PER GROUP (MAIN/RECOVERY STUDY) 18 MALES, 18 FEMALES PER GROUP FOR TOXICOKINETICS ON DAY 1 AND DAY 14 | INTRAVENOUS | 14 | MPIF | 0, 0.2, 2, AND 20 mg/kg | QUINTILES SCOTLAND | VRI 00202 |
| MOUSE | CD-1 | 10 MALES, 10 FEMALES | INTRAVENOUS | 25 | MPIF | 0, 0.2, 2, AND 20 mg/kg | QUINTILES SCOTLAND | VRI 00203 |

FIG.52

SUMMARY OF OBSERVATIONS FOR NONCLINICAL TOXICOLOGY STUDIES

| STUDY NUMBER | PRODUCT NAME DOSE LEVEL | DOSING CONDITIONS | CLINICAL OBSERVATIONS | NUMBER OF ANIMALS IN WHICH CLINICAL SIGNS WERE OBSERVED (GENDER) | UNIQUE ANIMAL NUMBERS |
|---|---|---|---|---|---|
| VRI 00201 | MPIF 0.2, 2, AND 20 mg/kg/DAY | INTRAVENOUS, 7 DAYS | THERE WERE NO FINDINGS IN EITHER SEX THAT WERE CONSIDERED DUE TO TEST ARTICLE | 0 | NONE |
| VRI 00202 | MPIF 0.2, 2, AND 20 mg/kg/DAY | INTRAVENOUS, 14 DAYS | THERE WERE NO FINDINGS IN EITHER SEX THAT WERE CONSIDERED DUE TO TEST ARTICLE | 0 | NONE |
| VRI 00203 | MPIF 0.2, 2, AND 20 mg/kg/DAY | INTRAVENOUS ON DAYS 0-4, 10-14, AND 20-24 | THERE WERE NO FINDINGS IN EITHER SEX THAT WERE CONSIDERED DUE TO TEST ARTICLE | 0 | NONE |

FIG.53

THE PHARMACOKINETIC PROFILE FROM 0 TO 24 HOURS

THE PHARMACOKINETIC PROFILE FROM 0 TO 4 HOURS

SHADED AREAS REPRESENT NORMAL HUMAN RANGE FOR INDICATED CELL TYPE

SHADED AREAS REPRESENT NORMAL HUMAN RANGE FOR INDICATED CELL TYPE

SHADED AREAS REPRESENT NORMAL HUMAN RANGE FOR INDICATED CELL TYPE

SHADED AREAS REPRESENT NORMAL HUMAN RANGE FOR INDICATED CELL TYPE

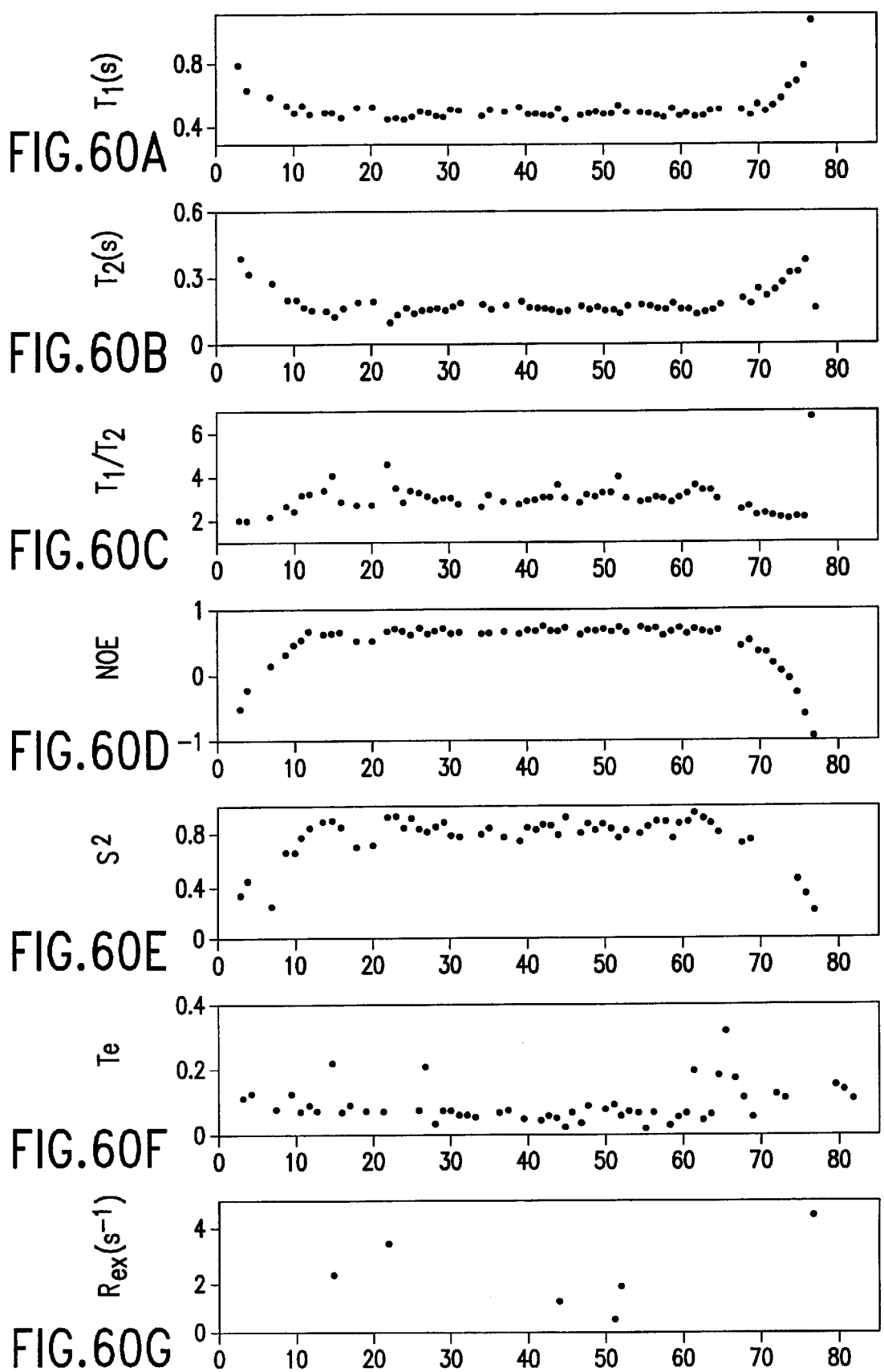

Amino Acid Sequence of MPIF-1 and related CC Chemokines

```
            5         10        15        20        25        30        35        40        45        50        55        60        65        70
MPIF1  LDRFHATSADCCISYTPRSIPCSLLESY-FETNSECSKPGVIFLTKKGRRFCANPSDKQVQVCMRMLKLDTRIKTRKN
HCC2        H-FAADCCTSYISQSIPCSLMKSY-FETSSECSKPGVIFLTKKGRQVCAKPSGPGVQDCMKKLKPYSI
HCC1   SSSRGPYHPSECCFTYTTYKIPRQRIMDY-YETNSQCSKPGIVFITKRGHSVCTNPSDKWVQDYIKDMKEN
MCP-1  QPDAINAPVTCCYNFTNRKISVQRLASYRRITSSKCPKEAVIFKTKLDKEICADPTQKWVQDSMDHLDKQTQTPKT
MCP-3  QPVGINTSTTCCYRFINKKIPKQRLESYRRTTSSHCPREAVIFKTKLDKEICADPTQKWVQDFMKHLDKKTQ--TPKI
Eotax       GPASVPTTCCFNLANRKIPLQRLESYRRITSGKCPQKAVIFKTKLAKDICADPKKKWVQDSMKYLDQSSPTPKP
MIP1β  APMGSDPPTACCFSYTARKLPRNFVVDY-YETSSLCSQPAVVFQTKRSKQVCADPSESWVQEYVYDLELN
MIP1α  ASLAADTPTACCFSYTSRQIPQNFIADY-FETSSQCSKPGVIFLTKRSRQVCADPSEEWVQKYVSDLELSA
RANTES SPYSSDTTPCCFAYIARPLPRAHIKEY-FYTSGKCSNPAVVFVTRKNRQVCANPEKKWVREYINSLEMS
MPIF1  LDRFHATSADCCISYTPRSIPCSLLESY-FETNSECSKPGVIFLTKKGRRFCANPSDKQVQVCMRMLKLDTRIKTRKN
```

FIG.62

METHODS OF INHIBITING HEMATOPOIETIC STEM CELLS USING HUMAN MYELOID PROGENITOR INHIBITORY FACTOR-1 (MPIF-1) (CKBETA-8/MIP-3)

CROSS-REFERENCE TO RELATED APPLICATIONS

This application claims the benefit of application Ser. Nos. 60/159,362, filed Oct. 14, 1999, 60/164,059, filed Nov. 8, 1999, Ser. No. 60/172,063, filed Dec. 23, 1999, Ser. No. 60/189,048, filed Mar. 14, 2000, Ser. No. 60/199,142, filed Apr. 24, 2000, Ser. No. 60/211,458, filed Jun. 13, 2000 and Ser. No. 60/212,658, filed Jun. 19, 2000, and is a continuation-in-part of Ser. No. 09/571,013, filed May 15, 2000 and a continuation-in-part of Ser. No. 09/334,951, filed Jun. 17, 1999; said Ser. No. 09/571,013 is a continuation of 08/941,020, filed Sep. 30, 1997 (abandoned); said Ser. No. 08/941,020 claims the benefit of Ser. Nos. 60/027,299 and 60/027,300, both filed Sep. 30, 1996, and is a continuation-in-part of Ser. No. 08/722,723, filed Sep. 30, 1996 (abandoned), and a continuation-in-part of Ser. No. 08/722,719, filed Sep. 30, 1996, U.S. Pat. No. 6,001,606; said Ser. No. 08/722,723 and said Ser. No. 08/722,719 is each a continuation-in-part of Ser. No. 08/468,775, filed Jun. 6, 1995 (abandoned), and a continuation-in-part of Ser. No. 08/465,682, filed Jun. 6, 1995 (abandoned), and a continuation-in-part of Ser. No. 08/446,881, filed May 5, 1995 (abandoned); said Ser. No. 08/468,775 and said Ser. No. 08/465,682 is each a continuation of said Ser. No. 08/446,881 and a continuation-in-part of Ser. No. 08/208,339, filed Mar. 8, 1994, U.S. Pat. No. 5,504,003; said Ser. No. 08/446,881 is a continuation-in-part of said Ser. No. 08/208,339; each of said applications is herein incorporated by reference.

BACKGROUND OF THE INVENTION

1. Field of the Invention

The present invention relates to novel methods of using human myeloid progenitor inhibitory factor-1 (MPIF-1) polypeptide (previously termed MIP-3 and chemokine β8 (CKβ8 or ckb-8)), as well as isolated polynucleotides encoding MPIF-1. Also provided are vectors, host cells and recombinant methods for producing MPIF-1.

2. Related Art

Chemokines, also referred to as intercrine cytokines, are a subfamily of structurally and functionally related cytokines. These molecules are 8–14 kd in size. In general, chemokines exhibit 20% to 75% homology at the amino acid level and are characterized by four conserved cysteine residues that form two disulfide bonds. Based on the arrangement of the first two cysteine residues, chemokines have been classified into two subfamilies, alpha and beta. In the alpha subfamily, the first two cysteines are separated by one amino acid and hence are referred to as the "C—X—C" subfamily. In the beta subfamily, the two cysteines are in an adjacent position and are, therefore, referred to as the —C—C— subfamily. Thus far, at least eight different members of this family have been identified in humans.

The intercrine cytokines exhibit a wide variety of functions. A hallmark feature is their ability to elicit chemotactic migration of distinct cell types, including monocytes, neutrophils, T lymphocytes, basophils and fibroblasts. Many chemokines have proinflammatory activity and are involved in multiple steps during an inflammatory reaction. These activities include stimulation of histamine release, lysosomal enzyme and leukotriene release, increased adherence of target immune cells to endothelial cells, enhanced binding of complement proteins, induced expression of granulocyte adhesion molecules and complement receptors, and respiratory burst. In addition to their involvement in inflammation, certain chemokines have been shown to exhibit other activities. For example, macrophage inflammatory protein I (MIP-1) is able to suppress hematopoietic stem cell proliferation, platelet factor-4 (PF-4) is a potent inhibitor of endothelial cell growth, Interleukin-8 (IL-8) promotes proliferation of keratinocytes, and GRO is an autocrine growth factor for melanoma cells.

In light of the diverse biological activities, it is not surprising that chemokines have been implicated in a number of physiological and disease conditions, including lymphocyte trafficking, wound healing, hematopoietic regulation and immunological disorders such as allergy, asthma and arthritis. An example of a hematopoietic lineage regulator is MIP-1. MIP-1 was originally identified as an endotoxin-induced proinflammatory cytokine produced from macrophages. Subsequent studies have shown that MIP-1 is composed of two different, but related, proteins MIP-1α and MIP-1β. Both MIP-1α and MIP-1β are chemoattractants for macrophages, monocytes and T lymphocytes. Interestingly, biochemical purification and subsequent sequence analysis of a multipotent stem cell inhibitor (SCI) revealed that SCI is identical to MIP-1β. Furthermore, it has been shown that MIP-1β can counteract the ability of MIP-1α to suppress hematopoietic stem cell proliferation. This finding leads to the hypothesis that the primary physiological role of MIP-1 is to regulate hematopoiesis in bone marrow, and that the proposed inflammatory function is secondary. The mode of action of MIP-1α as a stem cell inhibitor relates to its ability to block the cell cycle at the $G_2S$ interphase. Furthermore, the inhibitory effect of MIP-1α seems to be restricted to immature progenitor cells and it is actually stimulatory to late progenitors in the presence of granulocyte Hmacrophage-colony stimulating factor (GM-CSF).

Murine MIP-1 is a major secreted protein from lipopolysaccharide stimulated RAW 264.7, a murine macrophage tumor cell line. It has been purified and found to consist of two related proteins, MIP-1α and MIP-1β.

Several groups have cloned what are likely to be the human homologs of MIP-1α and MIP-1β. In all cases, cDNAs were isolated from libraries prepared against activated T-cell RNA.

MIP-1 proteins can be detected in early wound inflammation cells and have been shown to induce production of IL-1 and IL-6 from wound fibroblast cells. In addition, purified native MIP-1 (comprising MIP-1, MIP-1α and MIP-1β polypeptides) causes acute inflammation when injected either subcutaneously into the footpads of mice or intracisternally into the cerebrospinal fluid of rabbits (Wolpe and Cerami, *FASEB J.* 3:2565–73 (1989)). In addition to these proinflammatory properties of MIP-1, which can be direct or indirect, MIP-1 has been recovered during the early inflammatory phases of wound healing in an experimental mouse model employing sterile wound chambers (Fahey, et al. *Cytokine*, 2:92 (1990)). For example, PCT application U.S. Ser. No. 92/05198 filed by Chiron Corporation, discloses a DNA molecule which is active as a template for producing mammalian macrophage inflammatory proteins (MIPs) in yeast.

The murine MIP-1α and MIP-1β are distinct but closely related cytokines. Partially purified mixtures of the two proteins affect neutrophil function and cause local inflammation and fever. MIP-1α has been expressed in yeast cells and purified to homogeneity. Structural analysis confirmed that MIP-1α has a very similar secondary and tertiary structure to platelet factor 4 (PF-4) and interleukin 8 (IL-8) with which it shares limited sequence homology. It has also been demonstrated that MIP-1α is active in vivo to protect mouse stem cells from subsequent in vitro killing by tritiated thymidine. MIP-1α was also shown to enhance the proliferation of more committed progenitor granulocyte macrophage colony-forming cells in response to granulocyte macrophage colony-stimulating factor. (Clemens, J. M. et al., *Cytokine* 4:76–82 (1992)).

The olypeptide of the present invention, MPIF-1 (sometimes also referred to as MIP-3 and Ckβ-8), is a new member of the s chemokine family based on the amino acid sequence homology.

SUMMARY OF THE INVENTION

In accordance with one aspect of the present invention, there are provided novel methods of preventing or treating injury to cells, tissues and organs using full length or mature MPIF-1 polypeptides, as well as biologically active, diagnostically useful or therapeutically usefully fragments, analogs and derivatives thereof.

In another aspect, the invention provides methods of treatment or prevention using isolated polynucleotides encoding MPIF-1 polypeptides. The MPIF-1 of the present invention is preferably of animal origin, and more preferably of human origin.

The invention also provides MPIF-1 polypeptides and isolated polynucleotides (DNA or RNA) encoding such polypeptides, including mRNAs, DNAs, cDNAs, genomic DNA as well as biologically active and diagnostically or therapeutically useful fragments, analogs and derivatives thereof.

MPIF-1 Polynucleotides. The present invention also provides isolated nucleic acid molecules comprising, or alternatively consisting of, a polynucleotide encoding the MPIF-1 polypeptide having the amino acid sequence shown in FIG. 1 (SEQ ID NO:2) or the amino acid sequence encoded by the cDNA clone deposited as ATCC Deposit Number 75676 on Feb. 9, 1994. The nucleotide sequence determined by sequencing the deposited MPIF-1 clone, which is shown in FIG. 1 (SEQ ID NO:1), contains an open reading frame encoding a polypeptide of 120 amino acid residues, with a leader sequence of about 21 amino acid residues, and a predicted molecular weight for the mature protein of about 11 kDa in non-glycosylated form, and about 11–14 kDa in glycosylated form, depending on the extent of glycoslyation. The amino acid sequence of the mature MPIF-1 protein is shown in FIG. 1 (SEQ ID NO:2).

Thus, one aspect of the invention provides an isolated nucleic acid molecule comprising, or alternatively consisting of, a polynucleotide having a nucleotide sequence selected from the group consisting of: (a) a nucleotide sequence encoding an MPIF-1 polypeptide having the complete amino acid sequence in FIG. 1 (SEQ ID NO:2); (b) a nucleotide sequence encoding the MPIF-1 polypeptide having the complete amino acid sequence in FIG. 1 (SEQ ID NO:2) but minus the N-terminal methionine residue; (c) a nucleotide sequence encoding the mature MPIF-1 polypeptide having the amino acid sequence at positions 22–120 in FIG. 1 (SEQ ID NO:2); (d) a nucleotide sequence encoding the MPIF-1 polypeptide having the complete amino acid sequence encoded by the cDNA clone contained in ATCC Deposit No. 75676; (e) a nucleotide sequence encoding the mature MPIF-1 polypeptide having the amino acid sequence encoded by the cDNA clone contained in ATCC Deposit No. 75676; and (f) a nucleotide sequence complementary to any of the nucleotide sequences in (a), (b), (c), (d), or (e) above.

MPIF-1 Polynucleotide Variants. The present invention further relates to variants of the hereinabove described polynucleotides which encode for fragments, analogs and derivatives of the polypeptide having the deduced amino acid sequence of FIG. 1 (SEQ ID NO:2) or the polypeptides encoded by the cDNA of the deposited clone(s). The variants of the polynucleotides can be a naturally occurring allelic variant of the polynucleotides or a non-naturally occurring variant of the polynucleotides.

Homologous MPIF-1 Polynucleotides. Further embodiments of the invention include isolated nucleic acid molecules that comprise a polynucleotide having a nucleotide sequence at least 95%, 96%, 97%, 98% or 99% identical, to any of the nucleotide sequences in (a), (b), (c), (d), (e), or (f), above, or a polynucleotide which hybridizes under stringent hybridization conditions to a polynucleotide in (a), (b), (c), (d), (e), or (f), above. These polynucleotides which hybridize do not hybridize under stringent hybridization conditions to a polynucleotide having a nucleotide sequence consisting of only A residues or of only T residues.

Nucleic Acid Probes. In accordance with yet another aspect of the present invention, there are also provided nucleic acid probes comprising, or alternatively consisting of, nucleic acid molecules of sufficient length to specifically hybridize to the MPIF-1 nucleic acid sequences.

Recombinant Vectors, Host Cells and Expression. The present invention also relates to recombinant vectors, which include the isolated nucleic acid molecules of the present invention, and to host cells containing the recombinant vectors, as well as to methods of making such vectors and host cells and for using them for production of MPIF-1 polypeptides or peptides by recombinant techniques.

MPIF-1 Polypeptides. The invention further provides an isolated MPIF-1 polypeptide having an amino acid sequence selected from the group consisting of: (a) the amino acid sequence of the MPIF-1 polypeptide having the complete 120 amino acid sequence, including the leader sequence shown in FIG. 1 (SEQ ID NO:2); (b) the amino acid sequence of the MPIF-1 polypeptide having the complete 120 amino acid sequence, including the leader sequence shown in FIG. 1 (SEQ ID NO:2) but minus the N-terminal methionine residue; (c) the amino acid sequence of the mature MPIF-1 polypeptide (without the leader) having the amino acid sequence at positions 22–120 in FIG. 1 (SEQ ID NO:2); (d) the amino acid sequence of the MPIF-1 polypeptide having the complete amino acid sequence, including the leader, encoded by the cDNA clone contained in ATCC Deposit No. 75676; and (e) the amino acid sequence of the mature MPIF-1 polypeptide having the amino acid sequence encoded by the cDNA clone contained in ATCC Deposit No. 75676.

Homologous MPIF-Polypeptides. Polypeptides of the present invention also include homologous polypeptides having an amino acid sequence with at least 95% identity to those described in (a), (b), (c), (d), or (e) above, as well as polypeptides having an amino acid sequence at least 95%, 96%, 97%, 98% or 99% identical to those above.

MPIF-1 Epitope Bearing Polypeptides and Encoding Polynucleotides. An additional embodiment of this aspect of the invention relates to a peptide or polypeptide which has the amino acid sequence of an epitope-bearing portion of an MPIF-1 polypeptide having an amino acid sequence described in (a), (b), (c), (d), or (e), above. Peptides or polypeptides having the amino acid sequence of an epitope-bearing portion of an MPIF-1 polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

An additional nucleic acid embodiment of the invention relates to an isolated nucleic acid molecule comprising, or alternatively consisting of, a polynucleotide which encodes the amino acid sequence of an epitope-bearing portion of an MPIF-1 polypeptide having an amino acid sequence in (a), (b), (c), (d), or (e), above.

MPIF-1 Antibodies. In accordance with yet a further aspect of the present invention, there is provided an antibody against such polypeptides. In another embodiment, the invention provides an isolated antibody that binds specifically to an MPIF-1 polypeptide having an amino acid sequence described in (a), (b), (c), (d), or (e), above.

The invention further provides methods for isolating antibodies that bind specifically to an MPIF-1 polypeptide having an amino acid sequence as described herein. Such antibodies are useful diagnostically or therapeutically as described below.

MPIF-1 Antagonists and Methods. In accordance with yet another aspect of the present invention, there are provided antagonists or inhibitors of such polypeptides, which can be used to inhibit the action of such polypeptides, for example, in the treatment of arteriosclerosis, autoimmune and chronic inflammatory and infective diseases, histamine-mediated allergic reactions, hypereosinophilic syndrome, silicosis, sarcoidosis, inflammatory diseases of the lung, inhibition of IL-1 and TNF, aplastic anaemia, and myelodysplastic syndrome. Alternatively, such polypeptides can be used to inhibit production of IL-1 and TNF-α, to treat aplastic anemia, myelodysplastic syndrome, asthma and arthritis.

Diagnostic Assays. In accordance with still another aspect of the present invention, there are provided diagnostic assays for detecting diseases related to the underexpression and overexpression of the polypeptides and for detecting mutations in the nucleic acid sequences encoding such polypeptides.

In accordance with yet another aspect of the present invention, there is provided a process for utilizing such polypeptides, or polynucleotides encoding such polypeptides, as research reagents for in vitro purposes related to scientific research, synthesis of DNA and manufacture of DNA vectors, for the purpose of developing therapeutics and diagnostics for the treatment of human disease.

The present invention also provides a screening method for identifying compounds capable of enhancing or inhibiting a cellular response induced by an MPIF-1 polypeptide, which involves contacting cells which express the MPIF-1 polypeptide with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

For a number of disorders, it is believed that significantly higher or lower levels of MPIF-1 gene expression can be detected in certain tissues or bodily fluids (e.g, serum, plasma, urine, synovial fluid or spinal fluid) taken from an individual having such a disorder, relative to a "standard" MPIF-1 gene expression level, i. e., the MPIF-1 expression level in tissue or bodily fluids from an individual not having the disorder. Thus, the invention provides a diagnostic method useful during diagnosis of a disorder, which involves: (a) assaying MPIF-1 gene expression level in cells or body fluid of an individual; (b) comparing the MPIF-1 gene expression level with a standard MPIF-1 gene expression level, whereby an increase or decrease in the assayed MPIF-1 gene expression level compared to the standard expression level is indicative of a disorder. Such disorders include leukemia, chronic inflammation, autoimmune diseases, solid tumors, and toxicity from radiation and chemotherapy.

Pharmaceutical Compositions. The present invention also provides, in another aspect, pharmaceutical compositions comprising at least one of an MPIF-1 polynucleotide, probe, vector, host cell, polypeptide, fragment, variant, derivative, epitope bearing portion, antibody, antagonist, or agonist.

Therapeutic Methods. In accordance with yet a further aspect of the present invention, there is provided a process for utilizing such polypeptides, or polynucleotides encoding such polypeptides for therapeutic purposes, for example, to protect bone marrow stem cells from chemotherapeutic agents during chemotherapy, to remove leukemic cells, to stimulate an immune response, to regulate hematopoiesis and lymphocyte trafficking, treatment of psoriasis, solid tumors, to enhance host defenses against resistant and acute and chronic infection, and to stimulate wound healing.

An additional aspect of the invention is related to a method for treating an individual in need of an increased level of MPIF-1 activity in the body comprising administering to such an individual a composition comprising a therapeutically effective amount of an isolated MPIF-1 polypeptide of the invention or an agonist thereof, respectively.

A still further aspect of the invention is related to a method for treating an individual in need of a decreased level of MPIF-1 activity in the body comprising, administering to such an individual a composition comprising a therapeutically effective amount of an MPIF-1 antagonist.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIG. 1 displays the cDNA sequence encoding MPIF-1 (SEQ ID NO:1) and the corresponding deduced amino acid sequence (SEQ ID NO:2). The initial 21 amino acids represents the putative leader sequence. All the signal sequences were as determined by N-terminal peptide sequencing of the baculovirus expressed protein.

FIG. 2 illustrates the amino acid homology between MPIF-1 (top) (SEQ ID NO:2) and human MIP-1α (bottom) (SEQ ID NO:36). The four cysteines characteristic of all chemokines are shown.

FIGS. 3A–3B show a three-step purification of MPIF-1 in a baculovirus expression system. (A) Elution profile from HW50 column. (B) Photograph of an SDS-PAGE gel of fractions from the HW50 column.

FIG. 16 shows the effect of MPIF-1 pre-treatment of mice on the 5-Fu-induced reduction in the circulating WBC counts.

FIG. 18 shows the effect of administration of MPIF-1 prior to the second dose of 5-Fu on the HPP-CFC and LPP-CFC frequencies in the bone marrow.

FIG. 19 shows MPIF-1 variants. The first 80 out of 120 amino acids sequence of MPIF-1 (FIG. 1 (SEQ ID NO:2)) is shown using a single amino acid letter code of which the first 21 residues show characteristics of a signal sequence that is cleaved to give rise to a mature, wild type protein. Mutants-1 and -6 contain methionine as the N-terminal residue which is not present in the wild type. Also, the first four amino acids (HAAG) of Mutant-9 are not present in the wild type MPIF-1 protein. Mutants-1, -6 and, -9 correspond to SEQ ID NOS:3, 4 and 5, respectively. Mutant-2 corresponds to amino acid residues 46–120 in SEQ ID NO:2. Mutant-3 corresponds to amino acid residues 45–120 in SEQ ID NO:2. Mutant-4 corresponds to amino acid residues 48–120 in SEQ ID NO:2. Mutant-5 corresponds to amino acid residues 49–120 in SEQ ID NO:2. Mutant-7 corresponds to amino acid residues 39–120 in SEQ ID NO:2. Mutant-8 corresponds to amino acid residues 44–120 in SEQ ID NO:2.

FIGS. 20A–20B. FIG. 20A shows the nucleotide sequence of a human MPIF-1 splice variant cDNA (SEQ ID NO:6). This cDNA sequence is shown along with the open reading frame encoding for a protein of 137 amino acids (SEQ ID NO:7) using a single letter amino acid code. The N-terminal 21 amino acids which are underlined represent the putative leader sequence. The insertion of 18 amino acids sequence not represented in the MPIF-1 sequence but unique to the splice variant are high-lighted in italics. FIG. 20B shows the comparison of the amino acid sequence of the MPIF-1 variant (SEQ ID NO:7) with that of the wild type MPIF-1 molecule (SEQ ID NO:2).

FIG. 21 shows the concentrations of MPIF-1 mutant proteins required for 50% of maximal calcium mobilization response induced by MIP-1α in human monocytes.

FIGS. 22A–22B. The changes in the intracellular free calcium concentration was measured in human monocytes in response to the indicated proteins at 100 ng/ml as described in the legend to FIG. 21.

FIG. 23 shows the ability of MPIF-1 mutants to desensitize MIP-1α stimulated calcium mobilization in human monocytes (summary).

FIG. 24 shows the chemotactic responses of human peripheral blood mononuclear cells (PBMC) to MPIF-1 mutants. Numbers within the parenthesis reflect fold stimulation of chemotaxis above background observed at the indicate concentration range.

FIG. 25 shows the effect of MPIF-1 variants on the growth and differentiation of low Proliferative Potential Colony-forming Cells (LPP-CFC) in vitro.

FIG. 26 shows the stem cell mobilization in normal mice in response to the administration of MPIF-1.

Figure 27:
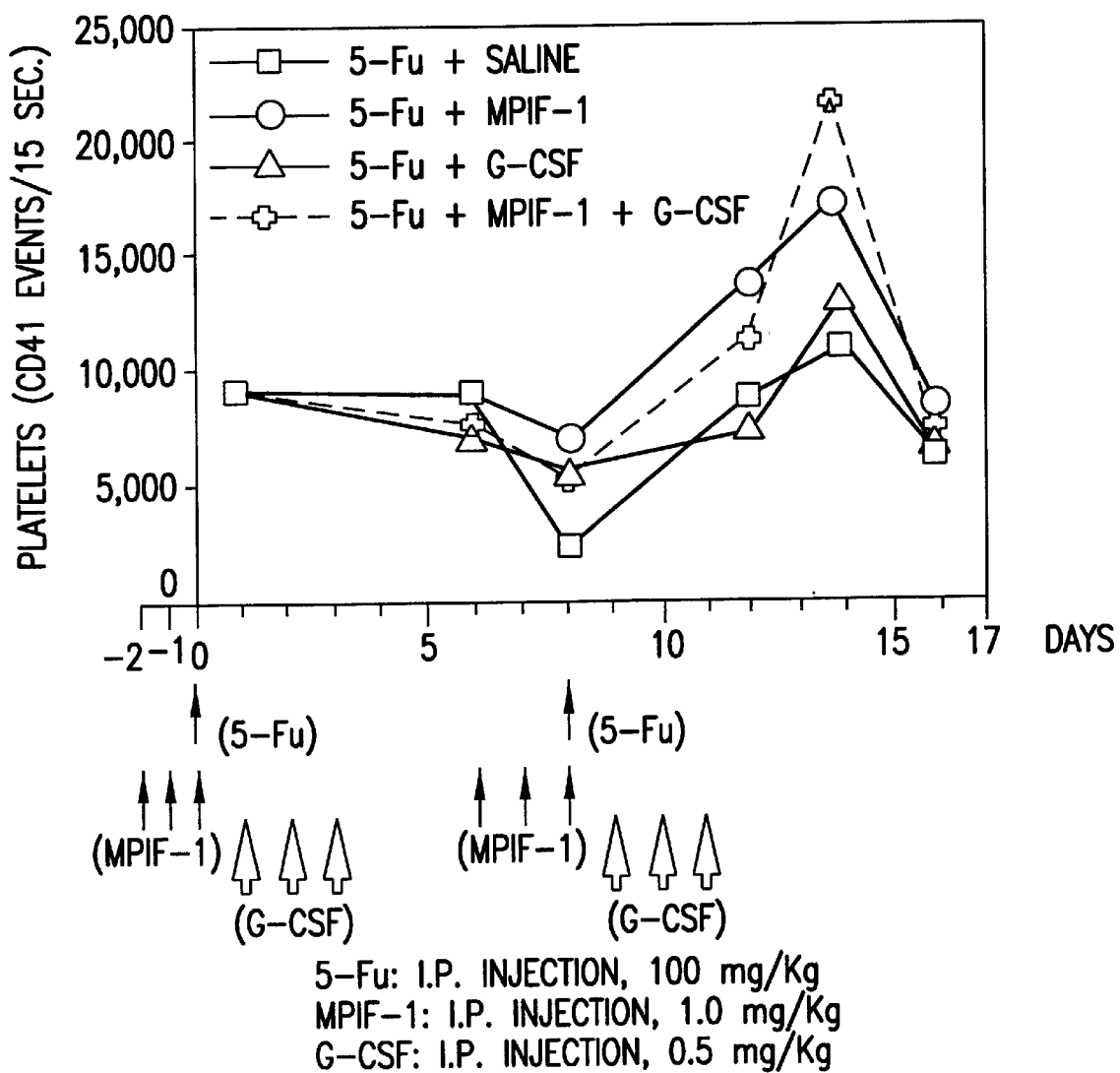

FIG. 27 shows a comparison of the effect of MPIF-1 with G-CSF on the recovery of platelets following two cycles of 5-Fu treatment as determined by FACS Vantage method.

Figure 28:
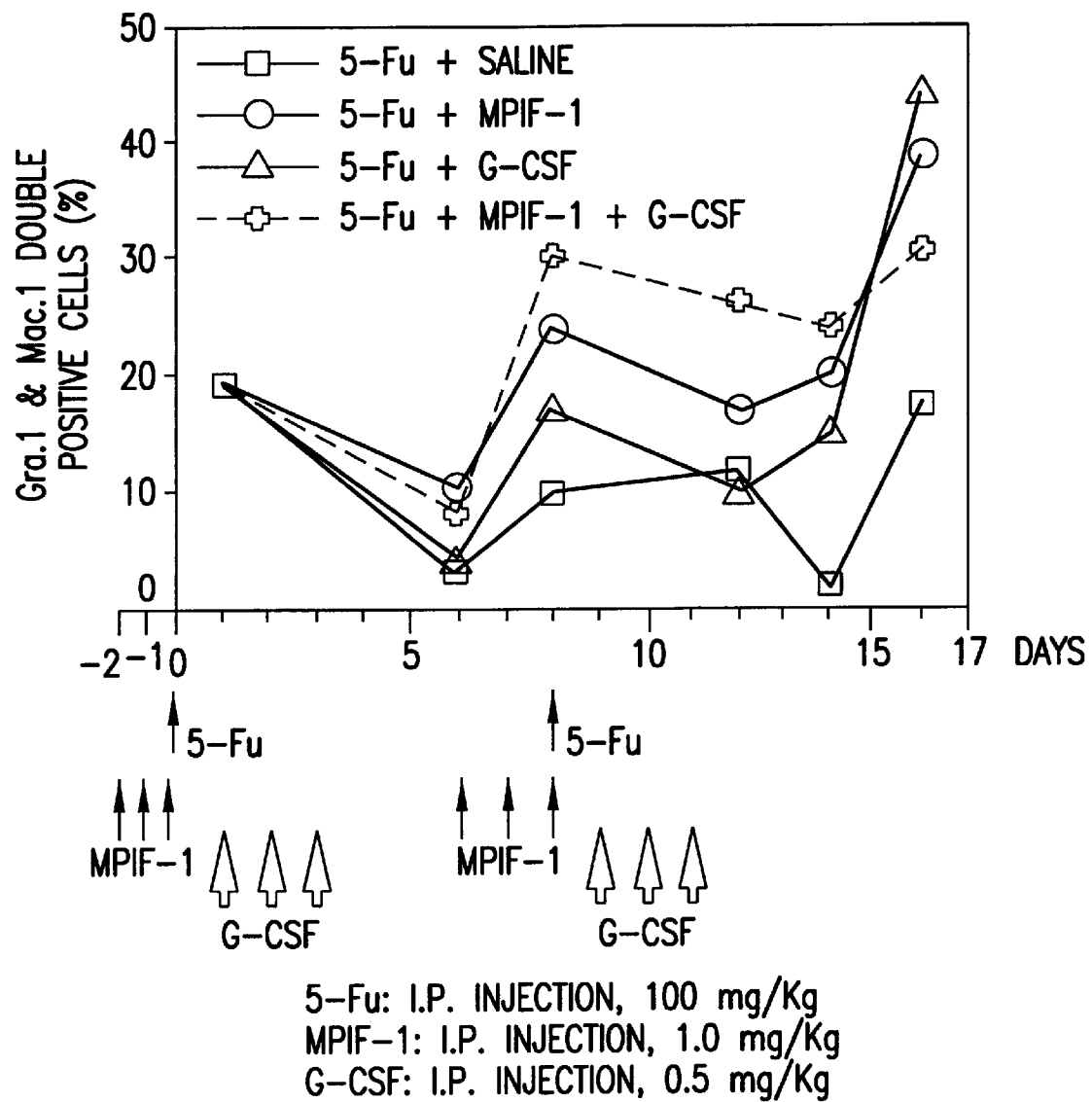

FIG. 28 shows a comparison of the effect of MPIF-1 with G-CSF on the recovery of Gra.1 and Mac.1 double positive cells in the blood following two cycles of 5-Fu treatment.

Figure 29:
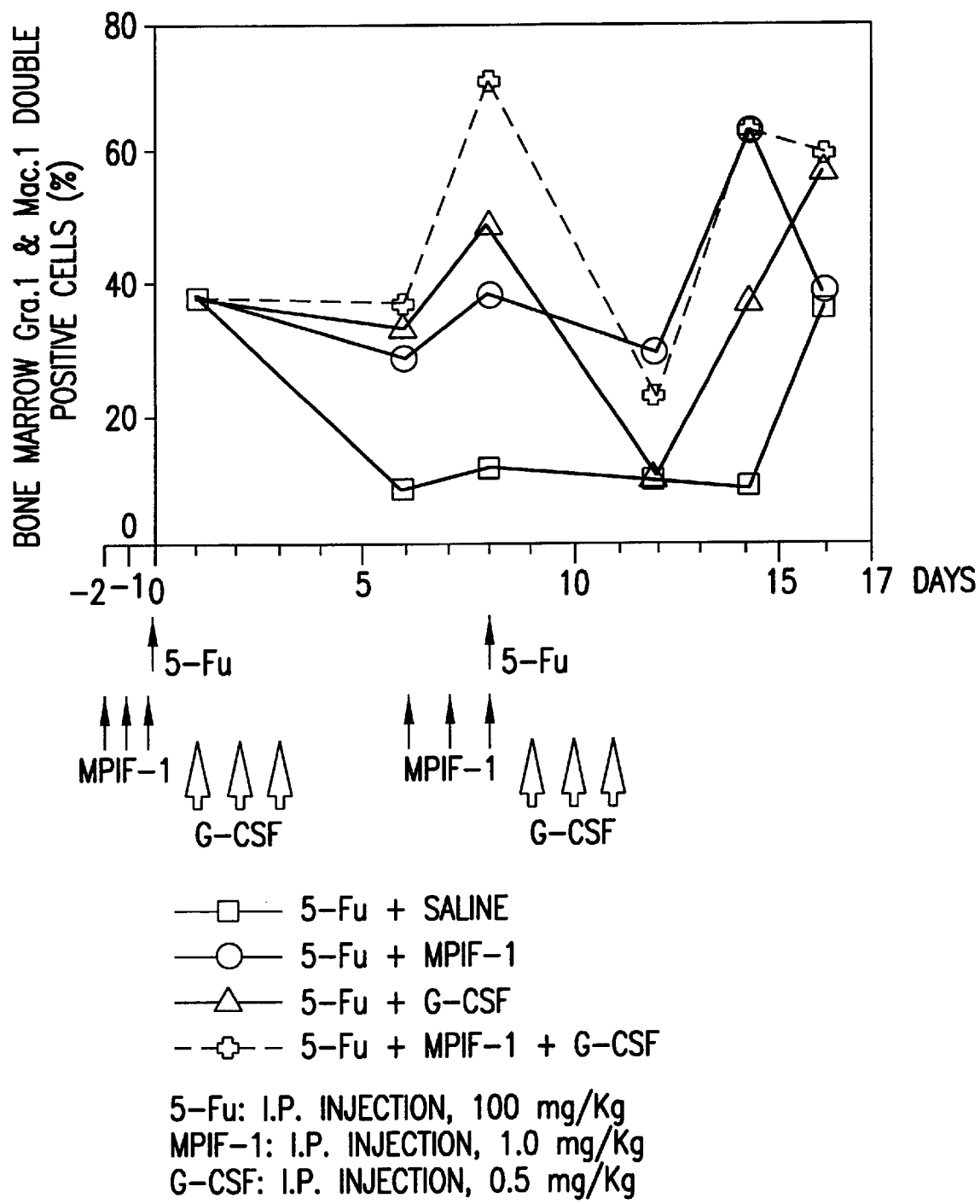

FIG. 29 shows a comparison of the effect of MPIF-1 with G-CSF on the recovery of Gra.1 and Mac.1 double positive cells in the bone marrow following two cycles of 5-Fu treatment as determined by FACS Vantage method.

Figure 30:
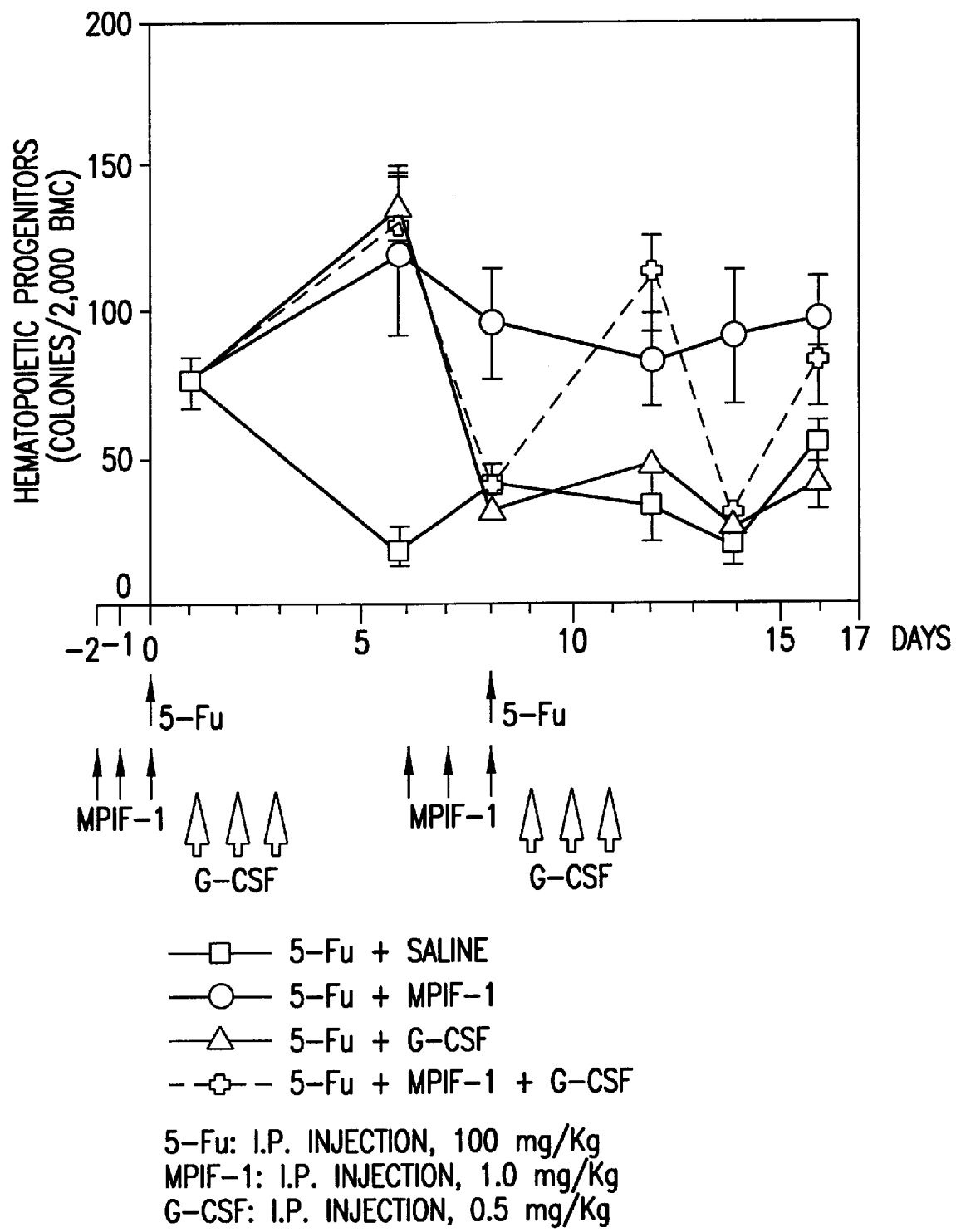

FIG. 30 shows a comparison of the effect of MPIF-1 with G-CSF on the recovery of hematopoietic progenitors in the bone marrow during following two cycles of 5-Fu treatment.

Figure 31:
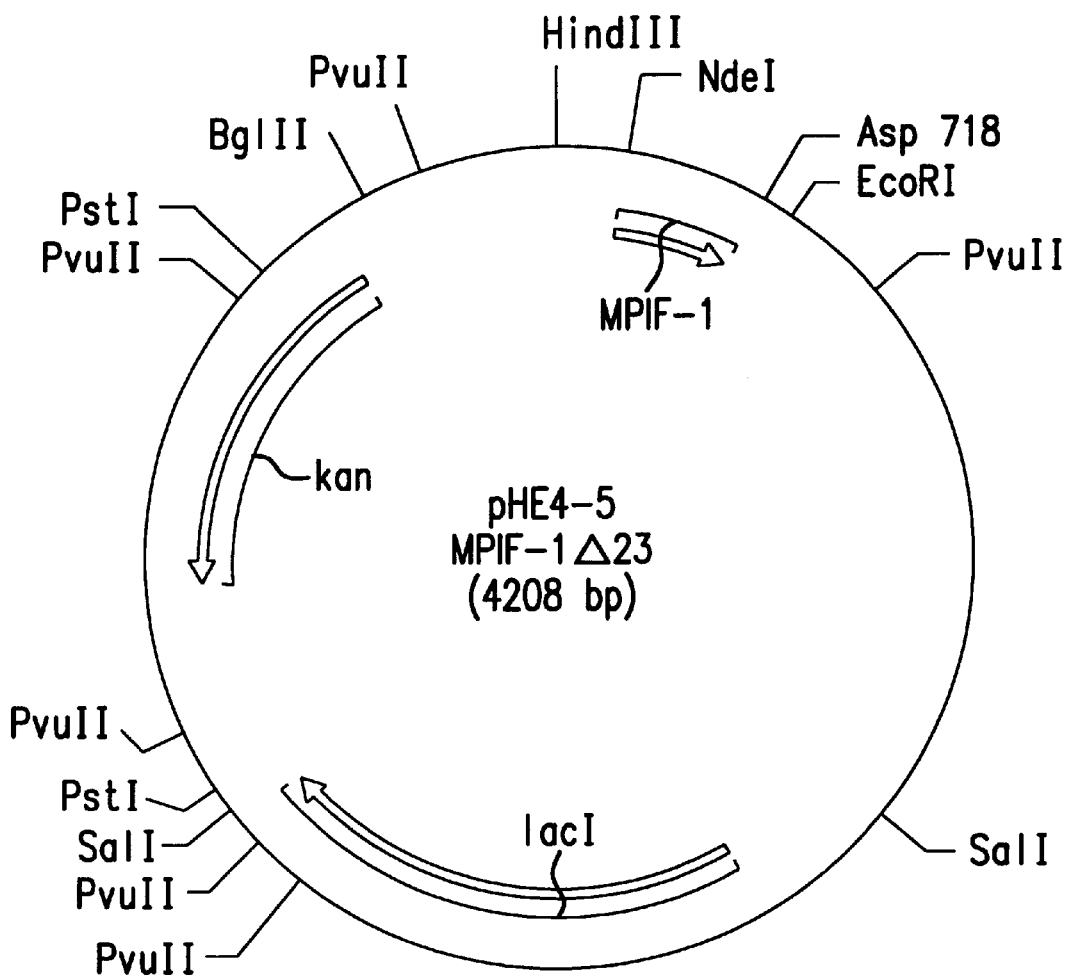

FIG. 31 shows a schematic representation of the pHE4–5 expression vector (SEQ ID NO:37) and the subcloned MPIF-1Δ23 cDNA coding sequence. The locations of the kanamycin resistance marker gene, the MPIF-1Δ23 coding sequence, the oriC sequence, and the lacIq coding sequence are indicated.

Figure 32:
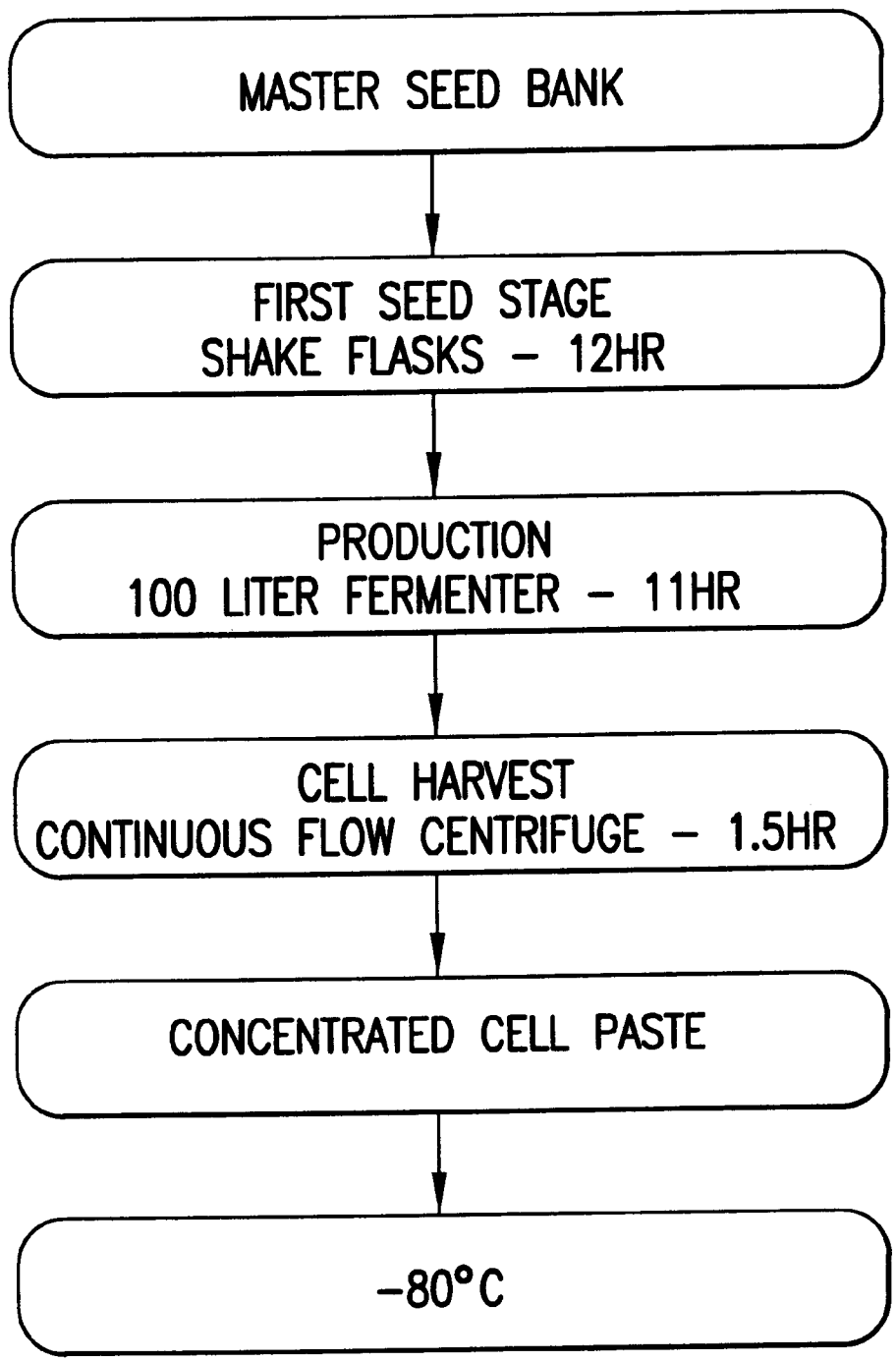

FIG. 32 shows an overview of the fermentation process for the production of MPIF-1Δ23.

Figure 33:
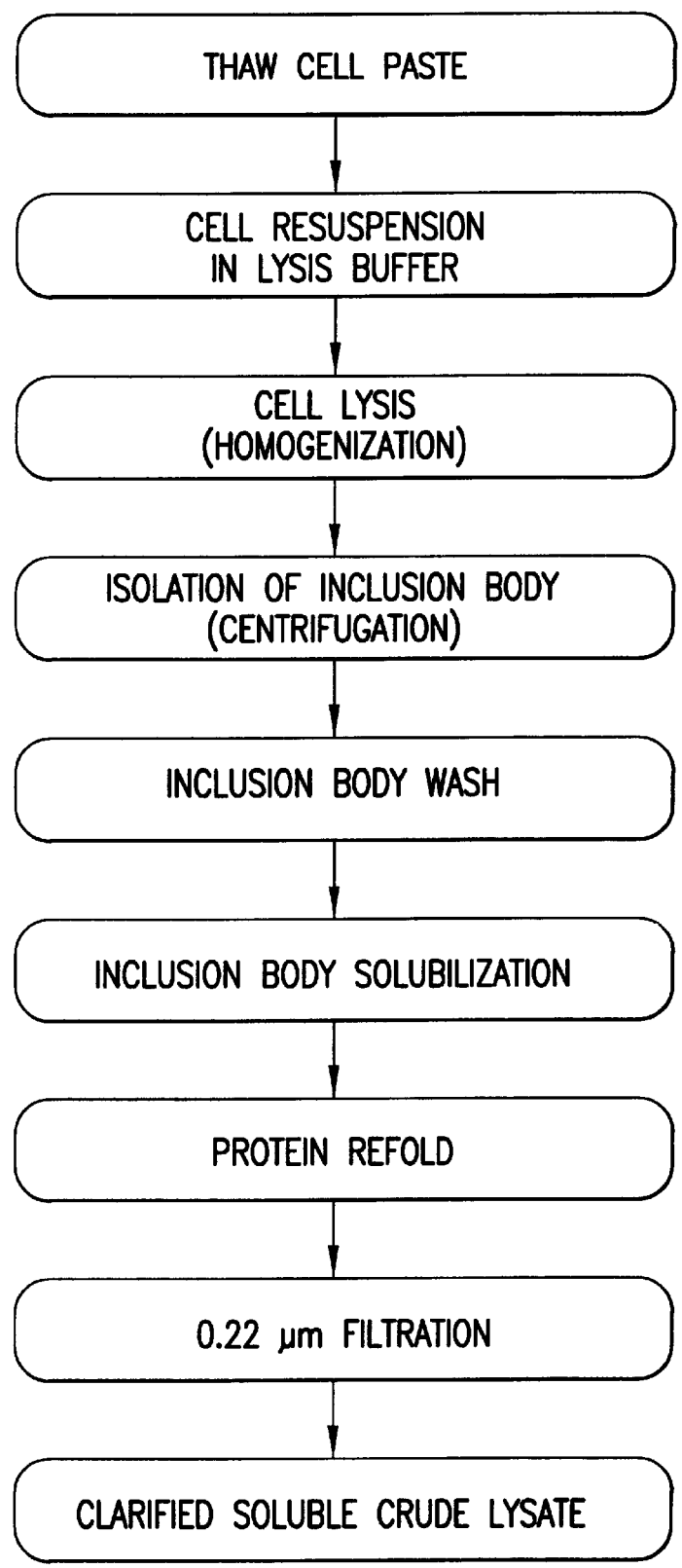

FIG. 33 shows a flow diagram of the methods used to recover MPIF-1Δ23 produced by the process shown in FIG. 32.

Figure 34:
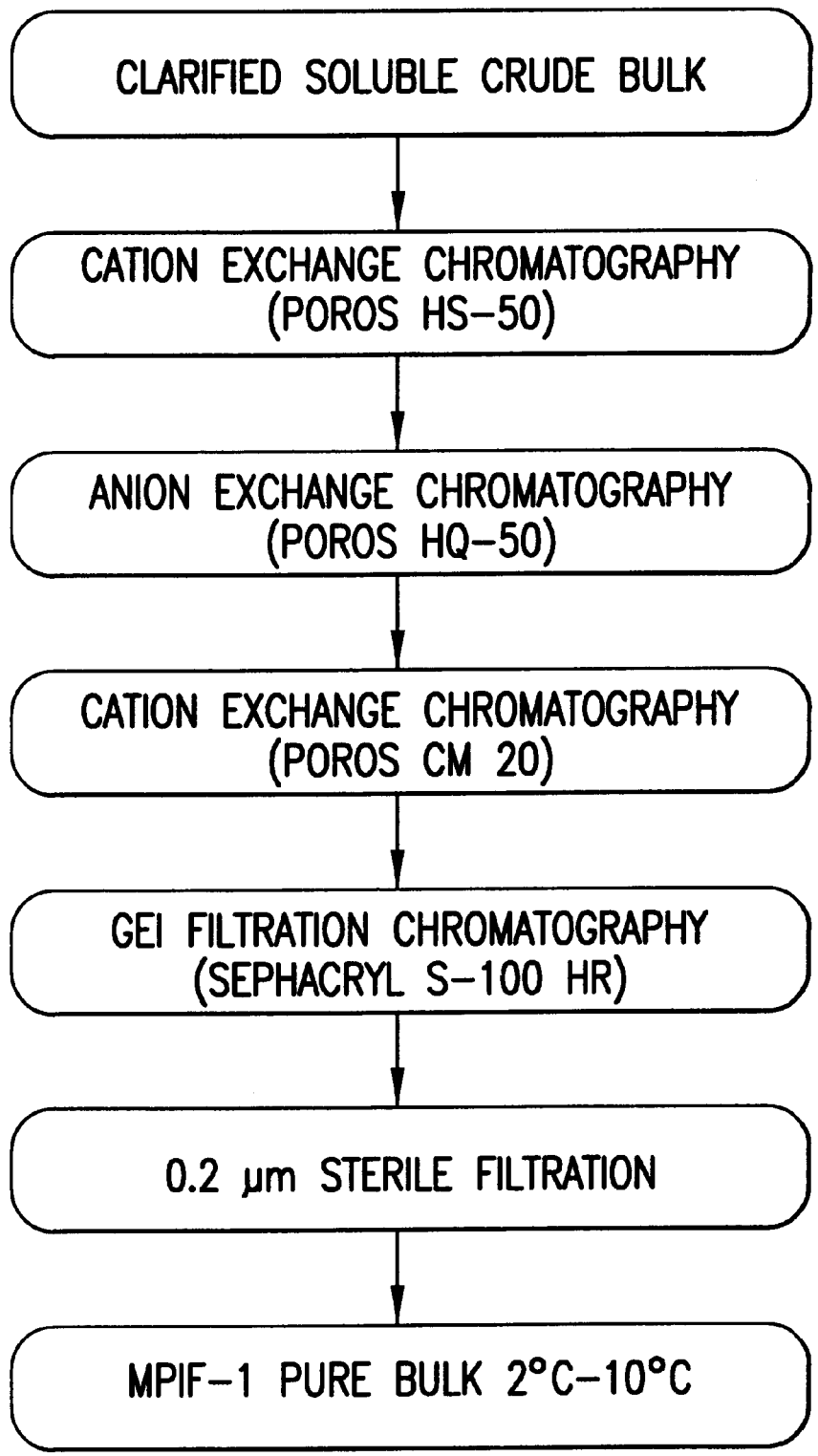

FIG. 34 shows the process for the purification of MPIF-1Δ23 produced and recovered by the processes shown in FIGS. 32 and 33.

FIG. 35 shows the nucleotide sequence of the regulatory elements of the pHE promoter (SEQ ID NO:38). The two lac operator sequences, the Shine-Delgarno sequence (S/D), and the terminal HindIII and NdeI restriction sites (italicized) are indicated.

Figure 36A:
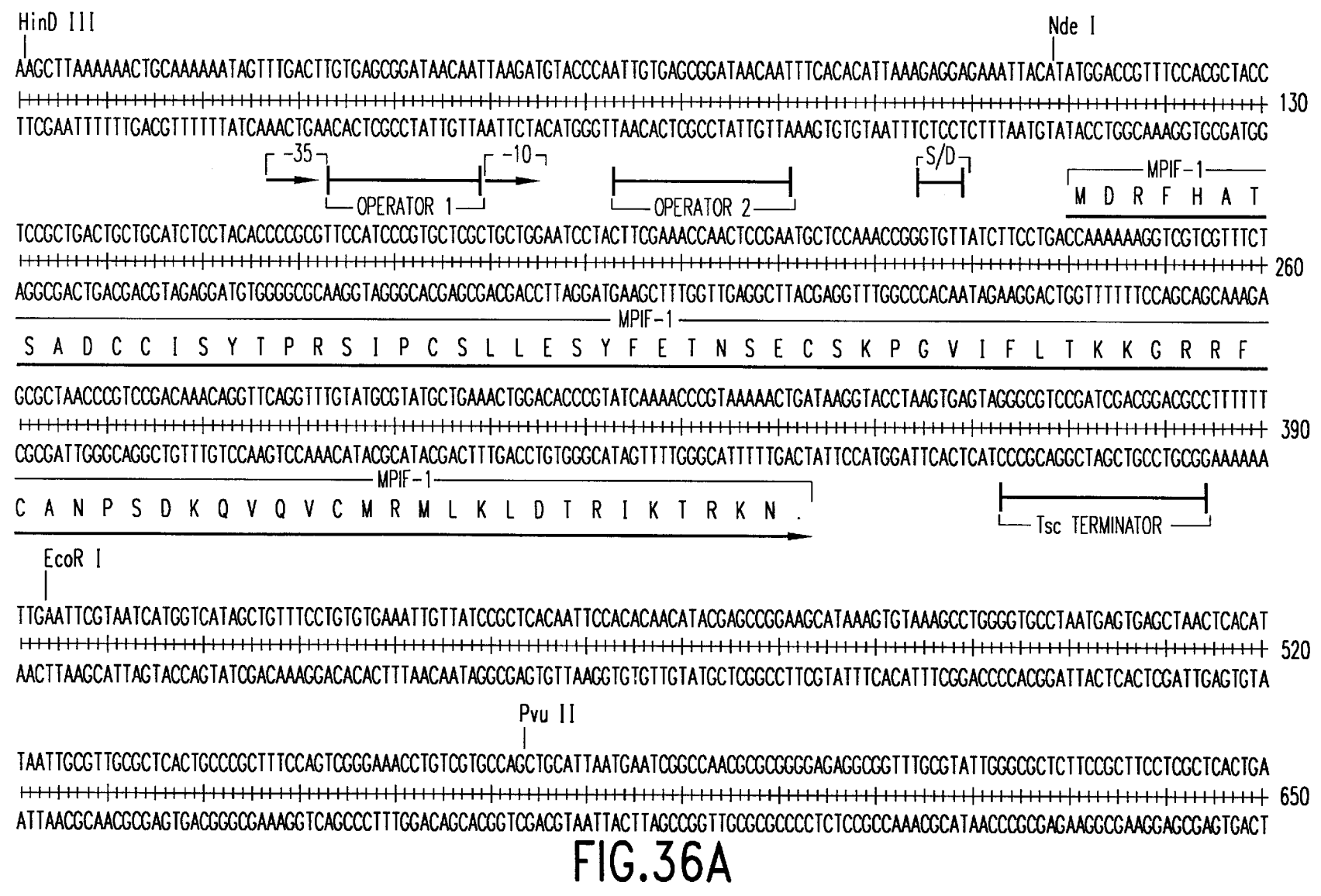
Figure 36C:
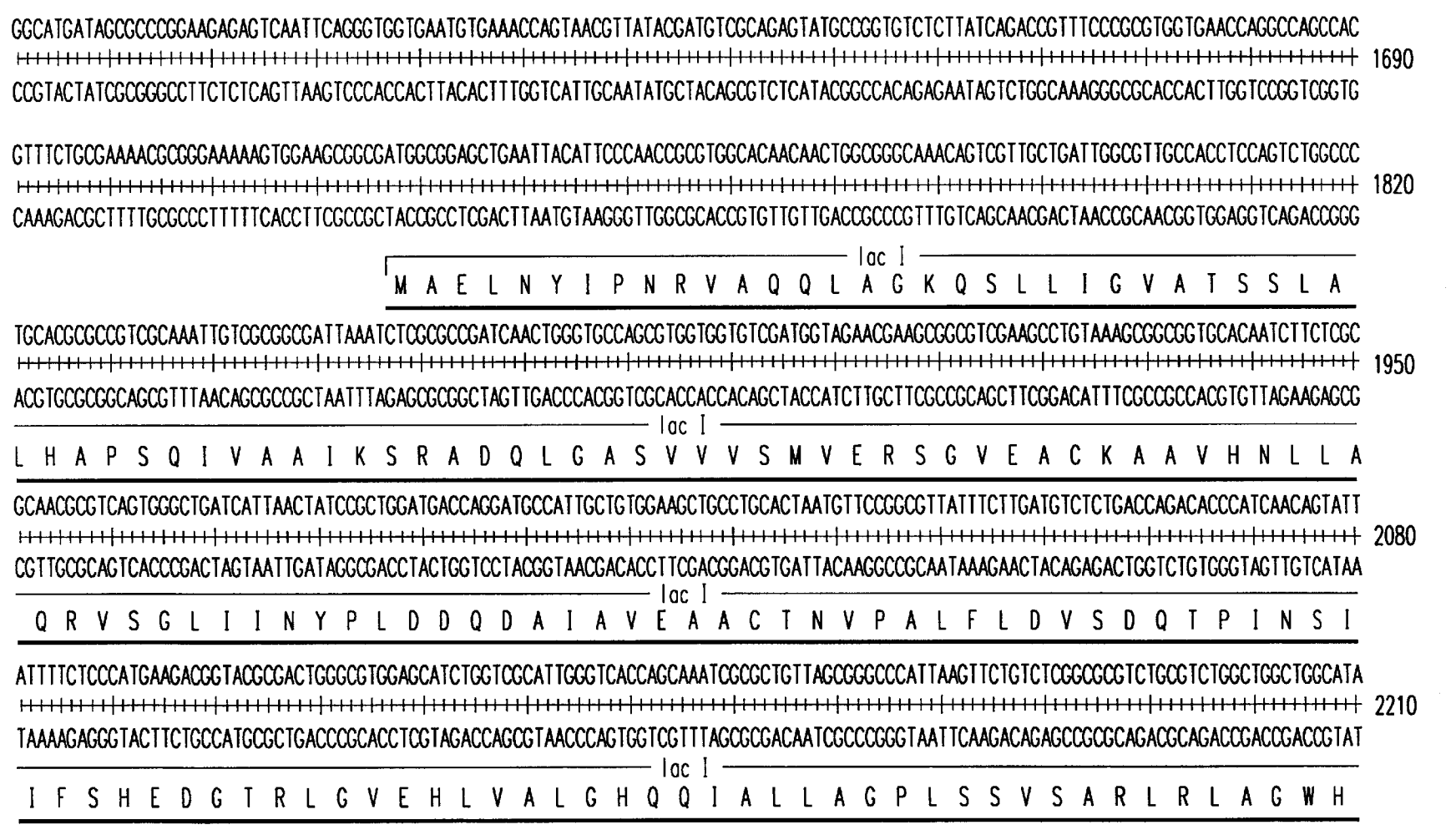
Figure 36F:
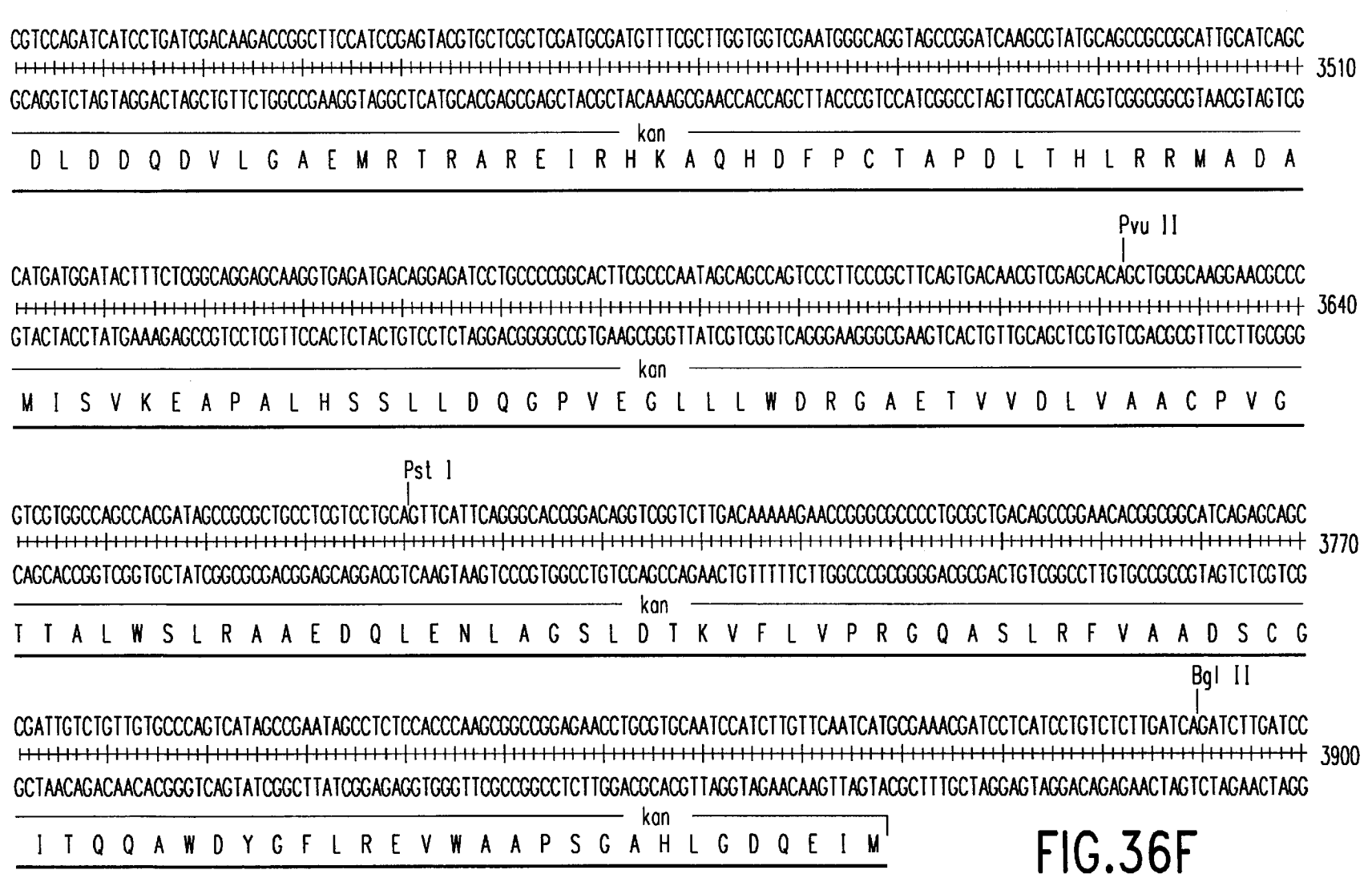

FIGS. 36A–36G show the complete nucleotide sequence of the pHE4–5 vector (SEQ ID NO:37).

FIG. 37 shows MPIF-1 protection of the gastrointestinal tract from radiation-induced damage during short-term monitoring. C57B1/6 female mice were treated before or after receiving a sub-lethal dose of irradiation (2×4.5 gy 4 hours apart from a $^{137}$Cs source). Mice were monitored for survival, condition and weight on the days shown. Data is shown the percent change in weight for each group based on each individual mouse's weight on the day indicated as a percentage of it's weight at the start of the experiment.

Figure 38:
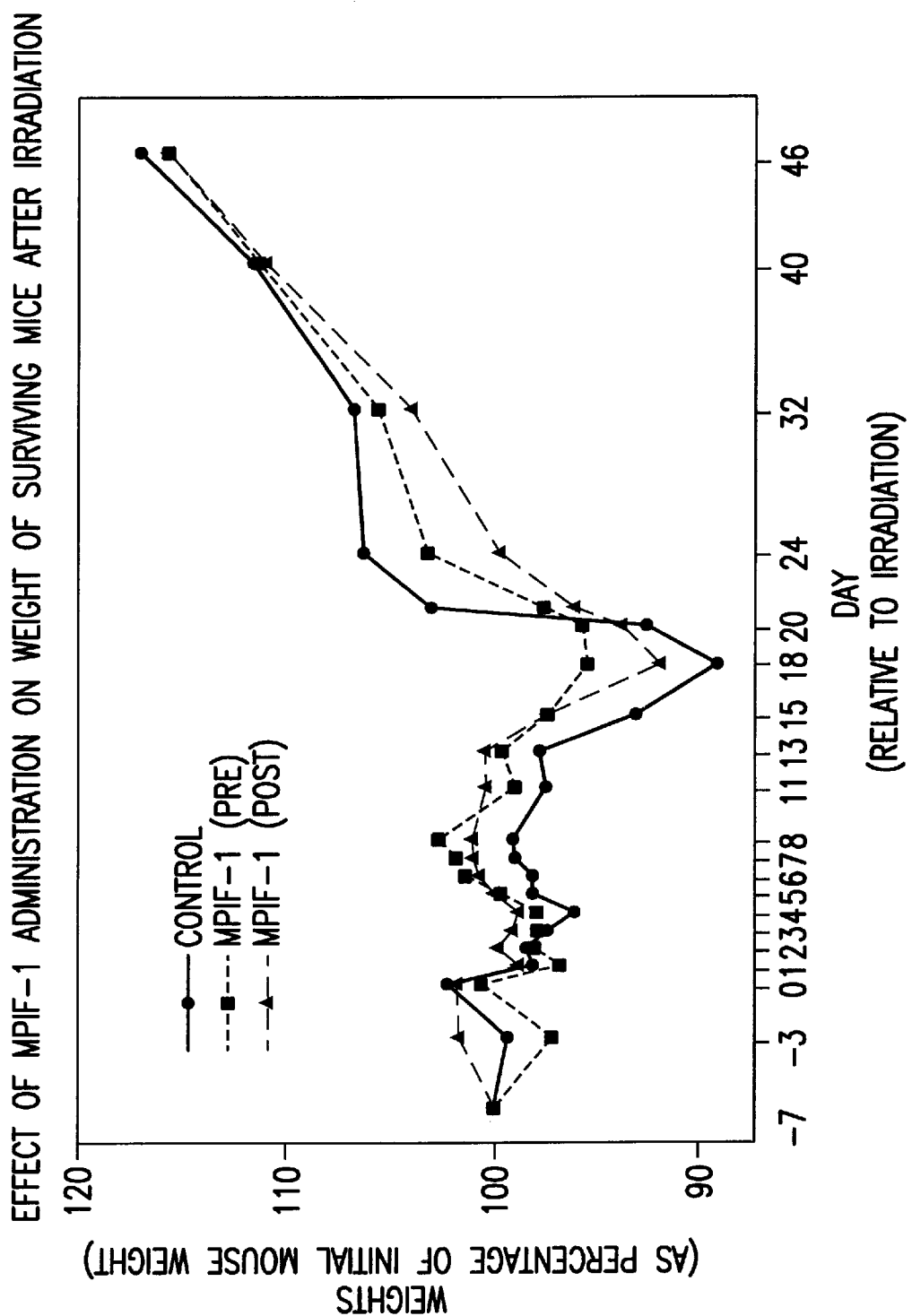

FIG. 38 shows MPIF-1 protection of the gastrointestinal tract from radiation-induced damage during long-term monitoring. C57B1/6 female mice were treated before or after receiving a sub-lethal dose of irradiation (2×4.5 gy 4 hours apart from a $^{137}$Cs source). Mice were monitored for survival, condition and weight on the days shown. Data is shown the percent change in weight for each group based on each individual mouse's weight on the day indicated as a percentage of it's weight at the start of the experiment. The curve is presented in two segments. The left segment represents changes within first 18 days and the right segment represents the weights in all groups at the termination days.

Figure 39:
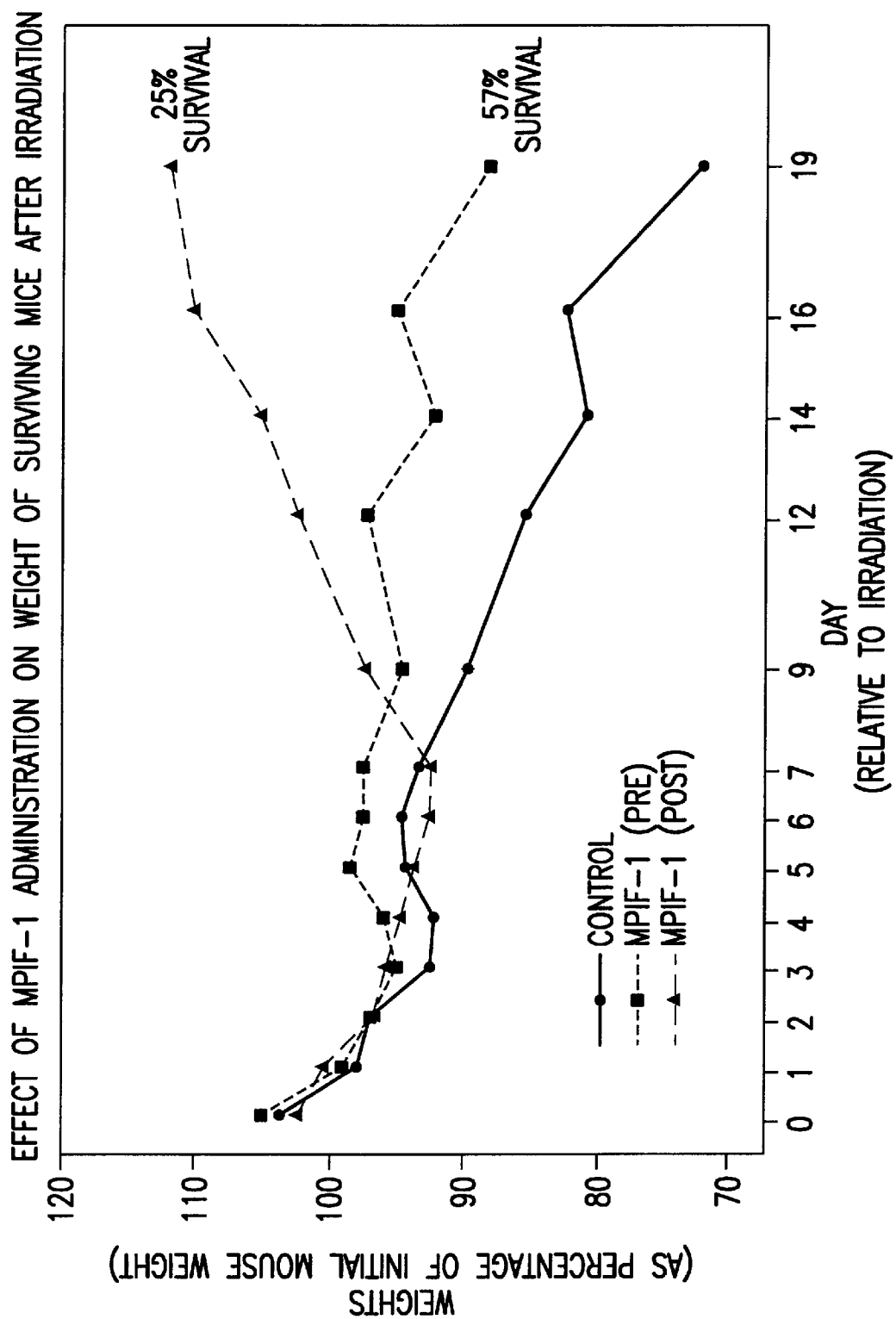

FIG. 39 shows MPIF-1 protection of the gastrointestinal tract from radiation-induced damage during short-term monitoring. C57B1/6 female mice were treated before or after receiving a sub-lethal dose of irradiation (2×5.5 gy, 4 hours apart using a $^{137}$Cs source). Mice were monitored for survival, condition and weight on the days shown. Data is shown the percent change in weight for each group based on each individual mouse's weight on the day indicated as a percentage of it's weight at the start of the experiment.

Figure 40:
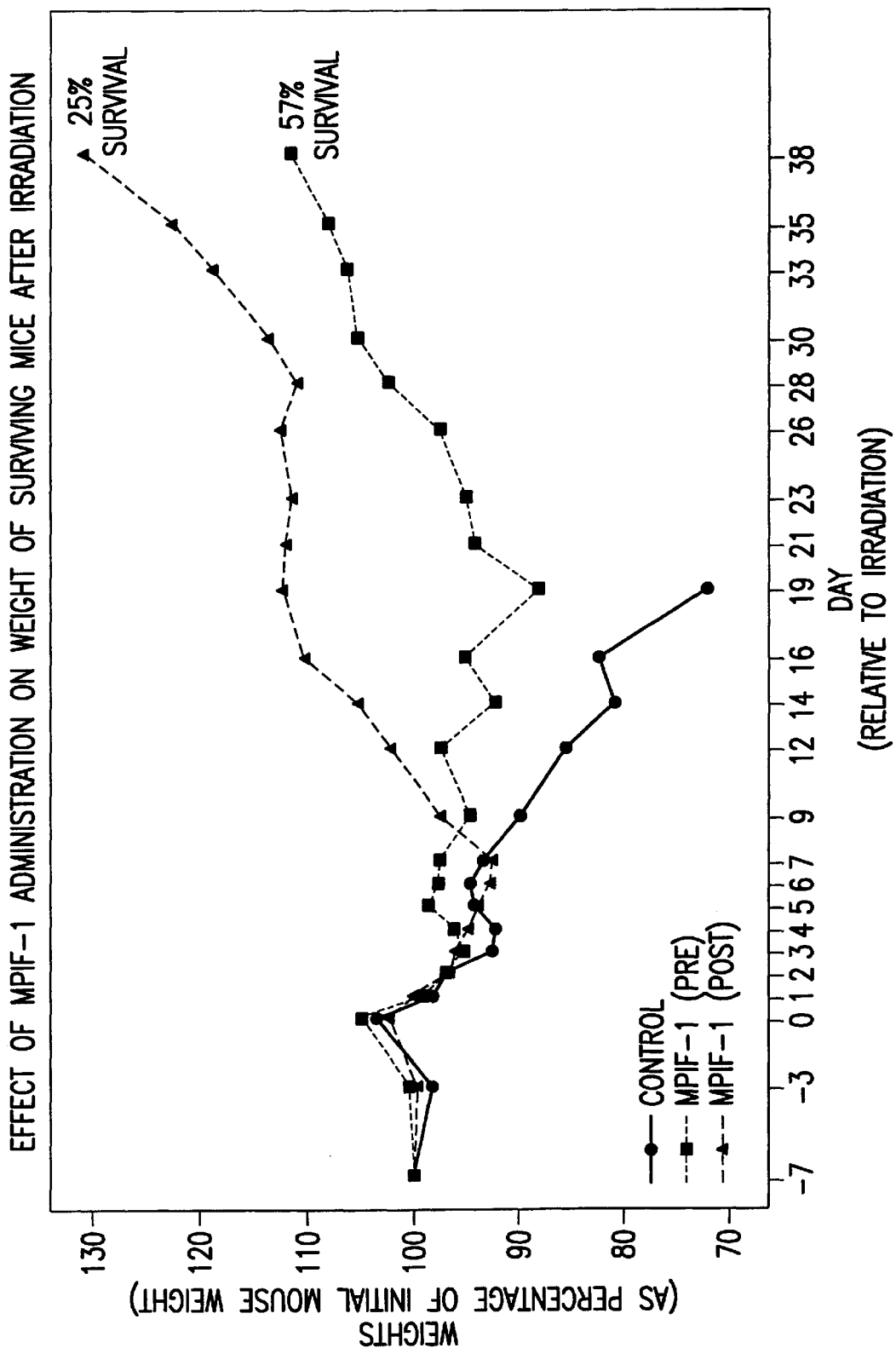

FIG. 40 shows MPIF-1 protection of the gastrointestinal tract from radiation-induced damage during long-term monitoring. C57B1/6 female mice were treated before or after receiving a sub-lethal dose of irradiation (2×5.5 gy, 4 hours apart using a $^{137}$Cs source). Mice were monitored for survival, condition and weight on the days shown. Data is shown the percent change in weight for each group based on each individual mouse's weight on the day indicated as a percentage of it's weight at the start of the experiment.

Figure 41:
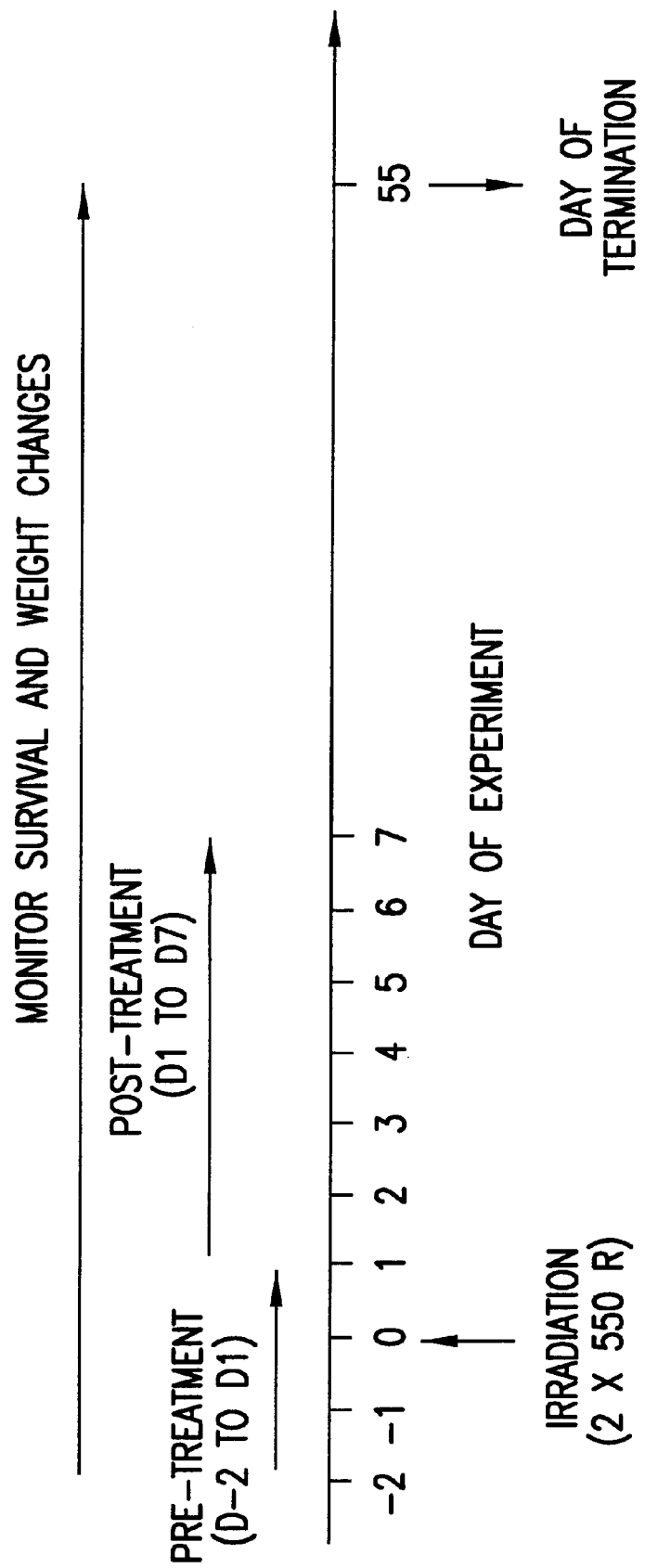

FIG. 41 shows a schematic of the treatment schedule for the in vivo model of protection against lethal irradiation in the mouse.

Figure 42:
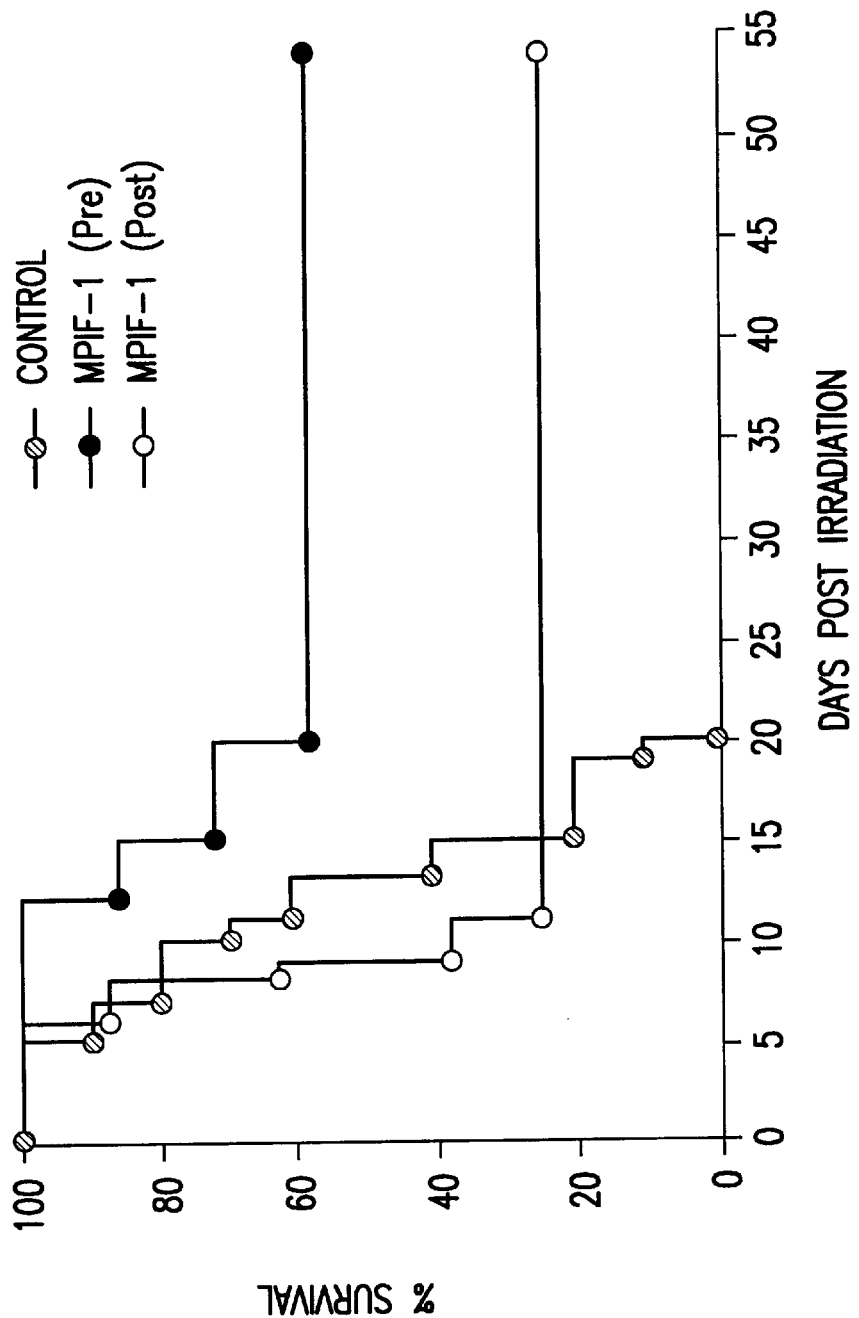

FIG. 42 shows that MPIF-1 enhances survival in lethally irradiated mice. Statistical analysis was performed using log-rank nonparametric and data are presented as a Kaplan-Meier survival curve. The experiment was terminated at day 54 post irradiation.

Figure 43:
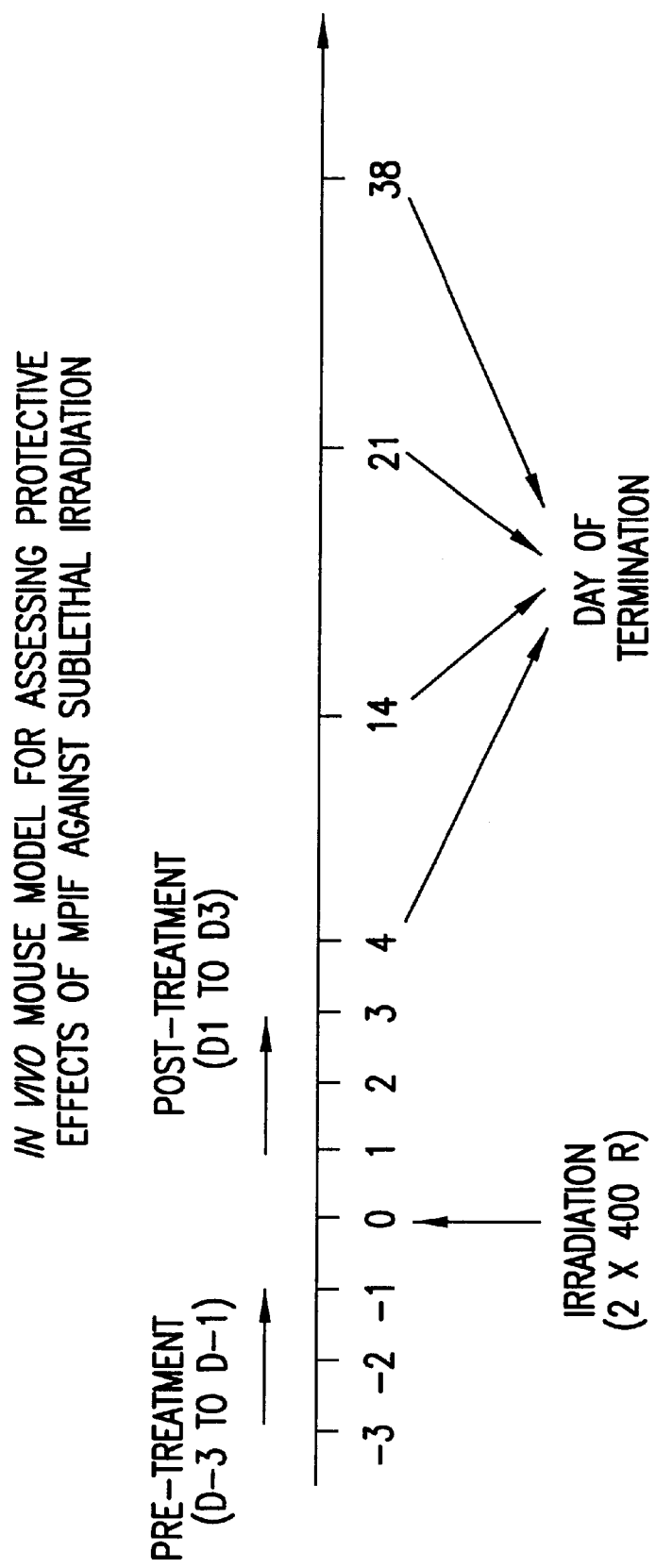

FIG. 43 shows a schematic of the treatment schedule for the in vivo model of protection against sublethal irradiation in the mouse.

Figure 44:
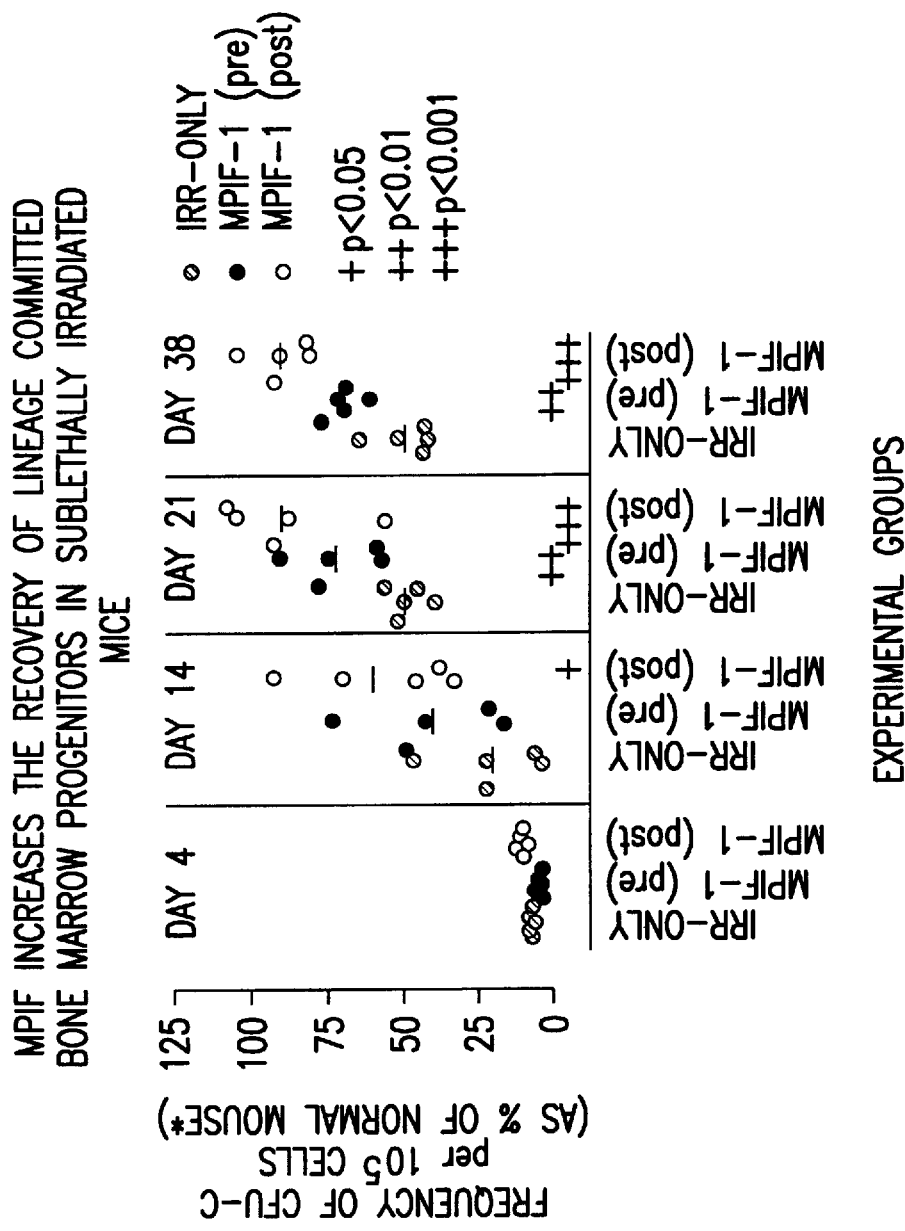

FIG. 44 shows that MPIF enhances the recovery of lineage committed bone marrow precursors in sublethally irradiated mice.

Figure 45:
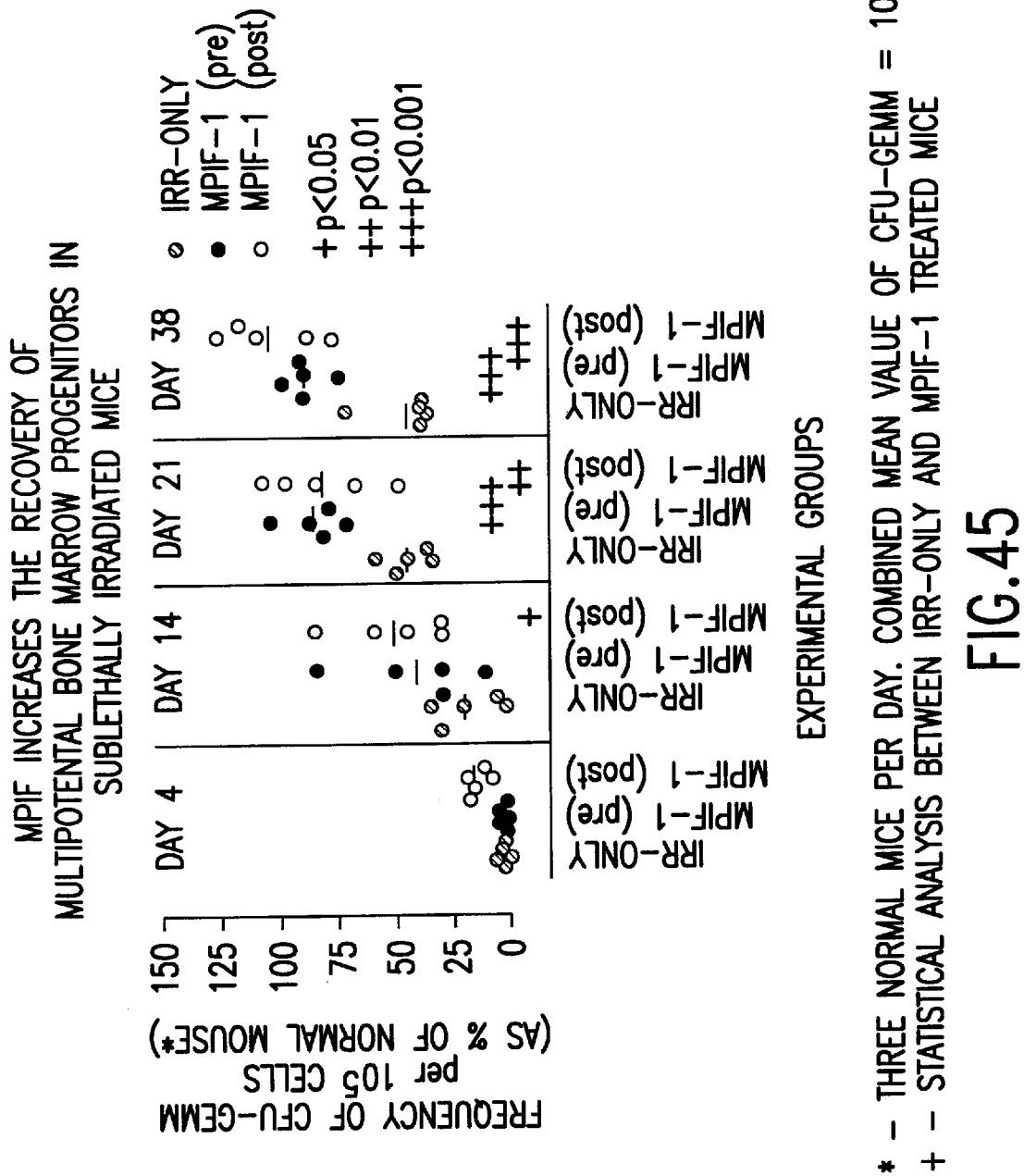

FIG. 45 shows that MPIF enhances the recovery of multipotential bone marrow progenitors in sublethally irradiated mice.

Figure 46:
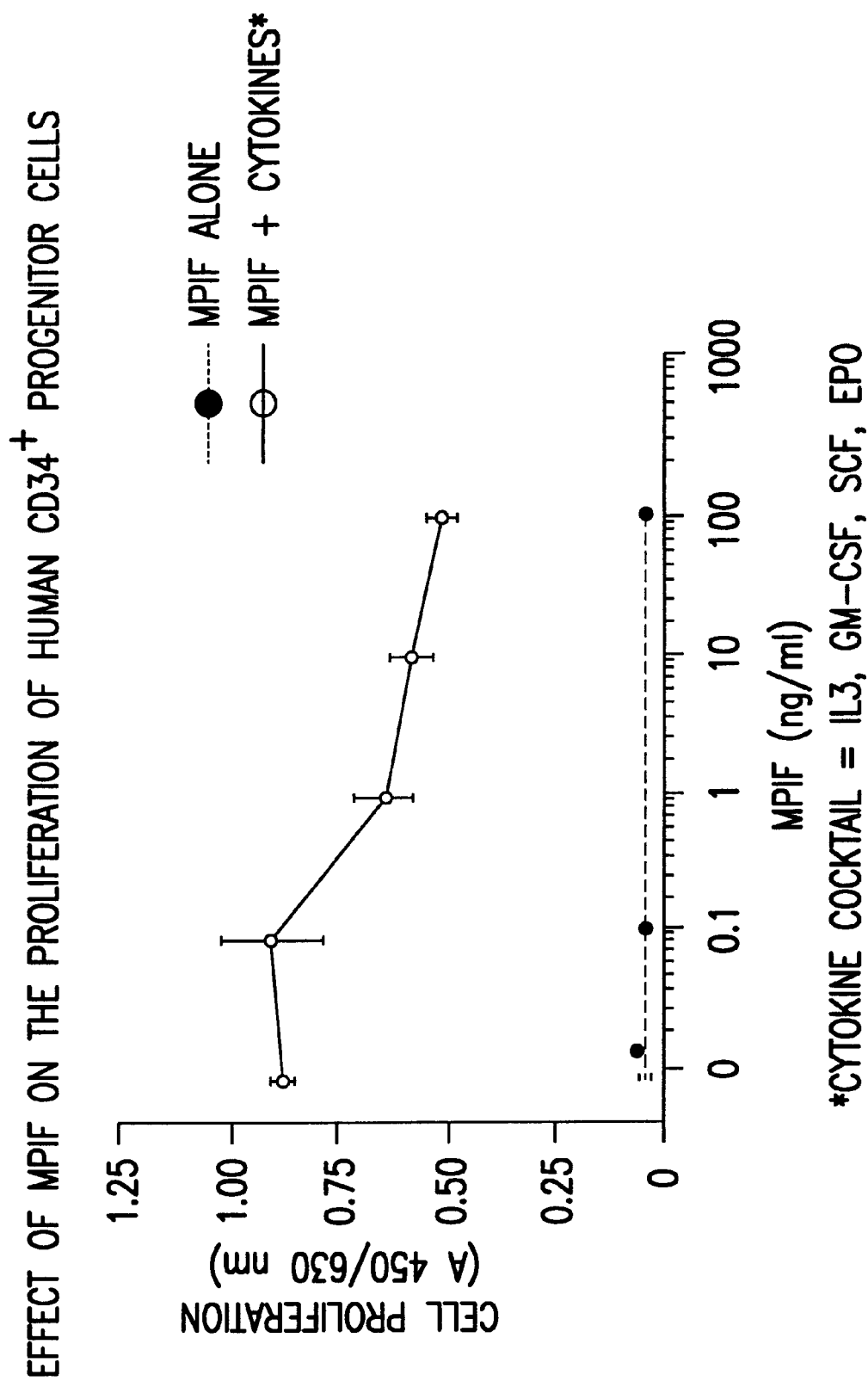

FIG. 46 shows the effect of MPIF on the proliferation of human CD34+progenitor cells in vitro.

Figure 47:
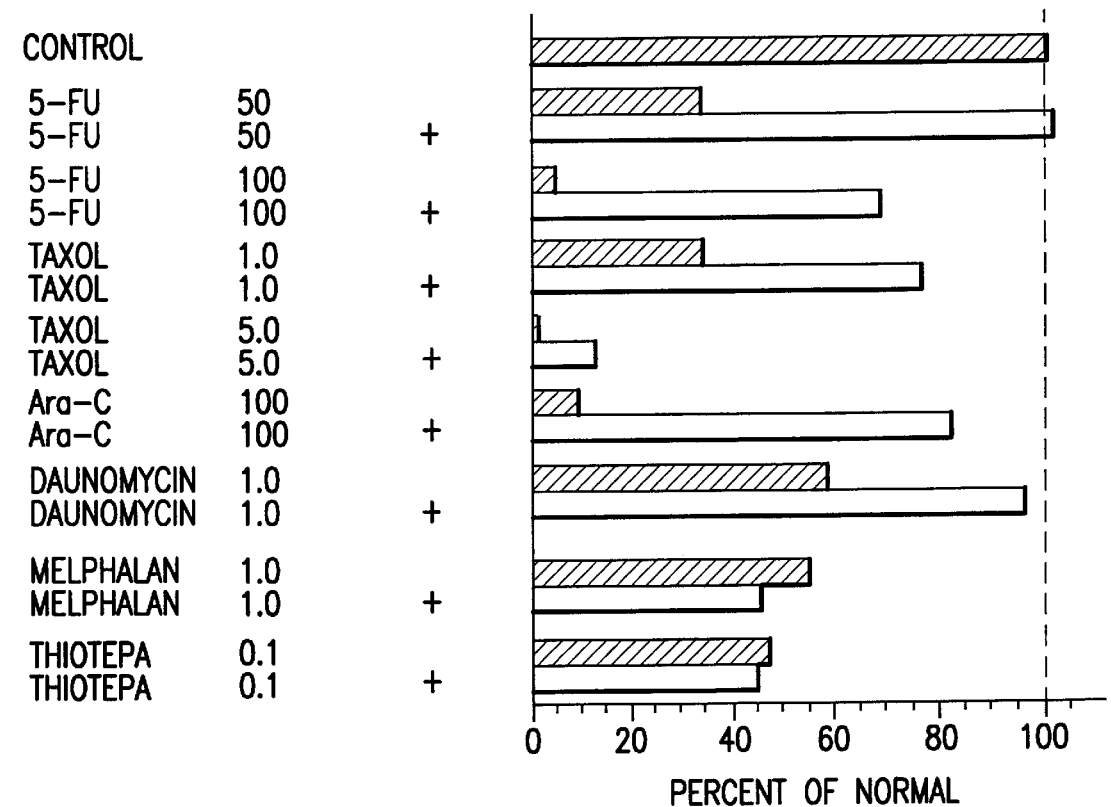

FIG. 47 shows the effect of MPIF on cytotoxic drug-induced killing in vitro.

Figure 48:
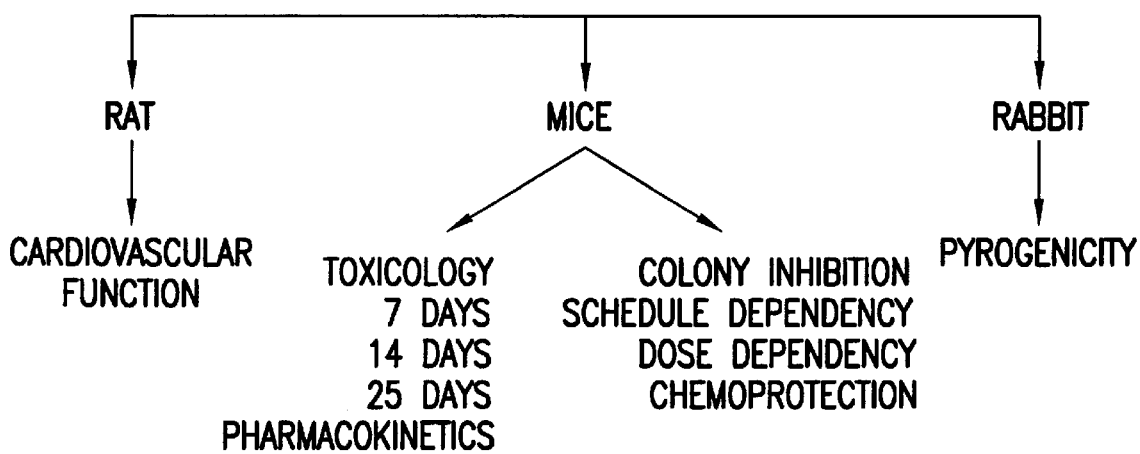

FIG. 48 shows a summary of the in vivo studies on MPIF.

Figure 49A:
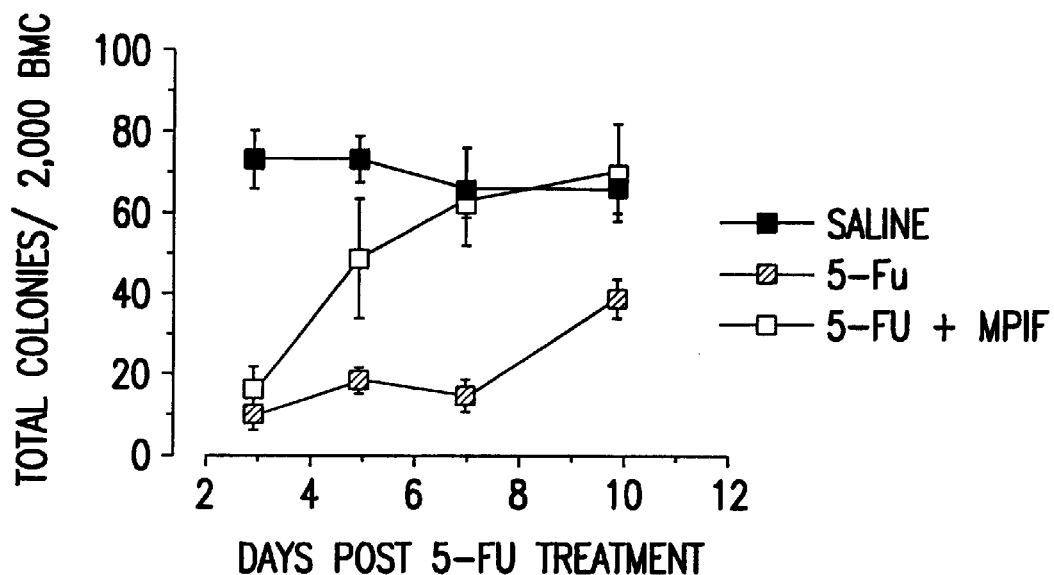
Figure 49B:
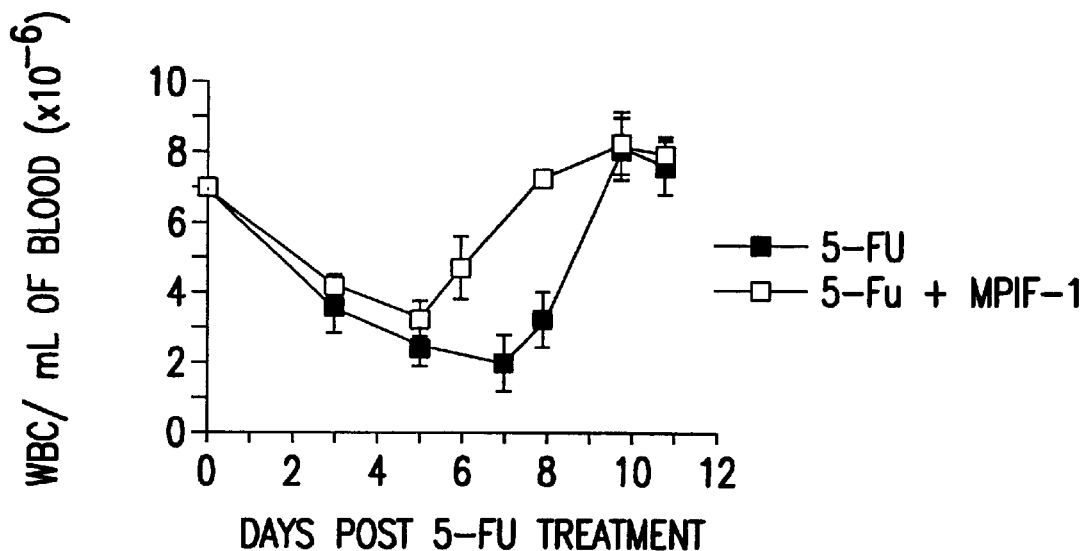

FIGS. 49A–49B show the effect of pretreatment with MPIF on 5-FU induced toxicity in myeloid progenitor cells in vivo. (A) The effect of MPIF on total colony formation. (B) The effect of MPIF on recovery of WBC. The results are the mean of eight experiments.

Figure 50:
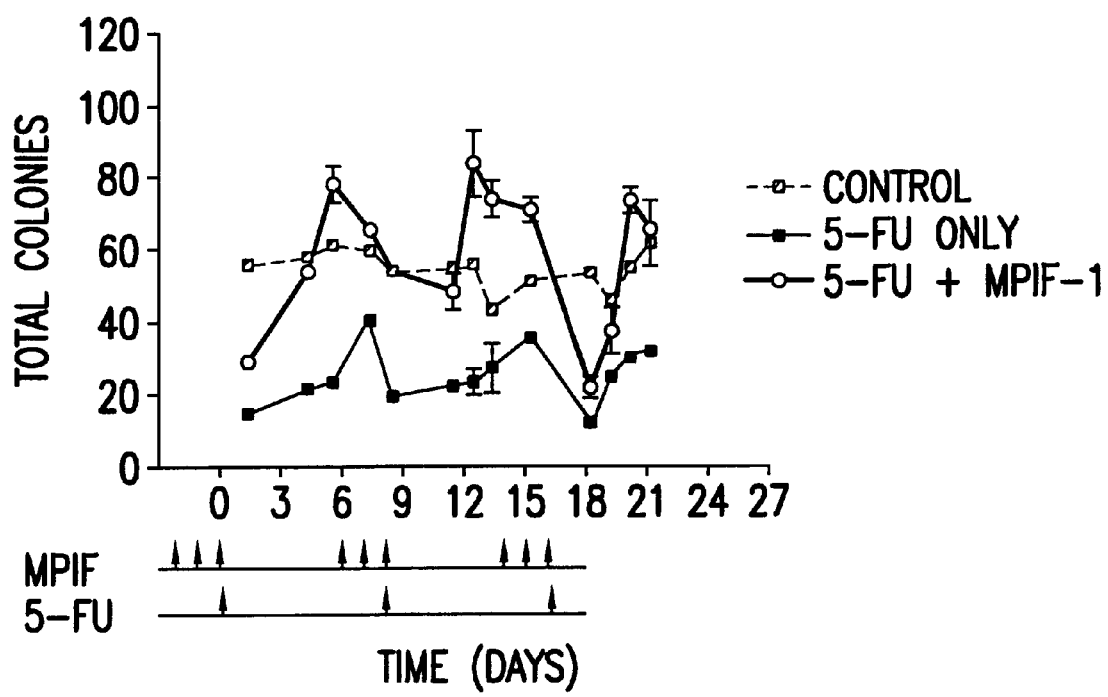

FIG. 50 shows the chemoprotective effect of MPIF on multiple cycles of therapy.

Figure 51:
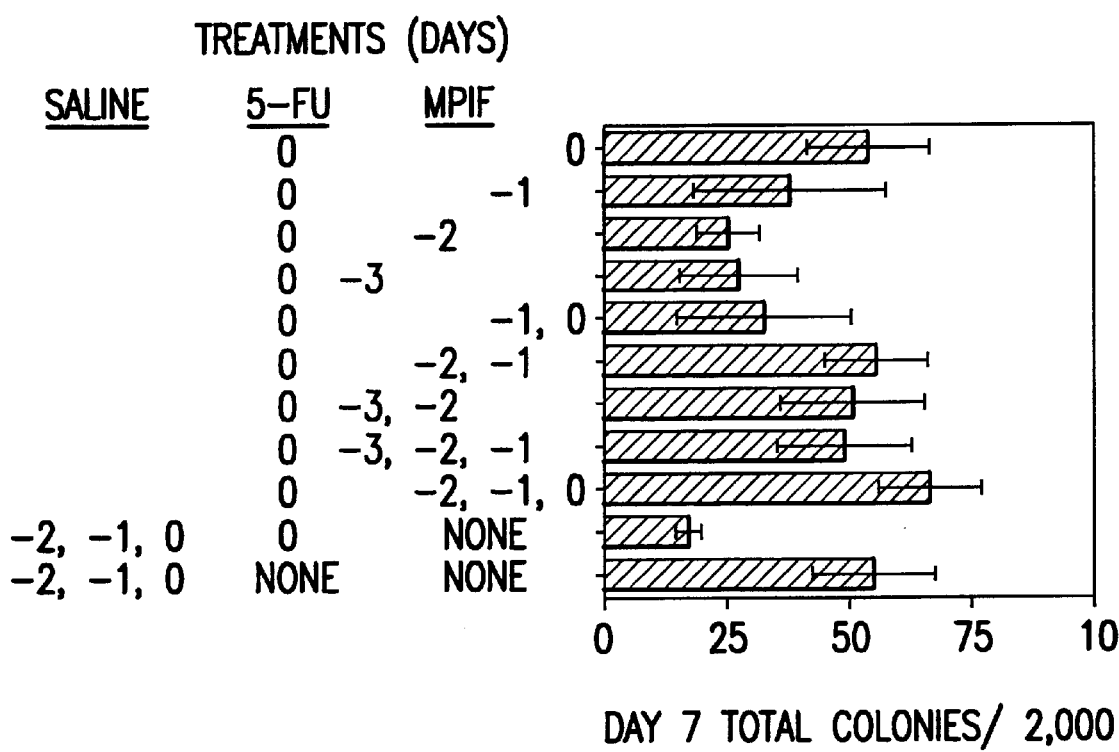

FIG. 51 shows the effect of the MPIF dosing schedule on the kinetics of bone marrow recovery after treatment with 5-FU.

FIG. 52 shows a summary of multiple dose toxicity studies.

FIG. 53 shows a summary of observations for nonclinical toxicology studies.

Figure 54A:
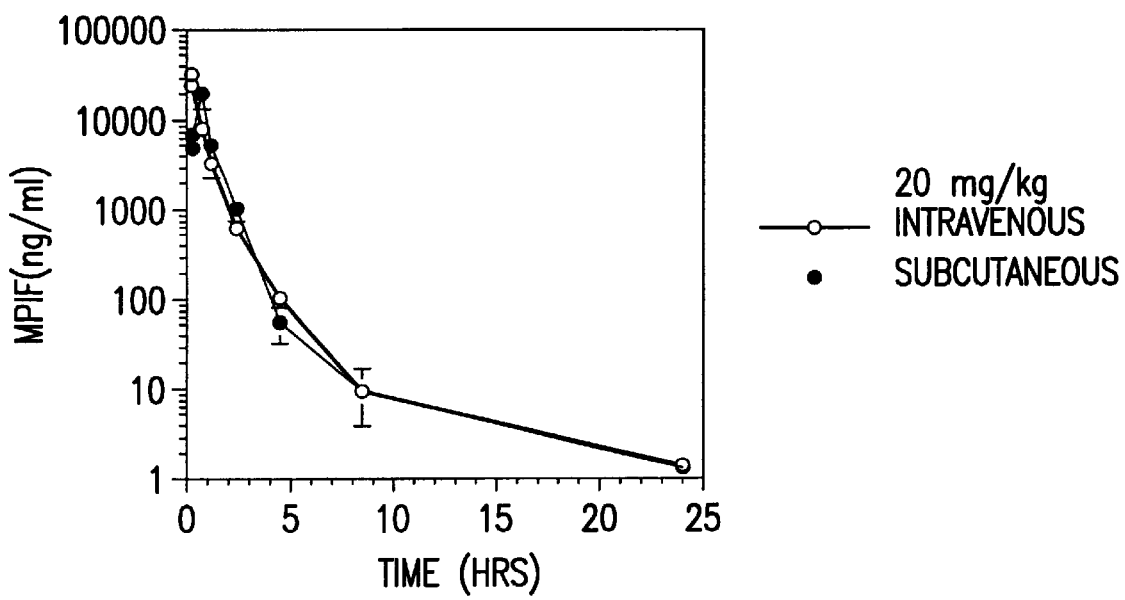
Figure 54B:
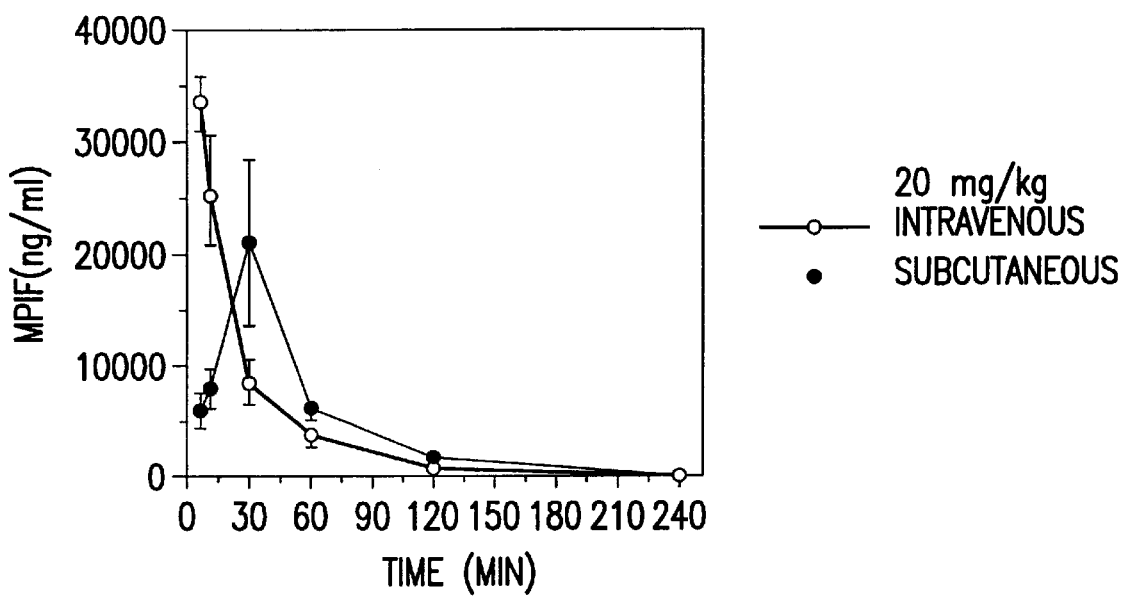
Figure 55A:
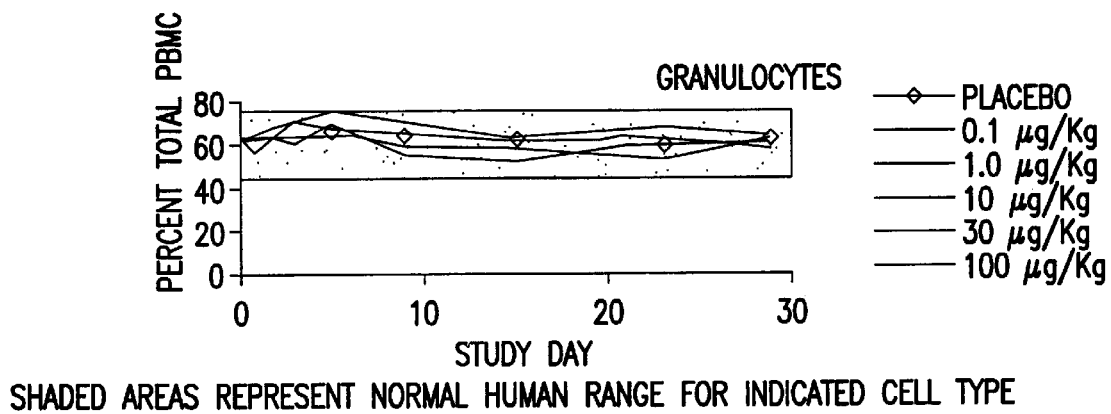
Figure 55B:
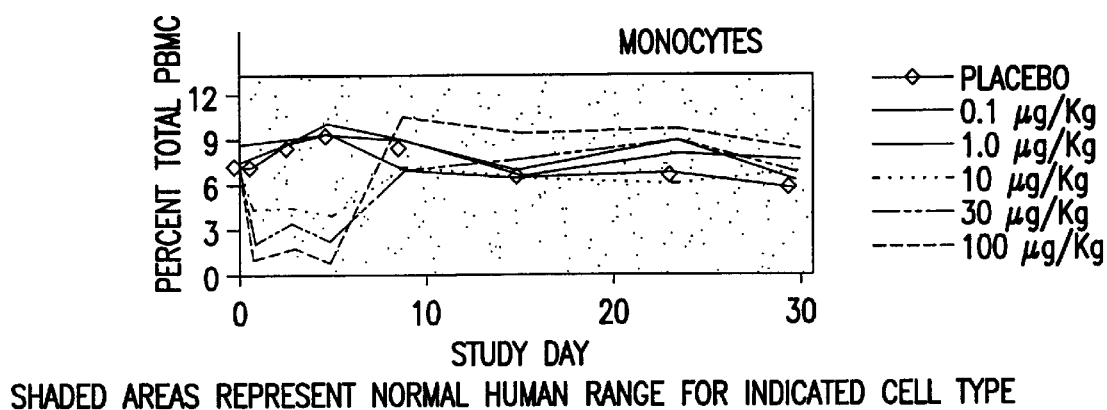
Figure 55C:
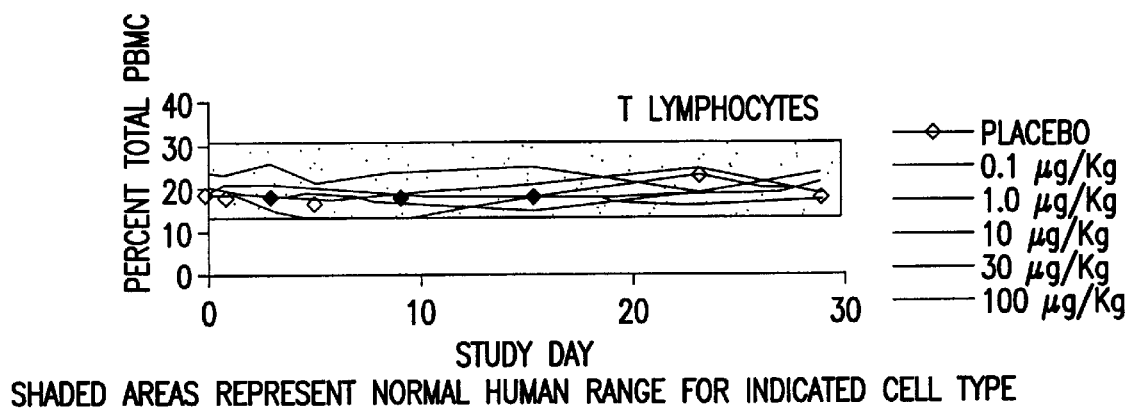
Figure 55D:
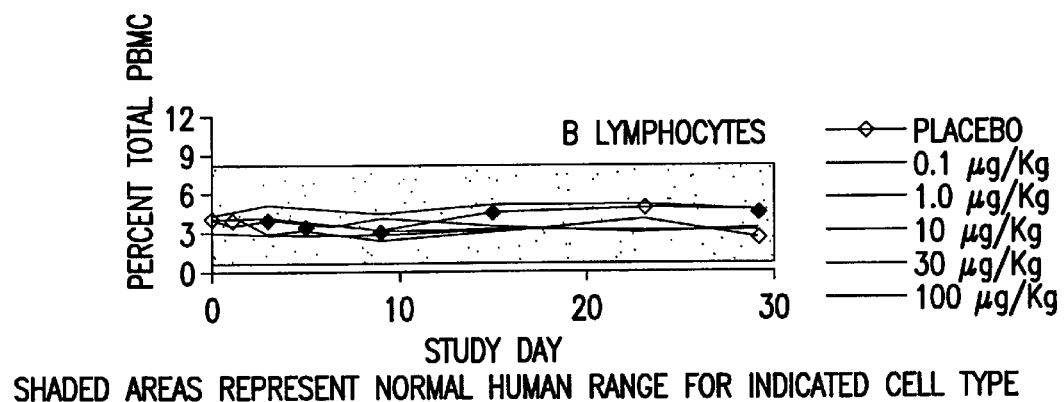

FIGS. 54A–54B show a comparison pf the pharmacokinetics of MPIF following intravenous or subcutaneous dosing. (A) Pharmacokinetic profile from 0 to 24 hours. (B) Profile from 0 to 4 hours. The MPIF dose was 20 mg/kg.

FIGS. 55A–55D show the evolution of peripheral blood cell composition in human subjects.

Figure 56:
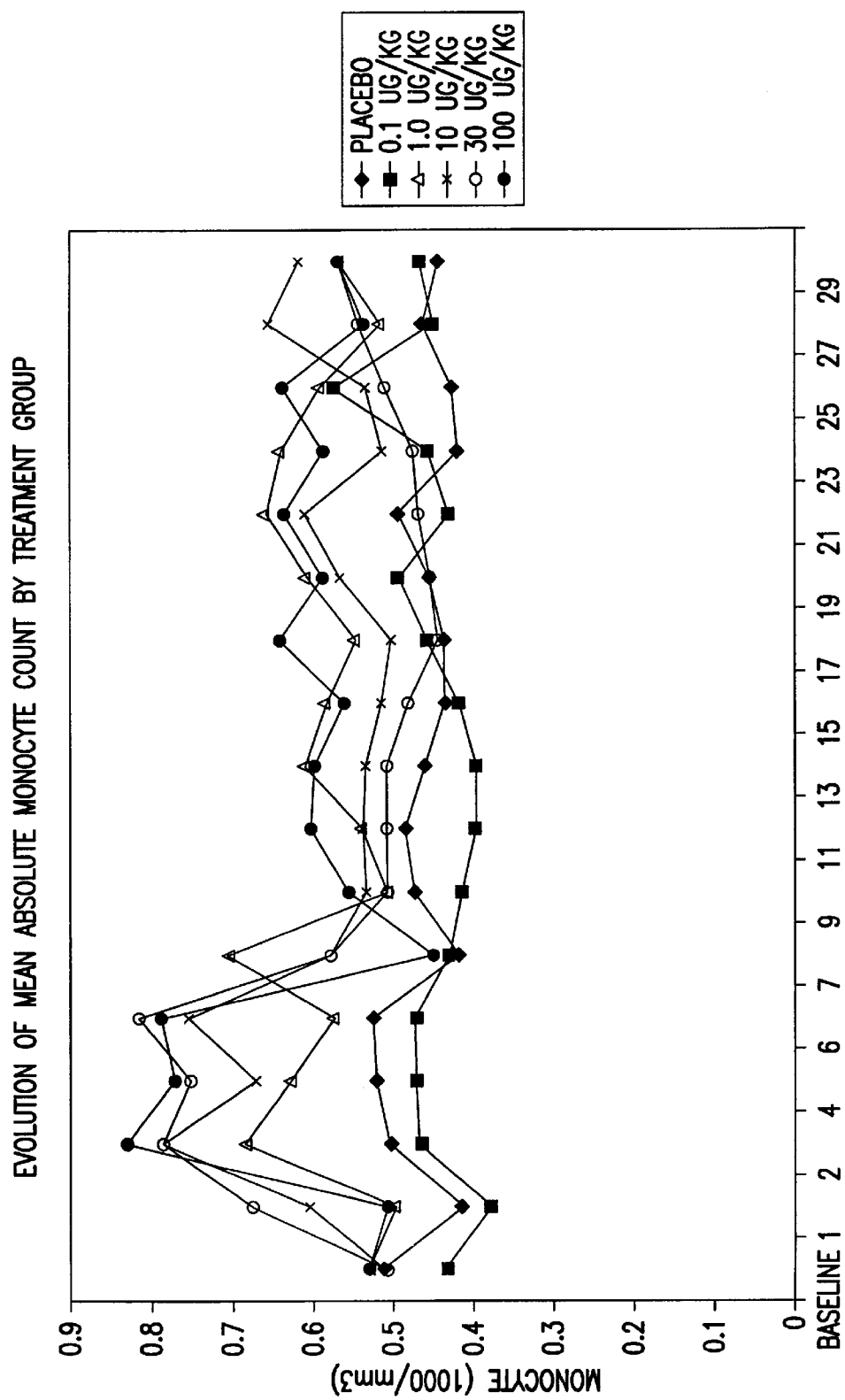

FIG. 56 shows the evolution of mean absolute monocyte count in healthy human volunteers by treatment group.

Figure 57:
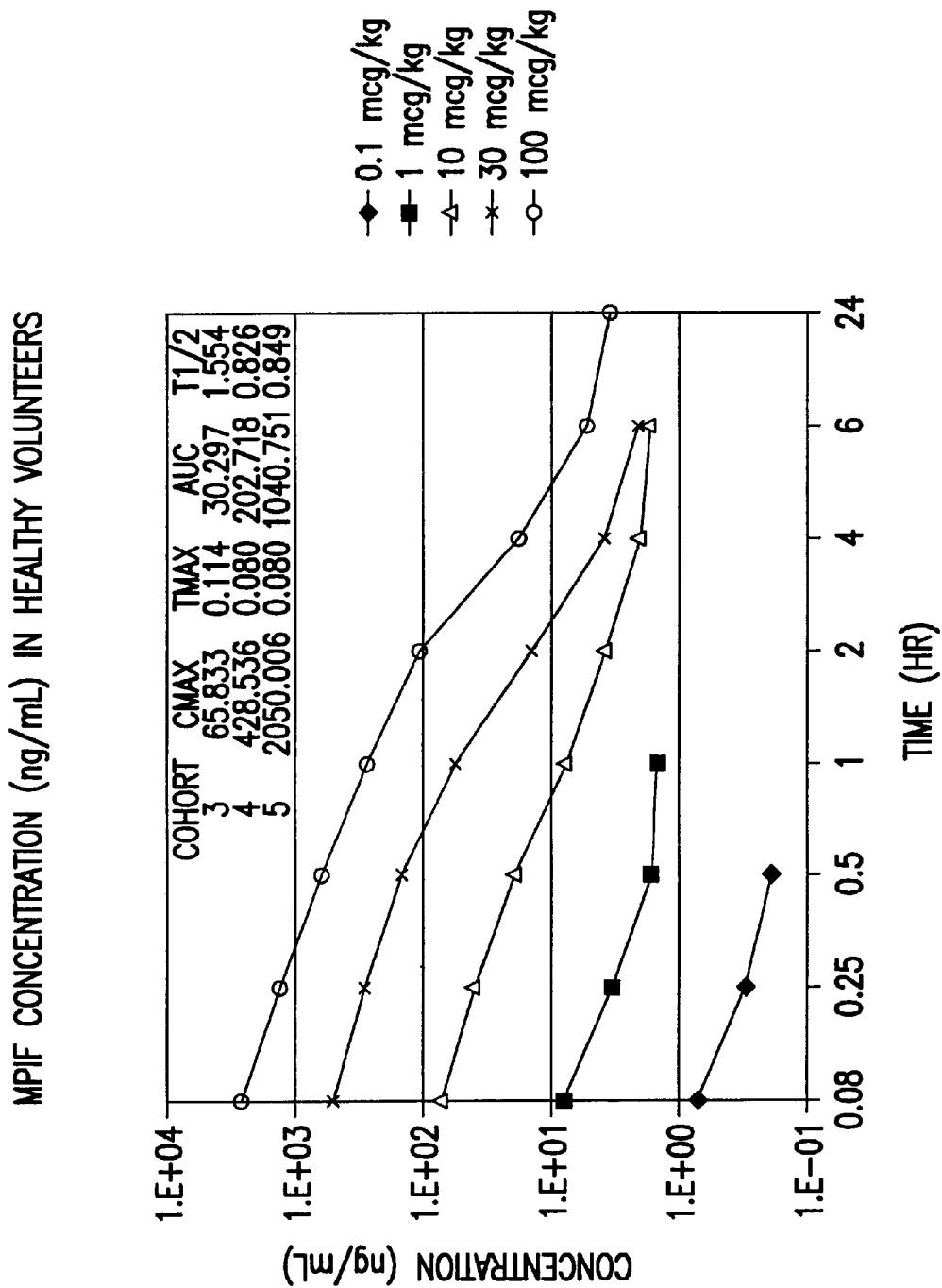

FIG. 57 shows the MPIF concentration (ng/ml) in healthy volunteers.

FIGS. 58A–58E show the structure of MPIF-1. (A) and (B) The superposition of the 30 simulated annealing (SA)

structures about the average structure of MPIF-1, residues 1–77. (C) The same as in A and B except the N-terminal (1–10) and the C-terminal (67–77) residues have been omitted for clarity. (D) and (E) A schematic representation of MPIF-1 in the same orientation as shown in panel C created using the program MOLMOL (Koradi, R., et al., *J. Mol. Graph.* 14:29–42 (1996)).

FIGS. 59A–59F show the atomic rms distribution of the 30 simulated annealing structures about the average structure best fitted for residues 11–66 for the backbone atoms (A) and all heavy atoms (B). Also shown are the angular order parameter (S) for $\phi$ (C), for $\psi$ (D), and $\chi1$ (E) and the fractional solvent accessible area (F).

FIGS. 60A–60G show the $^{15}N$ dynamics data of MPIF-1 as a function of residue. The $^{15}N$ $T_1$ $T_2$, $T_1/T_2$ ratio, and NOE are shown in panels A, B, C and D respectively. Dynamics parameters calculated from fitting the $^{15}N$ $T_1$ $T_2$, NOE data are shown in the remaining panels; order parameter, $S^2$ (E); internal correlation time,Te (F) and conformational exchange rate (G).

FIGS. 61A–61D show a comparison of MPIF-1 and other CC chemokine structures, MIP-1β, HCC-2, RANTES and MCP-1. Residues 11 to 66 of MPIF-1 are superimposed on residues 11 to 66 of MIP-1, residues 6 to 61 of HCC2, residues 10 to 65 of RANTES and residues 11 to 67 of MCP-3. For clarity, the N- and the C-termini residues are not displayed.

FIG. 62 shows the alignment of amino acid sequences of MPIF-1 and other related CC chemokines. The conserved cysteines are in bold-face type. The conserved hydrophobic and conserved charged residues are described in Example 36.

FIGS. 63A–63D show the surface charge distribution of MPIF-1 using the program MOLMOL (Koradi, R., et al.,*J. Mol. Graph.* 14:29–42 (1996)). Positive and negatively charged regions are shown in blue and red, respectively. For clarity, residues 1–10 and 69–77 are not shown.

DETAILED DESCRIPTION OF THE PREFERRED EMBODIMENTS

The present invention provides diagnostic or therapeutic compositions and methods that utilize isolated polynucleotide molecules encoding polypeptides, or the polypeptides themselves, as human myeloid progenitor inhibitory factor-1 (MPIF-1) polypeptides (previously termed MIP-3 and chemokine β8(CKβ8 or ckb-8)) and provides vectors, host cells and recombinant or synthetic methods for producing the same.

MPIF-1 Polynucleotides

In accordance with an aspect of the present invention, there are provided isolated nucleic acids (polynucleotides) which encode the full-length or mature MPIF-1 polypeptide having the deduced amino acid sequence of FIG. 1 (SEQ ID NO:2) and for the mature MPIF-1 polypeptide encoded by the cDNA of the clone deposited as ATCC Deposit No. 75676 on Feb. 9, 1994. The address of the American Type Culture Collection is Patent Depository, 10801 University Boulevard, Manassas, Va. 20110–2209. The deposited clone is contained in the pBluescript SK(–) plasmid (Stratagene, LaJolla, Calif.).

The deposit(s) referred to herein will be maintained under the terms of the Budapest Treaty on the International Recognition of the Deposit of Micro-Organisms for Purposes of Patent Procedure. These deposits are provided merely as convenience to those of skill in the art and are not an admission that a deposit is requiredunder 35 U.S.C. §112. The sequence of the polynucleotides contained in the deposited materials, as well as the amino acid sequence of the polypeptides encoded thereby, are incorporated herein by reference and are controlling in the event of any conflict with description of sequences herein. A license can be required to make, use or sell the deposited materials, and no such license is hereby granted.

Polynucleotides encoding polypeptides of the present invention are structurally related to the pro-inflammatory supergene "intercrine" which is in the cytokine or chemokine family. MPIF-1 is a MIP-1 homologue and is more homologous to MIP-1α than to MIP-1β. The polynucleotide encoding MPIF-1 was derived from an aortic endothelium cDNA library and contains an open reading frame encoding a polypeptide of 120 amino acid residues, which exhibits significant homology to a number of chemokines. The top match is to the human macrophage inflammatory protein 1 alpha, showing 36% identity and 66% similarity (FIG. 2).

The polynucleotides of the present invention can be in the form of RNA or in the form of DNA, which DNA includes cDNA, genomic DNA, and synthetic DNA. The DNA can be double-stranded or single-stranded, and if single stranded can be the coding strand or non-coding (anti-sense) strand. The coding sequence which encodes the mature polypeptide can be identical to the coding sequence shown in FIG. 1 or 20A (SEQ ID NO:1 or 6) or that of the deposited clone or can be a different coding sequence which coding sequence, as a result of the redundancy or degeneracy of the genetic code, encodes the same, mature polypeptide as the DNA of FIGS. 1 or 20A (SEQ ID NO:1 or 6) or the deposited cDNA.

The polynucleotides which code for the mature polypeptide of FIG. 1 (SEQ ID NO:2) or for the mature polypeptide encoded by the deposited cDNA can include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention is also directed to variants of the polynucleotide sequence disclosed in SEQ ID NO:1 or 6, the complementary strand thereto, and/or the cDNA sequence contained in a deposited clone.

"Variant" refers to a polynucleotide or polypeptide differing from the MPIF-1 polynucleotide or polypeptide, but retaining essential properties thereof. Generally, variants are overall closely similar, and, in many regions, identical to the MPIF-1 polynucleotide or polypeptide.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G , C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 or 6, as set forth using deoxyribonucleotide abbreviations, is intended to indicate an RNA molecule having a sequence in which each deoxyribonucleotide A, G or C of SEQ ID NO:1 or 6 has been replaced by the corresponding ribonucleotide A, G or C, and each deoxyribonucleotide T has been replaced by a ribonucleotide U.

Using the information provided herein, such as the nucleotide sequence in FIG. 1, a nucleic acid molecule of the present invention encoding an MPIF-1 polypeptide may be obtained using standard cloning and screening procedures, such as those for cloning cDNAs using mRNA as starting material.

The present invention further relates to variants of the hereinabove described polynucleotides which encode fragments, analogs and derivatives of the polypeptide having the deduced amino acid sequence of FIG. 1 (SEQ ID NO:2) or the polypeptides encoded by the cDNA of the deposited clone. The variants of the polynucleotides can be a naturally occurring allelic variant of the polynucleotides or a non-naturally occurring variant of the polynucleotides.

The present invention also includes polynucleotides encoding the same mature polypeptide as shown in FIG. 1 (SEQ ID NO:2) or the same mature polypeptides encoded by the cDNA of the deposited clone as well as variants of such polynucleotides which variants encode a fragment, derivative or analog of the polypeptide of FIG. 1 (SEQ ID NO:2) or the polypeptides encoded by the cDNA of the deposited clone. Such nucleotide variants include deletion variants, substitution variants and addition or insertion variants.

As hereinabove indicated, the polynucleotide can have a coding sequence which is a naturally occurring allelic variant of the coding sequence shown in FIG. 1 (SEQ ID NO:2) or of the coding sequence of the deposited clone. As known in the art, an allelic variant is an alternate form of a polynucleotide sequence which can have a substitution, deletion or addition of one or more nucleotides, which does not substantially alter the function of the encoded polypeptide.

The present invention also includes polynucleotides, wherein the coding sequence for the mature polypeptide can be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and can have the leader sequence cleaved by the host cell to form the mature form of the polypeptide. The polynucleotides can also encode a proprotein which is the mature protein plus additional N-terminal amino acid residues. A mature protein having a prosequence is a proprotein and is an inactive form of the protein. Once the prosequence is cleaved an active mature protein remains.

Thus, for example, the polynucleotides of the present invention can code for a mature protein, or for a protein having a prosequence or for a protein having both a prosequence and a presequence (leader sequence).

The polynucleotides of the present invention can also have the coding sequence fused in frame to a marker sequence which allows for purification of the polypeptides of the present invention. The marker sequence can be a hexa-histidine tag supplied by a pQE-9 vector to provide for purification of the mature polypeptide fused to the marker in the case of a bacterial host, or, for example, the marker sequence can be a hemagglutinin (HA) tag when a mammalian host, e.g. COS-7 cells, is used. The HA tag corresponds to an epitope derived from the influenza hemagglutinin protein (Wilson, I., et al., *Cell*, 37:767 (1984)).

The term "gene" means the segment of DNA involved in producing a polypeptide chain; it includes regions preceding and following the coding region (leader and trailer) as well as intervening sequences (introns) between individual coding segments (exons).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

The term "isolated" means that the material is removed from its original environment (e.g., the natural environment if it is naturally occurring). For example, a naturally-occurring polynucleotide or polypeptide present in a living animal is not isolated, but the same polynucleotides or DNA or polypeptides, separated from some or all of the coexisting materials in the natural system, is isolated. Such polynucleotides could be part of a vector and/or such polynucleotides or polypeptides could be part of a composition, and still be isolated in that such vector or composition is not part of its natural environment. Isolated RNA molecules include in vivo or in vitro RNA transcripts of the DNA molecules of the present invention. Isolated nucleic acid molecules according to the present invention further include such molecules produced synthetically. However, a nucleic acid contained in a clone that is a member of a library (e.g., a genomic or cDNA library) that has not been isolated from other members of the library (e. g., in the form of a homogeneous solution containing the clone and other members of the library) or which is contained on a chromosome preparation (e.g., a chromosome spread) or a nucleic acid present in a preparation of genomic DNA (e.g., intact, sheared, and/or cut with one or more restriction enzymes) that has not been isolated from other nucleic acids in the preparation, is not "isolated" for the purposes of this invention.

Isolated nucleic acid molecules of the present invention include DNA molecules comprising, or alternatively consisting of, an open reading frame (ORF) for a MPIF-1 cDNA; DNA molecules comprising, or alternatively consisting of, the coding sequence for a mature MPIF-1 protein; and DNA molecules which comprise a sequence substantially different from those described above but which, due to the degeneracy of the genetic code, still encode an MPIF-1 polypeptide. Of course, the genetic code is well known in the art. Thus, it would be routine for one skilled in the art to generate the degenerate variants described above.

The present invention further relates to polynucleotides which hybridize to the hereinabove-described sequences if there is at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which retain substantially the same biological function or activity as the mature polypeptide encoded by the cDNA of FIG. 1 (SEQ ID NO:1) or the deposited cDNA.

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

In another aspect, the invention provides an isolated nucleic acid molecule comprising, or alternatively consisting of, a polynucleotide which hybridizes under stringent hybridization conditions to a portion of the polynucleotide in a nucleic acid molecule of the invention described above, for instance, the cDNA clone contained in ATCC Deposit 75676 (MPIF-1). By "stringent hybridization conditions" is intended overnight incubation at 42° C. in a solution consisting of 50% formamide, 5×SSC (750 mM NaCi, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. Also intended is a polynucleotide hybridizing to at least about 15 nucleotides (nt), and more preferably at least about 20 nt, more preferably at least about 25 nt, still more preferably at least about 30 nt, and even more preferably about 30–70 (e.g., 30, 35, 40, 45, 50, 55, 60, 65, and/or 70 (of course, fragment lengths in addition to those recited herein are also useful)) nt of the reference polynucleotide. These are useful as diagnostic probes and primers as discussed above and in more detail below.

Of course, polynucleotides hybridizing to a larger portion of the reference polynucleotide (e.g. the deposited cDNA clone), for instance, a portion 50–750 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in SEQ ID NO:1 or 6 (MPIF-1). By a portion of a polynucleotide of "at least 20 nt in length," for example, is intended 20 or more contiguous nucleotides from the nucleotide sequence of the reference polynucleotide. As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual*, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since a MPIF-1 cDNA clone has been deposited and its determined nucleotide sequence is provided, generating polynucleotides which hybridize to a portion of the MPIF-1 cDNA molecule would be routine to the skilled artisan. For example, restriction endonuclease cleavage or shearing by sonication of a MPIF-1 cDNA clone could easily be used to generate DNA portions of various sizes which are polynucleotides that hybridize to a portion of the MPIF-1 cDNA molecule.

Alternatively, the hybridizing polynucleotides of the present invention could be generated synthetically according to known techniques. Of course, a polynucleotide which hybridizes only to a poly A sequence (such as the 3' terminal poly(A) tract of a cDNA, or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g practically any double-stranded cDNA clone).

As indicated, nucleic acid molecules of the present invention which encode an MPIF-1 polypeptide may include, but are not limited to those encoding the amino acid sequence of the mature polypeptide, by itself; the coding sequence for the mature polypeptide and additional sequences, such as those encoding the leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example— ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include an MPIF-1 polypeptide or fragment fused to Fc at the—or C-terminus.

The present invention further relates to variants of the nucleic acid molecules of the present invention, which encode portions, analogs or derivatives of an MPIF-1 polypeptide. Variants may occur naturally, such as a natural allelic variant. By an "allelic variant" is intended one of several alternate forms of a gene occupying a given locus on a chromosome of an organism. *Genes V*, Lewin, B., ed., Oxford University Press, New York (1994). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of an MPIF-1 polypeptide or portions thereof. Also especially preferred in this regard are conservative substitutions. Most highly preferred are nucleic acid molecules encoding the mature protein or the mature amino acid sequence encoded by the deposited cDNA clone, as described herein.

MPIF-1 Homolog Polynucleotides. The present invention is further directed to polynucleotides having at least 95% identity to apolynucleotide which encodes the polypeptide of SEQ ID NO:2 as well as fragments thereof, which fragments have at least 30 bases and preferably at least 50 bases and to polypeptides encoded by such polynucleotides.

Further embodiments of the invention include isolated nucleic acid molecules comprising—or alternatively, consisting of—a polynucleotide having a nucleotide sequence at least 80%, 85%, 90%, 92%, 95%, 96%, 97%, 98% or 99% identical to (a) a nucleotide sequence encoding an MPIF-1 polypeptide or fragment, having an amino acid sequence of SEQ ID NO:2 including the predicted leader sequence; (b) a nucleotide sequence encoding an MPIF-1 polypeptide or fragment, having an amino acid sequence of SEQ ID NO:2 including the predicted leader sequence, but minus the N-terminal methionine residue; (c) a nucleotide sequence encoding the mature MPIF-1 polypeptide (full-length polypeptide with the leader removed); (d) a nucleotide sequence encoding the full-length polypeptide having the complete amino acid sequence including the leader encoded by the deposited cDNA clone; (e) a nucleotide sequence encoding the mature polypeptide having the amino acid sequence encoded by the deposited cDNA clone; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding an MPIF-1 polypeptide is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 80%, 85%, 90%, 92%, 95%, 96%, 97%, 98% or 99% identical to, for instance, the nucleotide sequence shown in FIG. 1 or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

As a practical matter, whether any particular nucleic acid molecule or polypeptide is at least 80%, 85%, 90%, 92%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237–245 (1990).) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identify are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the lenght of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

Preferably, the programs described above are used to align a polynucleotide of the present invention (the reference sequence) and a second sequence, and the % identity is calculated manually. Percent identity is the number of individual nucleotides that are identical between two sequences, divided by the total number of nucleotide residues in the reference sequence, multiplied by 100%. For example, to determine the % identity of nucleotides 1 to 360 of SEQ ID NO:1 to a second sequence, the number of nucleotide mismatches (i.e., point mutations: insertions, deletions and substitutions) is counted and subtracted from 360 (the number of nucleotides in the reference sequence) to get the number of identical nucleotides. The resulting number is divided by 360 and then multiplied by 100%. If there are mismatches (i.e., point mutations: insertions, deletions and substitutions of individual nucleotides) at positions 1–5, 18, 201–210, 300, 302,318–328,330, 336, 341 and 349–352 of SEQ ID NO:1, the % identity would be 90%. (5+1+10+1+1+11+1+1+1+3=36. 360−36=324. 324/360=0.9. 0.9×100= 90%) Percent identity of polypeptides would be calculated in an analogous manner.

As one of ordinary skill would appreciate, due to the possibilities of sequencing errors discussed above, as well as the variability of cleavage sites for leaders in different known proteins, the mature MPIF-1 polypeptide encoded by the deposited cDNA comprises about 99 amino acids, but may be anywhere in the range of 75–120 amino acids; and the actual leader sequence of this protein is about 21 amino acids, but may be anywhere in the range of about 15 to about 35 amino acids.

The MPIF-1 variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. MPIF-1 polynucleotide variants can be produced for a variety of reasons, e.g., to optimize codon expression for a particular host (change codons in the human mRNA to those preferred by a bacterial host such as *E. coli*).

Naturally occurring MPIF-1 variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Nucleic Acid Probes. Such isolated molecules, particularly DNA molecules, are useful as probes for gene mapping, by in situ hybridization with chromosomes, and for detecting expression of a MPIF-1 gene in human tissue, for instance, by Northern blot analysis. The present invention is further directed to fragments of the isolated nucleic acid molecules described herein. By a fragment of an isolated nucleic acid molecule having the nucleotide sequence of the deposited MPIF-1 cDNA, or a nucleotide sequence shown in FIGS. 1 or 20A (SEQ ID NO:1 or 6) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–500 nt in length are also useful according to the present invention as are fragments corresponding to most, if not all, of a nucleotide sequence of the deposited MPIF-1 cDNA, or as shown in FIGS. 1 or 20A (SEQ ID NO:1 or 6). By a fragment at least 20 nt in length, for example, is intended fragments which include 20 or more contiguous bases from the nucleotide sequence of the deposited cDNA or the nucleotide sequence as shown in FIGS. 1 or 20A (SEQ ID NO:1 or 6). Since the gene has been deposited and the nucleotide sequence shown in FIGS. 1 or 20A (SEQ ID NO:1 or 6) is provided, generating such DNA fragments would be routine to the skilled artisan. For example, restriction endonuclease cleavage or shearing by sonication could easily be used to generate fragments of various sizes. Alternatively, such fragments could be generated synthetically.

The present application is directed to nucleic acid molecules at least 90%, 95%, 96%, 97%, 98% or 99% identical to the nucleic acid sequences disclosed herein, (e.g., encoding a polypeptide having the amino acid sequence of an N and/or C terminal deletion disclosed below as m-n of SEQ ID NO:2 or 7), irrespective of whether they encode a polypeptide having MPIF-1 functional activity. This is because even where a particular nucleic acid molecule does not encode a polypeptide having MPIF-1 functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having MPIF-1 functional activity include, inter alia, (1) isolating a MPIF-1 gene or allelic or splice variants thereof in a cDNA library; (2) in situ hybridization (e.g., "FISH") to metaphase chromosomal spreads to provide precise chromosomal location of the MPIF-1 gene, as described in Verma et al., *Human Chromosomes. A Manual of Basic Techniques*, Pergamon Press, New York (1988); and (3) Northern Blot analysis for detecting MPIF-1 mRNA expression in specific tissues.

Preferred, however, are nucleic acid molecules having sequences at least 90%, 95%, 96%, 97%, 98% or 99% identical to the nucleic acid sequences disclosed herein, which do, in fact, encode a polypeptide having MPIF-1 functional activity. By "a polypeptide having MPIF-1 functional activity" is intended polypeptides exhibiting activity similar, but not necessarily identical, to a functional activity of the MPIF-1 polypeptides of the present invention (e.g., complete (full-length) MPIF-1, mature MPIF-1 and soluble MPIF-1 (e.g., having sequences contained in the extracellular domain of MPIF-1) as measured, for example, in a particular immunoassay or biological assay. For example, a MPIF-1 functional activity can routinely be measured by determining the ability of a MPIF-1 polypeptide to bind a MPIF-1 ligand. MPIF-1 functional activity may also be measured by determining the ability of a polypeptide, such as cognate ligand which is free or expressed on a cell surface, to induce cells expressing the polypeptide.

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention is also directed to polynucleotide fragments of the polynucleotides of the invention. In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:1 or 6 or the complementary strand thereto, or is a portion of a polynucleotide sequence encoding the polypeptide of SEQ ID NO:2. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:1 or 6. In this context "about" includes the particularly recited value, a value larger or smaller by several (5, 4, 3, 2, or 1) nucleotides, at either terminus or at both termini. These nucleotide fragments have uses that include, but are not limited to, as diagnostic probes and primers as discussed herein. Of course, larger fragments (e.g., 50, 150, 500, 600, 2000 nucleotides) are preferred.

Further, the invention includes a polynucleotide comprising, or alternatively consisting of, any portion of at least about 25 nucleotides, at least about 30 nucleotides, at least about 35 nucleotides, at least about 40 nucleotides, at least about 45 nucleotides, preferably at least about 50 nucleotides, at least about 60 nucleotides, at least about 70 nucleotides, at least about 80 nucleotides, at least about 90 nucleotides, or at least about 100 nucleotides of SEQ ID NO:1 or 6 from residue 50–599, 100–599, 200–599, 300–599, 400–599, 500–599, 600–1800, 50–500, 100–500, 200–500, 300–500, 400–500, 50–400, 100–400, 200–400, 300–400, 50–300, 100–300, 200–300, 50–200, 100–200, and 50–100.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, or 551 to the end of SEQ ID NO:1 or 6, or the complementary strand thereto, or the cDNA contained in the deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Polynucleotides which hybridize to these nucleic acid molecules under stringent hybridization conditions or lower stringency conditions are also encompassed by the invention, as are polypeptides encoded by these polynucleotides. In the present invention, a "polypeptide fragment" refers to an amino acid sequence which is a portion of that contained in SEQ ID NO:2 or encoded by the cDNA contained in the deposited clone.

Vectors, Host Cells, and Protein Expression. The present invention also relates to vectors containing the isolated nucleic acid molecules of the present invention, genetically engineered host cells containing the recombinant vectors, and the production of MPIF-1 polypeptides or fragments thereof by recombinant techniques. The present invention further relates to novel expression vectors useful for the production of proteins in bacterial systems. These novel vectors are exemplified by the pHE4 series of vectors and, in particular, the pHE4–5 vector (FIGS. 31 and 36A–G).

The polynucleotide encoding the protein of the present invention may be joined to a vector containing a selectable marker for propagation in a host. As discussed in detail below, generally, a plasmid vector is introduced into a host cell in a precipitate, such as a calcium phosphate precipitate, or in a complex with a charged lipid. If the vector is a virus, it may be packaged in vitro using an appropriate packaging cell line and then transduced into host cells.

Preferred for use in the practice of the present invention are vectors comprising cis-acting control regions operatively linked to the polynucleotide of interest. Cis-acting control regions include operator and enhancer sequences. As used herein, the term "operator" refers to a nucleotide sequence, usually composed of DNA, which controls the transcription of an adjacent nucleotide sequence. Operator sequences are generally derived from bacterial chromosomes.

Transcription of the nucleotide sequences encoding the polypeptides of the present invention by higher eukaryotes may be increased by inserting an enhancer sequence into the vector. Enhancers are cis-acting elements usually about from 10 to 300 bp that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

Appropriate trans-acting factors may be supplied by the host, supplied by a complementing vector, or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives. Also preferred for the expression of MPIF-1 is the pHE4–5 vector described in Example 30.

Additional expression vectors useful in the present invention include chromosomal-, episomal- and virus-derived vectors, e.g. vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The appropriate nucleic acid sequence can be inserted into the vector by a variety of procedures. In general, the nucleic acid sequence is inserted into an appropriate restriction endonuclease site(s) by procedures known in the art. Such procedures and others are deemed to be within the scope of those skilled in the art.

The nucleic acid insert should be operably linked to an appropriate promoter, such as the phage lambda PL promoter, the *E. coli* lac, trp and tac promoters, the SV40 early and late promoters and promoters of retroviral LTRs, and other promoters known to control expression of genes in prokaryotic or eukaryotic cells or their viruses. Other suitable promoters will be known to the skilled artisan. As used herein, the term "promoter" refers to a nucleotide sequence or group of nucleotide sequences which, at a minimum, provides a binding site or initiation site for RNA polymerase action. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated. The vector can also include appropriate sequences for amplifying expression.

As used herein, the phrase "operably linked" refers to a linkage in which a nucleotide sequence is connected to another nucleotide sequence (or sequences) in such a way as to be capable of altering the functioning of the sequence (or sequences). For example, a protein coding sequence which is operably linked to a promoter/operator places expression of the protein coding sequence under the influence or control of these sequences. Two nucleotide sequences (such as a protein encoding sequence and a promoter region sequence linked to the 5' end of the encoding sequence) are said to be operatively linked if induction of promoter function results in the transcription of the protein encoding sequence mRNA and if the nature of the linkage between the two nucleotide sequences does not (1) result in the introduction of a frame-shift mutation nor (2) prevent the expression regulatory sequences to direct the expression of the mRNA or protein. Thus, a promoter region would be operably linked to a nucleotide sequence if the promoter were capable of effecting transcription of that nucleotide sequence.

As used herein, the phrase "cloning vector" refers to a plasmid or phage nucleic acid or other nucleic acid sequence which is able to replicate autonomously in a host cell, and which is characterized by one or a small number of endonuclease recognition sites at which such nucleic acid sequences may be cut in a determinable fashion without loss of an essential biological function of the vector, and into which nucleic acid may be spliced in order to bring about its replication and cloning. The cloning vector may further contain a marker suitable for use in the identification of cells transformed with the cloning vector. Markers, for example, are erythromycin and kanamycin resistance. The term "vehicle" is sometimes used for "vector."

As used herein, the phrase "expression vector" refers to a vector similar to a cloning vector which is capable of expressing a structural gene cloned into the expression vector, after transformation of the expression vector into a host. In an expression vector, the cloned structural gene (any coding sequence of interest) is placed under the control of (i.e., operably linked to) certain sequences which allow such gene to be expressed in a specific host. In the pHE4–5 vector, for example, the structural gene is operably linked to a T5 phage promoter sequence and two lac operator sequences. Expression control sequences will vary, and may additionally contain transcriptional elements such as termination sequences and/or translational elements such as initiation and termination sites.

As indicated above, the expression vectors will preferably include at least one selectable marker. Such markers include dihydrofolate reductase or neomycin resistance for eukaryotic cell culture and tetracycline, kanamycin, or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells (e.g, *Saccharomyces cerevisiae* or *Pichia pastoris* (ATCC Accession No. 201178)); insect cells such as Drosophila S2 and Spodoptera Sf9 cells; animal cells such as CHO, COS, 293 and Bowes melanoma cells; and plant cells. Appropriate culture mediums and conditions forthe above-described host cells are known in the art.

In addition to the use of expression vectors in the practice of the present invention, the present invention further includes novel expression vectors comprising operator and promoter elements operatively linked to nucleotide sequences encoding aproteinofinterest. One example of such avector is pHE4–5 (SEQ ID NO :37) which is described in detail both below and in Example 14. The pHE4–5 vector was deposited on Sep. 30, 1997 at the American Type Culture Collection, Patent Depository, 10801 University Boulevard, Manassas, Va. 20110–2209, and given ATCC accession number 209311.

As summarized in FIGS. 31 and 36, components of the pHE4–5 vector (SEQ ID NO:37) include: (1) a neomycin-phosphotransferase gene as a selection marker, (2) an *E. coli* origin of replication, (3) a T5 phage promoter sequence, (4) two lac operator sequences, (5) a nucleotide sequence encoding MPIF-1Δ23 (SEQ ID NO:27), (6) a Shine-Delgarno sequence, (7) the lactose operon repressor gene (lacIq). The origin of replication (oriC) is derived from pUC19 (LTI, Gaithersburg, Md.). The promoter sequence was and operator sequences were made synthetically. Synthetic production of nucleic acid sequences is well known in the art. Clontech 95/96 Catalog, pages 215–216, Clontech, 1020 East Meadow Circle, Palo Alto, Calif. 94303.

As noted above, the pHE4–5 vector contains a lacIq gene. LacIq is an allele of the lacI gene which confers tight regulation of the lac operator. Amann, E. et al., *Gene* 69.301–315 (1988); Stark, M., *Gene* 51:255–267 (1987). The lacIq gene encodes a repressor protein which binds to lac operator sequences and blocks transcription of down-stream (i.e., 3') sequences. However, the lacIq gene product dissociates from the lac operator in the presence of either lactose or certain lactose analogs, e.g., isopropyl B-D-thiogalactopyranoside (IPTG). MPIF-1Δ23 thus is not produced in appreciable quantities in uninduced host cells containing the pHE4–5 vector. Induction of these host cells by the additional of an agent such as IPTG, however, results in the expression of the MPIF-1Δ23 coding sequence.

The promoter/operator sequences (SEQ ID NO:38) of the pHE4–5 vector comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., Textbook of Biochemistry with Clinical Correlations, 4th Edition (1997), pages 802–807.

The pHE4 series of vectors contain all of the components of the pHE4–5 vector except for the MPIF-1Δ23 coding sequence. Features of the pHE4 vectors include optimized synthetic T5 phage promoter, lac operator, and Shine-Delagamo sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4–5 vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vectors useful for the production of the proteins of the present invention in bacteria. This aspect of the invention is exemplified by the pHE4–5 vector (SEQ ID NO:37) (ATCC Accession No. 20931) and variations thereof.

Additional vectors preferred for use in the expression of the proteins of the present invention in bacteria include pQE70, pQE60 and pQE-9, (Qiagen); pBS vectors, pD10, Phagescript vectors, pBluescript vectors, pNH8A, pNH16a, pNH18A, pNH46A, available from Stratagene; and ptrc99a, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia.

Other suitable vectors will be readily apparent to the skilled artisan and include pBR322 (ATCC 37017), pKK223-3 (Pharnacia Fine Chemicals, Uppsala, Sweden) and GEM1 (Promega Biotec, Madison, Wis., USA). These pBR322 "backbone" sections are combined with an appropriate promoter and the structural sequence to be expressed. Following transformation of a suitable host strain and growth of the host strain to an appropriate cell density, the selected promoter is induced by appropriate means (e.g, temperature shift or chemical induction) and cells are cultured for an additional period.

In a further embodiment, the present invention relates to host cells containing the above-described construct. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods in Molecular Biology (1986).

Recombinant constructs may be introduced into host cells using well known techniques such infection, transduction, transfection, transfection, electroporation and transformation. The vector may be, for example, a phage, plasmid, viral or retroviral vector. Retroviral vectors may be replication competent or replication defective. In the latter case, viral propagation generally will occur only in complementing host cells.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the MPIF-1, and genes. The culture conditions, such as temperature, pH and the like, are those previously used with the host cell selected for expression, and will be apparent to the ordinarily skilled artisan.

The polynucleotides of the present invention can be employed for producing polypeptides by recombinant techniques. Thus, for example, the polynucleotide sequence can be included in any one of a variety of expression vehicles, in particular vectors or plasmids for expressing a polypeptide. Such vectors include chromosomal, nonchromosomal and synthetic nucleic acid sequences, e.g., derivatives of SV40; bacterial plasmids; phage nucleic acid; yeast plasmids; vectors derived from combinations of plasmids and phage nucleic acid, viral nucleic acid such as vaccinia, adenovirus, fowl pox virus, alphaviruses and pseudorabies. However, any other plasmid or vector can be used as long they are replicable and viable in the host.

As noted above, the vector containing the appropriate nucleic acid sequence as hereinabove described, as well as an appropriate promoter or control sequence, can be employed to transform an appropriate host to permit the host to express the protein.

As representative examples of appropriate hosts, there can be mentioned: bacterial cells, such as *E. coli*, Streptomyces, *Salmonella typhimurium*; fungal cells, such as yeast; insect cells such as Drosophila and Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operatively linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia). However, any other plasmid or vector can be used as long as they are replicable and viable in the host.

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the nucleic acid constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural nucleic acid sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others can also be employed as a matter of choice.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. Nucleic acid sequences derived from the SV40 splice, and polyadenylation sites can be used to provide the required nontranscribed genetic elements.

MPIF-1 polypeptides, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the MPIF-1 polypeptides may be glycosylated or may be non-glycosylated. In addition, MPIF-1 polypeptides may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., MPIF-1 coding sequence), and/or to include genetic material (e.g., heterologous polynucleotide sequences) that is operably associated with MPIF-1 polynucleotides of the invention, and which activates, alters, and/or amplifies endogenous MPIF-1 polynucleotides. For example, techniques known in the art may be used to operably associate heterologous control regions (e.g., promoter and/or enhancer) and endogenous MPIF-1 polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:8932–8935 (1989); and Zijlstra et al., *Nature* 342:435–438 (1989), the disclosures of each of which are incorporated by reference in their entireties).

MPIF-1 Polypeptides

The invention further provides an isolated MPIF-1 polypeptide having the amino acid sequence encoded by the deposited cDNA, or the amino acid sequence in FIG. 1 (SEQ ID NO:2), or a peptide or polypeptide comprising, or alternatively consisting of, a portion of the above polypeptides. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus. The invention further provides for the proteins containing, or alternatively comprising, or alternatively consisting of, polypeptide sequences encoded by the polynucleotides of the invention.

The present invention also encompasses variants of the polypeptide sequence disclosed in SEQ ID NO:2 and/or encoded by a deposited clone.

"Variant" refers to a polynucleotide or polypeptide differing from the MPIF-1 polynucleotide or polypeptide, but retaining essential properties thereof. Generally, variants are overall closely similar, and, in many regions, identical to the MPIF-1 polynucleotide or polypeptide.

Preferably, the polynucleotide fragments of the invention encode a polypeptide which demonstrates a MPIF-1 functional activity. By a polypeptide demonstrating a MPIF-1 "functional activity" is meant, a polypeptide capable of displaying one or more known functional activities associated with a full-length (complete) MPIF-1 protein. Such functional activities include, but are not limited to, biological activity, antigenicity (ability to bind (or compete with a MPIF-1 polypeptide for binding) to an anti-MPIF-1 antibody), immunogenicity (ability to generate antibody which binds to a MPIF-1 polypeptide), ability to form multimers with MPIF-1 polypeptides of the invention, and ability to bind to a receptor or ligand for a MPIF-1 polypeptide.

The functional activity of MPIF-1 polypeptides, and fragments, variants derivatives, and analogs thereof, can be assayed by various methods.

For example, in one embodiment where one is assaying for the ability to bind or compete with full-length MPIF-1 polypeptide for binding to anti-MPIF-1 antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a MPIF-1 receptor or ligand is identified, or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E., et al., 1995, *Microbiol. Rev.* 59:94–123. In another embodiment, physiological correlates of MPIF-1 binding to its substrates (signal transduction) can be assayed.

In addition, assays described herein (see Examples) and otherwise known in the art may routinely be applied to measure the ability of MPIF-1 polypeptides and fragments, variants derivatives and analogs thereof to elicit MPIF-1 related biological activity (either in vitro or in vivo). Other methods will be known to the skilled artisan and are within the scope of the invention.

The MPIF proteins, or fragments thereof, of the invention may be in monomers or multimers (i.e., dimers, trimers, tetramers, and higher multimers). Accordingly, the present invention relates to monomers and multimers of the MPIF proteins of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only MPIF proteins of the invention (including MPIF fragments, variants, and fusion proteins, as described herein). These homomers may contain MPIF proteins having identical or different polypeptide sequences. In a specific embodiment, a homomer of the invention is a multimer containing only MPIF proteins having an identical polypeptide sequence. In another specific embodiment, a homomer of the invention is a multimer containing MPIF proteins having different polypeptide sequences. In specific embodiments, the multimer of the invention is a homodimer (e.g., containing MPIF proteins having identical or different polypeptide sequences) or a homotrimer (e.g., containing MPIF proteins having identical or different polypeptide sequences). In additional embodiments, the homomeric multimer of the invention is at least a homodimer, at least a homotrimer, or at least a homotetramer.

As used herein, the term heteromer refers to a multimer containing heterologous proteins (i.e., proteins containing only polypeptide sequences that do not correspond to a polypeptide sequences encoded by the MPIF gene) in addition to the MPIF proteins of the invention. In a specific embodiment, the multimer of the invention is a heterodimer, a heterotrimer, or a heterotetramer. In additional embodiments, the homomeric multimer of the invention is at least a homodimer, at least a homotrimer, or at least a homotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the MPIF proteins of the invention. Such covalent associations may involve one or more amino acid residues contained in the polypeptide sequence of the polypeptide sequence recited in SEQ ID NO:2 and contained in the polypeptide encoded by the cDNA clone contained in ATCC Deposit No. 75676. In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in an MPIF fusion protein. In one example, covalent associations are between the heterologous sequence contained in a fusion protein of the invention (see, e.g., U.S. Pat. No. 5,478,925). In a specific example, the covalent associations are between the heterologous sequence contained in an MPIF-Fc fusion protein of the invention (as described herein).

In another embodiment, the MPIF polypeptides of the present invention and the epitope-bearing fragments thereof are fused with a heterologous antigen (e.g., polypeptide, carbohydrate, phospholipid, or nucleic acid).

In specific embodiments, the heterologous antigen is an immunogen. In a more specific embodiment, the heterologous antigen is the gp120 protein of HIV, or a fragment thereof. Polynucleotides encoding these polypeptides are also encompassed by the invention.

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

In addition, proteins of the invention can be chemically synthesized using techniques known in the art (e.g., see Creighton, 1983, Proteins: Structures and Molecular Principles, W. H. Freeman & Co., NY, and Hunkapiller, M., et al., Nature 310:105–111(1984)). For example, a peptide corresponding to a fragment of the MPIF polypeptides of the invention can be synthesized by use of a peptide synthesizer. Furthermore, if desired, nonclassical amino acids or chemical amino acid analogs can be introduced as a substitution or addition into the MPIF polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., Nucl. Acids Res. 13:4331 (1986); and Zoller et al., Nucl. Acids Res. 10:6487 (1982)), cassette mutagenesis (see, e.g., Wells et al., Gene 34:315 (1985)), restriction selection mutagenesis (see, e.g., Wells et al., Philos. Trans. R. Soc. London SerA 317:415 (1986)).

The invention additionally, encompasses MPIF polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of MPIF which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59–72 (1996); Vorobjev et al., *Nucleosides Nucleotides* 18:2745–2750 (1999); and Caliceti et al. *Bioconjug. Chem.* 10:638–646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera Drug Carrier Sys.* 9:249–304 (1992); Francis et al., *Intern. J. of Hematol.* 68:1–18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

Figure 5:
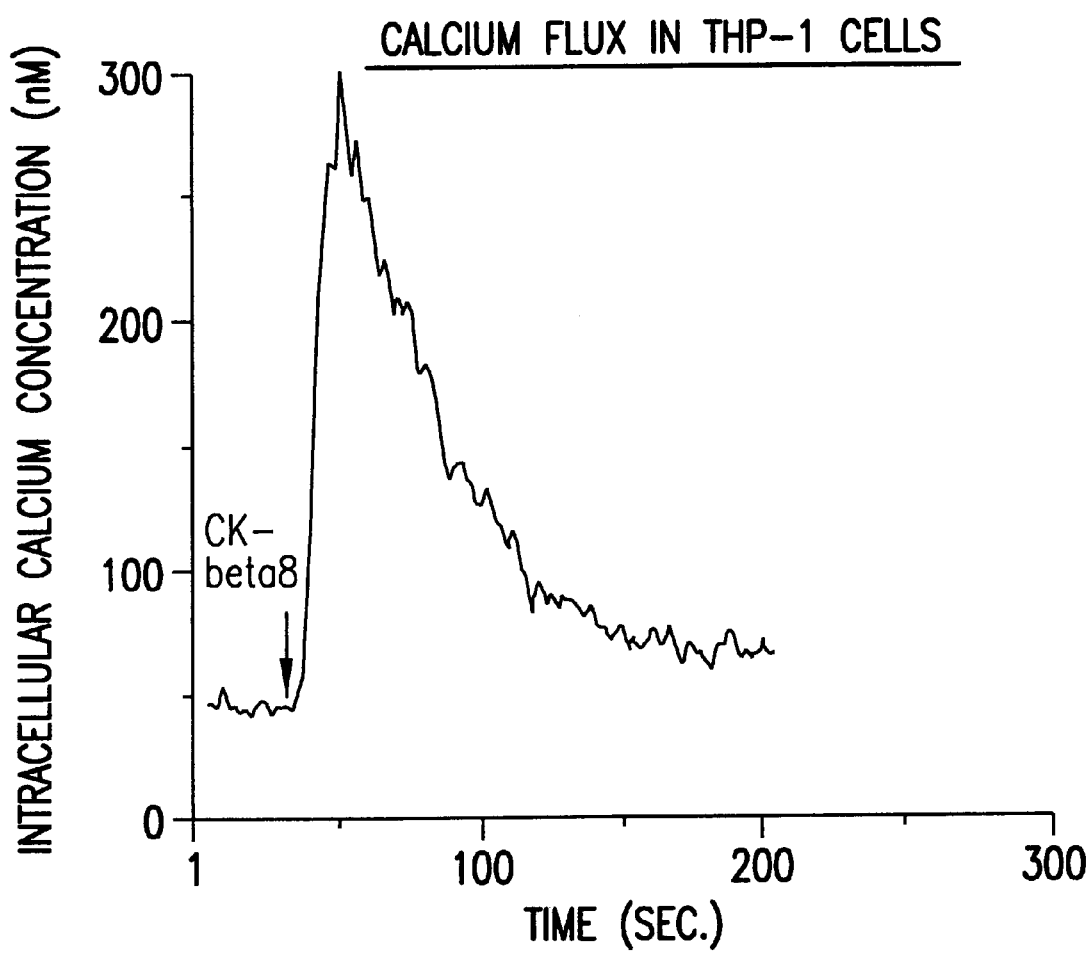
FIG. 5. Change in intracellular calcium concentration in response to MPIF-1 was determined using a Hitachi F-2000 fluorescence spectrophotometer. Bacterial expressed MPIF-1 was added to Indo-1 loaded THP-1 cells to a final concentration of 50 nM and the intracellular level of calcium concentration was monitored.

By "a polypeptide having MPIF-1 activity" is intended polypeptides exhibiting activity similar, but not necessarily identical, to an activity of the MPIF-1 protein of the invention (either the full-length protein or, preferably, the mature protein), as measured in a particular biological assay. MPIF-1 protein activity can be measured by the assays set forth in Examples 9, 10, as well as FIG. 5. For example, MPIF-1 protein activity measured using the in vitro myeloprotection assay disclosed in Example 9, infra.

Briefly, lineage-depleted populations of cells (Lin-cells) are isolated from mouse bone marrow and incubated in the presence of multiple cytokines with or without MPIF-1. After 48 hours, one set of each culture receives 5-Fu and the incubation is then continued for additional 24 hours, at which point the numbers of surviving low proliferative potential colony-forming cells (LPP-CFC) are determined by any suitable clonogenic assay known to those of skill in the art. A large percentage (e.g., $\geq$30–50%, such as $\geq$40%) of LPP-CFC are protected from the 5-Fu-induced cytotoxicity in the presence of MPIF-1, whereas little protection (<5%) of LPP-CFC will be observed in the absence of MPIF-1 in the presence of an unrelated protein. In such an assay, high proliferative potential colony-forming cells (HPP-CFC) can additionally be protected from the 5-Fu-induced cytotoxicity in the presence of MPIF-1, but in some cases are not. HPP-CFC are generally not protected when LPP-CFC are not protected.

MPIF-1 protein activity can also be measured by the sublethal and lethal models disclosed in Examples 16–18, and the cytoprotection method disclosed in Example 19.

Thus, "a polypeptide having MPIF-1 protein activity" includes polypeptides that exhibit MPIF-1 activity, in the above-described assay. Although the degree of activity need not be identical to that of the MPIF-1 protein, preferably, "a polypeptide having MPIF-1 protein activity" will exhibit substantially similar activity as compared to the MPIF-1 protein (i.e., the candidate polypeptide will exhibit greater activity or not more than about twenty-fold less and, preferably, not more than about ten-fold less activity relative to the reference MPIF-1 protein).

The present invention further relates to a MPIF-1 polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention can be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA can be (i) one in which one or more of the amino acid residues are substituted with a conserved or non-conserved amino acid residue (preferably a conserved amino acid residue) and such substituted amino acid residues is or is not be one encoded by the genetic code, or (ii) one in which one or more of the amino acid residues includes a substituent group, or (iii) one in which the mature polypeptides are fused with another compound, such as a compound to increase the half-life of the polypeptide (for example, polyethylene glycol), or (iv) one in which the additional amino acids are fused to the mature polypeptides, such as a leader or secretory sequence or a sequence which is employed for purification of the mature polypeptides or a proprotein sequence. Such fragments, derivatives and analogs are deemed to be within the scope of those skilled in the art from the teachings herein.

Any MPIF-1 polypeptide can be used to generate fusion proteins. For example, the MPIF-1 polypeptide, when fused to a second protein, can be used as an antigenic tag. Antibodies raised against the MPIF-1 polypeptide can be used to indirectly detect the second protein by binding to the MPIF-1. Moreover, because secreted proteins target cellular locations based on trafficking signals, the MPIF-1 polypeptides can be used as targeting molecules once fused to other proteins.

Examples of domains that can be fused to MPIF-1 polypeptides include not only heterologous signal sequences, but also other heterologous functional regions. The fusion does not necessarily need to be direct, but may occur through linker sequences.

The polypeptides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 95% similarity (still more preferably at least 95% identity) to the polypeptide of SEQ ID NO:2 and also include portions of such polypeptides with and also include portions of such polypeptides with at least 25 amino acids, at least 30 amino acids, at least 35 amino acids, at least 40 amino acids, at least 45 amino acids, and more preferably at least 50 amino acids, at least 55 amino acids, at least 60 amino acids, at least 65 amino acids, at least 70 amino acids, at least 75 amino acids, at least 80 amino acids, at least 85 amino acids, at least 90 amino acids, at least 95 amino acids, and at least 100 amino acids.

Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, or 161 to the end of the coding region. Moreover, polypeptide fragments can be about 20, 30,40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Even if deletion of one or more amino acids from the N-terminus of a protein results in modification of loss of one or more biological functions of the protein, other functional activities (e.g., biological activities, ability to multimerize, ability to bind MPIF-1 ligand) may still be retained. For example, the ability of shortened MPIF-1 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an MPIF-1 mutein with a large number of deleted N-terminal amino acid residues may retain some biological or immunogenic activities. In fact, peptides composed of as few as six MPIF-1 amino acid residues may often evoke an immune response.

Accordingly, polypeptide fragments include the secreted MPIF-1 protein as well as the mature form. Further preferred polypeptide fragments include the secreted MPIF-1 protein or the mature form having a continuous series of deleted residues from the amino or the carboxy terminus, or both. For example, any number of amino acids, ranging from 1–60, can be deleted from the amino terminus of either the secreted MPIF-1 polypeptide or the mature form. Similarly, any number of amino acids, ranging from 1–30, can be deleted from the carboxy terminus of the secreted MPIF-1 protein or mature form. Furthermore, any combination of the above amino and carboxy terminus deletions are preferred. Similarly,polynucleotides encoding these polypeptide fragments are also preferred.

As known in the art "similarity" between two polypeptides is determined by comparing the amino acid sequence and its conserved amino acid substitutes of one polypeptide to the sequence of a second polypeptide.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA (ATCC 75676) or the nucleic acid sequence shown in FIGS. 1 or 20A (SEQ ID NO:1 or 6) will encode a polypeptide "having MPIF-1 protein activity." In fact, since degenerate variants of this nucleotide sequence all encode the same polypeptide, this will be clear to the skilled artisan even without performing the above described comparison assay. It will be further recognized in the art that, for such nucleic acid molecules that are not degenerate variants, a reasonable number will also encode a polypeptide having MPIF-1 protein activity. This is because the skilled artisan is fully aware of amino acid substitutions that are either less likely or not likely to significantly effect protein function (e.g. replacing one aliphatic amino acid with a second aliphatic amino acid), as further described below.

As a practical matter, whether any particular polypeptide is at least 80%, 85%, 90%, 92%, 95%, 96%, 97%, 98% or 99% identical to, for instance, the amino acid sequences of SEQ ID NO:2 or to the amino acid sequence encoded by the cDNA contained in a deposited clone can be determined conventionally using known computer programs. A preferred method for determing the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237–245 (1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to—or C-terminal deletions, not because of internal deletions, a manual correction must be made to the results. This is because the FASTDB program does not account for—and C-terminal truncations of the subject sequence when calculating global percent identity. For subject sequences truncated at the—and C-termini, relative to the query sequence, the percent identity is corrected by calculating the number of residues of the query sequence that are—and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the—and C-termini of the subject sequence, which are not matched/aligned with the query sequence, are considered for the purposes of manually adjusting the percent identity score. That is, only query residue positions outside the farthest—and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the—and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the—or C-termini of the subject sequence which are not matched/aligned with the query. In this case the percent identity calculated by FASTDB is not manually corrected. Once again, only residue positions outside the—and C-terminal ends of the subject sequence, as displayed in the FASTDB alignment, which are not matched/aligned with the query sequence are manually corrected for. No other manual corrections are to made for the purposes of the present invention.

Preferably, the programs described above are used to align a polypeptide of the present invention (the reference sequence) and a second sequence, and the % identity is calculated manually. Percent identity is the number of individual amino acids that are identical between two sequences, divided by the total number of amino acid residues in the reference sequence, multiplied by 100%. For example, to determine the % identity of amino acids 1 to 100 of SEQ ID NO:2 to a second sequence, the number of amino acid mismatches (i.e., point mutations: insertions, deletions and substitutions) is counted and subtracted from 100 (the number of amino acids in the reference sequence) to get the number of identical amino acids. The resulting number is divided by 100 and then multiplied by 100%. If there are mismatches (i.e., point mutations: insertions, deletions and substitutions of individual amino acids) at positions 1,5, 21–23,41 and 96–100 of SEQ ID NO:2, the % identity would be 90%. (1+1+3+1+4=10. 100−10=90. 90/100=0.9. 0.9×100=90%)

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, *Science* 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Fragments or portions of the polypeptide of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from inmmunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

The MPIF-1 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

MPIF-1 Polypeptide Variants. It will be recognized in the art that some amino acid sequences of the MPIF-1 polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of an MPIF-1 polypeptide which show, respectively, substantial MPIF-1 polypeptide activity or which include regions of an MPIF-1 protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Of additional special interest are also substitutions of charged amino acids with another charged amino acid or with neutral amino acids. This may result in proteins with improved characteristics such as less aggregation. Prevention of aggregation is highly desirable. Aggregation of proteins cannot only result in a reduced activity but be problematic when preparing pharmaceutical formulations because they can be immunogenic (Pinckard et al., Clin. Exp. Immunol. 2:331–340 (1967), Robbins et al., Diabetes 36: 838–845 (1987), Cleland et al., Crit. Rev. Therapeutic Drug Carrier Systems 10:307–377 (1993).

The replacement of amino acids can also change the selectivity of the binding to cell surface receptors. Ostade et al., Nature 361: 266–268 (1993), described certain TNF alpha mutations resulting in selective binding of TNF alpha to only one of the two known TNF receptors.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247.1306–1310 (1990) (see Table 1).

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above and below. Generally speaking, the number of substitutions for any given MPIF-1 polypeptide or mutant thereof will not be more than 50, 40, 30, 20, 10, 5, or 3, depending on the objective. Specific MPIF-1 amino acid substitutions are described below.

A further aspect of the present invention also includes the substitution of amino acids. Of special interest are conservative amino acid substitutions that do not significantly affect the folding of the protein. Examples of conservative amino acid substitutions known to those skilled in the art are set forth Table 1, above.

Of additional special interest are also substitutions of charged amino acids with another charged amino acid or with neutral amino acids. This may result in proteins with improved characteristics such as less aggregation. Prevention of aggregation is highly desirable. Aggregation of proteins cannot only result in a reduced activity but be problematic when preparing pharmaceutical formulations because they can be immunogenic (Pinckard et al., *Clin. Exp. Immunol.* 2:331–340 (1967), Robbins et al., *Diabetes* 36:838–845 (1987), Cleland et al., *Crit. Rev. Therapeutic Drug Carrier Systems* 10:307–377 (1993).

The MPIF-1 protein may contain one or several amino acid substitutions, deletions or additions, either from natural mutation or human manipulation. Examples of some preferred mutations of the amino acid sequence shown in FIG. 1 (SEQ ID NO:2) are provided below. (By the designation, for example, Ala (21) Met is intended that the Ala at position 21 of FIG. 1 (SEQ ID NO:2) is replaced by Met.)

| | |
|---|---|
| Ala (21) Met | Asp (53) Ser |
| Thr (24) Ala | Asp (53) Thr |
| Lys (25) Asn | Asp (53) Met |
| Asp (26) Ala | Ser (51) Gly |
| Asp (45) Ala | Ser (34) Gly |
| Asp (45) Gly | Glu (30) Gln |
| Asp (45) Ser | Glu (28) Gln |
| Asp (45) Thr | Pro (60) Thr |
| Asp (45) Met | Ser (70) Ala |
| Asp (53) Ala | |
| Asp (53) Gly | |

For example, site directed changes at the amino acid level of MPIF-1 can be made by replacing a particular amino acid with a conservative amino acid. Preferred conservative mutations include: For example preferred complementary mutations include: MI replaced with A, G, I, L, S, T, or V; K2 replaced with H, or R; V3 replaced with A, G, I, L, S,T, or M; S4 replaced with A, G, I, L, T, M, or V; V5 replaced with A, G, I, L, S, T, or M; A6 replaced with G, I, L, S, T, M, or V; A7 replaced with G, I, L,S, T, M, or V; L8 replaced with A, G, 1, S, T, M, or V; S9 replaced with A, G, I, L, T, M, or V; L11 replaced with A, G, I, S, T, M, or V; M12 replaced with A, G, I, L, S, T, or V; L13 replaced with A, G, I, S, T, M, or V; V14 replaced with A, G, I, L, S, T, or M; T15 replaced with A, G, I, L, S, M, or V; A16replaced with G, I, L, S, T, M, or V; L17 replaced with A, G, I, S, T, M, or V; G18 replaced with A, I, L, S, T, M, or V; S19 replaced with A, G, I, L, T, M,or V; Q20 replaced with N; A21 replaced with G, I, L, S, T, M, or V; R22 replaced with H, or K; V23 replaced with A, G, I, L, S, T, or M; T24 replaced with A, G, I, L, S, M, or V; K25 replaced with H, or R; D26 replaced with E; A27 replaced with G, I, L, S, T, M, or V; E28 replaced with D; T29 replaced with A,G, I, L, S, M, or V; E30 replaced with D; F31 replaced with W, or Y; M32 replaced with A, G, I, L, S, T, or V; M33 replaced with A, G, I, L, S, T, or V; S34replaced with A, G, I, L, T, M, or V; K35 replaced with H, or R; L36 replaced with A, G, I, S, T, M, or V; L38 replaced with A, G, I, S, T, M, or V; E39replaced with D; N40 replaced with Q; V42 replaced with A, G, I, L, S, T, or M; L43 replaced with A, G, I, S, T, M, or V; L44 replaced with A, G, I, S, T,M, or V; D45 replaced with E; R46 replaced with H, or K; F47 replaced with W, or Y; H48 replaced with K, or R; A49 replaced with G, I, L, S, T, M, or V;T50 replaced with A, G, I, L, S, M, or V; S51 replaced with A, G, I, L, T, M, or V; A52 replaced with G, I, L, S, T, M, or V; D53 replaced with E; I56replaced with A, G, L, S, T, M, or V; S57 replaced with A, G, I, L, T, M, or V; Y58 replaced with F, or W; T59 replaced with A, G, I, L, S, M, or V; R61replaced with H, or K; S62 replaced with A, G, I, L, T, M, or V; 163 replaced with A, G, L, S, T, M, or V; S66 replaced with A, G, I, L, T, M, or V; L67replaced with A, G, I, S, T, M, or V; L68 replaced with A, G, I, S, T, M, or V; E69 replaced with D; S70 replaced with A, G, I, L, T, M, or V; Y71 replaced with F, or W; F72 replaced with W, or Y; E73 replaced with D; T74 replaced with A, G, I, L, S, M, or V; N75 replaced with Q; S76 replaced with A, G, I, L, T, M, or V; E77 replaced with D; S79 replaced with A, G, I, L, T, M, or V; K80 replaced with H, or R; G82 replaced with A, I, L, S, T, M, or V; V83replaced with A, G, I, L, S, T, or M; I84 replaced with A, G, L, S, T, M, or V; F85 replaced with W, or Y; L86 replaced with A, G, I, S, T, M, or V; T87replaced with A, G, I, L, S, M, or V; K88 replaced with H, or R; K89 replaced with H, or R; G90 replaced with A, I, L, S, T, M, or V; R91 replaced with H,or K; R92 replaced with H, or K; F93 replaced with W, or Y; A95 replaced with G, I, L, S, T, M, or V; N96 replaced with Q; S98 replaced with A, G, I, L, T,M, or V; D99 replaced with E; K100 replaced with H, or R; Q101 replaced with N; V102 replaced with A, G, I, L, S, T, or M; Q103 replaced with N; V104replaced with A, G, I, L, S, T, or M; M106 replaced with A, G, I, L, S, T, or V; R107 replaced with H, or K; M108 replaced with A, G, I, L, S, T, or V;L109 replaced with A, G, I, S, T, M, or V; K10 replaced with H, or R; L111 replaced with A, G, I, S, T, M, or V; D112 replaced with E; T113 replaced with A, G, I, L, S, M, or V; R114 replaced with H, or K; I115 replaced with A, G, L, S, T, M, or V; K116 replaced with H, or R; T117 replaced with A, G, I, L,S, M, or V; R118 replaced with H, or K; K119 replaced with H, or R; N120 replaced with Q.

The resulting constructs can be routinely screened for activities or functions described throughout the specification and known in the art. Preferably, the resulting constructs have an increased and/or a decreased MPIF-1 activity or function, while the remaining MPIF-1 activities or functions are maintained. More preferably, the resulting constructs have more than one increased and/or decreased MPIF-1 activity or function, while the remaining MPIF-1 activities or functions are maintained.

Besides conservative amino acid substitution, variants of MPIF-1 include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, MPIF-1 polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., *Clin. Exp. Immunol.* 2:331–340 (1967); Robbins et al., *Diabetes* 36: 838–845 (1987); Cleland et al., *Crit. Rev. Therapeutic Drug Carrier Systems* 10:307–377 (1993).)

For example, preferred non-conservative substitutions of MPIF-1 include: For example preferred non-complementary mutations include: M1 replaced with D, E, H, K, R, N, Q, F, W, Y, P, or C; K2 replaced with D, E, A, G, I, L, S,T, M, V, N, Q, F, W, Y, P, or C; V3 replaced with D, E, H, K, R, N, Q, F, W, Y, P, or C; S4 replaced with D, E, H, K, R, N, Q, F, W, Y, P, or C; V5replaced with D, E, H, K, R, N, Q, F, W, Y, P, or C; A6 replaced with D, E, H, K, R, N, Q, F, W, Y, P, or C; A7 replaced with D, E, H, K, R, N, Q, F,W, Y, P, or C; L8 replaced with D, E, H, K, R, N, Q, F, W, Y, P, or C; S9 replaced with D, E, H, K, R, N, Q, F, W, Y, P, or C; C10 replaced with D, E,H, K, R, A, G, I, L, S, T, M, V, N, Q, F, W, Y, or P; L11 replaced with D, E, H, K, R, N, Q, F, W, Y, P, or C; M12 replaced with D, E, H, K, R, N, Q,F, W, Y, P, or C; L13 replaced with D, E, H, K, R, N, Q, F, W, Y, P, or C; V14 replaced with D, E, H, K, R, N, Q, F, W, Y, P, or C; T15 replaced with D,E, H, K, R, N, Q, F, W, Y, P, or C; A16 replaced with D, E, H, K, R, N, Q, F, W, Y, P, or C; L17 replaced with D, E, H, K, R, N, Q, F, W, Y, P, or C;G18 replaced with D, E, H, K, R, N, Q, F, W, Y, P, or C; S19 replaced with D, E, H, K, R, N, Q, F, W, Y, P, or C; Q20 replaced with D, E, H, K, R, A,G, I, L, S, T, M, V, F, W, Y, P, or C; A21 replaced with D, E, H, K, R, N, Q, F, W, Y, P, or C; R22 replaced with D, E, A, G, I, L, S, T, M, V, N, Q, F,W, Y, P, or C; V23 replaced with D, E, H, K, R, N, Q, F, W, Y, P, or C; T24 replaced with D, E, H, K, R, N, Q, F, W, Y, P, or C; K25 replaced with D, E,A, G, I, L, S, T, M, V, N, Q, F, W, Y, P, or C; D26 replaced with H, K, R, A, G, I, L, S, T, M, V, N, Q, F, W, Y, P, or C; A27 replaced with D, E, H, K,R, N, Q, F, W, Y, P, or C; E28 replaced with H, K, R, A, G, I, L, S, T, M, V, N, Q, F, W, Y, P, or C; T29 replaced with D, E, H, K, R, N, Q, F, W, Y, P,or C; E30 replaced with H, K, R, A, G, I, L, S, T, M, V, N, Q, F, W, Y, P, or C; F31 replaced with D, E, H, K, R, N, Q, A, G, I, L, S, T, M, V, P, or C;M32 replaced with D, E, H, K, R, N, Q, F, W, Y, P, or C; M33 replaced with D, E, H, K, R, N, Q, F, W, Y, P, or C; S34 replaced with D, E, H, K, R, N,Q, F, W, Y, P, or C; K35 replaced with D, E, A, G, I, L, S, T, M, V, N, Q, F, W, Y, P, or C; L36 replaced with D, E, H, K, R, N, Q, F, W, Y, P, or C;P37 replaced with D, E, H, K, R, A, G, I, L, S, T, M, V, N, Q, F, W, Y, or C; L38 replaced with D, E, H, K, R, N, Q, F, W, Y, P, or C; E39 replaced with H, K, R, A, G, I, L, S, T, M, V, N, Q, F, W, Y, P, or C; N40 replaced with D, E, H, K, R, A, G, I, L, S, T, M, V, F, W, Y, P, or C; P41 replaced with D,E, H, K, R, A, G, I, L, S, T, M, V, N, Q, F, W, Y, or C; V42 replaced with D, E, H, K, R, N, Q, F, W, Y, P, or C; L43 replaced with D, E, H, K, R, N,Q, F, W, Y, P, or C; L44 replaced with D, E, H, K, R, N, Q, F, W, Y, P, or C; D45 replaced with H, K, R, A, G, I, L, S, T, M, V, N, Q, F, W, Y, P, or C;R46 replaced with D, E, A, G, I, L, S, T, M, V, N, Q, F, W, Y, P, or C; F47 replaced with D, E, H, K, R, N, Q, A, G, I, L, S, T, M, V, P, or C; H48replaced with D, E, A, G, I, L, S, T, M, V, N, Q, F, W, Y, P, or C; A49 replaced with D, E, H, K, R, N, Q, F, W, Y, P, or C; T50 replaced with D, E, H,K, R, N, Q, F, W, Y, P, or C; S51 replaced with D, E, H, K, R, N, Q, F, W, Y, P, or C; A52 replaced with D, E, H, K, R, N, Q, F, W, Y, P, or C; D53replaced with H, K, R, A, G, I, L, S, T, M, V, N, Q, F, W, Y, P, or C; C54 replaced with D, E, H, K, R, A, G, I, L, S, T, M, V, N, Q, F, W, Y, or P; C55replaced with D, E, H, K, R, A, G, I, L, S, T, M, V, N, Q, F, W, Y, or P; I56 replaced with D, E, H, K, R, N, Q, F, W, Y, P, or C; S57 replaced with D, E,H, K, R, N, Q, F, W, Y, P, or C; Y58 replaced with D, E, H, K, R, N, Q, A, G, I, L, S, T, M, V, P, or C; T59 replaced with D, E, H, K, R, N, Q, F, W,Y, P, or C; P60 replaced with D, E, H, K, R, A, G, I, L, S, T, M, V, N, Q, F, W, Y, or C; R61 replaced with D, E, A, G, I, L, S, T, M, V, N, Q, F, W, Y,P, or C; S62 replaced with D, E, H, K, R, N, Q, F, W, Y, P, or C; I63 replaced with D, E, H, K, R, N, Q, F, W, Y, P, or C; P64 replaced with D, E, H, K,R, A, G, I, L, S, T, M, V, N, Q, F, W, Y, or C; C65 replaced with D, E, H, K, R, A, G, I, L, S, T, M, V, N, Q, F, W, Y, or P; S66 replaced with D, E, H,K, R, N, Q, F, W, Y, P, or C; L67 replaced with D, E, H, K, R, N, Q, F, W, Y, P, or C; L68 replaced with D, E, H, K, R, N, Q, F, W, Y, P, or C; E69replaced with H, K, R, A, G, I, L, S, T, M, V, N, Q, F, W, Y, P, or C; S70 replaced with D, E, H, K, R, N, Q, F, W, Y, P, or C; Y71 replaced with D, E,H, K, R, N, Q, A, G, I, L, S, T, M, V, P, or C; F72 replaced with D, E, H, K, R, N, Q, A, G, I, L, S, T, M, V, P, or C; E73 replaced with H, K, R, A, G,I, L, S, T, M, V, N, Q, F, W, Y, P, or C; T74 replaced with D, E, H, K, R, N, Q, F, W, Y, P, or C; N75 replaced with D, E, H, K, R, A, G, I, L, S, T, M,V, F, W, Y, P, or C; S76 replaced with D, E, H, K, R, N, Q, F, W, Y, P, or C; E77 replaced with H, K, R, A, G, I, L, S, T, M, V, N, Q, F, W, Y, P, or C;C78 replaced with D, E, H, K, R, A, G, I, L, S, T, M, V, N, Q, F, W, Y, or P; S79 replaced with D, E, H, K, R, N, Q, F, W, Y, P, or C; K80 replaced with D, E, A, G, I, L, S, T, M, V, N, Q, F, W, Y, P, or C; P81 replaced with D, E, H, K, R, A, G, I, L, S, T, M, V, N, Q, F, W, Y, or C; G82 replaced with D,E, H, K, R, N, Q, F, W, Y, P, or C; V83 replaced with D, E, H, K, R, N, Q, F, W, Y, P, or C; I84 replaced with D, E, H, K, R, N, Q, F, W, Y, P, or C;F85 replaced with D, E, H, K, R, N, Q, A, G, I, L, S, T, M, V, P, or C; L86 replaced with D, E, H, K, R, N, Q, F, W, Y, P, or C; T87 replaced with D, E,H, K, R, N, Q, F, W, Y, P, or C; K88 replaced with D, E, A, G, I, L, S, T, M, V, N, Q, F, W, Y, P, or C; K89 replaced with D, E, A, G, I, L, S, T, M, V,N, Q, F, W, Y, P, or C; G90 replaced with D, E, H, K, R, N, Q, F, W, Y, P, or C; R91 replaced with D, E, A, G, I, L, S, T, M, V, N, Q, F, W, Y, P, or C;R92 replaced with D, E, A, G, I, L, S, T, M, V, N, Q, F, W, Y, P, or C; F93 replaced with D, E, H, K, R, N, Q, A, G, I, L, S, T, M, V, P, or C; C94replaced with D, E, H, K, R, A, G, I, L, S, T, M, V, N, Q, F, W, Y, or P; A95 replaced with D, E, H, K, R, N, Q, F, W, Y, P, or C; N96 replaced with D,E, H, K, R, A, G, I, L, S, T, M, V, F, W, Y, P, or C; P97 replaced with D, E, H, K, R, A, G, I, L, S, T, M, V, N, Q, F, W, Y, or C; S98 replaced with D,E, H, K, R, N, Q, F, W, Y, P, or C; D99 replaced with H, K, R, A, G, I, L, S, T, M, V, N, Q, F, W, Y, P, or C; K100 replaced with D, E, A, G, I, L, S, T,M, V, N, Q, F, W, Y, P, or C; Q101 replaced with D, E, H, K, R, A, G, I, L, S, T, M, V, F, W, Y, P, or C; V102 replaced with D, E, H, K, R, N, Q, F, W,Y, P, or C; Q103 replaced with D, E, H, K, R, A, G, I, L, S, T, M, V, F, W, Y, P, or C; V104 replaced with D, E, H, K, R, N, Q, F, W, Y, P, or C; C105 replaced with D, E, H, K, R, A, G, I, L, S, T, M, V, N, Q, F, W, Y, or P; M106 replaced with D, E, H, K, R, N, Q, F, W, Y, P, or C; R107 replaced with D, E, A, G, I, L, S, T, M, V, N, Q, F, W, Y, P, or C; M108 replaced with D, E, H, K, R, N, Q, F, W, Y, P, or C; L 109 replaced with D, E, H, K, R, N, Q,F, W, Y, P, or C; K110 replaced with D, E, A, G, I, L, S, T, M, V, N, Q, F, W, Y, P, or C; L111 replaced with D, E, H, K, R, N, Q, F, W, Y, P, or C;D112 replaced with H, K, R, A, G, I, L, S, T, M, V, N, Q, F, W, Y, P, or C; T113 replaced with D, E, H, K, R, N, Q, F, W, Y, P, or C; R114 replaced with D, E, A, G, I, L, S, T, M, V, N, Q, F, W, Y, P, or C; 1115 replaced with D, E, H, K, R, N, Q, F, W, Y, P, or C; K 16 replaced with D, E, A, G, I, L,S, T, M, V, N, Q, F, W, Y, P, or C; T117 replaced with D, E, H, K, R, N, Q, F, W, Y, P, or C; R118 replaced with D, E, A, G, I, L, S, T, M, V, N, Q, F,W, Y, P, or C; K 19 replaced with D, E, A, G, I, L, S, T, M, V, N, Q, F, W, Y, P, or C; N120 replaced with D, E, H, K, R, A, G, I, L.

The resulting constructs can be routinely screened for activities or functions described throughout the specification and known in the art. Preferably, the resulting constructs have an increased and/or decreased MPIF-1 activity or function, while the remaining MPIF-1 activities or functions are maintained. More preferably, the resulting constructs have more than one increased and/or decreased MPIF-1 activity or function, while the remaining MPIF-1 activities or functions are maintained.

Additionally, more than one amino acid (e.g., 2, 3, 4, 5, 6, 7, 8, 9 and 10) can be replaced with the substituted amino acids as described above (either conservative or nonconservative). The substituted amino acids can occur in the full length, mature, or proprotein form of MPIF-1 protein, as well as the N- and C-terminal deletion mutants, having the general formula m-n, listed below.

A further embodiment of the invention relates to a polypeptide which comprises the amino acid sequence of a MPIF-1 polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises the amino acid sequence of a MPIF-1 polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of FIG. 1 or fragments thereof (e.g., the mature form and/or other fragments described herein), is 1–5, 5–10, 5–25, 5–50, 10–50 or 50–150, conservative amino acid substitutions are preferable.

As mentioned above, the MPIF-1 polypeptides may comprise or consist of the amino acid sequence of SEQ ID NO:2, SEQ ID NO:7, or the amino acid sequences encoded by the deposited cDNA clones except for one or more acid substitutions, deletions, or additions. Also as described above, the MPIF-1 polypeptide may be at least 80%, 85%, 90%, 92%, 95%, 96%,97%,98% or 99% identical to SEQ ID NO:2, SEQ ID NO:7, or to the polypeptides encoded by the deposited cDNA clones. In one embodiment, such polypeptide variants also have a structure the same or substantially the same as that of MPIF-1 or at least one region thereof. The structure may, for example, be the solution structure as determined by NMR (see Ex. 37). Polynucleotides encoding these polypeptides are also encompassed by the invention.

For example, the MPIF-1 polypeptide may contain one or several amino acid changes (substitutions, deletions, or additions), but no changes at particular residues or positions. Positions at which substitutions, deletions, or additions may be excluded include conserved residues such as the four Cys residues at positions Cys-54 (Cys-11 in Ex. 37), Cys-55 (Cys-12 in Ex. 37), Cys-78 (Cys-35 in Ex. 37), and Cys-94 (Cys-51 in Ex. 37) of SEQ ID NO:2. Conserved residues also include the two Cys residues at positions Cys-65 (Cys-22 in Ex. 37), and Cys-105 (Cys-62 in Ex.37) of SEQ ID NO:2. Any one or a combination of these positions may be excluded from being substituted, deleted, or added to. Preferably, the MPIF-1 variant contains substitutions, deletions, or additions, except at each of the six Cys residues of MPIF-1.

Additional residues which may be excluded from being changed include conservatively substituted residues such as Ile-56 (Ile-13 in Ex. 37), Tyr-58 (Tyr-15 in Ex. 37), Arg-61 (Arg-18 in Ex. 37), and Ile-63 (Ile-20 in Ex. 37) of SEQ ID NO:2. Any one or a combination of these positions may be excluded from being substituted, deleted, or added to. Preferably, the MPIF-1 variant contains substitutions, deletions, or additions, except at each of these residues. Alternatively, such conservatively substituted residues may be changed by conservative substitutions.

Additional residues which may be excluded from being changed include conservatively substituted residues such as Ile-56 (Ile-13 in Ex. 37), Tyr-58 (Tyr-15 in Ex. 37), Arg-61 (Arg-18 in Ex. 37), Thr-74 (Thr-31 in Ex. 37) and Thr-87 (Thr-44 in Ex. 37) of SEQ ID NO:2. Any one or a combination of these positions may be excluded from being substituted, deleted, or added to. Preferably, the MPIF-1 variant contains substitutions, deletions, or additions, except at each of these residues. Alternatively, such conservatively substituted residues may be changed by conservative substitutions.

Additional residues which may be excluded from being changed include conservatively substituted residues such as Ile-56 (Ile-13 in Ex. 37), Tyr-58 (Tyr-15 in Ex. 37), Arg-61 (Arg-18 in Ex. 37), Ile-63 (Ile-20 in Ex. 37), Thr-74 (Thr-31 in Ex. 37) and Thr-87 (Thr-44 in Ex. 37) of SEQ ID NO:2. Any one or a combination of these positions may be excluded from being substituted, deleted, or added to. Preferably, the MPIF-1 variant contains substitutions, deletions, or additions, except at each of these residues. Alternatively, such conservatively substituted residues may be changed by conservative substitutions.

Conservatively substituted residues also include Ile-63 (Ile-20 in Ex. 37), Leu-68 (Leu-25 in Ex. 37), Tyr-71 (Tyr-28 in Ex. 37), Phe-72 (Phe-29 in Ex. 37), Val-83 (Val-40 in Ex. 37), Ile-84 (Ile-41 in Ex. 37), Phe-85 (Phe-42 in Ex. 37), Phe-93 (Phe-50 in Ex. 37), Ala-95 (Ala-52 in Ex. 37), Val-102 (Val-59 in Ex. 37), Met-106 (Met-63 in Ex. 37), and Leu-109 (Leu-66 in Ex. 37) of SEQ ID NO:2. Any one or a combination of these positions may be excluded from being substituted, deleted, or added to. Preferably, the MPIF-1 variant contains substitutions, deletions, or additions, except at each of these residues. Alternatively, such conservatively substituted residues may be changed by conservative substitutions.

Additional conservatively substituted residues include Ile-56 (Ile-13 in Ex. 37), Arg-61 (Arg-18 in Ex. 37), Tyr-58 (Tyr-15 in Ex. 37), Thr-74 (Thr-31 in Ex. 37), and Gly-82 (Gly-39 in Ex. 37) of SEQ ID NO:2. Any one or a combination of these positions may be excluded from being substituted, deleted, or added to. Preferably, the MPIF-1 variant contains substitutions, deletions, or additions, except at each of these residues. Alternatively, such conservatively substituted residues may be changed by conservative substitutions.

Further additional conservatively substituted residues include Pro-64 (Pro-21 in Ex. 37), and Pro-97 (Pro-54 in Ex. 37) of SEQ ID NO:2. Any one or a combination of these positions may be excluded from being substituted, deleted, or added to. Preferably, the MPIF-1 variant contains substitutions, deletions, or additions, except at all of these residues. Alternatively, such conservatively substituted residues may be changed by conservative substitutions.

Further additional conservatively substituted residues include Gln-101 (Gln-58 in Ex. 37) of SEQ ID NO:2. Preferably, this residue is excluded from being substituted, deleted, or added to. Preferably, it is conservatively substituted. More preferably, it is substituted with an amino acid lacking a bulky side chain. Thus, it preferably is substituted with an amino acid other than, for example, Trp.

Further additional conservatively substituted residues include Arg-61 (Arg-18 in Ex. 37), Lys-88 (Lys-45 in Ex. 37), and Arg-91 (Arg-48 in Ex. 37) of SEQ ID NO:2. Any one or a combination of these positions may be excluded from being substituted, deleted, or added to. Preferably, the MPIF-1 variant contains substitutions, deletions, or additions, except at all of these residues. Alternatively, such conservatively substituted residues may be changed by conservative substitutions.

Further additional conservatively substituted residues include Lys-89 (Lys-46 in Ex. 37), Lys-100 (Lys-57 in Ex. 37), Arg-107 (Arg-64 in Ex. 37), and Lys-110 (Lys-67 in Ex. 37) of SEQ ID NO:2. Any one or a combination of these positions may be excluded from being substituted, deleted, or added to. Preferably, the MPIF-1 variant contains substitutions, deletions, or additions, except at all of these residues. Alternatively, such conservatively substituted residues may be changed by conservative substitutions.

In addition to the preferred combinations above, a preferred combination of conserved and conservatively substituted residues includes Thr-74 (Thr-31 in Ex. 37), Gly-82 (Gly-39 in Ex. 37), Tyr-58 (Tyr-15 in Ex. 37), Cys-54 (Cys-11 in Ex. 37), Cys-55 (Cys-12 in Ex. 37), and Cys-94 (Cys-51 in Ex. 37) of SEQ ID NO:2. Preferably, the MPIF-1 variant contains substitutions, deletions, or additions, except at each of these residues. Alternatively, such residues may be changed by conservative substitutions.

Preferably, the MPIF-1 variant contains amino acid changes except for at least one or all of the above conservatively substituted residues. Alternatively, at least one or all of the above conservatively substituted residues may be changed by conservative substitutions.

Preferably, the MPIF-1 variant contains amino acid changes except for at least one or all of the above conserved residues (i.e., one or more Cys residue) and at least one or all of the conservatively substituted residues (i.e., one or more of the remaining residues above). Alternatively, at least one or all of the conservatively substituted residues may be changed by conservative substitutions.

MPIF-1 Splice Variant. In addition, variants of MPIF-1 have been identified and characterized. Several of these analogs comprise amino terminal truncations. In addition, an MPIF-1 analog apparently resulting from an alternative splice site has also been identified and characterized (FIG. 20 (SEQ ID NO:7)). Example 11 discloses the biological activities of these MPIF-1 analogs. The sequences of these analogs are shown in FIG. 19 (SEQ ID NOS:3, 4, and 5, as well amino acid residues 46–120, 45–120, 48–120, 49–120, 39–120, and 44–120 in SEQ ID NO:2).

In another aspect, the present invention includes amino acid substitutions in the 137 amino acid splice variant of MPIF-1. For example, conservative substitutions include: MI replaced with A, G, I, L, S, T, or V; K2 replaced with H, or R; V3 replaced with A, G, I, L, S, T, or M; S4 replaced with A, G, I, L, T, M, or V; V5 replaced with A, G, I, L, S, T, or M; A6 replaced with G, I, L, S, T, M, or V; A7 replaced with G, I, L, S, T, M, or V; L8 replaced with A, G, I, S, T, M, or V; S9 replaced with A, G, I, L, T, M, or V; L11 replaced with A, G, I, S, T, M, or V; M12 replaced with A, G, I, L, S, T, or V; L13 replaced with A, G, I, S, T, M, or V; V14 replaced with A, G, I, L, S, T, or M; T15 replaced with A, G, I, L, S, M, or V; A16 replaced with G, I, L, S, T, M, or V; L17 replaced with A, G, I, S, T, M, or V; G18 replaced with A, I, L, S, T, M, or V; S19 replaced with A, G, I, L, T, M, or V; Q20 replaced with N; A21 replaced with G, I, L, S, T, M, or V; R22 replaced with H, or K; V23 replaced with A, G, I, L, S, T, or M; T24 replaced with A, G, I, L, S, M, or V; K25 replaced with H, or R; D26 replaced with E; A27 replaced with G, I, L, S, T, M, or V; E28 replaced with D; T29 replaced with A, G, I, L, S, M, or V; E30 replaced with D; F31 replaced with W, or Y; M32 replaced with A, G, I, L, S, T, or V; M33 replaced with A, G, I, L, S, T, or V; S34 replaced with A, G, I, L, T, M, or V; K35 replaced with H, or R; L36 replaced with A, G, I, S, T, M, or V; L38 replaced with A, G, I, S, T, M, or V; E39 replaced with D; N40 replaced with Q; V42 replaced with A, G, I, L, S, T, or M; L43 replaced with A, G, I, S, T, M, or V; L44 replaced with A, G, I, S, T, M, or V; D45 replaced with E; M46 replaced with A, G, I, L, S, T, or V; L47 replaced with A, G, I, S, T, M, or V; W48 replaced with F, or Y; R49 replaced with H, or K; R50 replaced with H, or K; K51 replaced with H, or R; I52 replaced with A, G, L, S, T, M, or V; G53 replaced with A, I, L, S, T, M, or V; Q55 replaced with N; M56 replaced with A, G, I, L, S, T, or V; T57 replaced with A, G, I, L, S, M, or V; L58 replaced with A, G, I, S, T, M, or V; S59 replaced with A, G, I, L, T, M, or V; H60 replaced with K, or R; A61 replaced with G, I, L, S, T, M, or V; A62 replaced with G, I, L, S, T, M, or V; G63 replaced with A, I, L, S, T, M, or V; F64 replaced with W, or Y; H65 replaced with K, or R; A66 replaced with G, I, L, S, T, M, or V; T67 replaced with A, G, I, L, S, M, or V; S68 replaced with A, G, I, L, T, M, or V; A69 replaced with G, I, L, S, T, M, or V; D70 replaced with E; I73 replaced with A, G, L, S, T, M, or V; S74 replaced with A, G, I, L, T, M, or V; Y75 replaced with F, or W; T76 replaced with A, G, I, L, S, M, or V; R78 replaced with H, or K; S79 replaced with A, G, I, L, T, M, or V; I80 replaced with A, G, L, S, T, M, or V; S83 replaced with A, G, I, L, T, M, or V; L84 replaced with A, G, I, S, T, M, or V; L85 replaced with A, G, I, S, T, M, or V; E86 replaced with D; S87 replaced with A, G, I, L, T, M, or V; Y88 replaced with F, or W; F89 replaced with W, or Y; E90 replaced with D; T91 replaced with A, G, I, L, S, M, or V; N92 replaced with Q; S93 replaced with A, G, I, L, T, M, or V; E94 replaced with D; S96 replaced with A, G, I, L, T, M, or V; K97 replaced with H, or R; G99 replaced with A, I, L, S, T, M, or V; V100 replaced with A, G, I, L, S, T, or M; I101 replaced with A, G, L, S, T, M, or V; F102 replaced with W, or Y; L103 replaced with A, G, I, S, T, M, or V; T104 replaced with A, G, I, L, S, M, or V; K105 replaced with H, or R; K106 replaced with H, or R; G107 replaced with A, I, L, S, T, M, or V; R108 replaced with H, or K; R109 replaced with H, or K; F110 replaced with W, or Y; A112 replaced with G, I, L, S, T, M, or V; N113 replaced with Q; S115 replaced with A, G, I, L, T, M, or V; D116 replaced with E; K117 replaced with H, or R; Q118 replaced with N; V119 replaced with A, G, I, L, S, T, or M; Q120 replaced with N; V121 replaced with A, G, I, L, S, T, or M; M123 replaced with A, G, I, L, S, T, or V; R124 replaced with H, or K; M125 replaced with A, G, I, L, S, T, or V; L126 replaced with A, G, I, S, T, M, or V; K127 replaced with H, or R; L128 replaced with A, G, I, S, T, M, or V; D 129 replaced with E; T130 replaced with A, G, I, L, S, M, or V; R131 replaced with H, or K; I132 replaced with A, G, L, S, T, M, or V; K133 replaced with H, or R; T134 replaced with A, G, I, L, S, M, or V; R135 replaced with H, or K; K136 replaced with H, or R; and/or N137 replaced with Q of SEQ ID NO:7.

For example, non-conservative substitutions in the 137 amino acid splice variant include: M1 replaced with D, E, H, K, R, N, Q, F, W, Y, P, or C; K2 replaced with D, E, A, G, I, L, S, T, M, V, N, Q, F, W, Y, P, or C; V3 replaced with D, E, H, K, R, N, Q, F, W, Y, P, or C; S4 replaced with D, E, H, K, R, N, Q, F, W, Y, P, or C; V5 replaced with D, E, H, K, R, N, Q, F, W, Y, P, or C; A6 replaced with D, E, H, K, R, N, Q, F, W, Y, P, or C; A7 replaced with D, E, H, K, R, N, Q, F, W, Y, P, or C; L8 replaced with D, E, H, K, R, N, Q, F, W, Y, P, or C; S9 replaced with D, E, H, K, R, N, Q, F, W, Y, P, or C; C10 replaced with D, E, H, K, R, A, G, I, L, S, T, M, V, N, Q, F, W, Y, or P; L11 replaced with D, E, H, K, R, N, Q, F, W, Y, P, or C; M12 replaced with D, E, H, K, R, N, Q, F, W, Y, P, or C; L13 replaced with D, E, H, K, R, N, Q, F, W, Y, P, or C; V14 replaced with D, E, H, K, R, N, Q, F, W, Y, P, or C; T15 replaced with D, E, H, K, R, N, Q, F, W, Y, P, or C; A16 replaced with D, E, H, K, R, N, Q, F, W, Y, P, or C; L17 replaced with D, E, H, K, R, N, Q, F, W, Y, P, or C; G18 replaced with D, E, H, K, R, N, Q, F, W, Y, P, or C; S19 replaced with D, E, H, K, R, N, Q, F, W, Y, P, or C; Q20 replaced with D, E, H, K, R, A, G, I, L, S, T, M, V, F, W, Y, P, or C; A21 replaced with D, E, H, K, R, N, Q, F, W, Y, P, or C; R22 replaced with D, E, A, G, I, L, S, T, M, V, N, Q, F, W, Y, P, or C; V23 replaced with D, E, H, K, R, N, Q, F, W, Y, P, or C; T24 replaced with D, E, H, K, R, N, Q, F, W, Y, P, or C; K25 replaced with D, E, A, G, I, L, S, T, M, V, N, Q, F, W, Y, P, or C; D26 replaced with H, K, R, A, G, I, L, S, T, M, V, N, Q, F, W, Y, P, or C; A27 replaced with D, E, H, K, R, N, Q, F, W, Y, P, or C; E28 replaced with H, K, R, A, G, I, L, S, T, M, V, N, Q, F, W, Y, P, or C; T29 replaced with D, E, H, K, R, N, Q, F, W, Y, P, or C; E30 replaced with H, K, R, A, G, I, L, S, T, M, V, N, Q, F, W, Y, P, or C; F31 replaced with D, E, H, K, R, N, Q, A, G, I, L, S, T, M, V, P, or C; M32 replaced with D, E, H, K, R, N, Q, F, W, Y, P, or C; M33 replaced with D, E, H, K, R, N, Q, F, W, Y, P, or C; S34 replaced with D, E, H, K, R, N, Q, F, W, Y, P, or C; K35 replaced with D, E, A, G, I, L, S, T, M, V, N, Q, F, W, Y, P, or C; L36 replaced with D, E, H, K, R, N, Q, F, W, Y, P, or C; P37 replaced with D, E, H, K, R, A, G, I, L, S, T, M, V, N, Q, F, W, Y, or C; L38 replaced with D, E, H, K, R, N, Q, F, W, Y, P, or C; E39 replaced with H, K, R, A, G, I, L, S, T, M, V, N, Q, F, W, Y, P, or C; N40 replaced with D, E, H, K, R, A, G, I, L, S, T, M, V, F, W, Y, P, or C; P41 replaced with D, E, H, K, R, A, G, I, L, S, T, M, V, N, Q, F, W, Y, or C; V42 replaced with D, E, H, K, R, N, Q, F, W, Y, P, or C; L43 replaced with D, E, H, K, R, N, Q, F, W, Y, P, or C; L44 replaced with D, E, H, K, R, N, Q, F, W, Y, P, or C; D45 replaced with H, K, R, A, G, I, L, S, T, M, V, N, Q, F, W, Y, P, or C; M46 replaced with D, E, H, K, R, N, Q, F, W, Y, P, or C; L47 replaced with D, E, H, K, R, N, Q, F, W, Y, P, or C; W48 replaced with D, E, H, K, R, N, Q, A, G, I, L, S, T, M, V, P, or C; R49 replaced with D, E, A, G, I, L, S, T, M, V, N, Q, F, W, Y, P, or C; R50 replaced with D, E, A, G, I, L, S, T, M, V, N, Q, F, W, Y, P, or C; K51 replaced with D, E, A, G, I, L, S, T, M, V, N, Q, F, W, Y, P, or C; 152 replaced with D, E, H, K, R, N, Q, F, W, Y, P, or C; G53 replaced with D, E, H, K, R, N, Q, F, W, Y, P, or C; P54 replaced with D, E, H, K, R, A, G, I, L, S, T, M, V, N, Q, F, W, Y, or C; Q55 replaced with D, E, H, K, R, A, G, I, L, S, T, M, V, F, W, Y, P, or C; M56 replaced with D, E, H, K, R, N, Q, F, W, Y, P, or C; T57 replaced with D, E, H, K, R, N, Q, F, W, Y, P, or C; L58 replaced with D, E, H, K, R, N, Q, F, W, Y, P, or C; S59 replaced with D, E, H, K, R, N, Q, F, W, Y, P, or C; H60 replaced with D, E, A, G, I, L, S, T, M, V, N, Q, F, W, Y, P, or C; A61 replaced with D, E, H, K, R, N, Q, F, W, Y, P, or C; A62 replaced with D, E, H, K, R, N, Q, F, W, Y, P, or C; G63 replaced with D, E, H, K, R, N, Q, F, W, Y, P, or C; F64 replaced with D, E, H, K, R, N, Q, A, G, I, L, S, T, M, V, P, or C; H65 replaced with D, E, A, G, I, L, S, T, M, V, N, Q, F, W, Y, P, or C; A66 replaced with D, E, H, K, R, N, Q, F, W, Y, P, or C; T67 replaced with D, E, H, K, R, N, Q, F, W, Y, P, or C; S68 replaced with D, E, H, K, R, N, Q, F, W, Y, P, or C; A69 replaced with D, E, H, K, R, N, Q, F, W, Y. P, or C; D70 replaced with H, K, R, A, G, I, L, S, T, M, V, N, Q, F, W, Y, P, or C; C71 replaced with D, E, H, K, R, A, G, I, L, S, T, M, V, N, Q, F, W, Y, or P; C72 replaced with D, E, H, K, R, A, G, I, L, S, T, M, V, N, Q, F, W, Y, or P; 173 replaced with D, E, H, K, R, N, Q, F, W, Y, P, or C; S74 replaced with D, E, H, K, R, N, Q, F, W, Y, P, or C; Y75 replaced with D, E, H, K, R, N, Q, A, G, I, L, S, T, M, V, P, or C; T76 replaced with D, E, H, K, R, N, Q, F, W, Y, P, or C; P77 replaced with D, E, H, K, R, A, G, I, L, S, T, M, V, N, Q, F, W, Y, or C; R78 replaced with D, E, A, G, I, L, S, T, M, V, N, Q, F, W, Y, P, or C; S79 replaced with D, E, H, K, R, N, Q, F, W, Y, P, or C; I80 replaced with D, E, H, K, R, N, Q, F, W, Y, P, or C; P81 replaced with D, E, H, K, R, A, G, I, L, S, T, M, V, N, Q, F, W, Y, or C; C82 replaced with D, E, H, K, R, A, G, I, L, S, T, M, V, N, Q, F, W, Y, or P; S83 replaced with D, E, H, K, R, N, Q, F, W, Y, P, or C; L84 replaced with D, E, H, K, R, N, Q, F, W, Y, P, or C; L85 replaced with D, E, H, K, R, N, Q, F, W, Y, P, or C; E86 replaced with H, K, R, A, G, I, L, S, T, M, V, N, Q, F, W, Y, P, or C; S87 replaced with D, E, H, K, R, N, Q, F, W, Y, P, or C; Y88 replaced with D, E, H, K, R, N, Q, A, G, I, L, S, T, M, V, P, or C; F89 replaced with D, E, H, K, R, N, Q, A, G, I, L, S, T, M, V, P, or C; E90 replaced with H, K, R, A, G, I, L, S, T, M, V, N, Q, F, W, Y, P, or C; T91 replaced with D, E, H, K, R, N, Q, F, W, Y, P, or C; N92 replaced with D, E, H, K, R, A, G, I, L, S, T, M, V, F, W, Y, P, or C; S93 replaced with D, E, H, K, R, N, Q, F, W, Y, P, or C; E94 replaced with H, K, R, A, G, I, L, S, T, M, V, N, Q, F, W, Y, P, or C; C95 replaced with D, E, H, K, R, A, G, I, L, S, T, M, V, N, Q, F, W, Y, or P; S96 replaced with D, E, H, K, R, N, Q, F, W, Y, P, or C; K97 replaced with D, E, A, G, I, L, S, T, M, V, N, Q, F, W, Y, P, or C; P98 replaced with D, E, H, K, R, A, G, I, L, S, T, M, V, N, Q, F, W, Y, or C; G99 replaced with D, E, H, K, R, N, Q, F, W, Y, P, or C; V100 replaced with D, E, H, K, R, N, Q, F, W, Y, P, or C; I101 replaced with D, E, H, K, R, N, Q, F, W, Y, P, or C; F102 replaced with D, E, H, K, R, N, Q, A, G, I, L, S, T, M, V, P, or C; L103 replaced with D, E, H, K, R, N, Q, F, W, Y, P, or C; T104 replaced with D, E, H, K, R, N, Q, F, W, Y, P, or C; K105 replaced with D, E, A, G, I, L, S, T, M, V, N, Q, F, W, Y, P, or C; K106 replaced with D, E, A, G, I, L, S, T, M, V, N, Q, F, W, Y, P, or C; G107 replaced with D, E, H, K, R, N, Q, F, W, Y, P, or C; R108 replaced with D, E, A, G, I, L, S, T, M, V, N, Q, F, W, Y, P, or C; R109 replaced with D, E, A, G, I, L, S, T, M, V, N, Q, F, W, Y, P, or C; F110 replaced with D, E, H, K, R, N, Q, A, G, I, L, S, T, M, V, P, or C; C11 replaced with D, E, H, K, R, A, G, I, L, S, T, M, V, N, Q, F, W, Y, or P; A112 replaced with D, E, H, K, R, N, Q, F, W, Y, P, or C; N113 replaced with D, E, H, K, R, A, G, I, L, S, T, M, V, F, W, Y, P, or C; P114 replaced with D, E, H, K, R, A, G, I, L, S, T, M, V, N, Q, F, W, Y, or C; S115 replaced with D, E, H, K, R, N, Q, F, W, Y, P, or C; D116 replaced with H, K, R, A, G, I, L, S, T, M, V, N, Q, F, W, Y, P, or C; K117 replaced with D, E, A, G, I, L, S, T, M, V, N, Q, F, W, Y, P, or C; Q118 replaced with D, E, H, K, R, A, G, I, L, S, T, M, V, F, W, Y, P, or C; V119 replaced with D, E, H, K, R, N, Q, F, W, Y, P, or C; Q120 replaced with D, E, H, K, R, A, G, I, L, S, T, M, V, F, W, Y, P, or C; V121 replaced with D, E, H, K, R, N, Q, F, W, Y, P, or C; C122 replaced with D, E, H, K, R, A, G, I, L, S, T, M, V, N, Q, F, W, Y, or P; M123 replaced with D, E, H, K, R, N, Q, F, W, Y, P, or C; R124 replaced with D, E, A, G, I, L, S, T, M, V, N, Q, F, W, Y, P, or C; M125 replaced with D, E, H, K, R, N, Q, F, W, Y, P, or C; L126 replaced with D, E, H, K, R, N, Q, F, W, Y, P, or C; K127 replaced with D, E, A, G, I, L, S, T, M, V, N, Q, F, W, Y, P, or C; L128 replaced with D, E, H, K, R, N, Q, F, W, Y, P, or C; D129 replaced with H, K, R, A, G, I, L, S, T, M, V, N, Q, F, W, Y, P, or C; T130 replaced with D, E, H, K, R, N, Q, F, W, Y, P, or C; R131 replaced with D, E, A, G, I, L, S, T, M, V, N, Q, F, W, Y, P, or C; I132 replaced with D, E, H, K, R, N, Q, F, W, Y, P, or C; K133 replaced with D, E, A, G, I, L, S, T, M, V, N, Q, F, W, Y, P, or C; T134 replaced with D, E, H, K, R, N, Q, F, W, Y, P, or C; R135 replaced with D, E, A, G, I, L, S, T, M, V, N, Q, F, W, Y, P, or C; K136 replaced with D, E, A, G, I, L, S, T, M, V, N, Q, F, W, Y, P, or C; and/or N137 replaced with D, E, H, K, R, A, G,1, L, S, T, M, V, F, W, Y, P, or C of SEQ ID NO:7.

In order to improve or alter the characteristics of the MPIF-1 polypeptide(s), protein engineering may be employed. Recombinant DNA technology known to those skilled in the art can be used to create novel proteins. Muteins and deletions or fusion proteins can show, e.g., enhanced activity or increased stability. In addition, they could be purified in higher yields and show better solubility at least under certain purification and storage conditions. Set below are additional examples of mutations that can be constructed.

MPIF-1 Amino-terminal and Carboxy-terminal Deletions: Interferon gamma shows up to ten times higher activities by deleting 8–10 amino acid residues from the carboxy terminus of the protein (Dobeli et al., *J. of Biotechnology* 7:199–216 (1988). Ron et al., *J. Biol. Chem.*, 268 (4):2984–2988 (1993) reported modified KGF proteins that had heparin binding activity even if 3, 8, or 27 amino terminal amino acid residues were missing. Many other examples are known to anyone skilled in the art.

Particularly, N-terminal deletions of the MPIF-1 polypeptide can be described by the general formula m-120, where m is an integer from 2 to 115, where m corresponds to the position of the amino acid residue identified in SEQ ID NO:2. More in particular, the invention provides polynucleotides encoding polypeptides comprising, or alternatively consisting of, the amino acid sequence of residues: K-2 to N-120; V-3 to N-120; S-4 to N-120; V-5 to N-120; A-6 to N-120; A-7 to N-120; L-8 to N-120; S-9 to N-120; C-10 to N-120; L-11 to N-120; M-12 to N-120; L-13 to N-120; V-14 to N-120; T-15 to N-120; A-16 to N-120; L-17 to N-120; G-18 to N-120; S-19 to N-120; Q-20 to N-120; A-21 to N-120; R-22 to N-120; V-23 to N-120; T-24 to N-120; K-25 to N-120; D-26 to N-120; A-27 to N-120; E-28 to N-120; T-29 to N-120; E-30 to N-120; F-31 to N-120; M-32 to N-120; M-33 to N-120; S-34 to N-120; K-35 to N-120; L-36 to N-120; P-37 to N-120; L-38 to N-120; E-39 to N-120; N-40 to N-120; P-41 to N-120; V-42 to N-120; L-43 to N-120; L-44 to N-120; D-45 to N-120; R-46 to N-120; F-47 to N-120; H-48 to N-120; A-49 to N-120; T-50 to N-120; S-51 to N-120; A-52 to N-120; D-53 to N-120; C-54 to N-120; C-55 to N-120; I-56 to N-120; S-57 to N-120; Y-58 to N-120; T-59 to N-120; P-60 to N-120; R-61 to N-120; S-62 to N-120; I-63 to N-120; P-64 to N-120; C-65 to N-120; S-66 to N-120; L-67 to N-120; L-68 to N-120; E-69 to N-120; S-70 to N-120; Y-71 to N-120; F-72 to N-120; E-73 to N-120; T-74 to N-120; N-75 to N-120; S-76 to N-120; E-77 to N-120; C-78 to N-120; S-79 to N-120; K-80 to N-120; P-81 to N-120; G-82 to N-120; V-83 to N-120; I84 to N-120; F-85 to N-120; L-86 to N-120; T-87 to N-120; K-88 to N-120; K-89 to N-120; G-90 to N-120; R-91 to N-120; R-92 to N-120; F-93 to N-120; C-94 to N-120; A-95 to N-120; N-96 to N-120; P-97 to N-120; S-98 to N-120; D-99 to N-120; K-100 to N-120; Q-101 to N-120; V-102to N-120; Q-103 to N-120; V-104 to N-120; C-105 to N-120; M-106 to N-120; R-107 to N-120; M-108 to N-120; L-109 to N-120; K-110 to N-120; L-111 to N-120; D-112 to N-120; T-113 to N-120; R-114to N-120; I-115 to N-120; of SEQ ID NO:2. Polynucleotides encoding these polypeptides are also encompassed by the invention.

Also as mentioned above, even if deletion of one or more amino acids from the C-terminus of a protein results in modification of loss of one or more biological functions of the protein, other functional activities (e.g., biological activities, ability to multimerize, ability to bind MPIF-1 receptor) may still be retained. For example the ability of the shortened MPIF-1 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an MPIF-1 mutein with a large number of deleted C-terminal amino acid residues may retain some biological or immunogenic activities. In fact, peptides composed of as few as six MPIF-1 amino acid residues may often evoke an immune response.

Accordingly, the present invention further provides polypeptides having one or more residues deleted from the carboxy terminus of the amino acid sequence of the MPIF-1 polypeptide shown in FIG. 1 (SEQ ID NO:2), as described by the general formula 1-n, where n is an integer from 6 to 119, where n corresponds to the position of amino acid residue identified in SEQ ID NO:2. More in particular, the invention provides polynucleotides encoding polypeptides comprising, or alternatively consisting of, the amino acid sequence of residues: A-27to K-119; A-27to R-118; A-27 to T-117; A-27to K-116; A-27to I-115; A-27 to R-114; A-27 to T-113; A-27 to D-112; A-27 to L-111; A-27 to K-110; A-27 to L-109; A-27 to M-108; A-27 to R-107; A-27 to M-106; A-27 to C-105; A-27 to V-104; A-27 to Q-103; A-27 to V-102; A-27 to Q-101; A-27 to K-100; A-27 to D-99; A-27 to S-98; A-27 to P-97; A-27 to N-96; A-27 to A-95; A-27 to C-94; A-27 to F-93; A-27 to R-92; A-27 to R-91; A-27 to G-90; A-27; to K-89; A-27 to K-88; A-27 to T-87; A-27 to L-86; A-27 to F-85; A-27 to I-84; A-27 to V-83; A-27 to G-82; A-27 to P-81; A-27 to K-80; A-27 to S-79; A-27 to C-78; A-27 to E-77; A-27 to S-76; A-27 to N-75; A-27 to T-74; A-27 to E-73; A-27 to F-72; A-27 to Y-71; A-27 to S-70; A-27 to E-69; A-27 to L-68; A-27 to L-67; A-27 to S-66; A-27 to C-65; A-27 to P-64; A-27 to I-63; A-27 to S-62; A-27 to R-61; A-27 to P-60; A-27 to T-59; A-27 to Y-58; A-27 to S-57; A-27 to I-56; A-27 to C-55; A-27 to C-54; A-27 to D-53; A-27 to A-52; A-27 to S-51; A-27 to T-50; A-27 to A-49; A-27 to H-48; A-27 to F-47; A-27 to R-46; A-27 to D-45; A-27 to L-44; A-27 to L-43; A-27 to V-42; A-27 to P-41; A-27 to N-40; A-27 to E-39; A-27 to L-38; A-27 to P-37; A-27 to L-36; A-27 to K-35; A-27 to S-34; A-27 to M-33; A-27 to M-32; A-27 to F-31; A-27 to E-30; A-27 to T-29; A-27 to E-28; M-1 to D-26; M-1 to K-25; M-1 to T-24; M-1 to V-23; M-1 to R-22; M-1 to A-21; M-1 to Q-20; M-1 to S-19; M-1 to G-18; M-1 to L-17; M-1 to A-16; M-1 to T-15; M-1 to V-14; M-1 to L-13; M-1 to M-12; M-1 to L-11; M-1 to C-10; M-1 to S-9; M-1 to L-8; M-1 to A-7; of SEQ ID NO:2. Polynucleotides encoding these polypeptides are also encompassed by the invention.

Moreover, a signal sequence may be added to these C-terminal contructs. For example, amino acids 1–26 of SEQ ID NO:2, amino acids 2–26 of SEQ ID NO:2, amino acids 3–26 of SEQ ID NO:2, amino acids 4–26 of SEQ ID NO:2, amino acids 5–26 of SEQ ID NO:2, amino acids 6–26 of SEQ ID NO:2, amino acids 7–26 of SEQ ID NO:2, amino acids 8–26 of SEQ ID NO:2, amino acids 9–26 of SEQ ID NO:2, amino acids 10–26 of SEQ ID NO:2, amino acids 11–26 of SEQ ID NO:2, amino acids 12–26 of SEQ ID NO:2, amino acids 13–26 of SEQ ID NO:2, amino acids 14–26 of SEQ ID NO:2, amino acids 15–26 of SEQ ID NO:2, amino acids 16–26 of SEQ ID NO:2, amino acids 17–26 of SEQ ID NO:2, amino acids 18–26 of SEQ ID NO:2, amino acids 19–26 of SEQ ID NO:2, amino acids 20–26 of SEQ ID NO:2, amino acids 21–26 of SEQ ID NO:2, amino acids 22–26 of SEQ ID NO:2, amino acids 23–26 of SEQ ID NO:2, amino acids 24–26 of SEQ ID NO:2, amino acids 25–26 of SEQ ID NO:2, amino acids 26 of SEQ ID NO:2 can be added to the N-terminus of each C-terminal construct listed above.

In addition, any of the above listed N or C-terminal deletions can be combined to produce a N and C-terminal deleted MPIF-1 polypeptide. The invention also provides polypeptides having one or more amino acids deleted from both the amino and the carboxyl termini, which may be described generally as having residues m-n of SEQ ID NO:2, where n and m are integers as described above. Polynucleotides encoding these polypeptides are also encompassed by the invention.

Additional preferred polypeptide fragments comprise, or alternatively consist of, the amino acid sequence of residues: M-1 to T-15; K-2 to A-16; V-3 to L-17; S-4 to G-18; V-S to S-19; A-6 to Q-20; A-7 to A-21; L-8 to R-22; S-9 to V-23; C-10 to T-24; L-11 to K-25; M-12 to D-26; L-13 to A-27; V-14 to E-28; T-15 to T-29; A-16 to E-30; L-17 to F-31; G-18 to M-32; S-19 to M-33; Q-20 to S-34; A-21 to K-35; R-22 to L-36; V-23 to P-37; T-24 to L-38; K-25 to E-39; D-26 to N-40; A-27 to P-41; E-28 to V-42; T-29 to L-43; E-30 to L-44; F-31 to D-45; M-32 to R-46; M-33 to F-47; S-34 to H-48; K-35 to A-49; L-36 to T-50; P-37 to S-51; L-38 to A-52E-39 to D-53; N-40 to C-54; P-41 to C-55; V-42 to I-56; L-43 to S-57; L-44 to Y-58; D-45 to T-59; R-46 to P-60; F-47 to R-61; H-48 to S-62; A-49 to I-63; T-50 to P-64; S-51 to C-65; A-52 to S-66; D-53 to L-67; C-54 to L-68; C-55 to E-69; 1–56 to S-70; S-57 to Y-71; Y-58 to F-72; T-59 to E-73; P-60 to T-74; R-61 to N-75; S-62 to S-76; 1–63 to E-77; P-64 to C-78; C-65 to S-79; S-66 to K-80; L-67 to P-81; L-68 to G-82; E-69 to V-83; S-70 to I-84; Y-71 to F-85; F-72 to L-86; E-73 to T-87; T-74 to K-88; N-75 to K-89; S-76 to G-90; E-77 to R-91; C-78 to R-92; S-79 to F-93; K-80 to C-94; P-81 to A-95; G-82 to N-96; V-83 to P-97; 1–84 to S-98; F-85 to D-99; L-86 to K-100; T-87 to Q-101; K-88 to V-102; K-89 to Q-103; G-90 to V-104; R-91 to C-105; R-92 to M-106; F-93to R-107; C-94 to M-108; A-95 to L-109; N-96 to K-110; P-97 to L-111; S-98 to D-112; D-99 to T-113; K-100 to R-114; Q-101 to I-115; V-102 to K-116; Q-103 to T-117; V-104 to R-118; C-105 to K-119; M-106 to N-120. These polypeptide fragments may retain the biological activity of the MPIF-1 polypeptides of the invention and may be useful to generate antibodies, as described further below. Polynucleotides encoding these polypeptide fragments are also encompassed by the invention.

Also included are a nucleotide sequence encoding a polypeptide consisting of a portion of the complete MPIF-1 amino acid sequence encoded by the cDNA clone contained in ATCC Deposit No. 75676, where this portion excludes any integer of amino acid residues from 1 to about 110 amino acids from the amino terminus of the complete amino acid sequence encoded by the cDNA clone contained in ATCC Deposit No. 75676, or any integer of amino acid residues from 1 to about 110 amino acids from the carboxy terminus, or any combination of the above amino terminal and carboxy terminal deletions, of the complete amino acid sequence encoded by the cDNA clone contained in ATCC Deposit No. 75676. Polynucleotides encoding all of the above deletion mutant polypeptide forms also are provided.

The present application is also directed to proteins containing polypeptides at least 90%, 95%, 96%, 97%, 98% or 99% identical to the MPIF-1 polypeptide sequence set forth herein m-n. In preferred embodiments, the application is directed to proteins containing polypeptides at least 90%, 95%, 96%, 97%, 98% or 99% identical to polypeptides having the amino acid sequence of the specific MPIF-1 N and C-terminal deletions recited herein. Polynucleotides encoding these polypeptides are also encompassed by the invention.

Particularly preferred MPIF-1 polypeptides of the amino acid sequence shown in FIG. 1 (SEQ ID NO:2) are shown below:

| | |
|---|---|
| Val (23)-Asn (120) | Val (23)-Lys (119) |
| Thr (24)-Asn (120) | Thr (24)-Arg (118) |
| Lys (25)-Asn (120) | Lys (25)-Thr (117) |
| Asp (26)-Asn (120) | Asp (26)-Lys (116) |
| Ala (27)-Asn (120) | Ala (27)-Ile (115) |
| Glu (28)-Asn (120) | Glu (28)-Arg (114) |
| Thr (29)-Asn (120) | Thr (29)-Thr (113) |
| Glu (30)-Asn (120) | Thr (29)-Asp (112) |
| Phe (31)-Asn (120) | Thr (29)-Leu (111) |
| Met (32)-Asn (120) | Thr (29)-Lys (110) |
| Met (33)-Asn (120) | Met (33)-Leu (109) |
| Ser (34)-Asn (120) | Ser (34)-Met (108) |
| Lys (35)-Asn (120) | Ser (34)-Arg (107) |
| Leu (36)-Asn (120) | Ser (34)-Met (106) |
| Pro (37)-Asn (120) | Ser (34)-Cys (105) |
| Leu (38)-Asn (120) | Ser (34)-Val (104) |
| Glu (39)-Asn (120) | Ser (34)-Gln (103) |
| Asn (40)-Asn (120) | Ser (34)-Val (102) |
| Pro (41)-Asn (120) | Ser (34)-Gln (101) |
| Val (42)-Asn (120) | Ser (34)-Lys (100) |
| Leu (43)-Asn (120) | Ser (34)-Asp (99) |
| Leu (44)-Asn (120) | Ser (34)-Ser (98) |
| Asp (45)-Asn (120) | Ser (34)-Pro (97) |
| Arg (46)-Asn (120) | Ser (34)-Asn (96) |

-continued

| | |
|---|---|
| Phe (47)-Asn (120) | Ser (34)-Ala (95) |
| His (48)-Asn (120) | Ser (34)-Cys (94) |
| Ala (49)-Asn (120) | Ser (34)-Phe (93) |
| Thr (50)-Asn (120) | Ser (34)-Arg (92) |
| Ser (51)-Asn (120) | Ser (34)-Arg (91) |
| Ala (52)-Asn (120) | Ser (34)-Gly (90) |
| Asp (53)-Asn (120) | Ser (34)-Lys (89) |
| | Ser (34)-Ile (84) |
| | Ser (34)-Ser (79) |
| | Ser (34)-Asn (75) |
| | Ser (34)-Phe (72) |
| | Ser (34)-Leu (68) |

Thus, in one aspect, MPIF-1 N-terminal deletion mutants are provided by the present invention. Such mutants include those comprising, or alternatively consisting of, an amino acid sequence shown in FIG. 1 (SEQ ID NO:2) having a deletion of at least the first 22 N-terminal amino acid residues (i.e., a deletion of at least Met (1)—Arg (22)) but not more than the first 60 N-terminal amino acid residues of FIG. 1 (SEQ ID NO:2). Alternatively, the deletion will include at least the first 22 N-terminal amino acid residues but not more than the first 53 N-terminal amino acid residues of FIG. 1 (SEQ ID NO:2). Alternatively, the deletion will include at least the first 33 N-terminal amino acid residues but not more than the first 53 N-terminal amino acid residues of FIG. 1 (SEQ ID NO:2). Alternatively, the deletion will include at least the first 37 N-terminal amino acid residues (i.e., a deletion of at least Met (1)—Pro (37)) but not more than the first 53 N-terminal amino acid residues of FIG. 1 (SEQ ID NO:2). Alternatively, the deletion will include at least the first 48 N-terminal amino acid residues but not more than the first 53 N-terminal amino acid residues of FIG. 1 (SEQ ID NO:2).

In addition to the ranges of MPIF-1 N-terminal deletion mutants described above, the present invention is also directed to all combinations of the above described ranges, e.g., deletions of at least the first 22 N-terminal amino acid residues but not more than the first 48 N-terminal amino acid residues of FIG. 1 (SEQ ID NO:2); deletions of at least the first 37 N-terminal amino acid residues but not more than the first 48 N-terminal amino acid residues of FIG. 1 (SEQ ID NO:2); deletions of at least the first 22 N-terminal amino acid residues but not more than the first 37 N-terminal amino acid residues of FIG. 1 (SEQ ID NO:2); deletions of at least the first 22 N-terminal amino acid residues but not more than the first 33 N-terminal amino acid residues of FIG. 1 (SEQ ID NO:2); deletions of at least the first 33 N-terminal amino acid residues but not more than the first 37 N-terminal amino acid residues of FIG. 1 (SEQ ID NO:2); and deletions of at least the first 33 N-terminal amino acid residues but not more than the first 48 N-terminal amino acid residues of FIG. 1 (SEQ ID NO:2).

In another aspect, MPIF-1 C-terminal deletion mutants are provided by the present invention. Preferably, the N-terminal amino acid residue of said MPIF-1 C-terminal deletion mutants is amino acid residue 1 (Met) or 22 (Arg) of FIG. 1 (SEQ ID NO:2). Such mutants include those comprising, or alternatively consisting of, an amino acid sequence shown in FIG. 1 (SEQ ID NO:2) having a deletion of at least the last C-terminal amino acid residue (Asn (120)) but not more than the last 52 C-terminal amino acid residues (e.g., a deletion of amino acid residues Glu (69)—Asn (120) of FIG. 1 (SEQ ID NO:2)). Alternatively, the deletion will include at least the last 10 or 15 C-terminal amino acid residues but not more than the last 52 C-terminal amino acid residues of FIG. 1 (SEQ ID NO:2). Alternatively, the deletion will include at least the last 20 C-terminal amino acid residues but not more than the last 52 C-terminal amino acid residues of FIG. 1 (SEQ ID NO:2). Alternatively, the deletion will include at least the last 30 C-terminal amino acid residues but not more than the last 52 C-terminal amino acid residues of FIG. 1 (SEQ ID NO:2). Alternatively, the deletion will include at least the last 36 C-terminal amino acid residues but not more than the last 52 C-terminal amino acid residues of FIG. 1 (SEQ ID NO:2). Alternatively, the deletion will include at least the last 41 C-terminal amino acid residues but not more than the last 52 C-terminal amino acid residues of FIG. 1 (SEQ ID NO:2). Alternatively, the deletion will include at least the last 45 C-terminal amino acid residues but not more than the last 52 C-terminal amino acid residues of FIG. 1 (SEQ ID NO:2). Alternatively, the deletion will include at least the last 48 C-terminal amino acid residues but not more than the last 52 C-terminal amino acid residues of FIG. 1 (SEQ ID NO:2).

In addition to the ranges of C-terminal deletion mutants described above, the present invention is also directed to all combinations of the above described ranges, e.g., deletions of at least the last C-terminal amino acid residue but not more than the last 48 C-terminal amino acid residues of FIG. 1 (SEQ ID NO:2); deletions of at least the last C-terminal amino acid residue but not more than the last 45 C-terminal amino acid residues of FIG. 1 (SEQ ID NO:2); deletions of at least the last C-terminal amino acid residue but not more than the last 41 C-terminal amino acid residues of FIG. 1 (SEQ ID NO:2); deletions of at least the last C-terminal amino acid residue but not more than the last 36 C-terminal amino acid residues of FIG. 1 (SEQ ID NO:2); deletions of at least the last C-terminal amino acid residue but not more than the last 10 C-terminal amino acid residues of FIG. 1 (SEQ ID NO:2); deletions of at least the last 10 C-terminal amino acid residues but not more than the last 20 C-terminal amino acid residues of FIG. 1 (SEQ ID NO:2); deletions of at least the last 10 C-terminal amino acid residues but not more than the last 30 C-terminal amino acid residues of FIG. 1 (SEQ ID NO:2); deletions of at least the last 10 C-terminal amino acid residues but not more than the last 36 C-terminal amino acid residues of FIG. 1 (SEQ ID NO:2); deletions of at least the last 20 C-terminal amino acid residues but not more than the last 30 C-terminal amino acid residues of FIG. 1 (SEQ ID NO:2); etc. etc. etc.

In yet another aspect, also included by the present invention are MPIF-1 deletion mutants having amino acids deleted from both the—terminal and C-terminal residues. Such mutants include all combinations of the N-terminal deletion mutants and C-terminal deletion mutants described above. Such mutants include those comprising, or alternatively consisting of, an amino acid sequence shown in FIG. 1 (SEQ ID NO:2) having a deletion of at least the first 22 N-terminal amino acid residues but not more than the first 52 N-terminal amino acid residues of FIG. 1 (SEQ ID NO:2) and a deletion of at least the last C-terminal amino acid residue but not more than the last 52 C-terminal amino acid residues of FIG. 1 (SEQ ID NO:2). Alternatively, a deletion can include at least the first 33, 37, or 48 N-terminal amino acids but not more than the first 52 N-terminal amino acid residues of FIG. 1 (SEQ ID NO:2) and a deletion of at least the last 10, 20, 30, 36, 41, 45, or 48 C-terminal amino acid residues but not more than the last 52 C-terminal amino acid residues of FIG. 1 (SEQ ID NO:2). Further included are all combinations of the above described ranges.

Among the especially preferred fragments of the invention are fragments characterized by structural or functional attributes of MPIF-1. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, surface forming regions, and high antigenic index regions (i.e., containing four or more contiguous amino acids having an antigenic index of greater than or equal to 1.5, as identified using the default parameters of the Jameson-Wolf program) of complete (i.e., full-length) MPIF-1 (SEQ ID NO:2). Certain preferred regions are those set out in FIG. 14 and include, but are not limited to, regions of the aforementioned types identified by analysis of the amino acid sequence depicted in FIG. 1 (SEQ ID NO:2), such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In additional embodiments, the polynucleotides of the invention encode functional attributes of MPIF-1. Preferred embodiments of the invention in this regard include fragments that comprise alphahelix and alphahelix forming regions ("alpharegions"), betasheet and betasheet forming regions ("betaregions"), turn and turnforming regions ("turnregions"), coil and coilforming regions ("coilregions"), hydrophilic regions, hydrophobic regions, alpha amphipathic regions, beta amphipathic regions, flexible regions, surfaceforming regions and high antigenic index regions of MPIF-1.

Additional preferred regions are those set out in Example 37.

Figure 14:
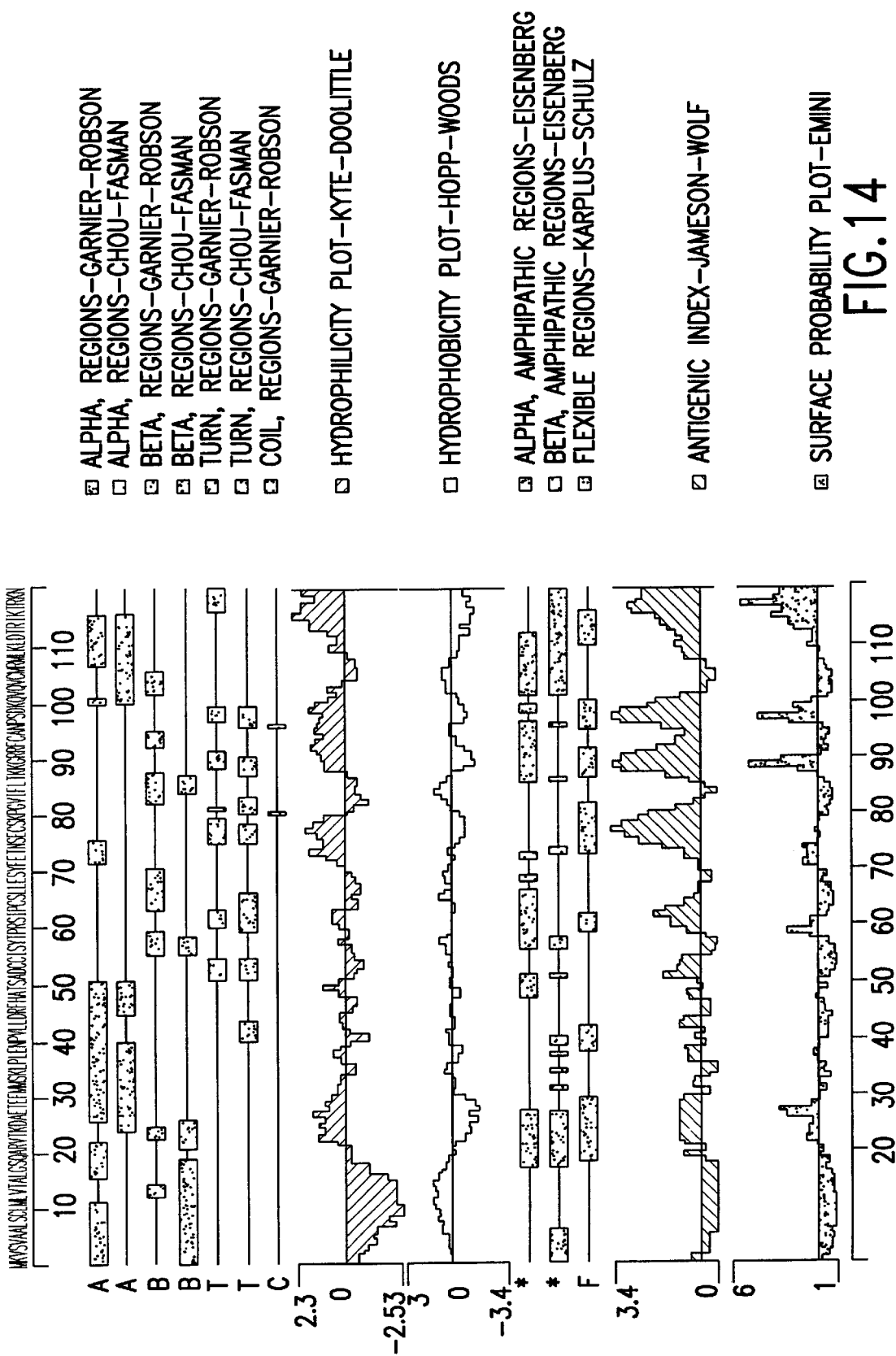
FIG. 14. Analysis of the MPIF-1 amino acid sequence (SEQ ID NO:2). Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues 21–30, 31–44, 49–55, 59–67, 72–83, 86–103 and 110–120 in FIG. 1 (SEQ ID NO:2), or any range or value therein, in FIG. 1 (SEQ ID NO:2) correspond to the shown highly antigenic regions of the MPIF-1 protein.

The data representing the structural or functional attributes of MPIF-1 set forth in FIG. 14 as described above, was generated using the various modules and algorithms of the DNA*STAR set on default parameters. In a preferred embodiment, the data presented in FIG. 14 can be used to determine regions of MPIF-1 which exhibit a high degree of potential for antigenicity. Regions of high antigenicity are determined from the data presented by choosing values which represent regions of the polypeptide which are likely to be exposed on the surface of the polypeptide in an environment in which antigen recognition may occur in the process of initiation of an immune response.

The abovementioned preferred regions set out in FIG. 14 include, but are not limited to, regions of the aforementioned types identified by analysis of the amino acid sequence set out in FIG. 1. As set out in FIG. 14, such preferred regions include Garnier Robson alpharegions, betaregions, tururegions, and coilregions, ChouFasman alpharegions, betaregions, and coilregions, KyteDoolittle hydrophilic regions and hydrophobic regions, Eisenberg alpha and betaamphipathic regions, KarplusSchulz flexible regions, Emini surfaceforming regions and JamesonWolf regions of high antigenic index.

Among highly preferred fragments in this regard are those that comprise regions of MPIF-1 that combine several structural features, such as several of the features set out above or below.

In one embodiment, MPIF-1 variants and/or fragments may have the same or substantially the same structure as MPIF-1 or at least one region thereof, for example, the solution structure as determined by nuclear magnetic resonance spectroscopy (NMR) (see Ex. 37) or the structure as determined by other techniques. Thus, the MPIF-1 variants and/or fragments may have an amino acid sequence differing from that of SEQ ID NO:2 or SEQ ID NO:7 or from the amino acid sequence of the polypeptides encoded by the deposited cDNA clones, but which nevertheless have the same or substantially the same structure as MPIF-1 or at least one region thereof. Polynucleotides encoding these polypeptides are also encompassed by the invention.

The MPIF-1 variant and/or fragment may have the same or substantially the same structure as at least one region of MPIF-1. Regions of MPIF-1 include the N-terminal loop, $3_{10}$ loop, first β strand, first type III turn, second β strand, type I turn, third β strand, second type III turn, and α helix described in Ex. 37, i.e., amino acids 56–63 (numbered 13–20 in Ex. 37), 64–67 (21–24 in Ex. 37), 70–74 (27–31 in Ex. 37), 75–81 (32–38 in Ex. 36), 82–87 (39–44 in Ex. 37), 88–90 (45–47 in Ex 36), 91–95 (48–52 in Ex. 37), 96–98 (53–55 in Ex. 37), and 99–109 (56–66 in Ex. 37) of SEQ ID NO:2. MPIF-1 regions also include amino acids 44–120 (1–77 in Ex. 37), 44–53 (1–10 in Ex. 37), 54–109 (11–66 in Ex. 37), 54–105 (11–62 in Ex. 37), 56–109 (13–66 in Ex. 37), 106–120 (63–77 in Ex. 37), 110–120 (67–77 in Ex. 37) of SEQ ID NO:2, the regions shown in FIG. 14, and others as described herein or predictable by amino acid sequence analysis. The MPIF-1 polypeptide variant and/or fragment may have the same or substantially the same structure as one or a combination of these MPIF-1 regions.

For an MPIF-1 variant and/or fragment having the same or substantially the same structure of more than one MPIF-1 region, the structures may be contiguous with one another. In one embodiment, the structures are not contiguous with one another, i.e., they are separated by one or more amino acid residues. Preferably, the structures align with those of MPIF-1. Preferably, the structures superimpose on those of MPIF-1. In a preferred embodiment, the structures have the same structure relative to each other (i.e., the same tertiary structure) as the corresponding structures in MPIF-1.

For example, the MPIF-1 variant and/or fragment may have the same or substantially the same structure as the N-terminal loop, first β strand, second β strand, third β strand, and α helix of MPIF-1. Thus, in a preferred combination, the MPIF-1 variant and/or fragment has the same or substantially the same structure as amino acids 56–63 (13–20 in Ex. 37), 70–74 (27–31 in Ex. 37), 82–87 (39–44 in Ex. 37), 91–95 (48–52 in Ex. 37), and 99–109 (56–66 in Ex. 37) of SEQ ID NO:2.

As another example, the MPIF-1 variant and/or fragment has the same or substantially the same structure as the N-terminal loop, 3 loop, first β strand, first type III turn, second β strand, type I turn, third β strand, second type III turn, and a helix of MPIF-1. Thus, the MPIF-1 variant and/or fragment has the same or substantially the same structure as amino acids 56–63 (numbered 13–20 in Ex. 37), 64–67 (21–24 in Ex. 37), 70–74 (27–31 in Ex. 37), 75–81 (32–38 in Ex. 36), 82–87 (39–44 in Ex. 37), 88–90 (45–47 in Ex 36), 91–95 (48–52 in Ex. 37), 96–98 (53–55 in Ex. 37), and 99–109 (56–66 in Ex. 37) of SEQ ID NO:2.

In a preferred embodiment, the MPIF-1 variant and/or fragment has the same or substantially the same structure as amino acids 56–109 (13–66 in Ex. 37) of SEQ ID NO:2.

In another embodiment, the MPIF-1 polypeptide may comprise or consist of the amino acid sequence of one or more regions of MPIF-1. For a polypeptide comprising or consisting of the amino acid sequence of two or more regions, the regions may be contiguous with one another. In one embodiment, the regions are not contiguous with one another, i.e., they are separated by one or more amino acid residues. Preferably, the amino acid sequences align with the amino acid sequences of the corresponding regions of MPIF-1 such that they are separated by the same number of amino acid residues as separate them in MPIF-1.

In yet another embodiment, MPIF-1 variants and/or fragments contain amino acid changes (substitutions, deletions, and insertions) in one or more of the above regions, but contain no changes in one or more other regions. Polynucleotides encoding these polypeptides are also encompassed by the invention.

Other preferred polypeptide fragments are biologically active MPIF-1 fragments. Biologically active fragments are those exhibiting activity similar, but not necessarily identical, to an activity of the MPIF-1 polypeptide. The biological activity of the fragments may include an improved desired activity, or a decreased undesirable activity. Polynucleotides encoding these polypeptide fragments are also encompassed by the invention.

However, many polynucleotide sequences, such as EST sequences, are publicly available and accessible through sequence databases. Some of these sequences are related to SEQ ID NO:1 or 6 and may have been publicly available prior to conception of the present invention. Preferably, such related polynucleotides are specifically excluded from the scope of the present invention. To list every related sequence might be cumbersome. Accordingly, preferably excluded from the present invention are one or more polynucleotides comprising, or alternatively consisting of, a nucleotide sequence described by the general formula of a-b, where a is any integer between 1 to 349 of SEQ ID NO:1, b is an integer of 15 to 363, where both a and b correspond to the positions of nucleotide residues shown in SEQ ID NO:1, and where the b is greater than or equal to a+14.

*Amino-terminal and carboxy-terminal deletions of the MPIF-1 137 amino acid splice variant*: As indicated above, the present invention further provides a human MPIF-1 splice variant. The cDNA sequence and the 137 amino acid sequence are shown in FIG. 20A (SEQ ID NOs:6 and 7, respectively). Using eukaryotic expression systems, the present inventions have discovered three N-terminal deletion mutants of this MPIF-1 splice variant. These include His (60)-Asn (137); Met (46)-Asn (137); and Pro (54)—Asn (137). Thus, in a further aspect, MPIF-1 splice variant N-terminal deletion mutants are provided by the present invention. Such mutants include those comprising, or alternatively consisting of, an amino acid sequence shown in FIG. 20A (SEQ ID NO:7) having a deletion of at least the first 45 N-terminal amino acid residues but not more than the first 59 N-terminal amino acid residues of FIG. 20A (SEQ ID NO:7). Alternatively, the deletion will include at least the first 53 N-terminal amino acid residues but not more than the first 59 N-terminal amino acid residues of FIG. 20A (SEQ ID NO:7). Alternatively, the deletion will include at least the first 45 N-terminal amino acid residues but not more than the first 53 N-terminal amino acid residues of FIG. 20A (SEQ ID NO:7).

Additional N-terminal deletions of the 137 amino acid splice variant polypeptide of the invention shown as SEQ ID NO:7 include polypeptides comprising, or alternatively consisting of, the amino acid sequence of residues: K-2 to N-137; V-3 to N-137; S-4 to N-137; V-5 to N-137; A-6 to N-137; A-7 to N-137; L-8 to N-137; S-9 to N-137; C-10 to N-137; L-11 to N-137; M-12 to N-137; L-13 to N-137; V-14 to N-137; T-15 to N-137; A-16 to N-137; L-17 to N-137; G-18 to N-137; S-19 to N-137; Q-20 to N-137; A-21 to N-137; R-22 to N-137; V-23 to N-137; T-24 to N-137; K-25 to N-137; D-26 to N-137; A-27 to N-137; E-28 to N-137; T-29 to N-137; E-30 to N-137; F-31 to N-137; M-32 to N-137; M-33 to N-137; S-34 to N-137; K-35 to N-137; L-36 to N-137; P-37 to N-137; L-38 to N-137; E-39 to N-137; N-40 to N-137; P-41 to N-137; V-42 to N-137; L-43 to N-137; L-44 to N-137; D-45 to N-137; M-46 to N-137; L-47 to N-137; W-48 to N-137; R-49 to N-137; R-50 to N-137; K-51 to N-137; 1–52 to N-137; G-53 to N-137; P-54 to N-137; Q-55 to N-137; M-56 to N-137; T-57 to N-137; L-58 to N-137; S-59 to N-137; H-60 to N-137; A-61 to N-137; A-62 to N-137; G-63 to N-137; F-64 to N-137; H-65 to N-137; A-66 to N-137; T-67 to N-137; S-68 to N-137; A-69 to N-137; D-70 to N-137; C-71 to N-137; C-72 to N-137; 1–73 to N-137; S-74 to N-137; Y-75 to N-137; T-76 to N-137; P-77 to N-137; R-78 to N-137; S-79 to N-137; I-80 to N-137; P-81 to N-137; C-82 to N-137; S-83 to N-137; L-84 to N-137; L-85 to N-137; E-86 to N-137; S-87 to N-137; Y-88 to N-137; F-89 to N-137; E-90 to N-137; T-91 to N-137; N-92 to N-137; S-93 to N-137; E-94 to N-137; C-95 to N-137; S-96 to N-137; K-97 to N-137; P-98 to N-137; G-99 to N-137; V-100 to N-137; I-101 to N-137; F-102 to N-137; L-103 to N-137; T-104 to N-137; K-105 to N-137; K-106 to N-137; G-107 to N-137; R-108 to N-137; R-109 to N-137; F-110 to N-137; C-111 to N-137; A-112 to N-137; N-113 to N-137; P-114 to N-137; S-115 to N-137; D-116 to N-137; K-117 to N-137; Q-118 to N-137; V-119 to N-137; Q-120 to N-137; V-121 to N-137; C-122 to N-137; M-123 to N-137; R-124 to N-137; M-125 to N-137; L-126 to N-137; K-127 to N-137; L-128 to N-137; D-129 to N-137; T-130 to N-137; R-131 to N-137; or I-132 to N-137 of SEQ ID NO:7.

Likewise, C-terminal deletions of the 137 amino acid splice variant polypeptide of the invention shown as SEQ ID NO:7 include polypeptides comprising the amino acid sequence of residues: M-1 to K-136; M-1 to R-135; M-1 to T-134; M-1 to K-133; M-1 to 1–132; M-1 to R-131; M-1 to T-130; M-1 to D-129; M-1 to L-128; M-1 to K-127; M-1 to L-126; M-1 to M-125; M-1 to R-124; M-1 to M-123; M-1 to C-122; M-1 to V-121; M-1 to Q-120; M-1 to V-119; M-1 to Q-118; M-1 to K-117; M-1 to D-116; M-1 to S-115; M-1 to P-114; M-1 to N-113; M-1 to A-112; M-1 to C-111; M-1 to F-110; M-1 to R-109; M-1 to R-108; M-1 to G-107; M-1 to K-106; M-1 to K-105; M-1 to T-104; M-1 to L-103; M-1 to F-102; M-1 to 1–101; M-1 to V-100; M-1 to G-99; M-1 to P-98; M-1 to K-97; M-1 to S-96; M-1 to C-95; M-1 to E-94; M-1 to S-93; M-1 to N-92; M-1 to T-91; M-1 to E-90; M-1 to F-89; M-1 to Y-88; M-1 to S-87; M-1 to E-86; M-1 to L-85; M-1 to L-84; M-1 to S-83; M-1 to C-82; M-1 to P-81; M-1 to I-80; M-1 to S-79; M-1 to R-78; M-1 to P-77; M-1 to T-76; M-1 to Y-75; M-1 to S-74; M-1 to I-73; M-1 to C-72; M-1 to C-71; M-1 to D-70; M-1 to A-69; M-1 to S-68; M-1 to T-67; M-1 to A-66; M-1 to H-65; M-1 to F-64; M-1 to G-63; M-1 to A-62; M-1 to A-61; M-1 to H-60; M-1 to S-59; M-1 to L-58; M-1 to T-57; M-1 to M-56; M-1 to Q-55; M-1 to P-54; M-1 to G-53; M-1 to 1–52; M-1 to K-51; M-1 to R-50; M-1 to R-49; M-1 to W-48; M-I to L-47; M-1 to M-46; M-I to D-45; M-1 to L-44; M-1 to L-43; M-1 to V-42; M-1 to P-41; M-1 to N-40; M-1 to E-39; M-1 to L-38; M-1 to P-37; M-1 to L-36; M-1 to K-35; M-1 to S-34; M-1 to M-33; M-1 to M-32; M-1 to F-31; M-1 to E-30; M-1 to T-29; M-1 to E-28; M-1 to A-27; M-1 to D-26; M-1 to K-25; M-I to T-24; M-1 to V-23; M-1 to R-22; M-1 to A-21; M-1 to Q-20; M-1 to S-19; M-1 to G-18; M-1 to L-17; M-1 to A-16; M-1 to T-15; M-1 to V-14; M-1 to L-13; M-1 to M-12; M-1 to L-11; M-1 to C-10; M-1 to S-9; M-1 to L-8; or M-1 to A-7 of SEQ ID NO:7.

The polypeptides of the present invention are preferably provided in an isolated form, and preferably are substantially purified. A recombinantly produced version of the MPIF-1 polypeptide can be substantially purified by the one-step method described in Smith and Johnson, Gene 67:31–40 (1988).

The polypeptides of the present invention include the polypeptide encoded by the deposited cDNA including the leader (i.e., the full length protein), the polypeptide encoded by the deposited cDNA minus the leader (i.e., the mature protein), the polypeptide of FIG. 1 (SEQ ID NO:2) including the leader, the polypeptide of FIG. 1 (SEQ ID NO:2) including the leader but minus the N-terminal methionine residue, the polypeptide of FIG. 1 (SEQ ID NO:2) minus the leader, as well as polypeptides which have at least 80%, 85%, 90%, 92%, or 95% similarity, and still more preferably at least 96%, 97%,98% or 99% similarity to those described above. Further polypeptides of the present invention include polypeptides at least 80%, 85%, 90% or 95% identical, still more preferably at least 96%, 97%, 98% or 99% identical to the polypeptide encoded by the deposited cDNA, to the polypeptide of FIG. 1 (SEQ ID NO:2) and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2:482–489, 1981) to find the best segment of similarity between two sequences.

By a polypeptide having an amino acid sequence at least, for example, 95% "identical" to a reference amino acid sequence of an MPIF-1 polypeptide is intended that the amino acid sequence of the polypeptide is identical to the reference sequence except that the polypeptide sequence may include up to five amino acid alterations per each 100 amino acids of the reference amino acid sequence of the MPIF-1 polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in FIG. 1 (SEQ ID NO:2) or to the amino acid sequence encoded by deposited cDNA clones can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting MPIF-1 protein expression as described below or as agonists and antagonists capable of enhancing or inhibiting MPIF-1 protein function. Further, such polypeptides can be used in the yeast two-hybrid system to "capture"MPIF-1 protein binding proteins which are also candidate agonist and antagonist according to the present invention. The yeast two hybrid system is described in Fields and Song, *Nature* 340:245–246 (1989).

MPIF-1 Epitope-Bearing Polypeptides. In another aspect, the invention provides a peptide or polypeptide comprising—or alternatively, consisting of—an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

Fragments which function as epitopes may be produced by any conventional means. (See, e.g., Houghten, R. A., *Proc. Natl. Acad. Sci. USA* 82:5131–5135 (1985) further described in U.S. Pat. No. 4,631,211.) As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, e.g., Sutcliffe, J. G., Shinnick, T. M., Green, N. and Learner, R. A., *Science* 219:660–666 (1983).

Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g. about 9 amino acids) can bind and displace the larger peptides in immunoprecipitation assays. See, for instance, Wilson et al., Cell 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising, or alternatively consisting of, a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

In the present invention,antigenic epitopes preferably contain a sequence of at least 4, at least 5, at least 6, at least 7, more preferably at least 8, at least 9, at least 10, at least 15, at least 20, at least 25, and most preferably between about 15 to about 30 amino acids. Preferred polypeptides comprising, or alternatively consisting of, immunogenic or antigenic epitopes are at least 10, 15, 20, 25, 30, 35, 40, 45, 50, 55, 60, 65, 70, 75, 80, 85, 90, 95, or 100 amino acid residues in length.

Non-limiting examples of antigenic polypeptides or peptides that can be used to generate MPIF-1-specific antibodies include: a polypeptide comprising, or alternatively consisting of, amino acid residues from about 21 to about 30 in SEQ ID NO:2; a polypeptide comprising, or alternatively consisting of, amino acid residues from about 31 to about 44 in SEQ ID NO:2; a polypeptide comprising amino acid residues from about 49 to about 55 in SEQ ID NO:2; a polypeptide comprising amino acid residues from about 59 to about 67 in SEQ ID NO:2; a polypeptide comprising amino acid residues from about 72 to about 83 in SEQ ID NO:2; a polypeptide comprising amino acid residues from about 86 to about 103 in SEQ ID NO;2; a polypeptide comprising amino acid residues from about 110 to about 120 in SEQ ID NO :2. As indicated above, the inventors have determined that the above polypeptide fragments are antigenic regions of the MPIF-1 protein.

Additional antigenic polypeptides or peptides that can be used to generate MPIF-1-specific antibodies include the N- and C-terminal deletions described above.

The invention also provides epitope fragments of the 137 amino acid splice variant of MPIF-1 (SEQ ID NO:7). More in particular, the invention provides polynucleotides having the amino acid sequence of residues: M-1 to T-15; K-2 to A-16; V-3 to L-17; S-4 to G-18; V-S to S-19; A-6 to Q-20; A-7 to A-21; L-8 to R-22; S-9 to V-23; C-10 to T-24; L-1 1 to K-25; M-12 to D-26; L-13 to A-27; V-14 to E-28; T-15 to T-29; A-16 to E-30; L-17 to F-3 1; G-18 to M-32; S-19 to M-33; Q-20 to S-34; A-21 to K-35; R-22 to L-36; V-23 to P-37; T-24 to L-38; K-25 to E-39; D-26 to N-40; A-27 to P-41; E-28 to V-42; T-29 to L-43; E-30 to L-44; F-31 to D-45; M-32 to M-46; M-33 to L-47; S-34 to W-48; K-35 to R-49; L-36 to R-50; P-37 to K-51; L-38 to 1–52; E-39 to G-53; N-40 to P-54; P-41 to Q-55; V-42 to M-56; L-43 to T-57; L-44 to L-58; D-45 to S-59; M-46 to H-60; L-47 to A-61; W-48 to A-62; R-49 to G-63; R-50 to F-64; K-51 to H-65; 1–52 to A-66; G-53 to T-67; P-54 to S-68; Q-55 to A-69; M-56 to D-70; T-57 to C-71; L-58 to C-72; S-59 to 1–73; H-60 to S-74; A-61 to Y-75; A-62 to T-76; G-63 to P-77; F-64 to R-78; H-65 to S-79; A-66 to 1–80; T-67 to P-81; S-68 to C-82; A-69 to S-83; D-70 to L-84; C-71 to L-85; C-72 to E-86; 1–73 to S-87; S-74 to Y-88; Y-75 to F-89; T-76 to E-90; P-77 to T-91; R-78 to N-92; S-79 to S-93; 1–80 to E-94; P-81 to C-95; C-82 to S-96; S-83 to K-97; L-84 to P-98; L-85 to G-99; E-86 to V-100; S-87 to 1–101; Y-88 to F-102; F-89 to L-103; E-90 to T-104; T-91 to K-105; N-92 to K-106; S-93 to G-107; E-94 to R-108; C-95 to R-109; S-96 to F-110; K-97 to C-111; P-98 to A-112; G-99 to N-113; V-100 to P-114; I-101 to S-115; F-102 to D-116; L-103 to K-117; T-104 to Q-118; K-105 to V-119; K-106 to Q-120; G-107 to V-121; R-108 to C-122; R-109 to M-123; F-110 to R-124; C-111 to M-125; A-112 to L-126; N-113 to K-127; P-114 to L-128; S-115 to D-129; D-116 to T-130; K-117 to R-131; Q-118 to I-132; V-119 to K-133; Q-120 to T-134; V-121 to R-135; C-122 to K-136; or M-123 to N-137 of SEQ ID NO:7.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A. (1985) General method for the rapid solid-phase synthesis of large numbers of peptides: specificity of antigen-antibody interaction at the level of individual amino acids. *Proc. Natl. Acad. Sci. USA* 82:5131–5135. This "Simultaneous Multiple Peptide Synthesis (SMPS)" process is further described in U.S. Pat. No. 4,631,211 to Houghten et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Preferred nucleic acid fragments of the present invention include nucleic acid molecules encoding epitope-bearing portions of the MPIF-1 protein.

In particular, such nucleic acid fragments of the MPIF-1 of the present invention include nucleic acid molecules encoding: a polypeptide comprising, or alternatively consisting of, amino acid residues from about 21 to about 30 in SEQ ID NO:2; a polypeptide comprising amino acid residues from about 31 to about 44 in SEQ ID NO:2; apolypeptide comprising amino acid residues from about 49 to about 55 in SEQ ID NO:2; apolypeptide comprising amino acid residues from about 59 to about 67 in SEQ ID NO:2; a polypeptide comprising amino acid residues from about 72 to about 83 in SEQ ID NO:2; a polypeptide comprising amino acid residues from about 86 to about 103 in SEQ ID NO:2; a polypeptide comprising amino acid residues from about 110 to about 120 in SEQ ID NO:2, or any range or value therein.

The inventors have determined that the above polypeptide fragments are antigenic regions of the MPIF-1 protein. Methods for determining other such epitope-bearing portions of the MPIF-1 protein are described in detail below.

Epitope bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.* 66:23472354 (1985). If in vivo immunization is used, animals may be immunized with free peptide; however, anti-peptide antibody titer may be boosted by coupling of the peptide to a macromolecular carrier, such as keyhole limpet hemacyanin (KLH) or tetanus to xoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a to pological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a to pographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear $C_1$–$C_7$-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Peptides" is hereby incorporated herein by reference.

As one of skill in the art will appreciate, MPIF-1 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric MPIF-1 protein or protein fragment alone (Fountoulakis et al., *J. Biochem* 270:3958–3964 (1995)).

As one of skill in the art will appreciate, and discussed above, the polypeptides of the present invention comprising, or alternatively consisting of, an immunogenic or antigenic epitope can be fused to heterologous polypeptide sequences. For example, the polypeptides of the present invention may be fused with the constant domain of immunoglobulins (IgA, IgE, IgG, IgM), or portions thereof ($CH_1$, $CH_2$, $CH_3$, any combination thereof including both entire domains and portions thereof) resulting in chimeric polypeptides. These fusion proteins facilitate purification, and show an increased half-life in vivo. This has been shown, e. g., for chimeric proteins consisting of the first two domains of the human CD4 polypeptide and various domains of the constant regions of the heavy or light chains of mammalian immunoglobulins. See, e.g., EPA 0,394,827; Traunecker et al., *Nature* 331:8486 (1988). Fusion proteins that have a disulfidelinked dimeric structure due to the IgG portion can also be more efficient in binding and neutralizing other molecules than monomeric polypeptides or fragments thereof alone. See, e.g., Fountoulakis et al., *J. Biochem.* 270:39583964 (1995). Nucleic acids encoding the above epitopes can also be recombined with a gene of interest as an epitope tag to aid in detection and purification of the expressed polypeptide.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides corresponding to SEQ ID NO:2 thereby effectively generating agonists and antagonists of the polypeptides. See, generally, U.S. Pat. Nos. 5,605,793, 5,811,238, 5,830,721, 5,834,252, and 5,837,458, and Patten, P. A., et al., *Curr. Opinion Biotechnol.* 8:724–33 (1997); Harayama, S., *Trends Biotechnol.* 16(2):76–82 (1998); Hansson, L. O., et al., *J. Mol. Biol.* 287:265–76 (1999); and Lorenzo, M. M. and Blasco, R., *Biotechniques* 24(2):308–13 (1998) (each of these patents and publications are hereby incorporated by reference). In one embodiment, alteration of polynucleotides corresponding to SEQ ID NO:1 or 6 and corresponding polypeptides may be achieved by DNA shuffling. DNA shuffling involves the assembly of two or more DNA segments into a desired molecule corresponding to SEQ ID NO:1 or 6 polynucleotides of the invention by homologous, or site-specific, recombination. In another embodiment, polynucleotides corresponding to SEQ ID NO:1 or 6 and corresponding polypeptides may be altered by being subjected to random mutagenesis by error-prone PCR, random nucleotide insertion or other methods prior to recombination. In another embodiment, one or more components, motifs, sections, parts, domains, fragments, etc., of coding polynucleotide corresponding to SEQ ID NO:1 or 6, or the polypeptide encoded thereby may be recombined with one or more components, motifs, sections, parts, domains, fragments, etc. of one or more heterologous molecules.

Polypeptide Purification and Isolation. MPIF-1 is recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention can be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention can be glycosylated with mammalian or other eukaryotic carbohydrates or can be non-glycosylated. Polypeptides of the invention can also include an initial methionine amino acid residue.

In addition, polypeptides of the invention can be chemically synthesized using techniques known in the art (e.g., see Creighton, 1983, Proteins: *Structures and Molecular Principles*, W. H. Freeman & Co., NY, and Hunkapiller et al., *Nature* 310:105–111 (1984)). For example, a polypeptide corresponding to a fragment of a MPIF-1 polypeptide can be synthesized by use of a peptide synthesizer. Furthermore, if desired, nonclassical amino acids or chemical amino acid analogs can be introduced as a substitution or addition into the MPIF-1 polypeptide sequence. Nonclassical amino acids include, but are not limited to, to the D-isomers of the common amino acids, 2,4-diaminobutyric acid, a-amino isobutyric acid, 4-aminobutyric acid, Abu, 2-amino butyric acid, gAbu, eAhx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses MPIF-1 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to GCSF), see also Malik et al., *Exp. Hematol.* 20:10281035 (1992) (reporting pegylation of GMCSF using tresyl chloride). For example, polyethylene glycol may be covalently bound through amino acid residues via a reactive group, such as, a free amino or carboxyl group. Reactive groups are those to which an activated polyethylene glycol molecule may be bound.

The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

Antibodies. MPIF-1 protein-specific antibodies for use in the present invention can be raised against the intact MPIF-1 protein or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to MPIF-1 protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain and humanized antibodies, as well as Fab fragments, or the product of an Fab expression library. Various procedures known in the art can be used for the production of such antibodies and fragments.

The present invention is also directed to polypeptide fragments comprising, or alternatively consisting of, an epitope of the polypeptide sequence shown in SEQ ID NO:2 or 7, or the polypeptide sequence encoded by the cDNA contained in a deposited clone. Polynucleotides encoding these epitopes (such as, for example, the sequence disclosed in SEQ ID NO:1or 6) are also encompassed by the invention, as is the nucleotide sequences of the complementary strand of the polynucleotides encoding these epitopes. And polynucleotides which hybridize to the complementary strand under stringent hybridization conditions or lower stringency conditions.

In the present invention, "epitopes" refer to polypeptide fragments having antigenic or immunogenic activity in an animal, especially in a human. A preferred embodiment of the present invention relates to a polypeptide fragment comprising, or alternatively consisting of, an epitope, as well as the polynucleotide encoding this fragment. A region of a protein molecule to which an antibody can bind is defined as an "antigenic epitope." In contrast, an "immunogenic epitope" is defined as a part of a protein that elicits an antibody response. (See, for instance, Geysen et al., *Proc. Natl. Acad. Sci. USA* 81:3998–4002 (1983).) Antigenic epitopes are useful, for example, to raise antibodies, including monoclonal antibodies, that specifically bind the epitope. (See, for instance, Wilson et al., *Cell* 37:767–778 (1984); Sutcliffe et al., *Science* 219:660–666 (1983).)

Similarly, immunogenic epitopes can be used, for example, to induce antibodies according to methods well known in the art. (See, for instance, Sutcliffe et al., supra; Wilson et al., supra; Chow et al., *Proc. Natl. Acad. Sci. USA* 82:910–914; and Bittle et al., *J. Gen. Virol.* 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.) The present invention further relates to antibodies and T-cell antigen receptors (TCR) which specifically bind the polypeptides of the present invention. The antibodies of the present invention include IgG (including IgG$_1$, IgG$_2$, IgG$_3$, and IgG$_4$), IgA (including IgA$_1$ and IgA$_2$), IgD, IgE, IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention and include, but are not limited to, Fab, Fab' and F(ab')$_2$, Fd, single-chain Fvs (scFv), single-chain antibodies, disulfide-linked Fvs (sdFv) and fragments comprising either a V$_L$ or V$_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, CH$_1$, CH$_2$, and CH$_3$ domains. Also included in the invention are any combinations of variable region(s) and hinge region, CH$_1$, CH$_2$, and CH$_3$ domains. The present invention further includes monoclonal, polyclonal, chimeric, humanized, and human monoclonal and human polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multi specificity. Multi specific antibodies may be specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, et al., *J. Immunol.* 147:60–69 (1991); U.S. Pat. Nos. 5,573,920, 4,474,893, 5,601,819, 4,714,681, 4,925,648; Kostelny et al., *J. Immunol.* 148:1547–1553 (1992).

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bindpolypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *Antibodies: a Laboratory Manual*, (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pa. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is nota limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art and taught in Harlow et al., *Antibodies: a Laboratory Manual*, (Cold Spring Harbor Laboratory Press, 2nd ed. 1988); Hammerling, et al., in: *Monoclonal Antibodies and T cell Hybridomas* 563681 (Elsevier, N.Y., 1981) (said references incorporated by reference in their entireties). Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA and phage display technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41–50 (1995); Ames et al., *J. Immunol. Methods* 184:177–186 (1995); Kettleborough et al., *Eur. J. Immunol.* 24:952–958 (1994); Persic et al., *Gene* 187:9–18 (1997); Burton et al., *Advances in Immunology* 57:191–280 (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax et al., *BioTechniques* 12(6):864–869 (1992); and Sawai et al., *AJRI* 34:26–34 (1995); and Better et al., *Science* 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46–88 (1991); Shu, L. et al., *PNAS* 90:7995–7999 (1993); and Skerra et al., *Science* 240:1038–1040 (1988). For some uses, including in vivo use of antibodies in humans and in vitro detection assays, it may be preferable to use chimeric, humanized, or human antibodies. Methods for producing chimeric antibodies are known in the art. See e.g., Morrison, Science 229:1202 (1985); Oi et al., *BioTechniques* 4:214 (1986); Gillies et al., *J. Immunol Methods* 125:191–202 (1989); and U.S. Pat. No. 5,807,715. Antibodies can be humanized using a variety of techniques including CDR-grafting (EP 0 239 400; WO 91/09967; U.S. Pat. No. 5,530,101; and 5,585,089), veneering or resurfacing (EP 0 592 106; EP 0 519 596; Padlan E.

A., *Molecular Immunology* 28(4/5):489–498 (1991); Studnicka et al., *Protein Engineering* 7(6):805–814 (1994); Roguska. et al., *PNAS* 91:969–973 (1994)), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; and WO 98/46645, WO 98/50433, WO 98/24893, WO 98/16654, WO 96/34096, WO 96/33735, and WO 91/10741 (said references incorporated by reference in their entireties).

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura et al., *Immunol. Lett.* 39:91–99 (1994); U.S. Pat. No. 5,474,981; Gillies et al., PNAS 89:1428–1432 (1992); Fell et al., *J. Immunol.* 146:2446–2452(1991) (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, $CH_1$ domain, $CH_2$ domain, and $CH_3$ domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi et al, *PNAS* 88:10535–10539 (1991); Zheng et al.,*J. Immunol.* 154:5590–5600 (1995); and Vil et al., *PNAS* 89:11337–11341(1992) (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also included are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng et al., *Blood* 92(6) :1981–1988 (1998); Chen, et al., *Cancer Res.* 58(16) :3668–3678 (1998); Harrop et al., *J. Immunol.* 161(4) :1786–1794 (1998); Zhu et al., *Cancer Res.* 58(15) :3209–3214 (1998); Yoon, et al., *J. Immunol.* 160(7) :3170–3179 (1998); Prat et al., *J. Cell. Sci.* 111(Pt2) :237–247 (1998); Pitard et al., *J. Immunol. Methods* 205(2) :177–190 (1997); Liautard et al., *Cytokine* 9(4):233–241 (1997); Carlson et al., *J. Biol. Chem.* 272(17):11295–11301 (1997); Taryman et al., *Neuron* 14(4):755–762 (1995); Muller et al., *Structure* 6(9):1153–1167 (1998); Bartunek et al., *Cytokine* 8(1):14–20 (1996) (said references incorporated by reference in their entireties).

As discussed above, antibodies to the polypeptides of the invention can, in turn, be utilized to generate anti-idiotype antibodies that "mimic" polypeptides of the invention using techniques well known to those skilled in the art. (See, e.g., Greenspan & Bona, *FASEB J.* 7(5):437–444; (1989) and Nissinoff, *J. Immunol.* 147(8):2429–2438 (1991)). For example, antibodies which bind to and competitively inhibit polypeptide multimerization and/or binding of a polypeptide of the invention to ligand can be used to generate anti-idiotypes that "mimic" the polypeptide mutimerization and/ or binding domain and, as a consequence, bind to and neutralize polypeptide and/or its ligand. Such neutralizing anti-idiotypes or Fab fragments of such anti-idiotypes can be used in therapeutic regimens to fneutralize polypeptide ligand. For example, such anti-idiotypic antibodies can be used to bind a polypeptide of the invention and/or to bind its ligands/receptors, and thereby block its biological activity.

Antibodies generated against the polypeptides corresponding to a sequence of the present invention or its in vivo receptor can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptides from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptides products of this invention.

The antibodies of the present invention may be prepared by any of a variety of methods. For example, cells expressing the MPIF-1 protein or an antigenic fragment thereof can be administered to an animal in order to induce the production of sera containing polyclonal antibodies. In a preferred method, a preparation of MPIF-1 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or MPIF-1 protein binding fragments thereof). Such monoclonal antibodies can be prepared using hybridoma technology (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, Elsevier, N.Y., (1981) pp. 563–681). In general, such procedures involve immunizing an animal (preferably a mouse) with an MPIF-1 protein antigen or, more preferably, with an MPIF-1 protein-expressing cell. Suitable cells can be recognized by their capacity to bind anti-MPIF-1 protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 μg/l of nonessential amino acids, about 1,000 U/ml of penicillin, and about 100 μg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP20), available from the American Type Culture Collection, Rockville, Md. After fusion, the resulting hybridoma cells are selectively maintained in HAT medium, and then cloned by limiting dilution as described by Wands et al. (*Gastroenterology* 80:225–232 (1981)). The hybridoma cells obtained through such a selection are then assayed to identify clones which secrete antibodies capable of binding the MPIF-1 protein antigen.

Alternatively, additional antibodies capable of binding to the MPIF-1 protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, MPIF-1 protein specific antibodies are used to immunize an animal, preferably a mouse. The splenocytes of such an animal are then used to produce hybridoma cells, and the hybridoma cells are screened to identify clones which produce an antibody whose ability to bind to the MPIF-1 protein-specific antibody can be blocked by the MPIF-1 protein antigen. Such antibodies comprise anti-idiotypic antibodies to the MPIF-1 protein-specific antibody and can be used to immunize an animal to induce formation of further MPIF-1 protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, MPIF-1 protein-binding fragments can be produced through the application of recombinant DNA technology or through synthetic chemistry.

It may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *Bio-Techniques* 4:214 (1986); Cabilly et al, U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the MPIF-1 protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$y, $^{67}$Cu, $^{217}$Ci, $^{211}$At, $^{212}$Pd, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins et al., *Eur. J. Nucl. Med.* 10:296–301 (1985); Carasquillo et al., *J. Nucl. Med.* 28:281–287 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy et al., *Clin. Chim. Acta* 70:1–31 (1976), and Schurs et al., *Clin. Chim. Acta* 81:1–40 (1977). Coupling techniques mentioned in the latter are the glutaraldehyde method, the periodate method, the dimaleimide method, the m-maleimidobenzyl-N-hydroxysuccinimide ester method, all of which methods are incorporated by reference herein.

Chromosome Assays. The nucleic acid molecules of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of an MPIF-1 protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. This assumes 1 megabase mapping resolution and one gene per 20 kb.

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

The present invention is further directed to inhibiting MPIF-1 in vivo by the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the polypeptides of the present invention, is used to design an antisense RNA oligonucleotide of from about 10 to 40 base pairs in length. A DNA oligonucleotide is designed to be complementary to a region of the gene involved in transcription (triple helix see Lee et al., Nucl. Acids Res., 6:3073 (1979); Cooney et al, Science, 241:456 (1988); and Dervan et al., Science, 251: 1360 (1991)), thereby preventing transcription and the production of MPIF-1. The antisense RNA oligonucleotide hybridizes to the mRNA in vivo and blocks translation of the mRNA molecule into MPIF-1 protein (antisense—Okano, *J. Neurochem.* 56:560 (1991); *Oligodeoxynucleotides as Antisense Inhibitors of Gene Expression*, CRC Press, Boca Raton, Fla. (1988)).

Alternatively, the oligonucleotides described above can be delivered to cells by procedures in the art such that the antisense RNA or DNA can be expressed in vivo to inhibit production of MPIF-1 in the manner described above.

Accordingly, antisense constructs to the MPIF-1 can be used to treat disorders which are either MPIF-1-induced or enhanced, for example, atherosclerosis, auto-immune, e.g. multiple sclerosis and insulin-dependent diabetes, and chronic inflammatory and infective diseases, histamine-mediated allergic reactions, rheumatoid arthritis, silicosis, sarcoidosis, idiopathic pulmonary fibrosis and other chronic inflammatory diseases of the lung, idiopathic hyper-eosinophilic syndrome, endotoxic shock, histamine-mediated allergic reactions, prostaglandin-independent fever, and aplastic anemia and other cases of bone marrow failure.

Antagonists, Agonists and Methods. This invention further provides methods for screening compounds to identify agonists and antagonists to the chemokine polypeptides of the present invention. An agonist is a compound which has similar biological functions, or enhances the functions, of the polypeptides, while antagonists block such functions. Chemotaxis may be assayed by placing cells, which are chemoattracted by either of the polypeptides of the present invention, on to p of a filter with pores of sufficient diameter to admit the cells (about 5 μm). Solutions of potential agonists are placed in the bottom of the chamber with an appropriate control medium in the upper compartment, and thus a concentration gradient of the agonist is measured by counting cells that migrate into or through the porous membrane over time.

When assaying for antagonists, the chemokine polypeptides of the present invention are placed in the bottom chamber and the potential antagonist is added to determine if chemotaxis of the cells is prevented.

Alternatively, a mammalian cell or membrane preparation expressing the receptors of the polypeptides would be incubated with a labeled chemokine polypeptide, e.g. radioactivity, in the presence of the compound. The ability of the compound to block this interaction could then be measured. When assaying for agonists in this fashion, the chemokines would be absent and the ability of the agonist itself to interact with the receptor could be measured.

Examples of potential MPIF-1 antagonists include antibodies, or in some cases, oligonucleotides, which bind to the polypeptides. Another example of a potential antagonist is a negative dominant mutant of the polypeptides. Negative dominant mutants are polypeptides which bind to the receptor of the wild-type polypeptide, but fail to retain biological activity.

Antisense constructs prepared using antisense technology are also potential antagonists. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple-helix, see Lee et al., *Nucl. Acids Res.* 6:3073 (1979); Cooney et al, *Science* 241:456 (1988); and Dervan et al., *Science* 251:1360 (1991)), thereby preventing transcription and the production of the chemokine polypeptides. The antisense RNA oligonucleotide hybridizes to the mRNA in vivo and blocks translation of the mRNA molecule into the polypeptides (antisense-Okano, *J. Neurochem.* 56:560 (1991); oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of the chemokine polypeptides.

Another potential chemokine antagonist is a peptide derivative of the polypeptides which are naturally or synthetically modified analogs of the polypeptides that have lost biological function yet still recognize and bind to the receptors of the polypeptides to thereby effectively block the receptors. Examples of peptide derivatives include, but are not limited to, small peptides or peptide-like molecules.

The antagonists may be employed to treat disorders which are either MPIF-1-induced or enhanced, for example, auto-immune and chronic inflammatory and infective diseases. Examples of auto-immune diseases include multiple sclerosis, and insulin-dependent diabetes.

The antagonists may also be employed to treat infectious diseases including silicosis, sarcoidosis, idiopathic pulmonary fibrosis by preventing the recruitment and activation of mononuclear phagocytes. They may also be employed to treat idiopathic hyper-eosinophilic syndrome by preventing eosinophil production and migration. Endotoxic shock may also be treated by the antagonists by preventing the migration of macrophages and their production of the chemokine polypeptides of the present invention.

The antagonists may also be employed for treating atherosclerosis, by preventing monocyte infiltration in the artery wall.

The antagonists may also be employed to treat histamine mediated allergic reactions and immunological disorders including late phase allergic reactions, chronic urticaria, and atopic dermatitis by inhibiting chemokine-induced mast cell and basophil degranulation and release of histamine. IgE-mediated allergic reactions such as allergic asthma, rhinitis, and eczema may also be treated.

The antagonists may also be employed to treat chronic and acute inflammation by preventing the attraction of monocytes to a wound area. They may also be employed to regulate normal pulmonary macrophage populations, since chronic and acute inflammatory pulmonary diseases are associated with sequestration of mononuclear phagocytes in the lung.

Antagonists may also be employed to treat rheumatoid arthritis by preventing the attraction of monocytes into synovial fluid in the joints of patients. Monocyte influx and activation plays a significant role in the pathogenesis of both degenerative and inflammatory arthropathies.

The antagonists may be employed to interfere with the deleterious cascades attributed primarily to IL-1 and TNF, which prevents the biosynthesis of other inflammatory cytokines. In this way, the antagonists may be employed to prevent inflammation. The antagonists may also be employed to inhibit prostaglandin-independent fever induced by chemokines.

The antagonists may also be employed to treat cases of bone marrow failure, for example, aplastic anemia and myelodysplastic syndrome.

The antagonists may also be employed to treat asthma and allergy by preventing eosinophil accumulation in the lung. The antagonists may also be employed to treat subepithelial basement membrane fibrosis which is aprominent feature of the asthmatic lung.

Agonists. MPIF-1 agonists include any small molecule that has an activity similar to any one or more of these polypeptides, as described herein. For example, MPIF-1 agonists can be used to enhance MPIF-1 activity. For example, to enhance MPIF-1 induced myeloprotection in patients undergoing chemotherapy or bone marrow transplantation.

Disease Diagnosis and Prognosis. Certain diseases or disorders, as discussed below, may be associated with enhanced levels of the MPIF-1 protein and mRNA encoding the MPIF-1 protein when compared to a corresponding "standard" mammal, i.e., a mammal of the same species not having the disease or disorder. Further, it is believed that enhanced levels of the MPIF-1 protein can be detected in certain body fluids (e.g. sera, plasma, urine, and spinal fluid) from mammals with a disease or disorder when compared to sera from mammals of the same species not having the disease or disorder. Thus, the invention provides a diagnostic method, which involves assaying the expression level of the gene encoding the MPIF-1 protein in mammalian cells or body fluid and comparing the gene expression level with a standard MPIF-1 gene expression level, whereby an increase in the gene expression level over the standard is indicative of certain diseases or disorders.

Where a disease or disorder diagnosis has already been made according to conventional methods, the present invention is useful as a prognostic indicator, whereby patients exhibiting enhanced MPIF-1 gene expression will experience a worse clinical outcome relative to patients expressing the gene at a lower level.

By "assaying the expression level of the gene encoding the MPIF-1 protein" is intended qualitatively or quantitatively measuring or estimating the level of the MPIF-1 protein or the level of the mRNA encoding the MPIF-1 protein in a first biological sample either directly (e.g. by determining or estimating absolute protein level or mRNA level) or relatively (e.g. by comparing to the MPIF-1 protein level or mRNA level in a second biological sample).

Preferably, the MPIF-1 protein level or mRNA level in the first biological sample is measured or estimated and compared to a standard MPIF-1 protein level or mRNA level, the standard being taken from a second biological sample obtained from an individual not having the disease or disorder. As will be appreciated in the art, once a standard MPIF-1 protein level or mRNA level is known, it can be used repeatedly as a standard for comparison.

By "biological sample" is intended any biological sample obtained from an individual, cell line, tissue culture, or other source which contains MPIF-1 protein or mRNA. Biological samples include mammalian body fluids (such as sera, plasma, urine, synovial fluid and spinal fluid) which contain secreted mature MPIF-1 protein, and also include ovarian, prostate, heart, placenta, pancreas, ascites, muscle, skin, glandular, kidney, liver, spleen, lung, bone, bone marrow, ocular, peripheral nervous, central nervous, breast and umbilical tissue. Methods for obtaining tissue biopsies and body fluids from mammals are well known in the art. Where the biological sample is to include mRNA, a tissue biopsy is the preferred source.

The present invention is useful for detecting disease in mammals. In particular the invention is useful during useful for diagnosis or treatment of various immune system-related disorders in mammals, preferably humans. Such disorders include tumors, cancers, and any disregulation of immune cell function including, but not limited to, autoimmunity, arthritis, leukemias, lymphomas, immunosuppression, sepsis, wound healing, acute and chronic infection, cell mediated immunity, humoral immunity, inflammatory bowel disease, myelosuppression, and the like. Preferred mammals include monkeys, apes, cats, dogs, cows, pigs, horses, rabbits and humans. Particularly preferred are humans.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the MPIF-1 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. MPIF-1 cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., *Cell* 49:357–367 (1987). To prepare probe DNA for use in S1 mapping, the sense strand of above-described cDNA is used as atemplate to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the MPIF-1 protein). Northern blot analysis can be performed as described above.

Preferably, levels of mRNA encoding the MPIF-1 protein are assayed using the RT-PCR method described in Makino et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on apolyacrylamide gel. After drying the gel, the radioactivity of the appropriate bands (corresponding to the mRNA encoding the MPIF-1 protein) is quantified using an imaging analyzer. RT and PCR reaction ingredients and conditions, reagent and gel concentrations, and labeling methods are well known in the art. Variations on the RT-PCR method will be apparent to the skilled artisan.

Any set of oligonucleotide primers which will amplify reverse transcribed target mRNA can be used and can be designed as described in the sections above.

Assaying MPIF-1 protein levels in a biological sample can occur using any art-known method. Preferred for assaying MPIF-1 protein levels in a biological sample are antibody-based techniques. For example, MPIF-1 protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g. with urea and neutral detergent, for the liberation of MPIF-1 protein for Western-blot or dot/slot assay (Jalkanen, M., et al., *J. Cell. Biol.* 101:976–985 (1985); Jalkanen, M., et al., *J. Cell. Biol.* 105:3087–3096 (1987)). In this technique, which is based on the use of cationic solid phases, quantitation of MPIF-1 protein can be accomplished using isolated MPIF-1 protein as a standard. This technique can also be applied to body fluids. With these samples, a molar concentration of MPIF-1 protein will aid to set standard values of MPIF-1 protein content for different body fluids, like serum, plasma, urine, spinal fluid, etc. The normal appearance of MPIF-1 protein amounts can then be set using values from healthy individuals, which can be compared to those obtained from a test subject.

Other antibody-based methods useful for detecting MPIF-1 gene expression include immunoassays, such as the enzyme linked immunosorbent assay (ELISA) and the radioimmunoassay (RIA). For example, an MPIF-1 protein-specific monoclonal antibodies can be used both as an immunoabsorbent and as an enzyme-labeled probe to detect and quantify the MPIF-1 protein. The amount of MPIF-1 protein present in the sample can be calculated by reference to the amount present in a standard preparation using a linear regression computer algorithm. In another ELISA assay, two distinct specific monoclonal antibodies can be used to detect MPIF-1 protein in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting MPIF-1 protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

The polypeptides of the present invention, and polynucleotides encoding such polypeptides, may be employed as research reagents for in vitro purposes related to scientific research, synthesis of DNA and manufacture of DNA vectors, and for the purpose of developing therapeutics and diagnostics for the treatment of human disease. For example, and MPIF-1 may be employed for the expansion of immature hematopoietic progenitor cells, for example, granulocytes, macrophages or monocytes, by temporarily preventing their differentiation. These bone marrow cells may be cultured in vitro.

Fragments of the full length MPIF-1 gene may be used as a hybridization probe for a cDNA library to isolate the full length gene and to isolate other genes which have a high sequence similarity to the gene or similar biological activity. Preferably, however, the probes have at least 30 bases and may contain, for example, 50 or more bases. The probe may also be used to identify a cDNA clone corresponding to a full length transcript and a genomic clone or clones that contain the complete genes including regulatory and promotor regions, exons, and introns. An example of a screen comprises isolating the coding region of the genes by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

This invention is also related to the use of the MPIF-1 gene as part of a diagnostic assay for detecting diseases or susceptibility to diseases related to the presence of mutations in the nucleic acid sequences. Such diseases are related to under-expression of the chemokine polypeptides.

Individuals carrying mutations in the MPIF-1 gene may be detected at the DNA level by avariety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., *Nature* 324:163–166 (1986)) prior to analysis. RNA or cDNA may also be used for the same purpose. As an example, PCR primers complementary to the nucleic acid encoding MPIF-1 and can be used to identify and analyze MPIF-1 and mutations. For example, deletions and insertions can be detected by a change in size of the amplified product in comparison to the normal genotype. Point mutations can be identified by hybridizing amplified DNA to radiolabeled MPIF-1 RNA or alternatively, radiolabeled MPIF-1 antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g. Myers et al., *Science* 230:1242 (1985)).

Sequence changes at specific locations may also be revealed by nuclease protection assays, such as RNase and S1 protection or the chemical cleavage method (e.g Cotton et al., *PNAS, USA* 85:4397–4401 (1985)).

Thus, the detection of a specific DNA sequence may be achieved by methods such as hybridization, RNase protection, chemical cleavage, direct DNA sequencing or the use of restriction enzymes, (e.g. Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of MPIF-1 protein in various tissues since an over-expression of the proteins compared to normal control tissue samples may detect the presence of a disease or susceptibility to a disease, for example, a tumor. Assays used to detect levels of MPIF-1 protein in a sample derived from a host are well-known to those of skill in the art and include radioimmunoassays, competitive-binding assays, Western Blot analysis, ELISA assays and "sandwich" assay. An ELISA assay (Coligan, et al., *Current Protocols in Immunology* 1(2), Chapter 6, (1991)) initially comprises preparing an antibody specific to the MPIF-1 antigens, preferably a monoclonal antibody. In addition a reporter antibody is prepared against the monoclonal antibody. To the reporter antibody is attached a detectable reagent such as radioactivity, fluorescence or, in this example, a horseradish peroxidase enzyme. A sample is removed from a host and incubated on a solid support, e.g. a polystyrene dish, that binds the proteins in the sample. Any free protein binding sites on the dish are then covered by incubating with a non-specific protein like BSA. Next, the monoclonal antibody is incubated in the dish during which time the monoclonal antibodies attach to any MPIF-1 proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to MPIF-1. Unattached reporter antibody is then washed out. Peroxidase substrates are then added to the dish and the amount of color developed in a given time period is a measurement of the amount of MPIF-1 protein present in a given volume of patient sample when compared against a standard curve.

A competition assay may be employed wherein antibodies specific to MPIF-1 are attached to a solid support and labeled MPIF-1 and a sample derived from the host are passed over the solid support and the amount of label detected, for example by liquid scintillation chromatography, can be correlated to a quantity of protein in the sample.

A "sandwich" assay is similar to an ELISA assay. In a "sandwich" assay MPIF-1 is passed over a solid support and binds to antibody attached to a solid support. A second antibody is then bound to the MPIF-1. A third antibody which is labeled and specific to the second antibody is then passed over the solid support and binds to the second antibody and an amount can then be quantified.

This invention provides a method for identification of the receptors for the chemokine polypeptides. The gene encoding the receptor can be identified by numerous methods known to those of skill in the art, for example, ligand panning and FACS sorting (Coligan, et al., *Current Protocols in Immun.* 1(2), Chapter 5, (1991)). Preferably, expression cloning is employed wherein polyadenylated RNA is prepared from a cell responsive to the polypeptides, and a cDNA library created from this RNA is divided into pools and used to transfect COS cells or other cells that are not responsive to the polypeptides. Transfected cells which are grown on glass slides are exposed to the labeled polypeptides. The polypeptides can be labeled by a variety of means including iodination or inclusion of a recognition site for a site-specific protein kinase. Following fixation and incubation, the slides are subjected to autoradiographic analysis. Positive pools are identified and sub-pools are prepared and retransfected using an iterative sub-pooling and rescreening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Therapeutics. Polypeptides of the present invention can be used in a variety of immunoregulatory and inflammatory functions and also in a number of disease conditions. MPIF-1 is in the chemokine family and therefore it is a chemo-attractant for leukocytes (such as monocytes, neutrophils, T lymphocytes, eosinophils, basophils, etc.).

Northern Blot analyses show that MPIF-1 is expressed predominantly in tissues of hemopoietic origin.

Figure 13:
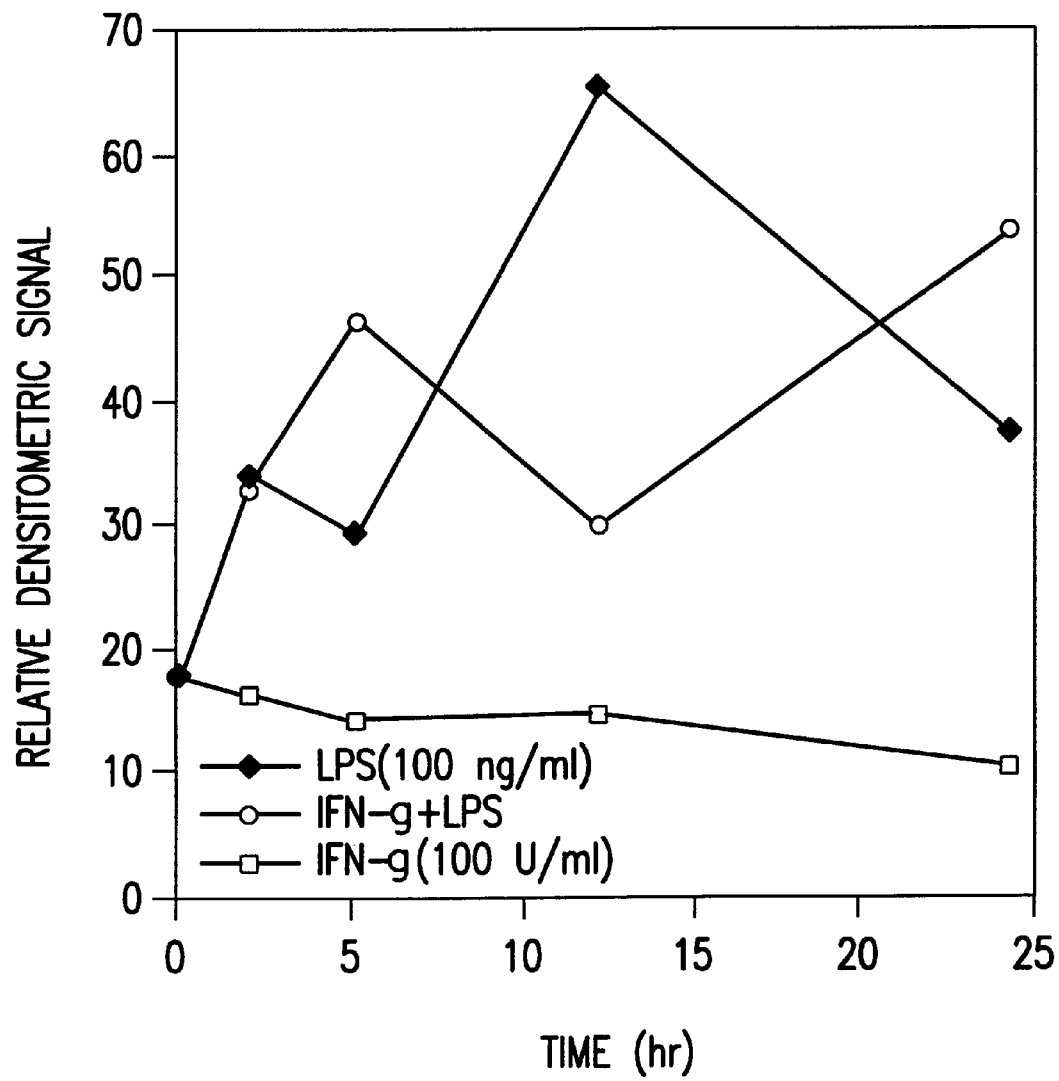
FIG. 13. Expression of RNA encoding MPIF-1 in human monocytes. Total RNA from fresh elutriated monocytes was isolated and treated with 100 U/ml hu rIFN-g, 100 ng/ml LPS, or both. RNA (8 μg) from each treatment was separated electrophoretically on a 1.2% agarose gel and transferred to a nylon membrane. MPIF-1 mRNA was quantified by probing with $^{32}$P-labeled cDNA and the bands on the resulting autoradiograph were quantified densitometrically.

MPIF-1 Therapeutic/DiagnosticApplications. MPIF-1 is shown to play an important role in the regulation of the immune response and inflammation. In FIG. 13, it is shown that lipopolysaccharide induces the expression of MPIF-1 from human monocytes. Accordingly, in response to the presence of an endotoxin, MPIF-1 is expressed from monocytes and, therefore, administration of MPIF-1 may be employed to regulate the immune response of a host. MPIF-1 could be used as an anti-inflammatory agent.

Figure 4A:
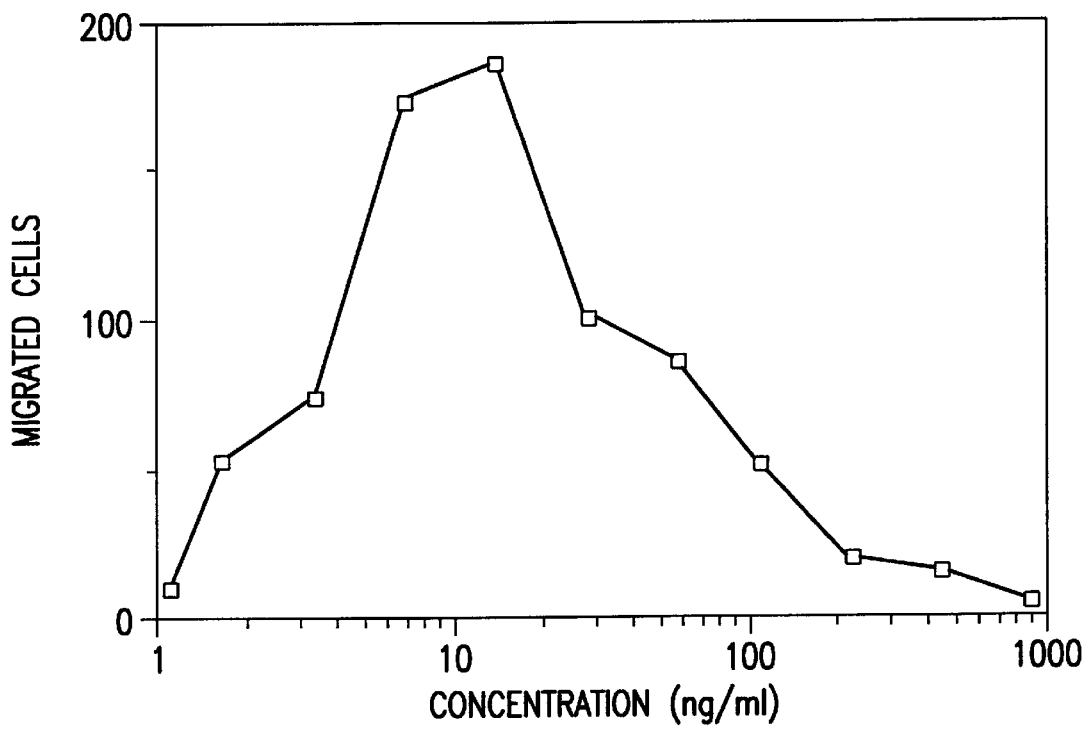
FIGS. 4A–4B. The chemoattractant activity of MPIF-1 was determined with chemotaxis assays using a 48-well microchamber device (Neuro Probe, Inc.). The experimental procedure was as described in the manufacturers manual. For each concentration of MPIF-1 tested, migration in 5 high-power fields was examined. The results presented represent the average values obtained from two independent experiments. The chemoattractant activity on THP-1 (A) cells and human PBMCs (B) is shown.
Figure 4B:
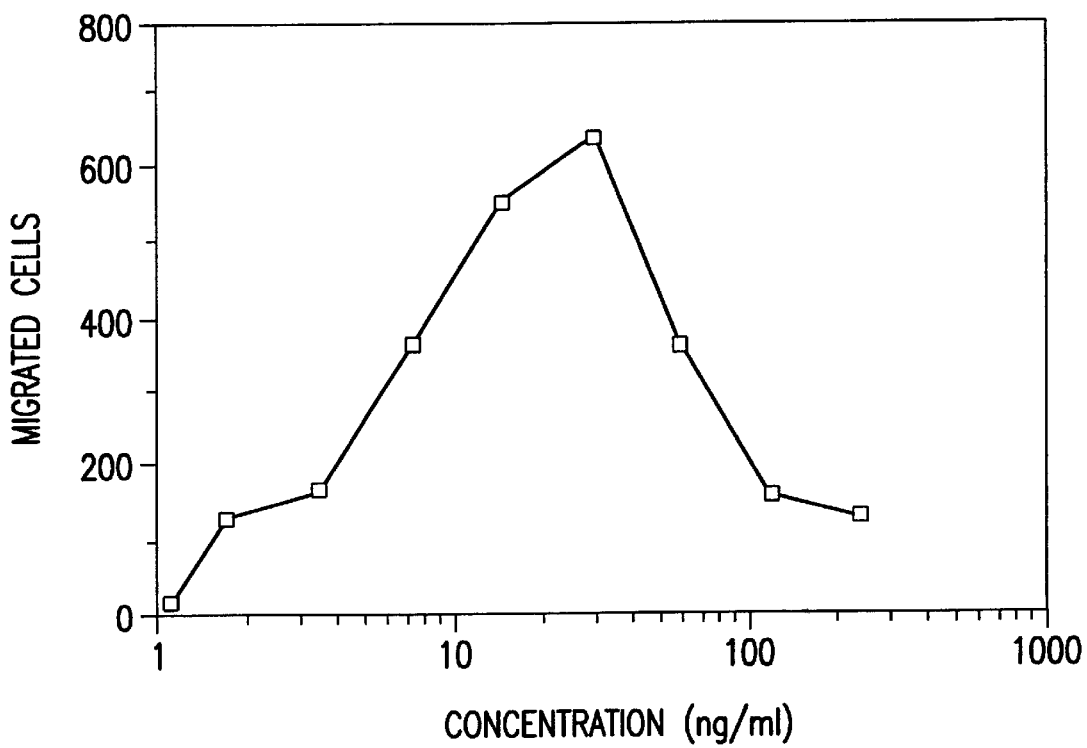

As illustrated in FIG. 4, the chemoattractant activity of MPIF-1 on THP-1 cells (A) and PBMCs (B) is significant. MPIF-1 also induces significant calcium mobilization in THP-1 cells (FIG. 5), showing that MPIF-1 has a biological effect on monocytes. Further, MPIF-1 produces a dose dependent chemotactic and calcium mobilization response in human monocytes and in dendritic cells.

Further, the polypeptides of the present invention can be useful in anti-tumor therapy since there is evidence that chemokine expressing cells injected into tumors have caused regression of the tumor, for example, in the treatment of Kaposi's sarcoma. MPIF-1 may induce cells to secrete TNF-α, which is a known agent for regressing tumors, in which case this protein could be used to induce tumor regression. MPIF-1 may also induce human monocytes to secrete other tumor and cancer inhibiting agents such as IL-6, IL-1 and G-CSF. Also, MPIF-1, and stimulate the invasion and activation of host defense (tumoricidal) cells, e.g., cytotoxic T-cells and macrophages via their chemotactic activity, and in this way can also be used to treat solid tumors.

Figure 6:
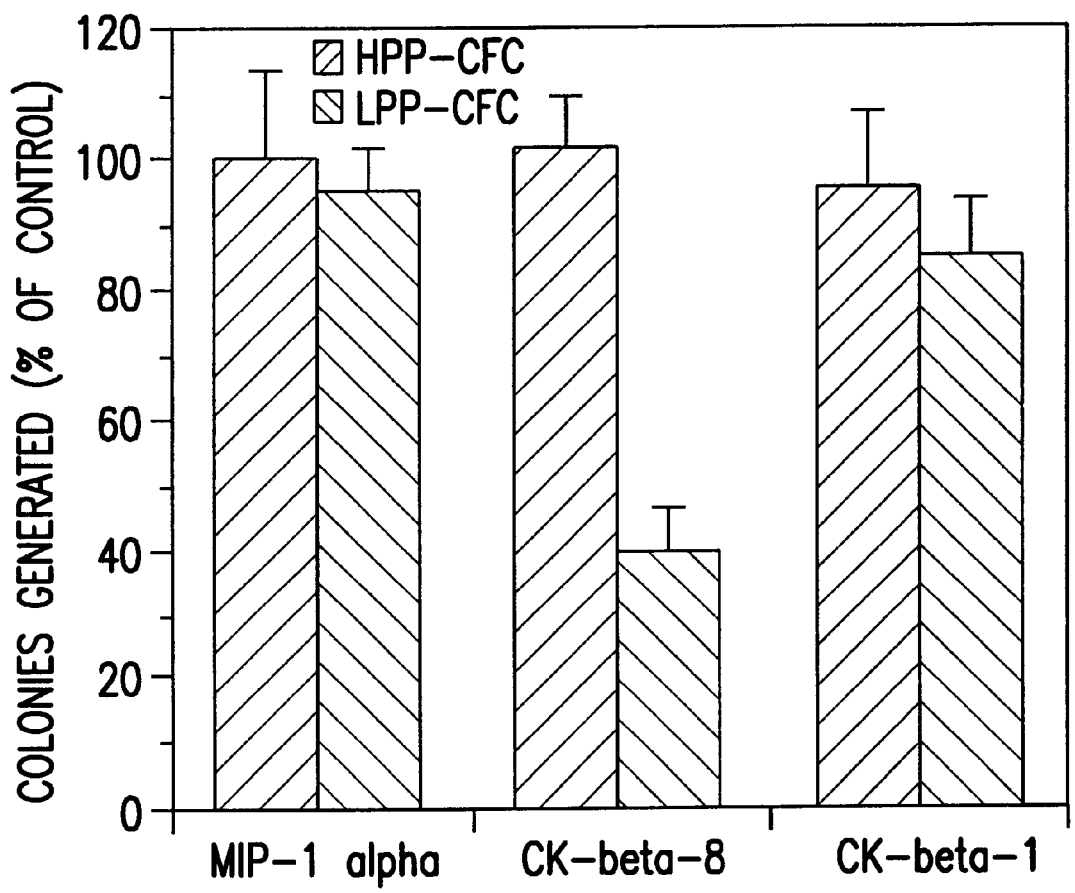
FIG. 6. A low density population of mouse bone marrow cells was plated (1,500 cells/dish) in agar containing-medium with or without the indicated chemokines (100 ng/ml), but in the presence of IL-3 (5 ng/ml), SCF (100 ng/ml), IL-1α (10 ng/ml), and M-CSF (5 ng/ml). The data shown represents the average obtained from two independent experiments (each performed in duplicate). Colonies were counted 14 days after plating. The number of colonies generated in the presence of chemokines is expressed as a mean percentage of those produced in the absence of any added chemokines.
Figure 7A:
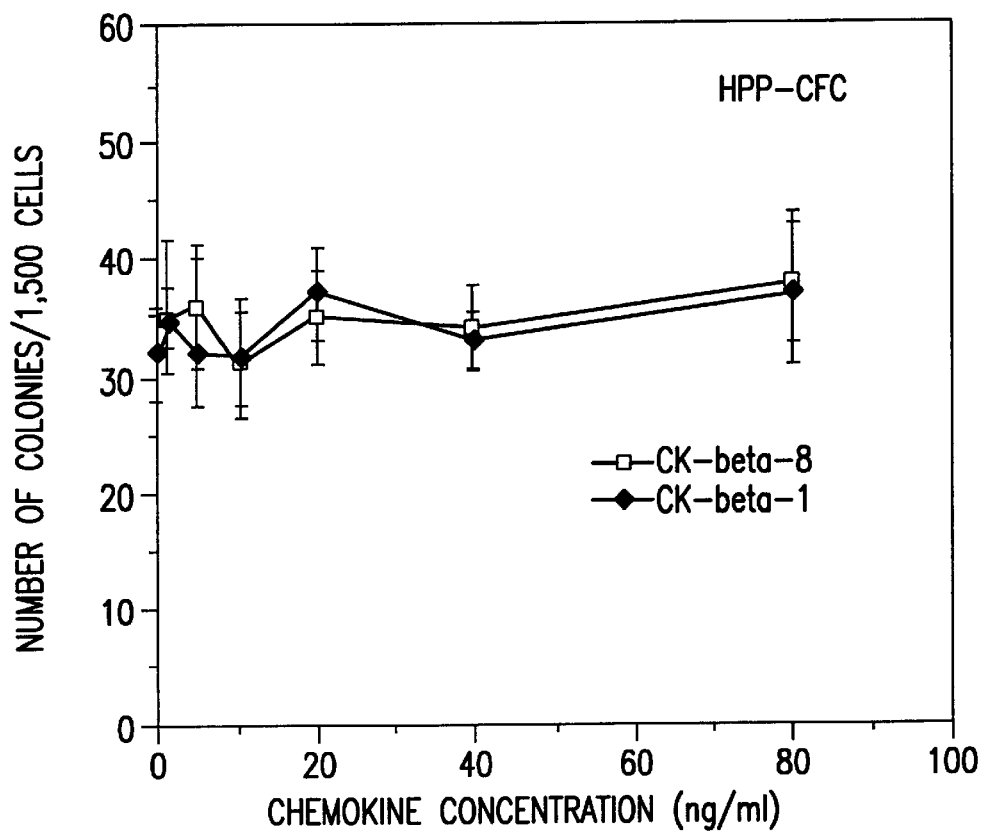
FIGS. 7A–7B illustrate the effect of MPIF-1 and M-CIF on mouse bone marrow colony formation by HPP-CFC (A) and LPP-CFC (B).
Figure 7B:
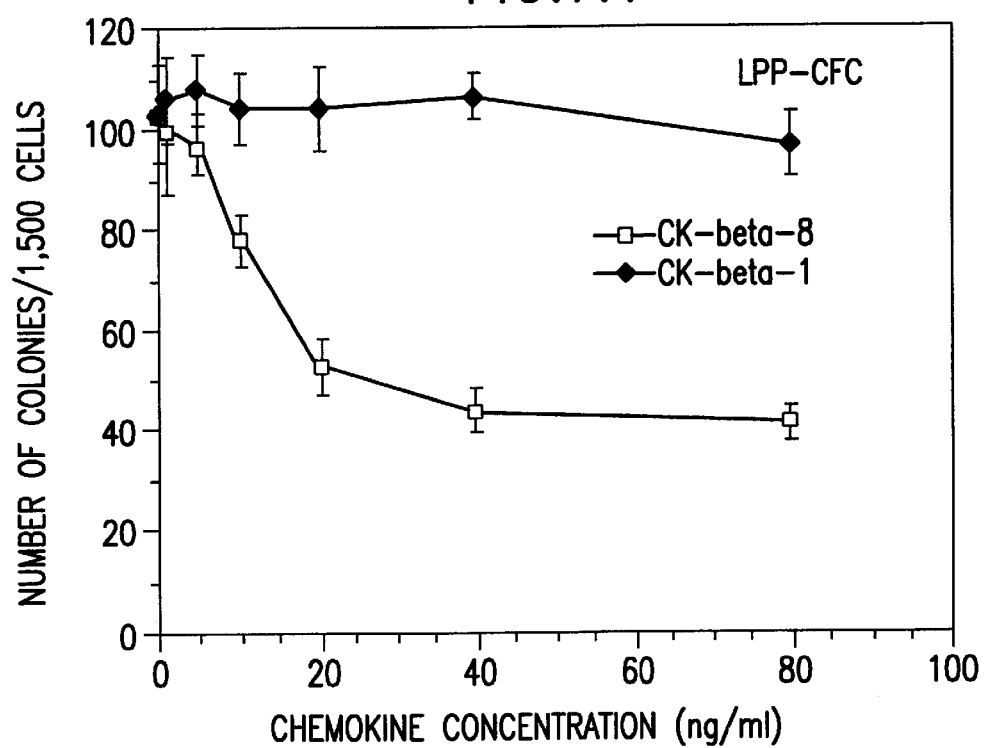
Figure 8:
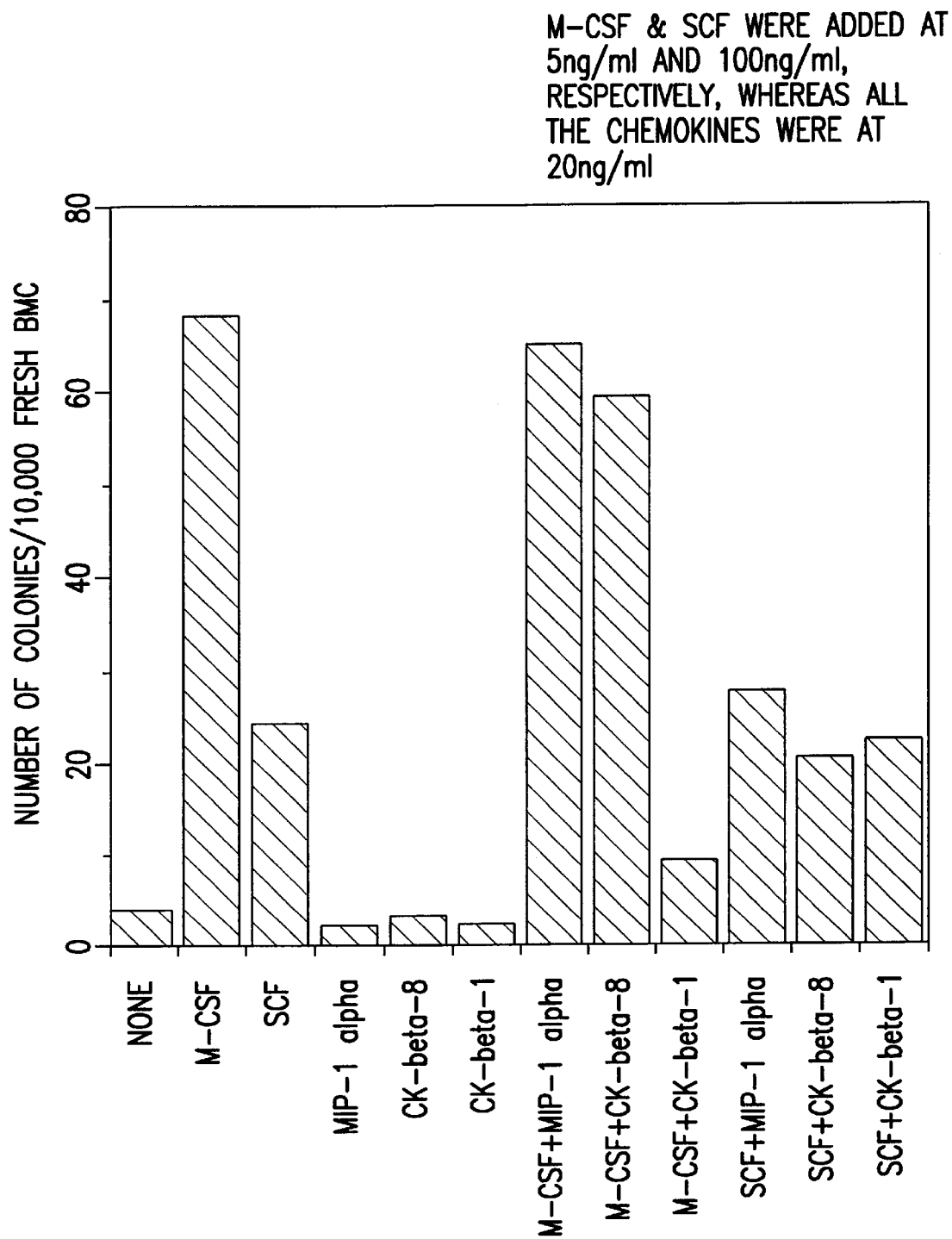
FIG. 8 illustrates the effect of baculovirus-expressed MPIF-1 and M-CIF on M-CFS and SCF-stimulated colony formation of freshly isolated bone marrow cells.

Myeloprotection. The polypeptides can be also be employed to inhibit the proliferation and differentiation of hematopoietic cells and therefore may be employed to protect bone marrow stem cells from chemotherapeutic agents during chemotherapy. FIGS. 6 and 7 illustrate that MPIF-1 inhibits colony formation by low proliferative potential colony forming cells (LPP-CFC). FIG. 8 illustrates that M-CIF specifically inhibits M-CSF-stimulated colony formation, while MPIF-1 does not. Since MPIF-1 significantly inhibits growth and/or differentiation of bone marrow cells, this antiproliferative effect may allow administration of higher doses of chemotherapeutic agents and, therefore, more effective chemotherapeutic treatment.

The inhibitory effect of MPIF-1 polypeptides on the subpopulation of committed progenitor cells, (for example granulocyte, and macrophage/monocyte cells) may be employed therapeutically to inhibit proliferation of leukemic cells.

Further, the inventors have found that MPIF-1, and variants thereof (e.g., MPIF-1Δ23), inhibit in vitro proliferation and differentiation of human myeloid and granulocyte precursors. Similarly, animal studies have shown that MPIF-1Δ23, for example, specifically inhibits the development of low proliferative potential-colony forming cells (LPP-CFCs) and granulocyte/monocyte committed progenitors both in vitro and in vivo. These findings indicate that MPIF-1 has therapeutic application as a chemoprotective agent that may spare early myeloid progenitors from the cytotoxic effects of commonly used chemotherapeutic drugs.

Because MPIF-1, and variants thereof, have the ability to selectively inhibit myeloid progenitor cells, MPIF-1 can be used to treat myeloproliferative disorders such as essential thrombocytosis (ET), polycythemia vera (PV), or agnogenic myeloid metaplasia (AMM), which are clinically closely related. Each disorder results from an acquired mutation of a single hematopoietic stem cell that gives the progeny of that stem cell a growth advantage. The pathophysiology of these disorders is distinct in that there is an overproduction of different cell types. In PV, there is an overproduction of erythrocytes, granulocytes, and megakaryocyte. In ET, there is, by definition, overproduction of platelets as well as leukocytes. AMM also shows thrombocytosis or leukocytosis in addition to bone marrow fibrosis.

Stabilization of PV patients can be addressed by removal of red cells by phlebotomy. However, there is no comparable therapy for elevated platelet levels in ET patients. Several myelosuppressive therapies have been studied for lowering the risk of thrombocytosis. Treatment with radioactive phosphorus, hydroxyurea, alkylating agents (busulfan and chlorambucil), interferons, or anagrelide have all shown significant side effects. In particular, there is an increased risk of acute leukemia with each myelosuppressive therapy except anagrelide. Anagrelide is a promising therapy. However, adverse reactions to anagrelide are a concern and its chronic toxicity potential has not been established. Interferons are, at present, considered second-line therapy because of expense, side effects, and the inconvenience of parenteral administration. These findings indicate that there is still a substantial need for therapy in these diseases.

In vivo studies in mice pretreated with MPIF-1Δ23 and then treated with 5-FU demonstrate an inhibition of platelet progenitor cell proliferation.

The present invention further encompasses the use of MPIF-1, and variants thereof, in combination with other myelosuppressive therapies and agents.

Figure 9:
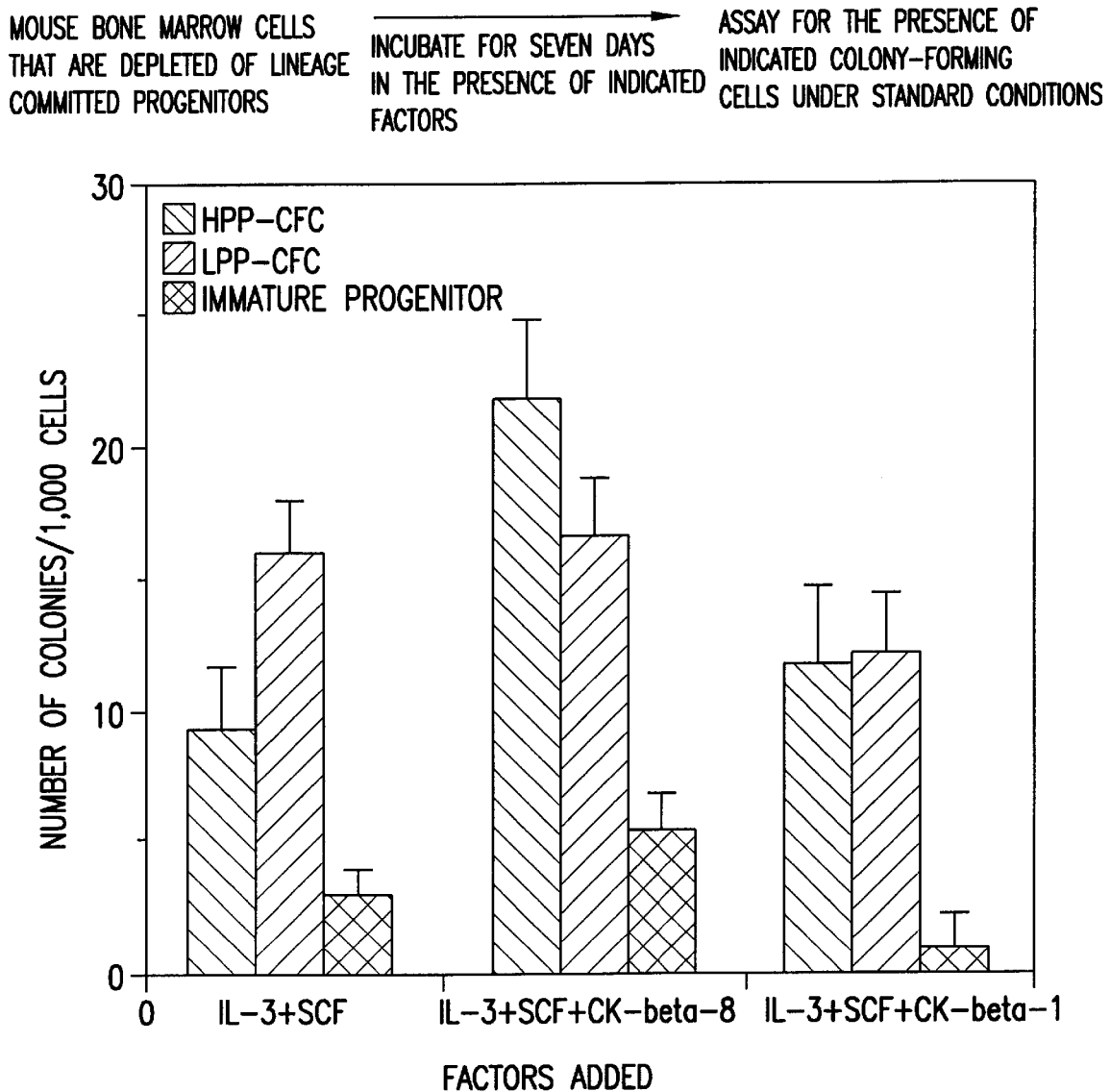
FIG. 9 illustrates the effect of MPIF-1 and M-CIF on IL3 and SCF-stimulated proliferation and differentiation of the line population of bone marrow cells.
Figure 10A:
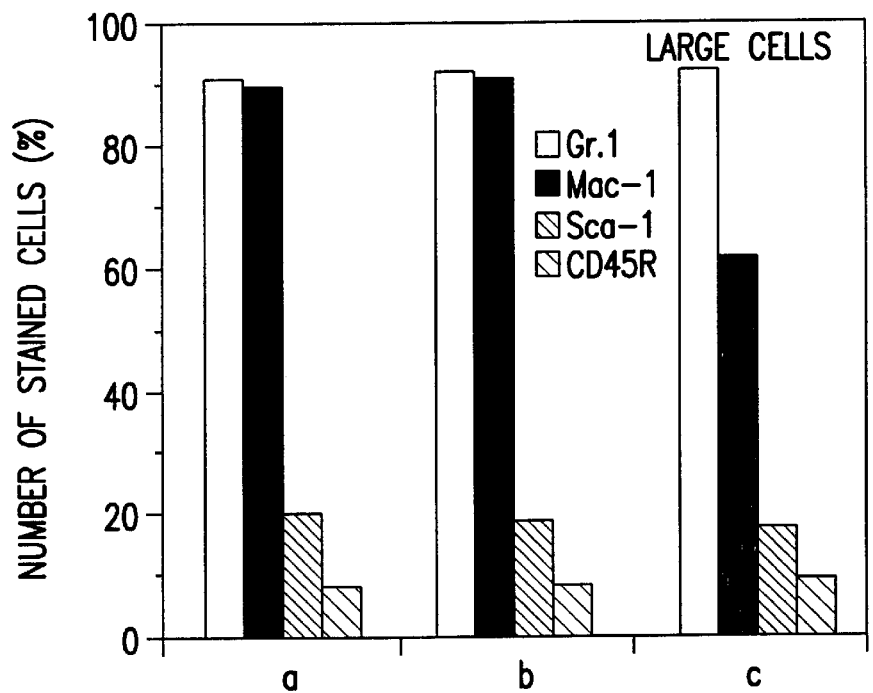
FIGS. 10A–10B show the effect of MPIF-1 and M-CIF on the generation of Gr.1 and Mac-1 (surface markers) positive population of cells from lineage depleted population of bone marrow cells. line cells were incubated in growth medium supplemented with IL-3 (5 ng/ml) and SCF (100 ng/ml) alone (a) with MPIF-1 (50 ng/ml) (b) or M-CIF (50 ng/ml) (c). Cells were then stained with Monoclonal antibodies against myeloid differentiation Gr.1, Mac-1, Sca-1, and CD45R surface antigens and analyzed by FACScan. Data is presented as percentage of positive cells in both large (FIG. 10A) and small (FIG. 10B) cell populations.
Figure 10B:
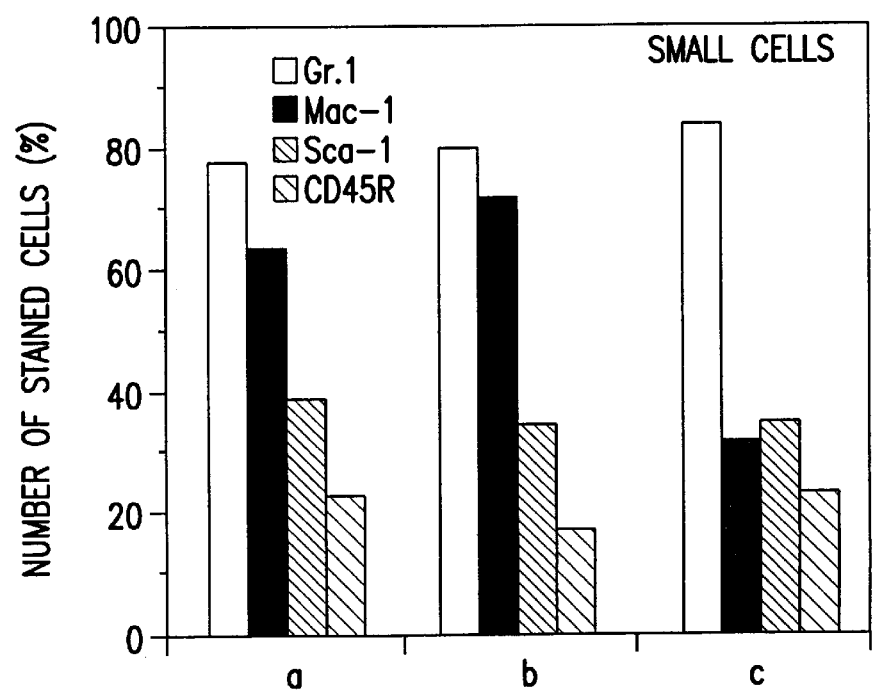
Figure 11:
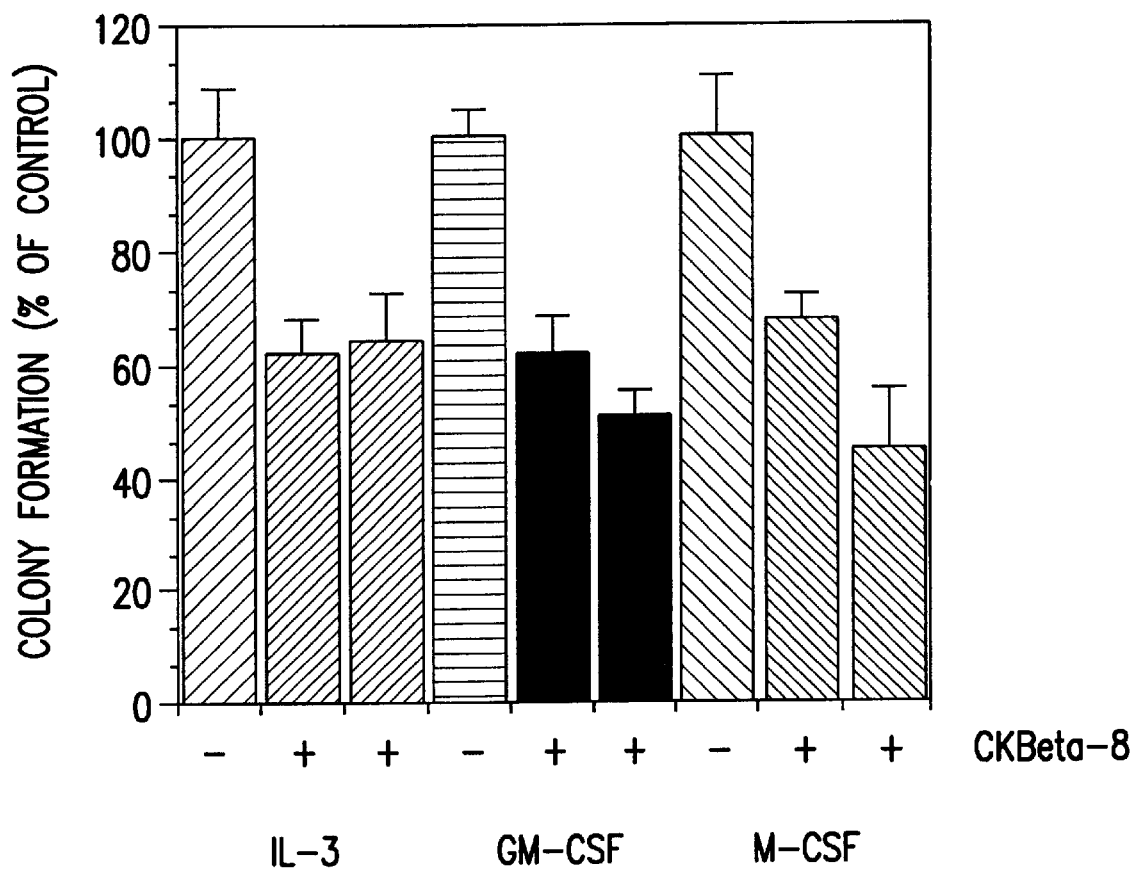
FIG. 11 illustrates that the presence of MPIF-1 protein inhibits bone marrow cell colony formation in response to IL3, M-CSF and GM-CSF.
Figure 12:
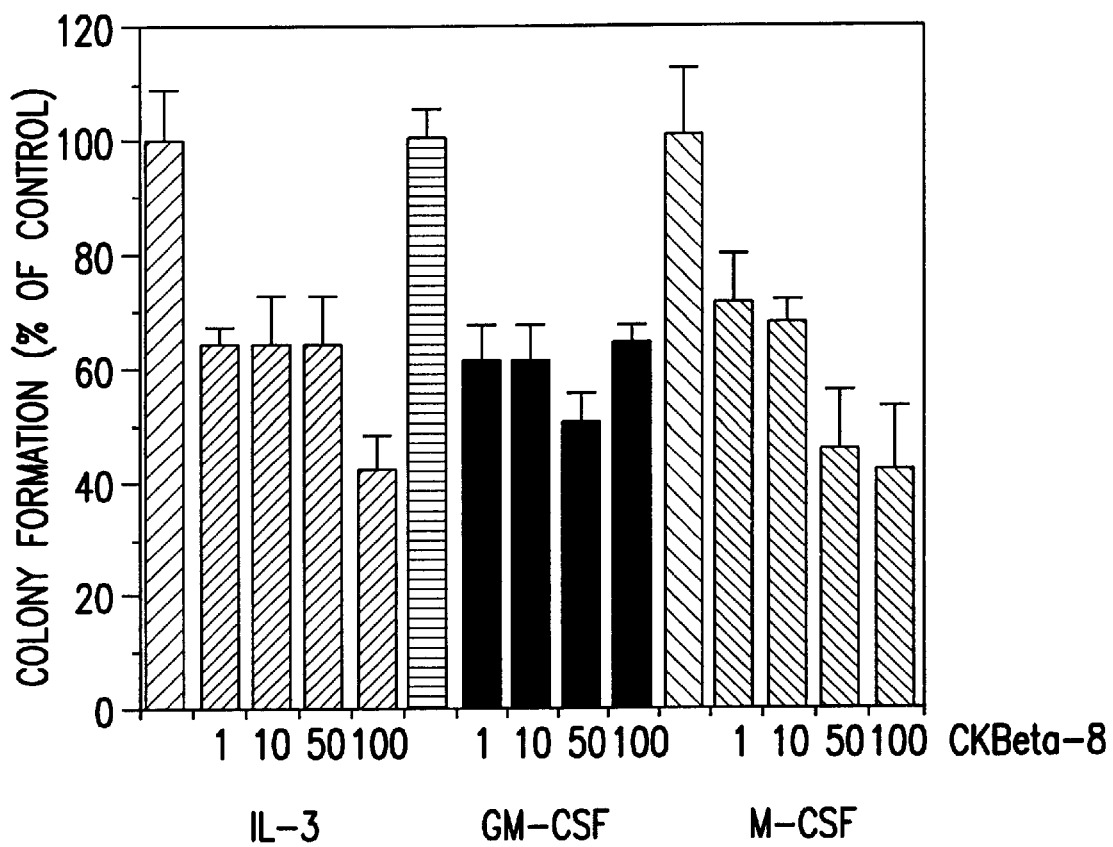
FIG. 12. Dose response of MPIF-1 inhibits bone marrow cell colony formation. Cells were isolated and treated as in FIG. 13. The treated cells were plated at a density of 1,000 cells/dish in agar-based colony formation assays in the presence of IL-3, GM-CSF or M-CSF (5 ng/ml) with or without MPIF-1 at 1, 10, 50 and 100 ng/ml. The data is presented as colony formation as a percentage of the number of colonies formed with the specific factor alone. The data is depicted as the average of duplicate dishes with error bars indicating the standard deviation.

In FIGS. 9, 10 and 11, the committed cells of the cell lineages utilized were removed and the resulting population of cells was contacted with M-CIF or MPIF-1. M-CIF causes a decrease in the Mac-I positive population of cells by nearly 50%, which is consistent with the results of FIG. 8 which shows M-CIF induces inhibition of M-CSF responsive colony-forming cells. MPIF-1, as shown in FIG. 11, inhibits the ability of committed progenitor cells to form colonies in response to IL-3, GM-CSF and M-CSF. Further, as shown in FIG. 12, a dose response of MPIF-1 is shown to inhibit colony formation. This inhibition could be due to a specific blockage of the differentiative signal mediated by these factors or to a cytotoxic effect on the progenitor cells. In addition, Examples 9 and 10 demonstrate that MPIF-1 has in vitro and in vivo myeloprotection activity against cytotoxicity of chemotherapeutic drugs. Thus, MPIF-1 can be useful as a myeloprotectant for patients undergoing chemotherapy.

As noted above, one major complication resulting from chemotherapy and radiation therapy is the destruction of non-pathological cell-types. The present invention provides methods for myeloprotection from radiation and chemotherapeutic agents by suppressing myeloid cell proliferation in an individual. These methods involve administering a myelosuppressive amount of MPIF-1 either alone or together with one or more chemokines selected from the group consisting of Macrophage Inflammatory Protein-1α (MIP-1α), Macrophage Inflammatory Protein-2α (MIP-2α), Platelet Factor 4 (PF4), Interleukin-8 (IL-8), Macrophage Chemotactic and Activating Factor (MCAF), and Macrophage Inflammatory Protein-Related Protein-2 (MRP-2) to an individual as part of a radiation treatment or chemotherapeutic regimen. The myelosuppressive compositions of the present invention thus provide myeloprotective effects and are useful in conjunction with therapies that have an adverse affect on myeloid cells. This is because the myelosuppressive compositions of the present invention place myeloid cells in a slow-cycling state thereby providing protection against cell damage caused by, for example, radiation therapy or chemotherapy using cell-cycle active drugs, such as cytosine arabinoside, hydroxyurea, 5-Fu and Ara-C. Once the chemotherapeutic drug has cleared the individual's system, it would be desirable to stimulate rapid amplification and differentiation of progenitor cells that were protected by MPIF-1 using, for example, myelostimulators, such as Interleukin-11 (IL-11), erythropoietin (EPO), GM-CSF, G-CSF, stem cell factor (SCF), and thrombopoietin (Tpo).

The ability of MPIF-1 to confer in vivo myeloprotection in the presence of a chemotherapeutic agent is demonstrated in Example 13. Example 13 shows that the administration of MPIF-1 to an individual prior to the administration of a chemotherapeutic agent accelerates the recovery of platelets in the blood even after multiple cycles of 5-Fu treatment. The experiments set forth in Example 13 also demonstrate that MPIF-1 treatment during multiple cycles of 5-Fu treatment results in the faster recovery of granulocytes. In addition, the results of Experiment 13 also suggest that MPIF-1 and G-CSF exert additive effects when co-administered.

As indicated, the inventors have found that MPIF-1, and variants thereof, exhibit potent in vitro suppression of low proliferation potential-colony forming cells (LPP-CFCs) from bone marrow. LPP-CFCs are bipotential hematopoietic progenitors that give rise to granulocyte and monocyte lineages. MPIF-1 also reversibly inhibits colony formation by human CD34$^+$ stem cell derived granulocyte and monocyte colony forming cells. The inventors' in vitro chemoprotection experiments have shown protection of these hematopoietic progenitors by MPIF-1Δ23 from the cytotoxic effects of the drugs 5-fluorouracil (5-Fu), cytosine arabinoside, and Taxol®.

The use of a MPIF-1 variant (Δ23) in an in vivo chemotherapeutic model has shown that it produces a more rapid recovery of both bone marrow progenitor cells and peripheral cell populations of neutrophils and platelets. Further, as shown in Examples 10 and 13, the administration of MPIF-1 results in the accelerated recovery from neutropenia and thrombocytopenia in experimental animals treated with 5-Fu. Thus, MPIF-1, and variants thereof, shorten the period of bone marrow aplasia, granulopenia, and thrombocytopenia associated with the chemotherapeutic agents and thereby reducing the likelihood of infection in patients undergoing treatment with such agents.

Thus, the invention relates to methods for protecting myeloid progenitor cells and to accelerating recovery of platelets and granulocytes which comprise the administration of MPIF-1 to an individual undergoing therapy which preferentially kills dividing cells (e.g., radiation therapy or treatment with a cell-cycle active drug). MPIF-1 is administered in sufficient quantity to provide in vivo myeloprotection against treatments and agents which preferentially kill dividing cells. By "MPIF-1 is administered" is meant that MPIF-1, an analog of MPIF-1, or combination thereof is administered in a therapeutically effective amount. Modes of administration of MPIF-1 are discussed in detail below.

MPIF-1 may be administered prior to, after, or during the therapy in which dividing cells are preferentially killed. In a preferred embodiment, MPIF-1 is administered prior to radiation therapy or administration of a cell-cycle active drug and sufficient time is allowed for MPIF-1 to suppress the proliferation of myeloid cells. Further contemplated by the present invention is the use of MPIF-1 to protect myeloid cells during multiple rounds of therapy in which dividing cells are preferentially killed. In such a case, MPIF-1 may be administered in either a single dose or multiple doses at different time points in the therapy or treatment regimen.

As indicated above, MPIF-1 may be used alone or in conjunction with one or more myelostimulators. Myelostimulators are currently used in the art to stimulate the proliferation of myeloid cells after their depletion in an individual undergoing radiation therapy or treatment with a cell-cycle active drug. See, e.g., Kannan, V. et al., *Int. J. Radiat. Oncol. Biol. Phys.* 37:1005–1010 (1997); Engelhardt, M. et al., *Bone Marrow Transplant* 19:529–537 (1997); Vadhan-Raj, S. et al., *Ann Intern Med.* 126:673–681 (1997); Harker, L. et al., *Blood* 89:155–165 (1997); Basser, R, et al., *Lancet* 348:1279–1281 (1996); Grossman, A. et al., *Blood* 88:3363–3370 (1996); Gordon, M. et al., *Blood* 87:3615–3624 (1996). MPIF-1 may, for example, be administered prior to therapy which kills dividing cells and one or more myelostimulators administered after or during the course of such therapy. In such a case, MPIF-1 will protect myeloid cells from the therapy and administration of the myelostimulator(s) will then result in expansion of the protected myeloid cell population.

Myelostimulators are typically administered to patients undergoing treatment with a chemotherapeutic agent in therapeutically effective amounts. Dosage formulation and mode of administration may vary with a number of factors including the individual being treated, the condition of the cells being stimulated, the stage of treatment in the chemotherapeutic regimen, and the myelostimulator(s) being used. GM-GSF and G-CSF, for examples, are therapeutically effective at dosages of about 1 μg/kilogram and 5 to 10 μg/kilogram of body weight, respectively, and may be administered daily by subcutaneous injection. See, e.g., Kannan, V. et al., Int. *J. Radiat. Oncol. Biol. Phys.* 37:1005–1010 (1997); Engelhardt, M. et al., *Bone Marrow Transplant* 19:529–537 (1997); Sniecinski, I. et al., *Blood* 89:1521–1528 (1997). IL-11 may be administered by daily subcutaneous injection at a dosage range of up to 100 µg/kilogram of body weight. Gordon, M. et al., supra. Doses of IL-11 below 10 µg/kilogram, however, are believed to be effective in reducing chemotherapy-induced thrombocytopenia. Tpo may be administered by intravenous injection at a dosage range of 0.3 to 2.5 µg/kilogram of body weight. See, e.g., Vadhan-Raj, S. et al., *Ann. Intern. Med.* 126:673–681 (1997); Harker, L. et al., *Blood* 89:155–165 (1997). As one skilled in the art would recognize, the optimal dosage formulation and mode of administration will vary with a number of factors including those noted above. Dosage formulation and mode of administration for additional myelostimulators are known in the art.

The timing of administration of myelostimulators as part of a treatment protocol involving therapy which preferentially kill dividing cells may also vary with the factors described above for dosage formulation and mode of administration. A number of reports have been published which disclose the administration of myelostimulators to individuals as part of treatment protocols involving radiation therapy or cell-cycle active drugs. Vadhan-Raj, S. et al., supra, for example, report the use of a single intravenous dose of Tpo three weeks prior to the administration of a chemotherapeutic agent. Papadimitrou, C. et al., *Cancer* 79:2391–2395 (1997) and Whitehead, R. et al., *J. Clin. Oncol.* 15:2414–2419 (1997) report chemotherapeutic treatment methods which involve the administration of chemotherapeutic agents over the course of several weeks. In each of these cases, doses of G-CSF are administered at multiple time points after the first day and before the last day of treatment with the chemotherapeutic agent. Similar usage of both IL-11 and GM-CSF are reported in Gordon, M. et al., supra, and Michael, M., et al., *Am. J. Clin. Oncol.* 20:259–262 (1997). One skilled in the art would recognize, however, that optimal timing of administration of myelostimulators will vary with the particular myelostimulators used and the conditions under which they are administered.

Thus, the administration of myelostimulators to alleviate cytotoxic effects that therapies which preferentially kill dividing cells have on myeloid cells is known in the art. The myelostimulators may be administered by several routes, including intravenous and subcutaneous injection. The concentrations of myelostimulators administered vary widely with numerous factors but generally range between 0.1 to 100 µg/kilogram of body weight and may be administered in a single dose or in multiple doses at various time points in the chemotherapeutic or radiological treatment regimen. Myelostimulators are generally administered, however, prior to or after administration of the chemotherapeutic agent or radiological treatment. As one skilled in the art would understand, the conditions under which myelostimulators are used will vary with both the particular myelostimulator and the treatment regimen.

As the skilled artisan will appreciate, MPIF-1 can be used as described above to enhance the effectiveness of hematopoietic growth factors generally. Such hematopoietic growth factors include erythropoietin, which stimulates production of erythrocytes, and IL-3, a multilineage growth factor that stimulates more primitive stem cells, thus increasing the number of all blood cell types. Others include stem cell factor; GM-CSF; and hybrid molecules of G-CSF and erythropoietin; IL-3 and SCF; and GM-CSF and G-CSF.

The myelosuppressive pharmaceutical compositions of the present invention are also useful in the treatment of leukemia, which causes a hyperproliferative myeloid cell state. Thus, the invention further provides methods for treating leukemia, which involve administering to a leukemia patient a myelosuppressive amount of MPIF-1 either alone or together with one or more chemokines selected from the group consisting of MIP-1α, MIP-2α, PF4, IL-8, MCAF, and MRP-2.

By "suppressing myeloid cell proliferation" is intended decreasing the cell proliferation of myeloid cells and/or increasing the percentage of myeloid cells in the slow-cycling phase. As above, by "individual" is intended mammalian animals, preferably humans. Preincubation of the myelosuppressive compositions of the present invention with acetonitrile (ACN) significantly enhances the specific activity of these chemokines for suppression of myeloid progenitor cells. Thus, preferably, prior to administration, the myelosuppresive compositions of the present invention are pretreated with ACN as described in Broxmeyer H. E., et al., *Ann-Hematol.* 71(5):235–46(1995) and PCT Publication WO 94/13321, the entire disclosures of which are hereby incorporated herein by reference.

The myelosuppressive compositions of the present invention may be used in combination with a variety of chemotherapeutic agents including alkylating agents such as nitrogen mustards, ethylenimines, methylmelamines, alkyl sulfonates, nitrosuoureas, and triazenes; antimetabolites such as folic acid analogs, pyrimidine analogs, in particular fluorouracil and cytosine arabinoside, and purine analogs; natural products such as vinca alkaloids, epipodophyllotoxins, antibiotics, enzymes and biological response modifiers; and miscellaneous products such as platinum coordination complexes, anthracenedione, substituted urea such as hydroxyurea, methyl hydrazine derivatives, and adrenocorticoid suppressant.

Chemotherapeutic agents can be administered at known concentrations according to known techniques. The myelosuppressive compositions of the present invention can be co-administered with a chemotherapeutic agent, or administered separately, either before or after chemotherapeutic administration.

Certain chemokines, such as MIP-1β, MIP-2β and GRO-α, inhibit (at least partially block) the myeloid suppressive affects of the myelosuppresive compositions of the present invention. Thus, in a further embodiment, the invention provides methods for inhibiting myelosuppression, which involves administering an effective amount of a myelosuppressive inhibitor selected from the group consisting of MIP-1β, MIP-2β and GRO-α to a mammal previously exposed to the myelosuppresive agent MPIF-1 either alone or together with one or more of MIP-1α, MIP-2α, PF4, IL-8, MCAF, and MRP-2.

Protection From Damage Induced by Cytotoxic Agents. The polypeptides of the present invention may also be employed to reduce or to prevent cytotoxic agent-induced damage/injury to cells, tissues and organs.

Damage to normal tissue occurs as a consequence of exposure to cytotoxic agents. Cytotoxic agents include radiation and chemotherapeutics. Radiation may be accidental, environmental, occupational, diagnostic, and therapeutic exposure to radiation. Normal tissue damage is also a common side effect of cancer treatment such as radiotherapy, chemotherapy, and combination radiotherapy and chemotherapy. This damage to normal tissue is commonly referred to as normal tissue "effects," tissue "toxicity," "morbidity," "complications" and tissue "reactions" (acute, subacute or late).

Thus, the present invention provides compositions and methods for treating and preventing normal tissue damage caused by radiation, radiation therapy, chemotherapy, and other cytotoxic agents.

Normal tissue toxicity, especially acute toxicity (i.e., occurring within days or weeks of treatment) causes pain and leads to further complications such as infection. Moreover, acute toxicity limits the dose of cancer therapeutic agent, thus compromising effective cancer treatment. Additionally, even when early toxic effects are subclinical (i.e., do not cause morbidity and are not dose-limiting), they can lead to late (also known as chronic) effects (i.e., occurring months or years after treatment). Late effects include, for example, sterility, late onset necrosis and fibrosis, and mitogen-induced cancer.

The present invention provides compositions and methods of treating and preventing acute, subacute, and late normal tissue toxicity.

Several pathways are involved in cytoxic agent-induced, such as radiation- and chemotherapy-induced, damage to normal cells and tissue. Damage may be direct or indirect. Direct damage results from the action of the cytotoxic agent on cell constituents and includes single-strand and double-strand breaks in chromosomes, and damage to cell membranes and other cell components from free-radicals and reactive oxygen species. Indirect damage results from events downstream from the initial action of the cytotoxic agent. Such downstream events include release of free-radicals by necrotic cells or tissue, vascular injury, normal immune responses and inflammatory responses.

The polypeptides and polynucleotides of the present invention treat and prevent cytotoxic agent-induced damage to cells, tissues, and organs by modulating at least one of the above direct and indirect pathways.

Damage may be caused by depletion of potentially mitotic cells (known as the stem cell model); vascular injury causing hypoxia and other effects; normal host repair responses including induction of immediate early genes such as Jun and EGR1, induction of proinflammatory cytokines such as interleukins and TNF, induction of inflammatory cytokines such as TGFβ, PDGF, BFGF, and induction of secondary cytokine cascade(s); effects of inflammatory responses; interactions between multiple cell types such as inflammatory cells, stromal functional cells and fibroblasts The polypeptides and polynucleotides of the present invention modulate at least one of the above causes of damage.

Fibrosis may be induced in one or more ways: monocytes and macrophages present in the irradiated tissue are induced to produce proinflammatory cytokines, thus recruiting additional macrophages in an inflammatory response; the initial loss of epithelial and stromal cells induces inflammation; irradiation induces expression of fibrogenic cytokines through induction of AP-1.

The polypeptides and polynucleotides of the present invention modulate at least one of the pathways leading to fibrosis.

Cells respond to radiation and other cytotoxic agents in several ways: formation of ceramide from membrane sphingomyelin activates the JNK pathway leading to apoptosis, marked by the formation of apoptotic bodies; apoptosis induced by other pathways; mitosis-linked death, marked by the formation of micronuclei (MN); and cytotoxin-induced senescence, in which cells are metabolically active but unable to divide.

The polypeptides and polynucleotides of the present invention modulate at least one of the above cellular responses to radiation and other cytotoxic agents.

Agents, such as the polypeptide of the present invention, that modulate normal tissue toxicity are referred to as chemical modifiers, toxicity protectants, protective agents, cytoprotectors and rescue agents. These agents are useful to reduce or prevent the side effects of cancer therapy, and to prevent or treat tissue damage from radiation exposure.

As used herein, the term cytotoxic agent refers to chemotherapeutic agents (also known as antineoplastic agents) and radiation such as accidental radiation, occupational radiation, environmental radiation, therapeutic radiation including, for example, fractionated radiotherapy, nonfractionated radiotherapy and hyperfractionated radiotherapy, and combination radiation and chemotherapy. Types of radiation also include ionizing (gamma) radiation, particle radiation, low energy transmission (LET), high energy transmission (HET), ultraviolet radiation, infrared radiation, visible light, and photosensitizing radiation. Cytotoxic agents include agents that preferentially kill neoplastic cells or disrupt the cell cycle of rapidly proliferating cells, and include agents used therapeutically to prevent or reduce the growth of neoplastic cells. Chemotherapeutic agents are also known as antineoplastic drugs, and are well known in the art. As used herein, chemotherapy includes treatment with a single chemotherapeutic agent or with a combination of agents. In a subject in need of treatment, chemotherapy may be combined with surgical treatment or radiation therapy, or with other antineoplastic treatment modalities.

Radiation also includes ionizing radiation which is high energy radiation, such as an X-ray or a gamma ray, which interacts to produce ion pairs in matter, high linear energy transfer irradiation, low linear energy transfer irradiation, alpha rays, beta rays, neutron beams, accelerated electron beams, and ultraviolet rays. Radiation also includes photon and fission-spectrum neutrons.

The polypeptides and polynucleotides of the present invention protect normal cells and tissues from the effects of cytotoxic agents, such as radiation and chemotherapeutics, described herein.

Exemplary chemotherapeutic agents are vinca alkaloids, epipodophyllotoxins, anthracycline antibiotics, actinomycin D, plicamycin, puromycin, gramicidin D, paclitaxel (Taxol®, Bristol Myers Squibb), colchicine, cytochalasin B, emetine, maytansine, and amsacrine (or "mAMSA"). The vinca alkaloid class is described in *Goodman and Gilman's The Pharmacological Basis of Therapeutics* ($7^{th}$ ed.), (1985), pp. 1277–1280. Exemplary of vinca alkaloids are vincristine, vinblastine, and vindesine. The epipodophyllotoxin class is described in *Goodman and Gilman's The Pharmacological Basis of Therapeutics* ($7^{th}$ ed.), (1985), pp. 1280–1281. Exemplary of epipodophyllotoxins are etoposide, etoposide orthoquinone, and teniposide. The anthracycline antibiotic class is described in *Goodman and Gilman's The Pharmacological Basis of Therapeutics* ($7^{th}$ ed.), (1985), pp. 1283–1285. Exemplary of anthracycline antibiotics are daunorubicin, doxorubicin, mitoxantraone, and bisanthrene. Actinomycin D, also called Dactinomycin, is described in *Goodmand and Gilman's The Pharmacological Basis of Therapeutics* ($7^{th}$ ed.), (1985), pp. 1281–1283. Plicamycin, also called mithramycin, is described in *Goodmand and Gilman's The Pharmacological Basis of Therapeutics* ($7^{th}$ ed), (1985), pp.1287–1288. Additional chemotherapeutic agents include cisplatin (Platinol®, Bristol Myers Squibb), carboplatin (Paraplatin®, Bristol Myers Squibb), mitomycin (Mutamycin®, Bristol Myers Squibb), altretamine (Hexalen®, U.S. Bioscience, Inc.), cyclophosphamide (Cytoxan®, Bristol Myers Squibb), lomustine (CCNU) (CeeNU®, Bristol Myers Squibb), carmustine (BCNU) (BiCNU®, Bristol Myers Squibb).

Additional therapeutic agents which may be administered in combination with polynucleotides and polypeptides of the invention also include aclacinomycin A, aclarubicin, acronine, acronycine, adriamycin, aldesleukin (interleukin-2), altretamine (hexamiethylmelamine), aminoglutethimide, aminoglutethimide (cytadren), aminoimidazole carboxamide, amsacrine (m-AMSA; amsidine), anastrazole (arimidex), ancitabine, anthracyline, anthramycin, asparaginase (elspar), azacitdine, azacitidine (ladakamycin), azaguanine, azaserine, azauridine, 1,1',1"-phosphinothioylidynetris aziridine, azirino(2', 3':3,4)pyrrolo (1,2-a)indole-4,7-dione, BCG (theracys), BCNU, BCNU chloroethyl nitrosoureas, benzamide, 4-(bis(2-chloroethyl) amino)benzenebutanoic acid, bicalutamide, bischloroethyl nitrosourea, bleomycin, bleomycin (blenozane), bleomycins, bromodeoxyuridine, broxuridine, busulfan (myleran), carbamic acid ethyl ester, carboplatin, carboplatin (paraplatin), carmustine, carmustine (BCNU; BiCNU), chlorambucil (leukeran), chloroethyl nitrosoureas, chorozotocin (DCNU), chromomycin A3, cis-retinoic acid, cisplatin (cis-ddpl; platinol), cladribine (2-chlorodeoxyadenosine; 2cda; leustatin), coformycin, cycloleucine, cyclophosphamide, cyclophosphamide anhydrous, chlorambucil, cytarabine, cytarabine, cytarabine HCl (cytosar-u), 2-deoxy-2-(((methylnitrosoamino)carbonyl) amino)-D-glucose, dacarbazine, dactinomycin (cosmegen), daunorubicin, Daunorubincin HCl (cerubidine), decarbazine, decarbazine (DTIC-dome), demecolcine, dexamethasone, dianhydrogalactitol, diazooxonorleucine, diethylstilbestrol, docetaxel (taxotere), doxorubicin HCl (adriamycin), doxorubicin hydrochloride, eflomithine, estramustine, estramustine phosphate sodium (emcyt), ethiodized oil, ethoglucid, ethyl carbamate, ethyl methanesulfonate, etoposide (VP16–213), fenretinide, floxuridine, floxuridine (fudr), fludarabine (fludara), fluorouracil (5-FU), fluoxymesterone (halotestin), flutamide, flutamide (eulexin), fluxuridine, gallium nitrate (granite), gemcitabine (gemzar), genistein, 2-deoxy-2-(3-methyl-3-nitrosoureido)-D-glucopyranose, goserelin (zoladex), hexestrol, hydroxyurea (hydra), idarubicin (idamycin), ifosfagemcitabine, ifosfamide (iflex), ifosfamide with mesna (MAID), interferon, interferon alfa, interferon alfa-2a, alfa-2b, alfa-n3, interleukin-2, iobenguane, iobenguane iobenguane, irinotecan (camptosar), isotretinoin (accutane), ketoconazole, 4-(bis(2-chloroethyl)amino)-L-phenylalanine, L-serine diazoacetate, lentinan, leucovorin, leuprolide acetate (LHRH-analog), levamisole (ergamisol), lomustine (CCNU; cee-NU), mannomustine, maytansine, mechlorethamine, mechlorethamine HCl (nitrogen mustard), medroxyprogesterone acetate (provera, depo provera), megestrol acetate (menace), melengestrol acetate, melphalan (alkeran), menogaril, mercaptopurin, mercaptopurine (purinethol), mercaptopurine anhydrous, MESNA, mesna (mesne), methanesulfonic acid, ethyl ester, methotrexate (mtx; methotrexate), methyl-ccnu, mimosine, misonidazole, mithramycin, mitoantrone, mitobronitol, mitoguazone, mitolactol, mitomycin (mutamycin), mitomycin C, mitotane (o,p'-DDD; lysodren), mitoxantrone, mitoxantrone HCl (novantrone), mopidamol, N,N-bis(2-chloroethyl)tetrahydro-2H-1,3,2-oxazaphosphorin-2-amine-2-oxide, N-(1-methylethyl)-4-((2-methylhydrazino)methyl) benzamide, N-methyl-bis(2-chloroethyl)amine, nicardipine, nilutamide (nilandron), nimustine, nitracrine, nitrogen mustard, nocodazole, nogalamycin, octreotide (sandostatin), pacilataxel (taxon), paclitaxel, pactamycin, pegaspargase (PEGx-1), pentostatin (2'-deoxycoformycin), peplomycin, peptichemio, photophoresis, picamycin (mithracin), picibanil, pipobroman, plicamycin, podofilox, podophyllotoxin, porfiromycin, prednisone, procarbazine, procarbazine HCl (matulane), prospidium, puromycin, puromycin aminonucleoside, PUVA (psoralen+ultraviolet a), pyran copolymer, rapamycin, s-azacytidine, 2,4,6-tris(1-aziridinyl)-s-triazine, semustine, showdomycin, sirolimus, streptozocin (zanosar), suramin, tamoxifen citrate (nolvadex), taxon, tegafur, teniposide (VM-26; vumon), tenuazonic acid, TEPA, testolactone, thio-tepa, thioguanine, thiotepa (thioplex), tilorone, topotecan, tretinoin (vesanoid), triaziquone, trichodermin, triethylene glycol diglycidyl ether, triethylenemelamine, triethylenephosphoramide, triethylenethiophosphoramide, trimetrexate (neutrexin), tris (1-aziridinyl)phosphine oxide, tris(1-aziridinyl)phosphine sulfide, tris(aziridinyl)-p-benzoquinone, tris(aziridinyl) phosphine sulfide, uracil mustard, vidarabine, vidarabine phosphate, vinblastine, vinblastine sulfate (velban), vincristine sulfate (oncovin), vindesine, vinorelbine, vinorelbine tartrate (navelbine), (1)-mimosine, 1-(2-chloroethyl)-3-(4-methylcyclohexyl)-1-nitrosourea, (8S-cis)-10-((3-amino-2, 3,6-trideoxy-alpha-L-lyxo-hexopyranosyl)oxy)-7,8,9,10-tetrahydro-6,8, 11-trihydroxy-8-(hydroxyacetyl)-1-methoxy-5,12-naphthacenedione, 131-meta-iodobenzyl guanidine (I-131 MIBG), 5-(3,3-dimethyl-1-triazenyl)-1H-imidazole-4-carboxamide, 5-(bis(2-chloroethyl)amino)-2,4 (1H,3H)-pyrimidinedione, 2,4,6-tris(1-aziridinyl)-s-thiazine, 2,3,5-tris(1-aziridinyl)-2,5-cyclohexadiene-1,4-dione, 2-chloro-N-(2-chloroethyl)-N-methylethanamine, N,N-bis(2-chloroethyl)tetrahydro-2H-1,3,2-oxazaphosphorin-2-amine-2-oxide, 3-deazauridine, 3-iodobenzylguanidine, 5,12-naphthacenedione, 5-azacytidine, 5-fluorouracil, (1aS,8S,8aR,8bS)-6-amino-8-(((aminocarbonyl)oxy)methyl)-1,1a, 2,8,8a,8b-hexahydro-8a-methoxy-5-methylazirino(2',3':3,4)pyrrolo(1,2-a)indole-4,7-dione, 6-azauridine, 6-mercaptopurine, 8-azaguanine, and combinations thereof.

Preferred therapeutic agents and combinations that may be administered in combination with polynucleotides and polypeptides of the invention include Doxorubicin and Doxetaxel, Topotecan, Paclitaxel, Carboplatin and Taxol, Taxol, Cisplatin and Radiation, 5-fluorouracil (5-FU), 5-FU and Radiation, Toxotere, Fludarabine, Ara C, Etoposide, Vincristine, and Vinblastin.

Exemplary chemotherapeutic agents also include doxetaxel (Toxotere®) and to potecan (Hycamtin®). Additional chemotherapeutic agents and other cytotoxic agents include those described below under "Pharmaceutical Compositions."

Additional chemotherapeutic agents and other cytotoxic agents include those described below under "Epitopes and Antibodies" and elsewhere herein, and others which are well-known in the art.

Polynucleotides and polypeptides of the invention may be used prophylactically and/or therapeutically for radiation damage.

Polynucleotides and polypeptides of the invention, administered prophylactically or therapeutically for the protection of cells, tissues, and organs against low, moderate, or high doses of radiation, would protect human or animal individuals and populations from damage due to radiation exposure. Such damage includes gastrointestinal system disorders, weight loss, radiation sickness, radiation burns, endocrine disorders, goiter, diseases of the eye such as dry eye syndrome, inflammatory diseases, psychological disorders, respiratory system disorders, genitourinary system disorders, circulatory system disorders, and cancers such as leukemia and thyroid carcinoma, as well as other disorders well-known in the art. Damage due to radiation exposure includes damage to cells and tissue such as those described above, damage to cellular DNA, disruption in cellular function such as by disrupting DNA function, cell death, cancer induction including therapy-induced secondary tumor induction and other cancer induction.

The proliferation of nuclear weapons and incidence of nuclear testing is on the increase in some areas of the world. Additionally, the use of nuclear power generation and the development of industries such as nuclear fuel treatment and dismantling of nuclear weapons has increased the risk of radiation exposure. For example, during the past 50 years four major industrial radioactive accidents were reported in Kistym (USSR) and Wind-Scale (England) in 1957, Three Mile Island (USA) in 1979 and in Chernobyl (USSR) in 1986. These releases of radiation resulted in widespread exposure to various levels of radioactivity. Due to the accident at the nuclear plant in Chernobyl, inhabitants and animals such as domestic animals in and outside of the region have undergone serious effects.

In the early 1950s it was found that cysteamine and related aminoalkyl thiols could protect organisms against radiation. In particular, when these substances were given to mice prior to exposure to x-rays, the substances reduced the lethal effect of the x-ray radiation. The search is underway to discover better radiation protecting agents. For example, amifostine and other aminoalkyl dihydrogen phosphorothioates (U.S. Pat. No. 3,892,824) were originally developed as protective agents, in particular to be used against x-ray or nuclear radiation which may be encountered during military conflicts. The most promising agent was amifostine (WR 2721 (S-2(3-aminopropylamino)-ethyl-phosphorothioic acid)), which breaks down in the body to an aminoalkyl thiol, and its effect is similar to that of cysteamine. However, the use of WR 2721 has been limited by poor clinical tolerance (Cairnie, *Radiation Res.* 94:221 (1983); Turrisi et al., in *Radioprotectors and Anticarcinogens*, Nygaard and Simic, Eds., Academic Press, New York, p.681–694 (1983); Blumberg, *Int. J. Radiation Oncology Biol. Phys.* 8:561 (1982)).

The present invention provides a method for protecting against radiation-induced damage which is be amenable to pre- and/or concurrent and/or post-radiation administration, and which is effective at relatively low non-toxic concentrations so as to allow use in mammals such as humans and also allows for multiple, as well as single, administrations, as described below.

As discussed above, polypeptides and polynucleotides of the invention protect, ameliorate, and treat cells, tissues, and organs from damage due to radiation or other cytotoxic agents, and increase the survival of individuals exposed to cytotoxic agents such as radiation. Polypeptides and polynucleotides of the invention, administered prior to, during, and/or after exposure, would eliminate or reduce the severity of damage caused by radiation.

Radiation exposure could be as a result of, for example, accidental, intentional, internal, external, occupational, environmental exposure, radon, nuclear contamination, and includes radiation released by, for example, a nuclear explosion, a nuclear accident, or a solar flare. Such exposure could occur, for example, in nuclear power industry workers, in military personnel, in civilians, in emergency personnel, in survivors of nuclear explosions and nuclear accidents, in workers in the health care field, in patients, and in astronauts. Polynucleotides and polypeptides of the invention may also be useful in providing treatment or protection against other sources of radiation such as may be encountered by emergency personnel, civilians, or military personnel, or by space travelers.

Thus, polynucleotides and polypeptides of the invention may be administered prophylactically and/or therapeutically to prevent, reduce, or treat damage due to radiation exposure.

The present invention provides a method for protecting or treating an individual from damage due to radiation comprising administering to the individual an effective amount of polypeptides or polynucleotides of the invention. Polypeptides and polynucleotides of the invention are protective agents against damage due to radiation, and can be administered prior to, during and/or subsequent to the radiation exposure. As described above and below, protective agents such as polynucleotides and polypeptides of the invention are useful in prophylactic and therapeutic methods of treatment.

Polypeptides and polynucleotides of the invention are useful for prophylactic and therapeutic treatment of individuals who are likely to be exposed to radiation such as workers in the nuclear power industry, military personnel, astronauts, workers in the medical field who are engaged in diagnostic and therapeutic methods involving radiation, or patients who have to be exposed to radiation for the purpose of diagnosis or treatment. As described elsewhere herein, polypeptides and polynucleotides of the invention are also useful as an adjunct in the radiotherapy of cancer in which the polypeptides or polynucleotides will selectively protect normal tissue allowing the cancerous tissue to be destroyed by the radiation therapy.

Therefore, polypeptides or polynucleotides of the invention may be administered prophylactically or therapeutically to individuals at risk of exposure to radiation. Prophylactic use will prevent or reduce possible radiation damage, and therapeutic use will treat or reduce present damage and slow, reduce, or prevent additional damage.

The effective amount should be understood as an amount of polypeptides or polynucleotides of the invention which is sufficient to achieve the desired effect. Such effect may be a prophylactic effect or a therapeutic effect or both. The effective amount depends on various factors including the type and amount of radiation to which the individual is exposed, and on the administration regimen, etc., as is well known in the art or described below. For example, dosages are those as described below and throughout the specification.

The polypeptides of the present invention have been shown to protect the gastrointestinal tract during treatment with chemotherapeutic agents and radiation. (See Examples 16–18.) Furthermore, the polypeptides of the present invention have been shown to reduce radiation induced damage in the gastrointestinal tract when administered after irradiation. (See Examples 16–18.) Thus, the polypeptides of the present invention may be employed to protect epithelium. "Epithelium" refers to the covering of internal and external surfaces of the body, including the lining of vessels and other small cavities. It consists of cells joined by small amounts of cementing substances. Epithelium is classified into types on the basis of the number of layers deep and the shape of the superficial cells. Epithelial cells include anterius corneae, Barrett's epithelium, capsular epithelium, ciliated epithelium, columnar epithelium, corneal epithelium, cubical epithelium, epithelium ductus semicircularis, enamel epithelium, false epithelium, germinal epithelium, gingival epithelium, glandular epithelium, glomerular epithelium, laminated epithelium, epithelium of the lend, mesenchymal epithelium, olfactory epithelium, pavement epithelium, pigmentary epithelium, protective epithelium, pseudostratified epithelium, pyramidal epithelium, respiratory epithelium, rod epithelium, seminiferous epithelium, sensory epithelium, simple epithelium, squamous epithelium, stratified epithelium, subcapsular epithelium, sulcular epithelium, tessellated epithelium, transitional epithelium, and epithelial cells of the eye, tongue, glands, oral mucosa, duodenum, ileum, jejunum, cecum, nasal passages, esophagus, colon, mammary glands, and the female and male reproductive systems.

"Glands" refer to an aggregation of cells, specialized to secrete or excrete materials not related to their ordinary metabolic needs. Examples of glands which may include epithelial cells include: absorbent clangs, accessory glands, acinar glands, acid glands, admaxillary glands, adrenal glands, aggregate glands, Albarran's gland, anal glands, alveolar glands, antepro static glands, aortic glands, apical glands of the tongue, apocrine glands, areolar glands, arterial glands, arteriococcygeal glands, arytenoid glands, Aselli's glands, Avicenna's glands, atribiliary gland, axillary glands, Bartholin's glands, Bauhin's glands, Baumgarten's glands, glands of the biliary mucosa, Blandin's glands, blood vessel glands, Boerhaave's glands, Bonnot's glands, Bowman's glands, brachial glands, bronchial glands, Bruch's glands, Brunner's glands, buccal glands, bulbocavernous glands, cardiac glands, carotid glands, celiac glands, ceruminous glands, cervical glands of the uterus, choroid glands, Ciaccio's glands, ciliary glands of the conjunctiva, circumanal glands, Cloquet's glands, Cobelli's glands, coccygeal glands, coil glands, compound glands, conglobate gland, conjunctival glands, Cowper's gland, cutaneous glands, cytogenic glands, ductless glands, duodenal glands, Duverney's gland, Ebner's gland, eccrine glands, Eglis' glands, endocrine glands, endoepithelial glands, esophageal glands, excretory glands, exocrine glands, follicular glands of the duct, fundus glands, gastric glands, gastroepiploic glands, glands of Gay, genital glands, gingival glands, Gley's glands, globate glands, glomerate glands, glossopalatine glands, Guerin's glands, guttural glands, glands of Haller, Harder's glands, haversian glands, hedonic glands, hemal glands, hemal lymph glands, hematopoietic glands, hemolymph glands, Henle's glands, hepatic glands, heterocrine glands, hibernating glands, holocrine glands and incretory glands.

Further examples of glands include intercarotid glands, intermediate glands, interscapular glands, interstitial glands, intestinal glands, intraepithelial glands, intramuscular glands of the tongue, jugular gland, Krause's glands, labial glands of the mouth, lacrimal glands, accessory lacrimal glands, lactiferous gland, glands of the large intestine, large sweat glands, laryngeal glands, lenticular glands of the stomach and tongue, glands of Lieberkuhn, lingual glands, anterior lingual glands, Littre's glands, Luschka's gland, lymph glands, extraparotid lymph glands, malar glands, mammary glands, accessory mammary glands, mandibular glands, Manz' glands, Mehlis' glands, meibomian glands, merocrine glands, mesenteric glands, mesocolic glands, mixed glands, molar glands, Moll's glands, monoptyphic glands, Montgomery's glands, Morgagni's glands, glands of the mouth, mucilaginous glands, muciparous glands, mucous glands, lingual mucous glands, mucous glands of the auditory tube, mucous glands of the duodenum, mucous glands of the eustachian tube, multicellular glands, myometrial glands, Naboth's glands, nabothian glands, nasal glands, glands of the neck, odoriferous glands of the prepuce, oil glands, olfactory glands, oxyntic glands, pacchionian glands, palatine glands, pancreaticosplenic glands, parafrenal glands, parathyroid glands, parurethral glands, parotid glands, accessory parotid glands, pectoral glands, peptic glands, perspiratory glands, Peyre's glands, pharyngeal glands, Philip's glands, pineal glands, and pituitary.

Other examples of glands include Poirier's glands, polyptychich glands, preen gland, pregnancy glands, prehyoid glands, preputial glands, prostate gland, puberty glands, pyloric glands, racemose glands, retrolingual glands, retromolar glands, Rivinus gland, Rosenmuller gland, saccular gland, salivary glands, abdominal salivary glands, external salivary glands, internal salivary glands, Sandstrom's glands, Schuller's glands, sebaceous glands, sebaceous glands of the conjunctiva, sentinal glands, seromucous glands, serous glands, Serres' glands, Sigmunds glands, Skene's glands, simple gland, glands of the small intestine, solitary glands of the large intestine, splenoid gland, Stahr's gland, staplyline glands, subauricular glands, sublingual glands, submandibular glands, suboriferous glands, suprarenal glands, accessory suprarenal glands, Suzanne's gland, sweat glands, synovial glands, tarsal glands, Theile's glands, thymus gland, thyroid gland, accessory thyroid glands, glands of the tongue, tracheal glands, tachoma glands, tubular glands, tubuloacinar glands, tympanic glands, glands of Tyson, unicellular glands, urethral glands, urethral glands of the female urethra, uropygial gland, uterine glands, utricular glands, vaginal glands, vascular glands, vestibular glands (greater and lesser), Virchow's gland, vitelline gland, bulbovaginal gland, Waldeyer's glands, Weber's glands, glands of Wolfring, glands of Zeis and Zuckerkandl's glands.

Additional examples of glands include albuminous glands, agminate glands, auditory tube glands, axillary sweat glands, bulbourethral glands, cardiac glands of the esophagus, glands of the eustachian tube, follicular glands, Galeati's glands, genal glands, Harver's glands, inguinal glands, interrenal glands, Knoll's gland, Luschka's cystic gland, malpighian glands, marrow-lymph glands, master glands, maxillary gland, Mery's glands, Nuhn's glands, palpebral glands, peritracheal glands, pileus glands, seminal glands, submaxillary gland, sudoriferous glands, suprahyoid gland, Terson's glands, Tiedemann's gland, tubuloalveolar gland, thachoma glands, vulvovaginal glands, Wasmann's glands, Wepfer's glands and Wolfer's gland.

Thus, MPIF-1 may be employed to protect any of these cells or cells within these glands.

MPIF-1 may be used to protect or reduce cytotoxic agent-induced injury in muscle cells such as cardiac muscle cells, skeletal muscle cells and smooth muscle cells; epithelial cells such as squamous epithelial cells, including endothelial cells, cuboid epithelial cells and columnar epithelial cells; nervous tissue cells such as neurons and neuroglia. MPIF-1 also may be used to protect or reduce cytotoxic agent-induced injury to muscle tissue, nervous tissue, epithelial tissue, endothelial tissue and connective tissue.

Further, MPIF-1 may be used to protect or reduce cytotoxic agent-induced injury to dividing cells, non dividing cells, terminally differentiated cells, pluripotent stem cells, committed progenitor cells and uncommitted stem cells.

Thus, MPIF-1 may be used to treat damage to nervous system cells such as: neurons, including cortical neurons, inter neurons, central effector neurons, peripheral effector neurons and bipolar neurons; and neuroglia, including Schwann cells, oligodendrocytes, astrocytes, microglia and ependyma.

Additionally, endocrine and endocrine-associated cells may also be treated or protected from cytotoxic agents using MPIF-1, such cells as: pituitary gland cells including epithelial cells, pituicytes, neuroglia, agranular chromophobes, granular chromophils (acidophils and basophils); adrenal gland cells including epinephrine-secreting cells, non-epinephrine-secreting cells, medullary cells, cortical cells (cells of the glomerulosa, fasciculata and reticularis); thyroid gland cells including epithelial cells (principal and parafollicular); parathyroid gland cells including epithelial cells (chief cells and oxyphils); pancreas cells including cells of the islets of Langerhans (alpha, beta and delta cells); pineal gland cells including parenchymal cells and neuroglial cells; thymus cells including parafollulicular cells; cells of the testes including seminiferous tubule cells, interstitial cells ("Leydig cells"), spermatogonia, spermatocytes (primary and secondary), spermatids, spermatozoa, Sertoli cells and myoid cells; cells of the ovary including ova, oogonia, oocytes, granulosa cells, theca cells (internal and external), germinal epithelial cells and follicle cells (primordial, vesicular, mature and atretic).

MPIF-1 may be used to treat cytotoxic-agent induced injury of muscle cells such as myofibrils, intrafusal fibers and extrafusal fibers. MPIF-1 may be used to treat cytotoxic-agent induced injury of skeletal system cells such as osteoblasts, osteocytes, osteoclasts and their progenitor cells.

Circulatory system cells may also be treated or protected from cytotoxic agents using MPIF-1, such cells as: heart cells (myocardial cells); cells of the blood and lymph including erythropoietin-sensitive stem cells, erythrocytes, leukocytes (such as eosinophils, basophils and neutrophils (granular cells) and lymphocytes and monocytes (agranular cells)), thrombocytes, tissue macrophages (histiocytes), organ-specific phagocytes (such as Kupffer cells, alveolar macrophages and microglia), B-lymphocytes, T-lymphocytes (such as cytotoxic T cells, helper T cells and suppressor T cells), megaloblasts, monoblasts, myeloblasts, lymphoblasts, proerythroblasts, megakaryoblasts, promonocytes, promyelocytes, prolymphocytes, early normoblasts, megakaryocytes, intermediate normoblasts, metamyelocytes (such as juvenile metamyelocytes, segmented metamyelocytes and polymorphonuclear granulocytes), late normoblasts, reticulocytes and bone marrow cells.

Respiratory system cells such as capillary endothelial cells and alveolar cells may also be treated with MPIF-1 to reduce or prevent cytotoxic agent-induced damage. Urinary system cells such as nephrons, capillary endothelial cells, granular cells, tubule endothelial cells and podocytes may also be treated or protected. Digestive system cells may also be treated or protected using MPIF-1, such as: simple columnar epithelial cells, mucosal cells, acinar cells, parietal cells, chief cells, zymogen cells, peptic cells, enterochromaffin cells, goblet cells, Argentaffen cells and G cells. Sensory cells such as: auditory system cells (hair cells); olfactory system cells including olfactory receptor cells and columnar epithelial cells; equilibrium/vestibular apparatus cells including hair cells and supporting cells; visual system cells including pigment cells, epithelial cells, photoreceptor neurons (rods and cones), ganglion cells, amacrine cells, bipolar cells and horizontal cells may be treated with MPIF-1 to prevent or reduce cytotoxic damage.

Additionally, mesenchymal cells, stromal cells, hair cells/follicles, adipose (fat) cells, cells of simple epithelial tissues (squamous epithelium, cuboidal epithelium, columnar epithelium, ciliated columnar epithelium and pseudostratified ciliated columnar epithelium), cells of stratified epithelial tissues (stratified squamous epithelium (keratinized and non-keratinized), stratified cuboidal epithelium and transitional epithelium), goblet cells, endothelial cells of the mesentery, endothelial cells of the small intestine, endothelial cells of the large intestine, endothelial cells of the vasculature capillaries, endothelial cells of the microvasculature, endothelial cells of the arteries, endothelial cells of the arterioles, endothelial cells of the veins, endothelial cells of the venules, etc., and endothelial cells of the bladder may be treated with MPIF-1 to reduce or prevent cytotoxic damage.

MPIF-1 also protects and treats cytoxic damage in cells of connective tissue such as loose connective (areolar) tissue including the dermis, dense fibrous connective tissue, elastic connective tissue, reticular connective tissue and adipose connective tissue. Cells of the connective tissue that are also protected by and treatable with MPIF-1 include chondrocytes, adipose cells, periosteal cells, endosteal cells, odontoblasts, osteoblasts, osteoclasts and osteocytes.

MPIF-1 also protects endothelial cells, hepatocytes, keratinocytes and basal keratinocytes, muscle cells, cells of the central and peripheral nervous systems, prostate cells, and lung cells.

MPIF-1 will also protect epithelial cells in the lung, breast, pancreas, stomach, small intestine, and large intestine. MPIF-1 can protect epithelial cells such as sebocytes, hair follicles, hepatocytes, type II pneumocytes, mucin-producing goblet cells, and other epithelial cells and their progenitors contained within the skin, lung, liver, and gastrointestinal tract.

MPIF-1 protects hepatocytes, thus MPIF-1 can be used prophylactically or therapeutically to prevent or attenuate acute or chronic hepatitis as well as fulminant or subfulminant liver failure caused by cancer therapy (e.g, chemotherapy and/or radiation therapy) and environmental or accidental radiation exposure.

MPIF-1 can also be used to reduce the side effects of gut toxicity that result from treatment with cytotoxic agents, such as radiation or chemotherapy. MPIF-1 has a cytoprotective effect on the small intestine mucosa. MPIF-1 may also be used prophylactically or therapeutically to prevent or attenuate mucositis and to reduce mucositis (e.g., oral, esophageal, intestinal, colonic, rectal, and anal ulcers) that results from chemotherapy and other cytotoxic agents.

Inflamamatory bowel diseases, such as Crohn's disease and ulcerative colitis, are diseases which result in destruction of the mucosal surface of the small or large intestine, respectively. Thus, MPIF-1 could be used to promote the resurfacing of the mucosal surface to aid more rapid healing and to prevent progression of inflammatory bowel disease. MPIF-1 treatment is expected to have a significant effect on the production of mucus throughout the gastrointestinal tract and could be used to protect the intestinal mucosa from cytotoxic agents. Thus the present invention also provides a method for preventing or treating diseases or pathological events of the mucosa, including ulcerative colitis, Crohn's disease, and other diseases where the mucosa is damaged, comprising the administration of an effective amount of MPIF-1. The present invention similarly provides a method for preventing or treating oral (including odynophagia associated with mucosal injury in the pharynx and hypopharynx), esophageal, gastric, intestinal, colonic and rectal mucositis caused by cytotoxic agents.

Moreover, MPIF-1 can be used to prevent and reduce damage to the lungs due to various agents. MPIF-1 could prevent or treat damage of alveoli and brochiolar epithelium. For example, inhalation injuries, i.e., resulting from smoke inhalation and radiation injury, that cause necrosis of the bronchiolar epithelium and alveoli could be effectively treated with MPIF-1. Also, MPIF-1 could be used to protect type II pneumocytes.

MPIF-1 may be clinically useful in treating or preventing damage of the dermis and epidermis, eye tissue, dental tissue, oral cavity and complications associated with systemic or local treatment with radiation therapy and antineoplastic drugs. MPIF-1 can also be used to treat dermal loss.

MPIF-1 can also be used to reduce the side effects of gut toxicity that result from radiation, chemotherapy or other cytotoxic treatments. MPIF-1 has a cytoprotective effect on the small intestine mucosa. MPIF-1 may also be used prophylactically or therapeutically to prevent or attenuate mucositis and to treat mucositis (e.g., oral, esophageal, intestinal, colonic, rectal, and anal ulcers) that results from chemotherapy, radiation and other cytotoxic agents. Thus, the present invention also provides a method for preventing or treating diseases or pathological events of the mucosa, including ulcerative colitis, Crohn's disease, and other diseases where the mucosa is damaged, comprising the administration of an effective amount of MPIF-1. The present invention similarly provides a method for preventing or treating oral (including odynophagia associated with mucosal injury in the pharynx and hypopharynx), esophageal, gastric, intestinal, colonic and rectal mucositis irrespective of the agent or modality causing this damage.

In addition, MPIF-1 could be used to treat and/or prevent blisters and bums due to chemicals; injury of the ovary due to treatment with chemotherapeutics, for example, radiation- or chemotherapy-induced cystitis, and high-dose chemotherapy-induced intestinal injury.

MPIF-1 can be used to prevent or reduce nephrotoxicity induced by chemotherapeutic agents, radiation or other cytotoxic agents.

The present invention also provides a method for protecting an individual from the effects of radiation, chemotherapy, or treatment with other cytotoxic agents comprising the administration of an effective amount of MPIF-1. The present invention further provides a method for reducing or preventing tissue damage which results from exposure to radiation, chemotherapeutic agents, or other cytotoxic agents comprising the administration of an effective amount of MPIF-1. An individual may be exposed to radiation for a number of reasons, including for therapeutic purposes (e.g., for the treatment of hyperproliferative disorders), as the result of an accidental release of a radioactive isotope into the environment, or during invasive or non-invasive medical diagnostic procedures (e.g., X-rays). Further, a substantial number of individuals are exposed to radioactive radon in their work places and homes. Long-term continuous environmental exposure has been used to calculate estimates of lost life expectancy. Johnson, W. and Kearfott, K., *Health Phys.* 73:312–319 (1997). As shown in Examples 17–18, the proteins of the present invention enhance the survival of animals exposed to radiation. Thus, MPIF-1 can be used to increase survival rate of individuals suffering radiation-induced injuries, to protect individuals from sub-lethal doses of radiation, and to increase the therapeutic ratio of irradiation in the treatment of afflictions such as hyperproliferative disorders.

MPIF-1 may also be used to protect individuals against dosages of radiation, chemotherapeutic drugs or other cytotoxic agents which normally would not be tolerated. When used in this manner, or as otherwise described herein, MPIF-1 may be administered prior to, after, and/or during radiation therapy/exposure, chemotherapy, or treatment with/exposure to other cytotoxic agents. High dosages of radiation and chemotherapeutic agents may be especially useful when treating an individual having an advanced stage of an affliction such as a hyperproliferative disorder.

In another aspect, the present invention provides a method for preventing or treating conditions such as radiation-induced oral and gastrointestinal injury, mucositis, intestinal fibrosis, proctitis, radiation-induced pulmonary fibrosis, radiation-induced pneumonitis, radiation-induced pleural retraction, radiation-induced hemopoietic syndrome and radiation-induced myelotoxicity, comprising administering an effective amount of MPIF-1 to an individual.

Thus, MPIF polynucleotides or polypeptides of the invention are used to inhibit normal cell damage, including damage to bone marrow progenitors, during radiation therapy, chemotherapy, and targeted radiotherapy such as radioimmunotherapy of malignancies, metastases, and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, gastric cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma. Such disorders also include metastatic medullary thyroid cancer, anaplastic astrocytoma, glioblastoma, follicular lymphomas, colon cancer, cardiac tumors, lung cancer, intestinal cancer, testicular cancer, stomach cancer, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer. Additional disorders that may be treated using the polypeptides, polypeptide fragments and variants, agonists and antagonists (including antibodies) and other antibodies of the invention are well known in the art and may also be disclosed herein.

MPIF-1 may be used alone or in conjunction with one or more additional agents which confer protection against radiation or other agents. A number of cytokines (e.g., IL-1, TNF, IL-6, IL-12) have been shown to confer such protection. See, e.g., Neta, R. et al., *J. Exp. Med.* 173:1177 (1991). Additionally, IL-11 has been shown to protect small intestinal mucosal cells after combined irradiation and chemotherapy, Du, X.X. et al., *Blood* 83:33 (1994), and radiation-induced thoracic injury. Redlich, C. A. et al., *J. Immun.* 157:1705–1710 (1996). Several growth factors have also been shown to confer protection to radiation exposure, e.g., fibroblast growth factor and transforming growth factor beta-3. Ding, I. et al., *Acta Oncol.* 36:337–340 (1997); Potten, C. et al., *Br. J. Cancer* 75:1454–1459 (1997).

Additional radiation protecting agents that may be administered with polypeptides and polynucleotides of the invention include calcium antagonists (WO 93/02670), polyethylene glycol (U.S. Pat. No. 4,676,979), polyvinylpyrrolidone (U.S. Pat. No. 4,676,979), polyethyleneglycolmonomethylether (U.S. Pat. No. 4,676,979), amides and amines and salts of methoxypolyethylene glycols and chelating agents such as EDTA, DTPA, and EGTA (WO 98/47858), manganese and othermetallothionein-inducing substances (U.S. Pat. No. 5,008,119), WR-2721 (U.S. Pat. No. 5,424,471), WR-1065, other phosphorothioates (U.S. Pat. No. 5,869,338), polyamide thiols (U.S. Pat. No. 5,217,964), SCF/IL-3/GM-CSF combination or single therapeutic regimens (U.S. Pat. No. 5,620,685), beta carotene and Dunaliella algae preparations (U.S. Pat. No. 5,948, 823), phosphorous derivatives of alkaloids (U.S. Pat. No. 5,981,512), thymalin and L-Glu-L-Trp (U.S. Pat. No. 5,770, 576), cytokines such as IL-1, tumor necrosis factor, stem cell factor and IL-12 (Neta, *Stem Cells* 15(Suppl 2):207–10 (1997)), copper chelates (Sorenson et al., *Proc. Soc. Exp. Biol. Med.* 210:191–204 (1995)), D-factor/growth hormone/IL-1/tumor necrosis factor combination or single therapeutic regimens (U.S. Pat. No. 5,843,422), Actihaemyl (CAS RN No. 37239-28-4), Amifostine (WR2721), 2-aminoethanethiol dihydrogen phosphate (ester) monosodium salt (cystaphos, phosphocysteamine), 3-(bis(2-chloroethyl) carbamate) estradiol (estramustine), 2-amino-ethanethiol (cysteamine), 2,2'-dithiobis(ethylamine) (cystamine), S-2-aminoethylthiouronium bromide hydrobromide (AET), copper chelates such as Cu(II)2(3,5-diisopropylsalicylate)4 (Cu (II)2(3,5,-DIPS)4), essential metalloelement chelates of Fe, Mn, and Zn (Sorenson et al., *Proc. Soc. Exp. Biol. Med.* 210:191–204 (1995), 2-(allylthio) pyrazine, phosphorus derivatives of alkaloids (Austrian Patent Nos. 377 988 and 354 644; U.S. Pat. No. 5,981,512), etc., and combinations thereof.

Polynucleotides and polypeptides of the invention may also be administered with antiemetics such as 2-(ethylthio)-10-(3-(4-methyl-1-piperazinyl) propyl)-10H-phenothiazine (ethylthioperazine), 1-(p-chloro-alpha-phenylbenzyl)-4-(m-methylbenzyl)-piperazine (meclozine, meclizine), etc., and combinations thereof. Polynucleotides and polypeptides of the invention may also be administered with other therapeutic agents, and combinations thereof, disclosed herein or known in the art.

Hemorrhagic cystitis is a syndrome associated with certain disease states as well as exposure to drugs, viruses, and to xins. It manifests as diffuse bleeding of the endothelial lining of the bladder. Known treatments include intravesical, systemic, and nonpharmacologic therapies (West, N.J., *Pharmacotherapy* 17:696–706 (1997). Some cytotoxic agents used clinically have side effects resulting in the inhibition of the proliferation of the normal epithelial in the bladder, leading to potentially life-threatening ulceration and breakdown in the epithelial lining. For example, cyclophosphamide is a cytotoxic agent which is biotransformed principally in the liver into active alkylating metabolites by a mixed function microsomal oxidase system. These metabolites interfere with the growth of susceptible rapidly proliferating malignant cells. The mechanism of action is believed to involve cross-linking of tumor cell DNA (Physicians' Desk Reference, 1997).

Cyclophosphamide is one example of a cytotoxic agent which causes hemorrhagic cystitis in some patients, a complication which can be severe and in some cases fatal. Fibrosis of the urinary bladder may also develop with or without cystitis. This injury is thought to be caused by cyclophosphamide metabolites excreted in the urine. Hematuria caused by cyclophosphamide usually is present for several days, but may persist. In severe cases medical or surgical treatment is required. Instances of severe hemorrhagic cystitis result in discontinued cyclophosphamide therapy. In addition, urinary bladder malignancies generally occur within two years of cyclophosphamide treatment and occurs in patients who previously had hemorrhagic cystitis (See Cytoxan package insert). Cyclophosphamide has toxic effects on the prostate and male reproductive systems. Cyclophosphamide treatment can result in the development of sterility, and result in some degree of testicular atrophy.

One of ordinary skill will appreciate that effective amounts of the MPIF-1 polypeptides for treating an individual in need of an increased level of MPIF-1 activity (including amounts of MPIF-1 polypeptides effective for myelosuppression with or without myelosuppressive agents or myelosuppressive inhibitors) can be determined empirically for each condition where administration of MPIF-1 is indicated. The polypeptide having MPIF-1 activity my be administered in pharmaceutical compositions in combination with one or more pharmaceutically acceptable excipients.

MPIF-1 may also be employed to treat leukemia and abnormally proliferating cells such as tumor cells by inducing apoptosis. MPIF-1 induces apoptosis in a population of hematopoietic progenitor cells.

MPIF-1 may be employed for the expansion of immature hematopoietic progenitor cells such as granulocytes, macrophages or monocytes, by temporarily preventing their differentiation. These bone marrow cells may be cultured in vitro. Thus, MPIF-1 can also be useful as a modulator of hematopoietic stem cells in vitro for the purpose of bone marrow transplantation and/or gene therapy. Since stem cells are rare and are most useful for introducing genes into for gene therapy, MPIF can be used to isolate enriched populations of stem cells. Stem cells can be enriched by culturing cells in the presence of cytotoxins, such as 5-Fu, which kills rapidly dividing cells, where as the stem cells will be protected by MPIF-1. These stem cells can be returned to a bone marrow transplant patient or can then be used for transfection of the desired gene for gene therapy. In addition, MPIF-1 can be injected into individuals which results in the release of stem cells from the bone marrow of the individual into the peripheral blood. These stem cells can be isolated for the purpose of autologous bone marrow transplantation or manipulation for gene therapy. After the patient has finished chemotherapy or radiation treatment, the isolated stem cells can be returned to the patient.

In addition, since MPIF-1 has effects on T-lymphocytes as well as macrophages, MPIF-1 may enhance the capacity of antigen presenting cells (APCs) to take up virus, bacteria or other foreign substances, process them and present them to the lymphocytes responsible for immune responses. MPIF-1 may also modulate the interaction of APCs with T-lymphocytes and B-lymphocytes. MPIF-1 may provide a costimulatory signal during antigen presentation which directs the responding cell to survive, proliferate, differentiate, secrete additional cytokines or soluble mediators, or selectively removes the responding cell by inducing apoptosis or other mechanisms of cell death. Since APCs have been shown to facilitate the transfer of HIV to CD4+ T-lymphocytes, MPIF-1 may also influence this ability and prevent infection of lymphocytes by HIV or other viruses mediated through APCs. This is also true for the initial infection of APCs, T-lymphocytes or other cell types by HIV, EBV, or any other such viruses.

In addition, recent demonstration that the MIP-1α (receptor serves as a cofactor in facilitating the entry of HIV into human monocytes and T-lymphocytes raises an interesting possibility that MPIF-1 and its variants might interfere with the process of HIV entry into the cells. (See Example 11). Thus, MPIF-1 can be useful as an antiviral agent for viruses and retroviruses whose entry is facilitated by the MIP-1α receptor.

MPIF-1 may act as an immune enhancement factor by stimulating the intrinsic activity of T-lymphocytes to fight bacterial and viral infection as well as other foreign bodies. Such activities are useful for the normal response to foreign antigens such as infection of allergies as well as immunoresponses to neoplastic or benign growth including both solid tumors and leukemias.

For these reasons the present invention is useful for diagnosis or treatment of various immune system-related disorders in mammals, preferably humans. Such disorders include tumors, cancers, and any disregulation of immune cell function including, but not limited to, autoimmunity, arthritis, leukemias, lymphomas, immunosuppression, sepsis, wound healing, acute and chronic infection, cell mediated immunity, humoral immunity, inflammatory bowel disease, myelosuppression, and the like.

Accordingly, MPIF-1 can be used to facilitate wound healing by controlling infiltration of target immune cells to the wound area. In a similar fashion, the polypeptides of the present invention can enhance host defenses against chronic infections, e.g. mycobacterial, via the attraction and activation of microbicidal leukocytes.

The polypeptides of the present invention, and polynucleotides encoding such polypeptides, may be employed as research reagents for in vitro purposes related to scientific research, synthesis of DNA and manufacture of DNA vectors, and for the purpose of developing therapeutics and diagnostics for the treatment of human disease. For example, and MPIF-1 may be employed for the expansion of immature hematopoietic progenitor cells, for example, granulocytes, macrophages or monocytes, by temporarily preventing their differentiation. These bone marrow cells may be cultured in vitro.

Another use of the polypeptides is the inhibition of T-cell proliferation via inhibition of IL-2 biosynthesis, for example, in auto-immune diseases and lymphocytic leukemia.

MPIF-1 can also be useful for inhibiting epidermal keratinocyte proliferation which has utility in psoriasis (keratinocyte hyper-proliferation) since Langerhans cells in skin have been found to produce MIP-1α.

MPIF-1 can be used to prevent scarring during wound healing both via the recruitment of debris-cleaning and connective tissue-promoting inflammatory cells and by its control of excessive TGFβ-mediated fibrosis, in addition this polypeptide can be used to treat stroke, thrombocytosis, pulmonary emboli and myeloproliferative disorders, since MPIF-1 increases vascular permeability.

Pharmaceutical Compositions. The MPIF-1 polypeptide pharmaceutical composition comprises an effective amount of an isolated MPIF-1 polypeptide of the invention, particularly a mature form of the MPIF-1 effective to increase the MPIF-1 activity level in such an individual. Such compositions can be formulated and dosed in a fashion consistent with good medical practice, taking into account the clinical condition of the individual patient (especially the side effects of treatment with MPIF-1 polypeptide alone), the site of delivery of the MPIF-1 polypeptide composition, the method of administration, the scheduling of administration, and other factors known to practitioners. The "effective amount" of MPIF-1 polypeptide for purposes herein is thus determined by such considerations.

Polypeptides, antagonists or agonists of the present invention can be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The MPIF-1 polypeptide is also suitably administered by sustained-release systems. Suitable examples of sustained-release compositions include semi-permeable polymer matrices in the form of shaped articles, e.g. films, or microcapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(-)-3-hydroxybutyric acid (EP 133,988). Sustained-release MPIF-1 polypeptide compositions also include liposomally entrapped MPIF-1 polypeptide. Liposomes containing MPIF-1 polypeptide are prepared by methods known per se: DE 3,218,121; Epstein et al., *Proc. Natl. Acad. Sci.* (*USA*) 82:3688–3692 (1985); Hwang et al., *Proc. Natl. Acad. Sci.* (*USA*) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal MPIF-1 polypeptide therapy.

For parenteral administration, in one embodiment, the MPIF-1 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the MPIF-1 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g. polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The MPIF-1 polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of MPIF-1 polypeptide salts.

When MPIF-1, and/or a variant thereof, is administered as a myeloprotectant as part of a chemotherapeutic regimen for the treatment of hyperproliferative disorders in humans, a suitable dosage range for intravenous administration is 0.01 $\mu$g/kg to 10 $\mu$g/kg of body weight. Further, MPIF-1 may be administered intravenously at doses of 0.1, 1.0, 10, and 100 $\mu$g/kg of body weight. Extrapolation of data from animal studies indicates that a dosage of MPIF-1 suitable for myeloprotection in humans is 0.016 $\mu$g/kg of body weight.

When MPIF-1, and/or a variant thereof, is administered as a treatment for cytoxic damage to cells, tissues and organs, it may be administered to a human after exposure to the cytotoxic agent. When used as a preventive for cytotoxic damage to cells, tissues and organs, MPIF-1 and/or a variant thereof may be administered before exposure, or it may be administered both before and after exposure to the cytoxic agent.

Further, MPIF-1, and/or a variant thereof, may be administered once daily for a specified number of days (e.g., three days). In addition, when used in a chemotherapeutic regimen, MPIF-1 may be administered to a human prior to the administration of the chemotherapeutic agent(s). For example, MPIF-1 may be administered two days before, one day before and the day of administration of a chemotherapeutic agent(s).

When MPIF-1, and/or a variant thereof, is administered to a human for the treatment of myeloproliferative disorders the dosages administered may be the same as when MPIF-1 is used as a myeloprotectant. When administered to a human for the treatment of myeloproliferative disorders, MPIF-1 may be administered subcutaneously.

MPIF-1 polypeptide to be used for therapeutic administration must be sterile. Sterility is readily accomplished by filtration through sterile filtration membranes (e.g., 0.2 micron membranes). Therapeutic MPIF-1 polypeptide compositions generally are placed into a container having a sterile access port, for example, an intravenous solution bag or vial having a stopper pierceable by a hypodermic injection needle.

MPIF-1 polypeptide ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous MPIF-1 polypeptide solution, and the resulting mixture is lyophilized. The infusion solution is prepared by reconstituting the lyophilized MPIF-1 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

The invention also provides methods of treatment and/or prevention of diseases or disorders (such as, for example, any one or more of the diseases or disorders disclosed herein) by administration to a subject of an effective amount of a Therapeutic. By therapeutic is meant polynucleotides or polypeptides (including fragments and variants), agonists or antagonists thereof, and/or antibodies thereto, in combination with a pharmaceutically acceptable carrier type (e.g., a sterile carrier).

MPIF-1 will be formulated and dosed in a fashion consistent with good medical practice, taking into account the clinical condition of the individual patient (especially the side effects of treatment with MPIF-1 alone), the site of delivery, the method of administration, the scheduling of administration, and other factors known to practitioners. The "effective amount" for purposes herein is thus determined by such considerations.

As a general proposition, the total pharmaceutically effective amount of MPIF-1 administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, MPIF-1 is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

MPIF-1 can be administered orally, rectally, parenterally, intracistemally, intravaginally, intraperitoneally, to pically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral"as used herein refers to modes of administration which include intravenous, intramuscular, intraperitoneal, intrastemal, subcutaneous and intraarticular injection and infusion.

MPIF-1 is also suitably administered by sustained-release systems. Suitable examples of sustained-release MPIF-1 are administered orally, rectally, parenterally, intracistemally, intravaginally, intraperitoneally, to pically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrastemal, subcutaneous and intraarticular injection and infusion.

MPIF-1 is also suitably administered by sustained-release systems. Suitable examples of sustained-release MPIF-1 include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained release matrices include polylactides (U.S. Pat. No. 3,773,919, EP 58,481), copolymers of L-glutamic acid and gamma-ethyl-L-glutamate (Sidman, et al., *Biopolymers* 22:547–556 (1983)), poly (2-hydroxyethyl methacrylate) (Langer, et al., *J. Biomed. Mater. Res.* 15:167–277 (1981); Langer, *Chem. Tech.* 12:98–105 (1982)), ethylene vinyl acetate (Langer et al., Id.) or poly-D-(–)-3-hydroxybutyric acid (EP 133,988).

Sustained-release MPIF-1 also include liposomally entrapped MPIF-1 (see generally, Langer, *Science* 249:1527–1533 (1990); Treat, et al., in *Liposomes in the Therapy of Infectious Disease and Cancer*, Lopez-Berestein and Fidler (eds.), Liss, New York, pp.317–327 and 353–365 (1989)). Liposomes containing MPIF-1 are prepared by methods known per se: DE 3,218,121; Epstein, et al., *Proc. Natl. Acad. Sci. (USA)* 82:3688–3692 (1985); Hwang, et al., *Proc. Natl. Acad. Sci. (USA)* 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal therapeutic.

In yet an additional embodiment, MPIF-1 is delivered by way of a pump (see Langer, supra; Sefton, *CRC Crit. Ref. Biomed. Eng.* 14:201 (1987); Buchwald, et al., *Surgery* 88:507(1980); Saudek, et al., *N. Engl. J. Med.* 321:574 (1989)).

Other controlled release systems are discussed in the review by Langer (*Science* 249:1527–1533 (1990)).

For parenteral administration, in one embodiment, MPIF-1 is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to MPIF-1.

Generally, the formulations are prepared by contacting MPIF-1 uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

MPIF-1 is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). MPIF-1 generally is placed into a container having a sterile access port, for example, an intravenous solution bag or vial having a stopper pierceable by a hypodermic injection needle.

MPIF-1 ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous MPIF-1 solution, and the resulting mixture is lyophilized. The infusion solution is prepared by reconstituting the lyophilized MPIF-1 using bacteriostatic Water-for-Injection.

The invention also provides a pharmaceutical pack or kit comprising one or more containers filled with one or more of the ingredients of MPIF-1. Associated with such container(s) can be a notice in the form prescribed by a governmental agency regulating the manufacture, use or sale of pharmaceuticals or biological products, which notice reflects approval by the agency of manufacture, use or sale for human administration. In addition, the MPIF-1 may be employed in conjunction with other therapeutic compounds.

MPIF-1 may be administered alone or in combination with adjuvants. Adjuvants that may be administered with MPIF-1 include, but are not limited to, alum, alum plus deoxycholate (ImmunoAg), MTP-PE (Biocine Corp.), QS21 (Genentech, Inc.), BCG, and MPL. In a specific embodiment, MPIF-1 is administered in combination with alum. In another specific embodiment, MPIF-1 is administered in combination with QS-21. Further adjuvants that may be administered with MPIF-1 include, but are not limited to, monophosphoryl lipid immunomodulator, Adju-Vax 100a, QS-21, QS-18, CRL1005, aluminum salts, MF-59, and virosomal adjuvant technology. Vaccines that may be administered with MPIF-1 include, but are not limited to, vaccines directed to ward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

MPIF-1 may be administered alone or in combination with other therapeutic agents. Therapeutic agents that may be administered in combination with MPIF-1, include but not limited to, other members of the TNF family, cytotoxic agents, chemotherapeutic agents, radiation, radiation sensitizers, targeted radiotherapy, antibiotics, antivirals, steroidal and non-steroidal anti-inflammatories, immunotherapeutic agents, radioimmunodetection agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, MPIF-1 is administered in combination with members of the TNF family. TNF, TNF-related or TNF-like molecules that may be administered with MPIF-1 include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

In certain embodiments, MPIF-1 is administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with MPIF-1, include, but are not limited to, RETROVIR™ (zidovudine/AZT), VIDEX™ (didanosine/ddl), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with MPIF-1, include, but are not limited to, VIRAMUNE™ (nevirapine), RESCRIPTOR™ (delavirdine), and SUSTIVA™ (efavirenz). Protease inhibitors that may be administered in combination with MPIF-1, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with MPIF-1 to treat AIDS and/or to prevent or treat HIV infection.

In other embodiments, MPIF-1 may be administered in combination with anti-opportunistic infection agents. Anti-opportunistic agents that may be administered in combination with MPIF-1, include, but are not limited to, TRIMETHOPR-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, MPIF-1 is used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, MPIF-1 is used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, MPIF-1 is used in any combination with RIFABUTIN™, CLARITHROMYCIN™, and/or AZITHROMYCIN™ to prophylactically treat or prevent an opportunistic Mycobacterium tuberculosis infection. In another specific embodiment, MPIF-1 is used in any combination with GANCICLOVIR™, FOSCARNET™, and/or CIDOFOVIR™ to prophylactically treat or prevent an opportunistic cytomegalovirus infection. In another specific embodiment, MPIF-1 is used in any combination with FLUCONAZOLE™, ITRACONAZOLE™, and/or KETOCONAZOLE™ to prophylactically treat or prevent an opportunistic fungal infection. In another specific embodiment, MPIF-1 is used in any combination with ACYCLOVIR™ and/or FAMCICOLVIR™ to prophylactically treat or prevent an opportunistic herpes simplex virus type I and/or type II infection. In another specific embodiment, MPIF-1 is used in any combination with PYRIMETHAMINE™ and/or LEUCOVORIN™ to prophylactically treat or prevent an opportunistic *Toxoplasma gondii* infection. In another specific embodiment, MPIF-1 is used in any combination with LEUCOVORIN™ and/or NEUPOGEN™ to prophylactically treat or prevent an opportunistic bacterial infection.

In a further embodiment, MPIF-1 is administered in combination with an antiviral agent. Antiviral agents that may be administered with MPIF-1 include, but are not limited to, acyclovir, ribavirin, amantadine, and remantidine.

In a further embodiment, MPIF-1 is administered in combination with an antibiotic agent. Antibiotic agents that may be administered with MPIF-1 include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with MPIF-1 include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, MPIF-1 is administered in combination with immunosuppressants. Immunosuppressants preparations that may be administered with MPIF-1 include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, MPIF-1 is administered alone or in combination with one or more intravenous immune globulin preparations. Intravenous immune globulin preparations that may be administered with MPIF-1 include, but not limited to, GAMMAR™, IVEEGAM™, SANDOGLOBULIN™, GAMMAGARD S/D™, and GAMIMUNE™. In a specific embodiment, MPIF-1 is administered in combination with intravenous immune globulin preparations in transplantation therapy (e.g., bone marrow transplant).

In an additional embodiment, MPIF-1 is administered alone or in combination with an anti-inflammatory agent. Anti-inflammatory agents that may be administered with MPIF-1 include, but Ire not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, MPIF-1 compositions are administered in combination with a chemotherapeutic agent. Chemotherapeutic agents that may be administered with MPIF-1 include, but are not limited to, antibiotic derivatives (e.g., doxorubicin (Adriamycin™), bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, MPIF-1 is administered in combination with CHOP (cyclophosphamide, doxorubicin, vincristine, and prednisone) or any combination of the components of CHOP. In another embodiment, MPIF-1 is administered in combination with Rituximab. In a further embodiment, MPIF-1 is administered with Rituxmab and CHOP, or Rituxmab and any combination of the components of CHOP.

In an additional embodiment, MPIF-1 is administered in combination with cytokines. Cytokines that may be administered with MPIF-1 include, but are not limited to, IL2, IL3, IL4, IL5, IL6, IL7, IL10, IL12, IL13, IL15, anti-CD40, CD40L, IFN-gamma and TNF-alpha. In another embodiment, MPIF-1 may be administered with any interleukin, including, but not limited to, IL-1 alpha, IL-1 beta, IL-2, IL-3, IL-4, IL-5, IL-6, IL-7, IL-8, IL-9, IL-10, IL-11, IL-12, IL-13, IL-14, IL-15, IL-16, IL-17, IL-1 8, IL-19, IL-20, and IL-21.

In an additional embodiment, MPIF-1 is administered in combination with angiogenic proteins. Angiogenic proteins that may be administered with MPIF-1 include, but are not limited to, Glioma Derived Growth Factor (GDGF), as disclosed in European Pat. No. EP-399816; Platelet Derived Growth Factor-A (PDGF-A), as disclosed in European Pat. No. EP-682110; Platelet Derived Growth Factor-B (PDGF-B), as disclosed in European Patent Number EP-282317; Placental Growth Factor (PIGF), as disclosed in International Publication Number WO 92/06194; Placental Growth Factor-2 (PIGF-2), as disclosed in Hauser, et al., *Gorwth Factors* 4:259–268 (1993); Vascular Endothelial Growth Factor (VEGF), as disclosed in International Publication Number WO 90/13649; Vascular Endothelial Growth Factor-A (VEGF-A), as disclosed in European Pat. No. EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B 186), as disclosed in International Publication Number WO 96/26736; Vascular Endothelial Growth Factor-D (VEGF-D), as disclosedin International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Pat. No. DE19639601. The above mentioned references are incorporated herein by reference herein.

In an additional embodiment, MPIF-1 is administered in combination with hematopoietic growth factors. Hematopoietic growth factors that may be administered with MPIF-1 include, but are not limited to, LEUKINE™ (SARGRAMOSTIM™) and NEUPOGEN™ (FILGRASTIM™).

In an additional embodiment, MPIF-1 is administered in combination with Fibroblast Growth Factors. Fibroblast Growth Factors that may be administered with MPIF-1 include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, MPIF-1 is administered in combination with other therapeutic or prophylactic regimens, such as, for example, radiation therapy.

In additional embodiments, the polynucleotides, polypeptides, agonists and/or agonists of the present invention may also be administered along with anti-angiogenic factors. Representative examples of anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., *Cancer Res.* 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2-(3-H)-oxazolone; Methotrexate; Mitoxantrone; Heparin; Interferons; 2 Macroglobulin-serum; ChIMP-3 (Pavloff et al., *J. Bio. Chem.* 267:17321–17326, 1992); Chymostatin (Tomkinson et al., *Biochem J.* 286:475–480, 1992); Cyclodextrin Tetradecasulfate; Eponemycin; Camptothecin; Fumagillin (Ingber et al., *Nature* 348:555–557, 1990); Gold Sodium Thiomalate ("GST"; Matsubara and Ziff, *J. Clin. Invest.* 79:1440–1446, 1987); anticollagenase-serum; alpha2-antiplasmin (Holmes et al., *J. Biol. Chem.* 262(4): 1659–1664, 1987); Bisantrene (National Cancer Institute); Lobenzarit disodium (N-(2)-carboxyphenyl-4-chloroanthronilic acid disodium or "CCA"; Takeuchi et al., *Agents Actions* 36:312–316, 1992); Thalidomide; Angostatic steroid; AGM-1470; carboxynaminolmidazole; and metalloproteinase inhibitors such as BB94.

Modes of administration. It will be appreciated that conditions caused by a decrease in the standard or normal level of MPIF-1 activity in an individual, can be treated by administration of MPIF-1 protein. Thus, the invention further provides a method of treating an individual in need of an increased level of MPIF-1 activity comprising administering to such an individual a pharmaceutical composition comprising an effective amount of an isolated MPIF-1 polypeptide of the invention, particularly amature form of the MPIF-1 effective to increase the MPIF-1 activity level in such an individual.

The amounts and dosage regimens of MPIF-1 administered to a subject will depend on a number of factors such as the mode of administration, the nature of the condition being treated and the judgment of the prescribing physician. The pharmaceutical compositions are administered in an amount which is effective for treating and/or prophylaxis of the specific indication. In general, the polypeptides will be administered in an amount of at least about 10 µg/kg body weight and in most cases they will be administered in an amount not in excess of about 10 mg/kg body weight per day and preferably the dosage is from about 10 µg/kg body weight daily, taking into account the routes of administration, symptoms, etc.

As a general proposition, the total pharmaceutically effective amount of MPIF-1 polypseptide administered parenterally per dose will more preferably be in the range of about 1 µg/kg/day to 10 mg/kg/day of patient body weight, although, as noted above, this will be subject to therapeutic discretion. Even more preferably, this dose is at least 0.01 mg/kg/day, and most preferably for humans between about 0.01 and 1 mg/kg/day. If given continuously, the MPIF-1 polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the MPIF-1 of the invention may be administered orally, rectally, parenterally, intracistemally, intravaginally, intraperitoneally, to pically (as by powders, ointments, drops or transdermal patch), bucally, or as an oral or nasal spray.

Gene Therapy. The chemokine polypeptides, and agonists or antagonists which are polypeptides, may be employed in accordance with the present invention by expression of such polypeptides in vivo, which is often referred to as "gene therapy."

Thus, for example, cells from a patient can be engineered with a polynucleotide (DNA or RNA) encoding a polypeptide ex vivo, with the engineered cells then being provided to a patient to be treated with the polypeptides. Such methods are well-known in the art. For example, cells can be engineered by procedures known in the art by use of a retroviral particle containing RNA encoding the polypeptides of the present invention.

Similarly, cells can be engineered in vivo for expression of a polypeptides in vivo by, for example, procedures known in the art. As known in the art, a producer cell for producing a retroviral particle containing RNA encoding the polypeptides of the present invention can be administered to a patient for engineering the cells in vivo and expression of the polypeptides in vivo. These and other methods for administering polypeptides of the present invention by such method should be apparent to those skilled in the art from the teachings of the present invention. For example, the expression vehicle for engineering cells can be other than a retrovirus, for example, an adenovirus which can be used to engineer cells in vivo after combination with a suitable delivery vehicle.

The retroviral plasmid vectors may be derived from retroviruses which include, but are not limited to, Moloney Murine Sarcoma Virus, Moloney Murine Leukemia Virus, spleen necrosis virus, Rous Sarcoma Virus and Harvey Sarcoma Virus.

In a preferred embodiment the retroviral expression vector, pMV-7, is flanked by the long terminal repeats (LTRS) of the Moloney murine sarcoma virus and contains the selectable drug resistance gene neo under the regulation of the herpes simplex virus (HSV) thymidine kinase (tk) promoter. Unique EcoRI and HindIII sites facilitate the introduction of coding sequence (Kirschmeier, P. T. et al., *DNA* 7:219–25 (1988)).

The vectors include one or more suitable promoters which include, but are not limited to, the retroviral LTR; the SV40 promoter; and the human cytomegalovirus (CMV) promoter described in Miller, et al., *Biotechniques*, Vol. 7, No. 9:980–990 (1989), or any other promoter (e.g cellular promoters such as eukaryotic cellular promoters including, but not limited to, the histone, pol III, and β-actin promoters). The selection of a suitable promoter will be apparent to those skilled in the art from the teachings contained herein.

The nucleic acid sequence encoding the polypeptide of the present invention is under the control of a suitable promoter which includes, but is not limited to, viral thymidine kinase promoters, such as the Herpes Simplex thymidine kinase promoter; retroviral LTRs, the β-actin promoter, and the native promoter which controls the gene encoding the polypeptide.

The retroviral plasmid vector is employed to transduce packaging cell lines to form producer cell lines. Examples of packaging cells which may be transfected include, but are not limited to, the PE501, PA317 and GP+am12. The vector may transduce the packaging cells through any means known in the art. Such means include, but are not limited to, electroporation, the use of liposomes, and $CaPO_4$ precipitation.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced, include but are not limited to, fibroblasts and endothelial cells.

Another aspect of the present invention is gene therapy methods for treating disorders, diseases and conditions. The gene therapy methods relate to the introduction of nucleic acid (DNA, RNA and antisense DNA or RNA) sequences into an animal to achieve expression of the MPIF-1 polypeptide of the present invention. This method requires a polynucleotide which codes for a MPIF-1 polypeptide operatively linked to a promoter and any other genetic elements necessary for the expression of the polypeptide by the target tissue. Such gene therapy and delivery techniques are known in the art, see, for example, WO 90/11092, which is herein incorporated by reference.

Thus, for example, cells from a patient may be engineered with a polynucleotide (DNA or RNA) comprising a promoter operably linked to a MPIF-1 polynucleotide ex vivo, with the engineered cells then being provided to a patient to be treated with the polypeptide. Such methods are well-known in the art. For example, see Belldegrun, A., et al., *J. Natl. Cancer Inst.* 85: 207–216 (1993); Ferrantini, M. et al., *Cancer Research* 53:1107–1112 (1993); Ferrantini, M. et al., *J. Immunology* 153: 4604–4615 (1994); Kaido, T., et al., *Int. J. Cancer* 60: 221–229 (1995); Ogura, H., et al., *Cancer Research* 50: 5102–5106 (1990); Santodonato, L., et al., *Human Gene Therapy* 7:1–10 (1996); Santodonato, L., et al., *Gene Therapy* 4:1246–1255 (1997); and Zhang, J.-F. et al., *Cancer Gene Therapy* 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the MPIF-1 polynucleotide constructs can be delivered by any method that delivers injectable materials to the cells of an animal, such as, injection into the interstitial space of tissues (heart, muscle, skin, lung, liver, and the like). The MPIF-1 polynucleotide constructs may be delivered in a pharmaceutically acceptable liquid or aqueous carrier.

In one embodiment, the MPIF-1 polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the MPIF-1 polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The MPIF-1 polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of MPIF-1 polynucleotide sequence. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for MPIF-1.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The MPIF-1 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, nondividing cells which are differentiated, although delivery and expression may be achieved in nondifferentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked MPIF-1 DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the MPIF-1 polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., *Proc. Natl. Acad. Sci. USA* 84:74137416(1987), which is herein incorporated by reference); mRNA (Malone et al., *Proc. Natl. Acad. Sci. USA* 86:60776081 (1989), which is herein incorporated by reference); and purified transcription factors (Debs et al., *J. Biol. Chem.* 265:1018910192 (1990), which is herein incorporated by reference), in functional form.

Cationic liposomes are readily available. For example, N-[12,3-dioleyloxy)-propyl]-N,N,N-triethylammonium (DOTMA) liposomes are particularly useful and are available under the trademark Lipofectin, from GIBCO BRL, Grand Island, N.Y. (See, also, Felgner et al., *Proc. Natl Acad. Sci. USA* 84:74137416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., *Proc. Natl. Acad. Sci. USA* 84:74137417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially available dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposomenucleic acid complexes are prepared using methods well known in the art. See, e.g., Straubinger et al., *Methods of Immunology* 101:512527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., *Biochim. Biophys. Acta* 394:483 (1975); Wilson et al., *Cell* 17:77 (1979)); ether injection (Deamer, D. and Bangham, A., *Biochim. Biophys. Acta* 443:629 (1976); Ostro et al., *Biochem. Biophys. Res. Commun.* 76:836 (1977); Fraley et al., *Proc. Natl. Acad. Sci. USA* 76:3348 (1979)); detergent dialysis (Enoch, H. and Strittmatter, P., *Proc. Natl. Acad. Sci. USA* 76:145 (1979)); and reversephase evaporation (REV) (Fraley et al., *J. Biol. Chem.* 255:10431 (1980); Szoka, F. and Papahadjopoulos, D., *Proc. Natl. Acad. Sci. USA* 75:145 (1978); SchaeferRidder et al., *Science* 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding MPIF-1. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+envAm12, and DAN cell lines as described in Miller, *Human Gene Therapy* 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding MPIF-1. Such retroviral vector particles then may be employed, to transduce eukaryotic cells, either in vitro or in vivo. The transduced eukaryotic cells will express MPIF-1.

In certain other embodiments, cells are engineered, ex vivo or in vivo, with MPIF-1 polynucleotide contained in an adenovirus vector. Adenovirus can be manipulated such that it encodes and expresses MPIF-1, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. *Am. Rev. Respir. Dis.* 109:233–238 (1974)). Finally, adenovirus mediated gene transfer has been demonstrated in a number of instances including transfer of alpha1 antitrypsin and CFTR to the lungs of cotton rats (Rosenfeld, M. A. et al. *Science* 252:431–434 (1991); Rosenfeld et al, *Cell* 68:143–155 (1992)). Furthermore, extensive studies to attempt to establish adenovirus as a causative agent in human cancer were uniformly negative (Green, M. et al. *Proc. Natl. Acad. Sci. USA* 76:6606 (1979)).

Suitable adenoviral vectors useful in the present invention are described, for example, in Kozarsky and Wilson, *Curr. Opin. Genet. Devel.* 3:499–503 (1993); Rosenfeld et al., *Cell* 68:143–155 (1992); Engelhardt et al., *Human Genet. Ther.* 4:759–769 (1993); Yang et al., *Nature Genet.* 7:362–369 (1994); Wilson et al., *Nature* 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., *Curr. Topics in Microbiol. Immunol.* 158:97 (1992)). It is also one of the few viruses that may integrate its DNA into nondividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The MPIF-1 polynucleotide construct is inserted into the AAV vector using standard cloning methods, such as those found in Sambrook et al., *Molecular Cloning: A Laboratory Manual*, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the MPIF-1 polynucleotide construct. These viral particles are then used to transduce eukaryotic cells, either ex vivo or in vivo. The transduced cells will contain the MPIF-1 polynucleotide construct integrated into its genome, and will express MPIF-1.

Another method of gene therapy involves operably associating heterologous control regions and endogenous polynucleotide sequences (e.g. encoding MPIF-1) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:89328935 (1989); and Zijlstra et al., *Nature* 342:435438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the MPIF-1 desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, to pical administration, catheter infusion, particle accelerators, etc. The methods are described in more detail below.

The promoter-targeting sequence construct is taken up by cells. Homologous recombination between the construct and the endogenous sequence takes place, such that an endogenous MPIF-1 sequence is placed under the control of the promoter. The promoter then drives the expression of the endogenous MPIF-1 sequence.

The polynucleotides encoding MPIF-1 may be administered along with other polynucleotides encoding an angiogenic protein. Examples of angiogenic proteins include, but are not limited to, acidic and basic fibroblast growth factors, VEGF-1, VEGF-2, VEGF-3, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding MPIF-1 contains a secretory signal sequence that facilitates secretion of the protein. Typically, the signal sequence is positioned in the coding region of the polynucleotide to be expressed to wards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or to pical applications during surgery. For example, direct injection of naked calcium phosphateprecipitated plasmid into rat liver and rat spleen or a proteincoated plasmid into the portal vein has resulted in gene expression of the foreign gene in the rat livers (Kaneda et al., *Science* 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., *Proc. Natl. Acad. Sci. USA* 189:11277–11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Antisense and Ribozyme (Antagonists). In specific embodiments, antagonists according to the present invention are nucleic acids corresponding to the sequences contained in SEQ ID NO:1 or 6, or the complementary strand thereof, and/or to nucleotide sequences contained in the deposited clone 75676. In one embodiment, antisense sequence is generated internally, by the organism, in another embodiment, the antisense sequence is separately administered (see, for example, O'Connor, *J. Neurochem.* 56:560 (1991); Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, *J. Neurochem.* 56:560 (1991); Oligodeoxynucleotides as Antisense Inhibitors of Gene Expression, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrometal. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2×ligation buffer (20 mM Tris HCl pH 7.5, 10 mM $MgCl_2$, 10 mM dithiothreitol (DTT) and 0.2 mM ATP) and then ligated to the EcoRI/HindIII site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the MPIF-1 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the MPIF-1 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding MPIF-1, or fragments thereof, can be by any promoter known in the art to act in vertebrate, preferably human cells. Such promoters can be inducible or constitutive. Such promoters include, but are not limited to, the SV40 early promoter region (Bemoist and Chambon, Nature 29:304–310 (1981), the promoter contained in the 3' long terminal repeat of Rous sarcoma virus (Yamamoto et al., *Cell* 22:787–797 (1980), the herpes thymidine promoter (Wagner et al., *Proc. Natl. Acad. Sci. U.S.A.* 78:1441–1445 (1981), the regulatory sequences of the metallothionein gene (Brinster, et al., *Nature* 296:39–42 (1982)), etc.

The antisense nucleic acids of the invention comprise a sequence complementary to at least a portion of an RNA transcript of a MPIF-1 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded MPIF-1 antisense nucleic acids, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with a MPIF-1 RNA it may contain and still form a stable duplex (or triplex as the case may be). One skilled in the art can ascertain a to lerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, *Nature* 372:333–335. Thus, oligonucleotides complementary to either the 5'- or 3'- non-translated, non-coding regions of MPIF-1 shown in FIG. 20 could be used in an antisense approach to inhibit translation of endogenous MPIF-1 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of MPIF-1 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553–6556 (1989); Lemaitre et al., *Proc. Natl. Acad. Sci.* 84:648–652 (1987); PCT Publication No. WO88/098 10, published Dec. 15, 1988) or the blood-brain barrier (see, e.g., PCT Publication No. WO89/10134, published Apr. 25, 1988), hybridization-triggered cleavage agents. (See, e.g., Krol et al., *BioTechniques* 6:958–976 (1988)) or intercalating agents. (See, e.g., Zon, *Pharm. Res.* 5:539–549(1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-isopentenyladenine, 1-methylguanine, 1-methylinosine, 2,2-dimethylguanine, 2-methyladenine, 2-methylguanine, 3-methylcytosine, 5-methylcytosine, N-6-adenine, 7-methylguanine, 5-methylaminomethyluracil, 5-methoxyaminomethyl-2-thiouracil, beta-D-mannosylqueosine, 5'methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3(3-amino-3-N2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an aanomeric oligonucleotide. An a-anomeric oligonucleotide forms specific double-stranded hybrids with complementary RNA in which, contrary to the usual bunits, the strands run parallel to each other (Gautier et al., *Nucl. Acids Res.* 15:6625–6641(1987)). The oligonucleotide is a 2'-0-methylribonucleotide (Inoue et al., *Nucl. Acids Res.* 15:6131–6148(1987)), or a chimeric RNA-DNA analogue (Inoue et al., *FEBS Lett.* 215:327–330(1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, *Nucl. Acids Res.* 16:3209), methylphosphonate oligonucleotides can be prepared by use of controlled pore glass polymer supports (Sarin et al., *Proc. Natl. Acad. Sci. U.S.A.* 85:7448–7451 (1988)), etc.

While antisense nucleotides complementary to the MPIF-1 coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al., *Science* 247:1222–1225 (1990). While ribozymes that cleave mRNA at site specific recognition sequences can be used to destroy MPIF-1 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585–591 (1988). There are numerous potential hammerhead ribozyme cleavage sites within the nucleotide sequence of MPIF-1 (FIG. 1A–B). Preferably, the ribozyme is engineered so that the cleavage recognition site is located near the 5' end of the MPIF-1 mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express MPIF-1 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous MPIF-1 messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to treat the diseases described herein.

Thus, the invention provides a method of treating disorders or diseases, including but not limited to the disorders or diseases listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Epitopes and Antibodies

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in ATCC deposit NO. 75676 or encoded by apolynucleotide that hybridizes to the complement of the sequence of SEQ ID NO:1 or 6 or contained in ATCC deposit No. 75676 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1 or 6), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., *Proc. Natl. Acad. Sci. USA* 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, *Proc. Natl. Acad. Sci. USA* 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., *Cell* 37:767–778 (1984); Sutcliffe et al., *Science* 219:660–666 (1983)).

Similarly, immunogenic epitopes can be used, for example, to induce antibodies according to methods well known in the art. (See, for instance, Sutcliffe et al., supra; Wilson et al., supra; Chow et al., *Proc. Natl. Acad. Sci. USA* 82:910–914; and Bittle et al., *J. Gen. Virol.* 66:2347–2354 (1985). Preferred immunogenic epitopes include the immunogenic epitopes disclosed herein, as well as any combination of two, three, four, five or more of these immunogenic epitopes. The polypeptides comprising, or alternatively consisting of, one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.*, 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof ($CH_1$, $CH_2$, $CH_3$, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., *Nature*, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., *J. Biochem.*, 270:3958–3964 (1995). Nucleic acids encoding the above epitopes can also be recombined with an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, *Proc. Natl. Acad. Sci. USA* 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., *Curr. Opinion Biotechnol.* 8:724–33 (1997); Harayama, *Trends Biotechnol.* 16(2): 76–82 (1998); Hansson, et al., *J. Mol. Biol.* 287:265–76 (1999); and Lorenzo and Blasco, Biotechniques 24(2): 308–13 (1998) (each of these patents and publications are hereby incorporated by reference in its entirety). In one embodiment, alteration of polynucleotides corresponding to SEQ ID NO:1 or 6 and the polypeptides encoded by these polynucleotides may be achieved by DNA shuffling. In another embodiment, alteration of polynucleotides encoding the polypeptide shown in SEQ ID NO:2 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies. Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA, and IgY), class (e.g., $IgG_1$, $IgG_2$, $IgG_3$, $IgG_4$, $IgA_1$, and $IgA_2$) or subclass of immunoglobulin molecule.

Most preferably the antibodies are human antigen-binding antibody fragments of the present invention and include, but are not limited to, Fab, Fab' and $F(ab')_2$, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, may comprise the variable region(s) alone or in combination with the entirety or a portion of the following: hinge region, $CH_1$, $CH_2$, and $CH_3$ domains. Also included in the invention are antigen-binding fragments also comprising any combination of variable region(s) with a hinge region, $CH_1$, $CH_2$, and $CH_3$ domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or as listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$M, $10^{-2}$ M, $5\times10^{-3}$ M, $10^{-3}$M, $5\times10^{-4}$ M, $10^{-4}$ M, $5\times10^{-5\ M}$, $10^{-5}$ M, $5\times10^{-6}$ M, $10^{-6}$M, $5\times10^{-7}$M, $10^{7}$ M, $5\times10^{-8}$ M, $10^{-8}$M, $5\times10^{-9}$ M, $10^{-9}$ M, $5\times10^{-10}$M, $10^{-10}$M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

The invention also provides antibodies that competitively inhibit the binding of a monoclonal antibody to a polypeptide of the invention, preferably the polypeptide of SEQ ID NO:2. Competitive inhibition can be determined by any method known in the art, for example, using the competitive binding assays described herein. In preferred embodiments, the antibody competitively inhibits the binding of a monoclonal antibody of the invention by at least 90%, at least 80%, at least 70%, at least 60%, or at least 50% to the polypeptide of SEQ ID NO:2.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., *Blood* 92(6):1981–1988 (1998); Chen et al., *Cancer Res.* 58(16):3668–3678 (1998); Harrop et al., *J. Immunol.* 161 (4):1786–1794 (1998); Zhu et al., *Cancer Res.* 58(15): 3209–3214 (1998); Yoon et al., *J. Immunol.* 160(7): 3170–3179 (1998); Prat et al., *J. Cell. Sci.* 111(Pt2): 237–247 (1998); Pitard et al., *J. Immunol. Methods* 205(2): 177–190 (1997); Liautard et al., *Cytokine* 9(4):233–241 (1997); Carlson et al., *J. Biol. Chem.* 272(17):11295–11301 (1997); Taryman et al., *Neuron* 14(4):755–762 (1995); Muller et al., *Structure* 6(9):1153–1167 (1998); Bartunek et al., *Cytokine* 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *Antibodies. A Laboratory Manual*, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or to xins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples (e.g., Examples 22 and 30). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding apolypeptide of the invention. Ascites fluid, which generally contains high levels of antibodies, can be generated by immunizing mice with positive hybridoma clones.

Accordingly, the present invention provides methods of generating monoclonal antibodies, as well as antibodies produced by the methods, comprising culturing a hybridoma cell secreting an antibody of the invention wherein, preferably, the hybridoma is generated by fusing splenocytes from a mouse immunized with an antigen of the invention with myeloma cells, and then screening the hybridomas resulting from the fusion for hybridoma clones that secrete an antibody able to bind a polypeptide of the invention.

Antibody fragments which recognize specific epitopes may be generated by known techniques. For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the $CH_1$ domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41–50 (1995); Ames et al., *J. Immunol. Methods* 184:177–186 (1995); Kettleborough et al., *Eur. J. Immunol.* 24:952–958 (1994); Persic et al., *Gene* 187:9–18(1997); Burton et al., *Advances in Immunology* 57:191–280 (1994); PCT application No. PCT/GB91/01134; PCT publications WO 90/02809; WO 91/10737; WO 92/01047; WO 92/18619; WO93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT publication WO 92/22324; Mullinax et al., *BioTechniques* 12(6):864–869 (1992); and Sawai et al., *AJRI* 34:26–34 (1995); and Better et al., *Science* 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46–88 (1991); Shu et al., *PNAS* 90:7995–7999 (1993); and Skerra et al., *Science* 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, *Science* 229:1202 (1985); Oi et al., *BioTechniques* 4:214 (1986); Gillies et al., *J. Immunol. Methods* 125:191–202 (1989); U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and one or more framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, *Molecular Immunology* 28(4/5):489–498 (1991); Studnicka et al., *Protein Engineering* 7(6):805–814 (1994); Roguska. et al., *PNAS* 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos.4,444,887 and 4,716,111; and PCT publications WO 98/46645, WO 98/50433, WO98/24893, WO98/16654, WO 96/34096, WO96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM, and IgE antibodies. For an overview of this technology for producing human antibodies, see Lonberg and Huszar, *Int. Rev. Immunol.* 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Pat. No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, *FASEB J*. 7(5):437–444; (1989) and Nissinoff, *J., Immunol.* 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The term "bind(ing) of a polypeptide of the invention to a ligand" includes, but is not limited to, the binding of a ligand polypeptide of the present invention to a receptor; the binding of a receptor polypeptide of the present invention to a ligand; the binding of an antibody of the present invention to an antigen or epitope; the binding of an antigen or epitope of the present invention to an antibody; the binding of an antibody of the present invention to an anti-idiotypic antibody; the binding of an anti-idiotypic antibody of the present invention to a ligand; the biding of an anti-idiotypic antibody of the present invention to a receptor; the binding of an anti-anti-idiotypic antibody of the present invention to a ligand, receptor or antibody, etc.

As another example, antibodies which bind to and competitively activate the polypeptide of the invention or its ligand can be used to generate anti-idiotypic antibodies that mimic the polypeptide binding domain and/or activation domain and, as a consequence, bind to and activate the polypeptide and/or its ligand. Such activating anti-idiotypes or Fab fragments of such anti-idiotypes can be used in therapeutic regimens to activate polypeptide ligand. For example, such anti-idiotypic antibodies can be used to bind a polypeptide of the invention to thereby activate its biological activity and/or bind a ligand/receptor of the polypeptide of the invention to thereby activate its biological activity.

Polynucleotides Encoding Antibodies. The invention further provides polynucleotides comprising, or alternatively consisting of, a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A$^+$ RNA, isolated from, any tissue or cells expressing the antibody, such as hybridoma cells selected to express an antibody of the invention) by PCR amplification using synthetic primers hybridizable to the 3' and 5' ends of the antibody coding sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., *Molecular Cloning, A Laboratory Manual*, 2d Ed., Cold Spring Harbor Laboratory, Cold Spring Harbor, N.Y. (1990) and Ausubel et al., eds., *Current Protocols in Molecular Biology*, John Wiley & Sons, NY, (1998) which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al, *J. Mol. Biol.* 278:457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., *Proc. Natl. Acad. Sci.* 81:851–855 (1984); Neuberger et al., *Nature* 312:604–608 (1984); Takeda et al., *Nature* 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, *Science* 242:423–42 (1988); Huston et al., *Proc. Natl. Acad. Sci. USA* 85:5879–5883 (1988); and Ward et al., *Nature* 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., *Science* 242:1038–1041 (1988)).

Methods of Producing Antibodies. The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; to bacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, *Nucleic Acids Res.* 13:3101–3109 (1985); Van Heeke & Schuster, *J. Biol. Chem.* 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa califomica nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, *Proc. Natl. Acad. Sci. USA* 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker but no functional or intact viral origin. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al, *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Natl. Acad. Sci. USA* 77:357 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 *Clinical Pharmacy* 12:488–505; Wu and Wu, *Biotherapy* 3:87–95 (1991); Tolstoshev, *Ann. Rev. Pharmacol. Toxicol.* 32:573–596 (1993); Mulligan, *Science* 260:926–932 (1993); and Morgan and Anderson, *Ann. Rev. Biochem.* 62:191–217 (1993); May, 1993, *TIB TECH* 11(5): 155–215); and hygro, which confers resistance to hygromycin (Santerre et al., *Gene* 30:147 (1984)). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression, A Laboratory Manual*, Stockton Press, NY (1990); and in Chapters 12 and 13, Dracopoli et al. (eds), *Current Protocols in Human Genetics*, John Wiley & Sons, NY (1994); Colberre-Garapin et al., *J. Mol. Biol.* 150:1 (1981), which are incorporated by reference herein in their entireties.

The expression levels of an antibody molecule can be increased by vector amplification (for a review, see Bebbington and Hentschel, "The use of vectors based on gene amplification for the expression of cloned genes in mammalian cells," in *DNA Cloning*, Vol.3, (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, *Nature* 322:52 (1986); Kohler, *Proc. Natl. Acad. Sci. USA* 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalent and non-covalent conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., *Immunol. Lett.* 39:91–99 (1994); U.S. Pat. No. 5,474,981; Gillies et al., *PNAS* 89:1428–1432 (1992); Fell et al., *J. Immunol.* 146:2446–2452(1991), which are incorporated by reference in their entireties.

Conjugates and Chelates. The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH, domain, $CH_2$ domain, and $CH_3$ domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., *Proc. Natl. Acad. Sci. USA* 88:10535–10539 (1991); Zheng, et al., *J. Immunol.* 154:5590–5600 (1995); and Vil et al., *Proc. Natl. Acad. Sci. USA* 89:11337–11341(1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., *Nature* 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., *J. Biochem.* 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., *J. Molecular Recognition* 8:52–58 (1995); Johanson et al., *J. Biol. Chem.* 270:9459–9471 (1995).

Moreover, the antibodies, or fragments thereof, of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 3 7:767 (1984)) and the "flag" tag.

As indicated above, antibodies which specifically bind at least one epitope of MPIF-1 are included, and antibodies which specifically bind any epitope or polypeptide of the present invention may also be excluded. Thus, the antibodies may be specific for MPIF-1 or may be specific for polypeptides and epitopes other than MPIF-1.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission to mographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriaziny-lamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$, or $^{99}Tc$.

Further, an antibody or fragment thereof may be conjugated to a therapeutic moiety such as a cytotoxin, e.g., a cytotoxic, cytostatic or cytocidal agent, a therapeutic agent or a radioactive metal ion, e.g., alpha-emitters such as, for example, $^{213}Bi$. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, and the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Further, MPIF polypeptides, variants, fragments, agonists, and antagonists thereof, may be conjugated to a diagnostic or therapeutic agent such as those above and herein or others well known in the art. MPIF conjugates may be used for diagnostic or therapeutic purposes described herein and well known in the art.

For example, MPIF may be conjugated to a radioisotope and used for diagnosis or therapy.

Techniques for conjugating such therapeutic moiety to antibodies are well known, see, e.g., Amon et al., "Monoclonal Antibodies For Immunotargeting Of Drugs In Cancer Therapy," in *Monoclonal Antibodies And Cancer Therapy*, Reisfeld et al. (eds.), Alan R. Liss, Inc. (1985), pp. 243–56; Hellstrom et al., "Antibodies For Drug Delivery", in *Controlled Drug Delivery* (2nd Ed.), Robinson et al. (eds.), Marcel Dekker, Inc. (1987), pp. 623–53; Thorpe, "Antibody Carriers Of Cytotoxic Agents In Cancer Therapy: A Review", in *Monoclonal Antibodies '84: Biological And Clinical Applications*, Pinchera, et al. (eds.), (1985), pp.475–506; "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press (1985), pp. 303–16; and Thorpe et al., *Immunol. Rev.* 62:119–58 (1982).

Antibodies, proteins, including polypeptides of the invention, and small molecules may be used as targeting and pretargeting molecules. Such molecules of the present invention may be radiolabeled by methods well known to those of ordinary skill in the art, which include, but are not limited to, radiolabeled chelation of the antibody and antibody phage libraries for targeting radioimmunotherapeutics. See e.g., DeNardo, et al., *Clin. Cancer Res.* 5(10S):3213s–3218s (1999); Quadri, et al., *Q.J. Nucl. Med.* 42:250–261 (1998); the contents of each of which are incorporated by reference in its entirety.

For chelation, different chemical linkages can be inserted between the antibody and the radiolabeled chelate. Radiolabeled monoclonal antibodies reactive with a target antigen can selectively deliver cytotoxic or diagnostic isotopes to malignant cells in vivo. The construction of pretargeting molecules can be provided using the diversity and malleability of antibody genes. Diverse arrays of single chain antibody fragments (i.e., scFvs) can be obtained that are reactive with a target antigen by selection from human naive phage antibody libraries. ScFvs can also be cloned directly from hybridoma for construction of phage libraries that facilitate susequent manipulation: e.g., affinity maturation and modification of specificity. ScFvs affinity selected from these sources to their specific antigen targets have demonstrated a wide spectrum of binding characteristics. Antibody heavy (V(H)) and light (V(L)) genes from selected ScFvs may be cloned as cassettes into diabody molecules. This application is discussed further, below, in the method for specific destruction of cells by administering polypeptides of the invention in association with to xins or cytotoxic prodrugs.

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Antibodies, proteins and small molecules which are radiolabeled are cytotoxic agents and may be employed in targeted radiotherapy such as radioimmunotherapy, or in radioimmunodetection such as radioimmunodiagnosis and radioimaging. To protect or treat normal tissues, cells, and organs, MPIF-1 may be administered prior to, during, or after administration of radiolabeled antibodies, proteins or small molecules.

As indicated above, antibodies which specifically bind at least one epitope of MPIF-1 are included, and antibodies which specifically bind any epitope or polypeptide of the present invention may also be excluded. Thus, the antibodies may be specific for MPIF-1 or may be specific for polypeptides and epitopes other than MPIF-1. In one embodiment, a radiolabeled antibody, protein or small molecule is administered in combination with an MPIF polypeptide during radioimmunotherapy for cancer or another disease. The MPIF polypeptide protects and/or treats normal cells such as bone marrow progenitors, and other normal cells, tissues and organs from damage when administered prior to, during, or after administration of the radioimmunotherapeutic agent.

In another preferred embodiment, the compositions of the invention are administered in combination with Rituximab (anti-CD20 monoclonal antibody; Rituxan™), Ibritumomab tiuxetan (anti-CD20 monoclonal antibody conjugated with $^{90}$Y; Zevalin™), Tositumomab (conjugated to $^{131}$I; Bexxar™), Rituximab (Rituxan™), Trastuzumab (Herceptin™), OvaRex MoAb (monoclonal antibody to CA 125 in ovarian cancer), Denileukin difitox (diphtheria toxin conjugate; Ontak®), AA98 (monoclonal Ab that binds microvasculature but not normal tissue(Xiyun et al., *Clin Cancer Res.* 5(suppl):abstract 82 (1999)), Adrecolomab (anti-panadenocarcinoma antigen), anti-CEA antibodies (conjugated with $^{131}$I (Behr et al., Amer. Soc. of Clin. Oncol. 35th Annual Meeting, Atlanta; abstract 1025 (1999)), anti-TAG72 glycoprotein antibodies, anti-PMSA antibodies, anti-HLA-DR10β antibodies, anti-VEGF antibodies, anti-CXCR4 antibodies, CH225 (chimerized anti-EGFr antibody (Mendelsohn et al., Amer. Soc. of Clin. Oncol. 35th Ann. Meeting, Atlanta; abstract 1502 (1999)), CP-358,774 (Karp et al., Amer. Soc. Clin. Onc. 35th Ann. Meeting, Atlanta, Ga.; abstract 1499 (1999)) and ZD 1839 (Karp et al., Amer. Soc. Clin. Onc. 35th Ann. Meeting, Atlanta, Ga.; abstract 1500 (1999)) (both are small-molecule inhibitors of EGFr), IDEC-Y2B8 (anti-CD20 antibody conjugated to a molecule which binds $^{90}$Y (Witzig et al., "Phase I/II trial of IDEC-Y2B8 radioimmunotherapy for treatment of relapsed or refractory CD20-positive B-cell non-Hodgkin's lymphoma," *J Clin Oncol.* 1999 (in press); Bastion et al., *Blood.* 1995;86:3257–3262.), $^{131}$I-MN-14 F(ab)$_2$ anti-carcinoembryonic antigen monoclonal antibody (Juweid et al., *J Nucl Med* 2000 January;41(1):93–103; comment in: *J Nucl Med* 2000 January;41(1):104–6), $^{67}$Cu-21T-BAT-Lym-1 (Lym-1 is a mouse monoclonal antibodythat preferentially targets malignant lymphocytes; the chelating agent is 1,4,7,11-tetraazacyclotetradecane-N,N',N'',N'''-tetraacetic acid, which binds $^{67}$CU (O'Donnell et al., *J Nucl Med* 1999 December;40(12):2014–20)), rhenium-188-labeled anti-NCA antigen antibody BW 250/183 (anti-granulocyte; direct radiolabeling method using tris-(2-carboxyethyl) phosphine (TCEP) (Seitz et al., Eur *J Nucl Med* 1999 October;26(10):1265–73)), IDEC-Y2B8 ($^{90}$Y ibritumomab tiuxetan; a murine IgG$_1$ kappa anti-CD20 monoclonal antibody that covalently binds MX-DTPA (tiuxetan), which chelates the radioisotope yttrium-90 (Witzig J Clin Oncol 1999 December;17(12):3793–803)), $^{213}$Bi-HuM195 (anti-CD33 (Sgouros et al., *J Nucl Med* 1999 November;40(11): 1935–46)), $^{67}$Copper-2-iminothiolane-6-[p-(bromoacetamido)benzyl]-TETA-Lym-1 (O'Donnell et al., *Clin Cancer Res* 1999 October;5(10 Suppl):3330s–3336s)), $^{90}$Y-BC-4 (murine MAb that recognizes tenascin; stable $^{90}$Y-labeled MAb conjugates can be prepared using the chelator p-isothiocyanatobenzyl derivative of diethylenetriaminepentaacetic acid (ITC-Bz-DTPA)(Riva et al., *Clin Cancer Res* 1999 October;5(10 Suppl):3275s–3280s)), $^{131}$I-labeled cG250 chimeric monoclonal antibody G250 (cG250) (Steffens et al., *Clin Cancer Res* 1999 October;5(10 Suppl):3268s–3274s)), bispecific anti-carcinoembryonic antigen/anti-diethylenetriaminepentaacetic acid (DTPA) antibody and $^{131}$I Di-DTPA hapten (Vuillez et al., *Clin Cancer Res* 1999 October;5(10 Suppl):3259s–3267s)), and additional targets for radioimmunotherapy include HLA-DR, CD19, and CD22.

Methods for analyzing protection of normal tissue by compositions of the invention during radioimmunotherapy are well know in the art and include in vivo models for studying bone marrow damage using infusion of 89-Strontium, which seeks bone and thus irradiates marrow constituents. The following review articles also provide guidance for use of antibodies, radiotherapy and immunoradiotherapy: "Physical and biological targeting of radiotherapy" *Acta Oncol.* 1999;38 Suppl 13:75–83; "Radioimmunodiagnosis and therapy" *Cancer Treat Rev.* 2000 February;26(1):3–10; "Antibodies in the therapy of colon cancer" *Semin Oncol.* 1999 December;26(6):683–90; "Overview of the clinical development of rituximab: first monoclonal antibody approved for the treatment of lymphoma" *Semin Oncol.* 1999 October;26(5 Suppl 14):66–73; "Radiolabeled antibody therapy of B-cell lymphomas" *Semin Oncol.* 1999 October;26(5 Suppl 14):58–65; "Strategies for developing effective radioimmunotherapy for solid tumors" *Clin Cancer Res.* 1999 October;5(10 Suppl) :3219s–3223s; "Technical advances in radiotherapy of head and neck tumors" *Hematol Oncol Clin North Am.* 1999 August;13(4):811–23; and "Use of monoclonal antibodies for the diagnosis and treatment of bladder cancer"*Hybridoma.* 1999 June;18(3):219–24.

In another embodiment, the invention provides a method of delivering compositions containing the polypeptides of the invention (e.g., compositions containing MPIF polypeptides or anti-MPIF antibodies associated with heterologous polypeptides, heterologous nucleic acids, to xins, or prodrugs) to targeted cells, such as, for example, B or T cells, monocytes, macrophages, and neutrophils expressing MPIF. MPIF polypeptides or anti-MPIF antibodies of the invention may be associated with heterologous polypeptides, heterologous nucleic acids, to xins, or prodrugs via hydrophobic, hydrophilic, ionic and/or covalent interactions.

In one embodiment, the invention provides a method for the specific delivery of compositions of the invention to cells by administering polypeptides of the invention (e.g., MPIF polypeptides or anti-MPIF antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., MPIF polypeptides or anti-MPIF antibodies) in association with toxins or cytotoxic prodrugs.

For example, MPIF conjugated to a radioisotope may be administered to destroy leukemic cells, thus treating leukemia.

In a specific embodiment, the invention provides a method for the specific destruction of cells of T or B cell lineage (e.g., T or B cell related leukemias or lymphomas) by administering MPIF polypeptides in association with toxins or cytotoxic prodrugs.

In another specific embodiment, the invention provides a method for the specific destruction of cells of monocytic lineage (e.g., monocytic leukemias or lymphomas) by administering anti-MPIF antibodies in association with toxins or cytotoxic prodrugs.

In another embodiment, the invention provides a method for the specific destruction of cells (e.g., the destruction of cellular mediators of inflammation) by administering polypeptides of the invention (e.g., MPIF polypeptides or anti-MPIF antibodies) in association with toxins or cytotoxic prodrugs. Cellular mediators of inflammation include, for example, T cells, monocytes, dendritic cells, astrocytes, kidney mesangial cells, macrophages, neutrophils, and cells involved in graft rejection (acute or chronic).

In an another embodiment, non-MPIF molecules in association with toxins or cytotoxic prodrugs are administered in combination with MPIF-1, such that MPIF-1 prevents or treats normal cell, tissue, or organ damage, or protects bone marrow progenitor cells.

By "toxin" is meant compounds that bind and activate endogenous cytotoxic effector systems, radioisotopes, holotoxins, modified toxins, catalytic subunits of toxins, other cytoxic agents, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. "Toxin" also includes a cytoxic, cytostatic or cytocidal agent, a therapeutic agent or a radio-active metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$y, $^{51}$Cr, $^{54}$Mn, $^{Se}$, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Additional preferred embodiments of the invention include, but are not limited to, the use of MPIF polypeptides, MPIF polynucleotides, and functional agonists thereof, in the applications that follow below.

In a specific embodiment, an MPIF polypeptide(s) or polynucleotide(s) of the invention, or agonist(s) or antagonist(s) (e.g., anti-MPIF antibodies) thereof, are administered to treat, prevent, detect, and/or diagnose chronic myelogenous leukemia, acute myelogenous leukemia, leukemia, hystiocytic leukemia, monocytic leukemia (e.g., acute monocytic leukemia), leukemic reticulosis, Shilling Type monocytic leukemia, and/or other leukemias derived from monocytes and/or monocytic cells and/or tissues.

Thus, an MPIF polypeptide(s) or polynucleotide(s) of the invention, or agonist(s) or antagonist(s) (e.g., anti-MPIF antibodies) thereof, are administered to treat, prevent, detect, and/or diagnose leukemias such as acute lymphoblastic (lymphocytic) leukemia (ALL), which may include undifferentiated B cell forms, common B cell forms, pre-B cell forms, and B cell forms; acute myelogenous (myeloid or myelocytic) leukemia (AML) which may include undifferentiated myeloblastic forms, differentiated myeloblastic forms, promyelocytic forms (APL), myelomonoblastic forms, monoblastic forms, erythroleukemic forms, and megakaryoblastic forms; chronic lymphocytic (lymphatic) leukemia (CLL) which may include B cell forms, T cell forms, prolymphocytic forms, Sezary syndrome (leukemic phase of cutaneous T cell lymphoma), hairy cell forms, and lymphoma leukemia (i.e., leukemic changes seen in advanced stages of malignant lymphoma); and chronic myelocytic (myeloid, myelogenous or granulocytic) leukemia (CML), for example wherein the neoplastic clone is a red blood cell, megakaryocyte, monocyte, T cell, or B cell.

In another specific embodiment, an MPIF polypeptide(s) or polynucleotide(s) of the invention, or agonist(s) or antagonist(s) therof, is administered to treat, prevent, diagnose, and/or ameliorate monocytic leukemoid reaction, as seen, for example, with tuberculosis.

In another specific embodiment, an MPIF polypeptide(s) or polynucleotide(s) of the invention, or agonist(s) or antagonist(s) thereof, is administered to treat, prevent, diagnose, and/or ameliorate monocytic leukocytosis, monocytic leukopenia, monocytopenia, and/or monocytosis.

In another specific embodiment, an MPIF polypeptide(s) or polynucleotide(s) of the invention, or agonist(s) or antagonist(s) thereof, is administered to treat, prevent, diagnose, and/or ameliorate graft versus host disease or transplant rejection.

In another specific embodiment, an MPIF polypeptide(s) or polynucleotide(s) of the invention, or agonist(s) or antagonist(s) thereof, is administered to treat, prevent, diagnose, and/or ameliorate anemia.

In another specific embodiment, an MPIF polypeptide(s) or polynucleotide(s) of the invention, or agonist(s) or antagonist(s) thereof, is administered to treat, prevent, diagnose, and/or ameliorate B cell malignancies such as ALL, Hodgkins disease, non-Hodgkins lymphoma, Chronic lymphocyte leukemia, plasmacytomas, multiple myeloma, Burkitt's lymphoma, and EBV-transformed diseases.

In another embodiment, an MPIF polypeptide(s) or polynucleotide(s) of the invention, or agonist(s) or antagonist(s) thereof, is used to treat, prevent, and/or diagnose fibroses and conditions associated with fibroses, such as, for example, but not limited to, pulmonary fibrosis, cystic fibrosis (including such fibroses as cystic fibrosis of the pancreas, Clarke-Hadfield syndrome, fibrocystic disease of the pancreas, mucoviscidosis, and viscidosis), endomyocardial fibrosis, idiopathic retroperitoneal fibrosis, leptomeningeal fibrosis, mediastinal fibrosis, nodular subepidermal fibrosis, pericentral fibrosis, perimuscular fibrosis, pipestem fibrosis, replacement fibrosis, subadventitial fibrosis, and Symmers' clay pipestem fibrosis.

In a highly preferred embodiment, an MPIF polypeptide (s) or polynucleotide(s) of the invention, or agonist(s) or antagonist(s) thereof is used to treat, prevent, and/or diagnose mucositis, especially as associated with chemotherapy or radiation therapy.

MPIF polynucleotides or polypeptides of the invention and/or agonists and/or antagonists thereof, may also be used to treat, prevent, and/or diagnose organ rejection or graft-versus-host disease (GVHD) and/or conditions associated therewith. Organ rejection occurs by host immune cell destruction of the transplanted tissue through an immune response. Similarly, an immune response is also involved in GVHD, but, in this case, the foreign transplanted immune cells destroy the host tissues. The administration of MPIF polynucleotides or polypeptides of the invention and/or agonists and/or antagonists thereof, that inhibits an immune response, particularly the proliferation, differentiation, or chemotaxis of T-cells, monocytes or other mediators of inflammation, may be an effective therapy in preventing organ rejection or GVHD. Moreover, it has been shown that deletion of the CCR1 receptor, which binds MPIF-1, in mice resulted in prolonged allograft survival. (Gao et al., "Targeting of the chemokine receptor CCR1 suppresses development of acute and chronic cardiac allograft rejection," *J. Clin. Invest.* 2000 January; 105(1):35–44.) Thus, blocking the interaction of MPIF-1 or other CCR1 ligands with their CCR1 receptor, via an MPIF-1 antagonist for example, will be useful to prevent acute and chronic graft rejection.

Similarly, MPIF polynucleotides or polypeptides of the invention and/or agonists and/or antagonists thereof, may also be used to modulate inflammation. For example, MPIF polynucleotides or polypeptides of the invention and/or agonists and/or antagonists thereof, may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthrtis, complement-mediated hyperacute rejection, nephritis, cytokine or chemokine induced lung injury, inflammatory bowel disease, Crohn's disease, or resulting from over production of cytokines (e.g., TNF or IL-1.)

In a specific embodiment, anti-MPIF antibodies of the invention are used to treat, prevent, modulate, detect, and/or diagnose inflammation.

In a specific embodiment, anti-MPIF antibodies of the invention are used to treat, prevent, modulate, detect, and/or diagnose inflammatory disorders.

In a preferred embodiment, the compositions of the invention are administered in combination with CD40 ligand (CD40L), a soluble form of CD40L (e.g., AVRENDT™), biologically active fragments, variants, or derivatives of CD40L, anti-CD40L antibodies (e.g,. agonistic or antagonistic antibodies), and/or anti-CD40 antibodies (e.g, agonistic or antagonistic antibodies).

As is recognized in the art, the conjugates and chelates described above and herein in reference to antibodies apply equally to conjugates and chelates of MPIF polypeptides.

Immunophenotyping. The antibodies of the inventionmay be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding. The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel, et al., eds., *Current Protocols in Molecular Biology*, Vol. 1, John Wiley & Sons, Inc., New York (1994), which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1%

Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel, et al., eds., *Current Protocols in Molecular Biology*, Vol. 1, John Wiley & Sons, Inc., New York (1994) at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), contacting/probing/incubating the membrane with primary antibody (the antibody of interest) diluted in blocking buffer, washing the membrane in washing buffer, contacting/probing/incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds., *Current Protocols in Molecular Biology*, Vol. 1, John Wiley & Sons, Inc., New York (1994), at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well (i.e., sandwich ELISA). One of skill in the art would be knowledgeable as to the parameters that can be modified to increase the signal detected as well as other variations of ELISAs known in the art. For further discussion regarding ELISAs see, e.g., Ausubel et al., eds., *Current Protocols in Molecular Biology*, Vol. 1, John Wiley & Sons, Inc., New York (1994), at 11.1.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3$H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by Scatchard plot analysis. Competition with a second antibody can also be determined using radioimmunoassays. In this case, the antigen is incubated with antibody of interest conjugated to a labeled compound (e.g., $^3$H or $^{125}$I) in the presence of increasing amounts of an unlabeled second antibody.

Therapeutic-Antibodies. The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M.

Antibody Gene Therapy. In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., *Clinical Pharmacy* 12:488–505 (1993); Wu and Wu, *Biotherapy* 3:87–95 (1991); Tolstoshev, *Ann. Rev. Pharmacol. Toxicol.* 32:573–596(1993); Mulligan, *Science* 260:926–932 (1993); and Morgan and Anderson, *Ann. Rev. Biochem.* 62:191–217 (1993); May, *TIBTECH* 11(5): 155–215 (1993). Methods commonly known in the art of recombinant DNA technology which can be used are described in Ausubel et al. (eds.), *Current Protocols in Molecular Biology*, John Wiley & Sons, NY (1993); and Kriegler, *Gene Transfer and Expression, A Laboratory Manual*, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, *Proc. Natl. Acad. Sci. USA* 86:8932–8935 (1989); Zijlstra et al., *Nature* 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, *J. Biol. Chem.* 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, *Proc. Natl. Acad. Sci. USA* 86:8932–8935 (1989); Zijlstra et al., *Nature* 342:435–438 (1989)).

In a specific embodiment, viral vectors that contains nucleic acid sequences encoding an antibody of the invention are used. For example, a retroviral vector can be used (see Miller et al., *Meth. Enzymol.* 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., *Biotherapy* 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644–651 (1994); Kiem et al., *Blood* 83:1467–1473 (1994); Salmons and Gunzberg, *Human Gene Therapy* 4:129–141 (1993); and Grossmanand Wilson, *Curr. Opin. in Genetics and Devel.* 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499–503 (1993) present a review of adenovirus-based gene therapy. Bout et al., *Human Gene Therapy* 5:3–10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431–434(1991); Rosenfeld et al., *Cell* 68:143–155(1992); Mastrangeli et al., *J. Clin. Invest.* 91:225–234(1993); PCT Publication WO94/12649; and Wang, et al., *Gene Therapy* 2:775–783 (1995). In a preferred embodiment, adenovirus vectors are used.

Adeno-associated virus (AAV) has also been proposed for use in gene therapy (Walsh et al., *Proc. Soc. Exp. Biol. Med.* 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, *Meth. Enzymol.* 217:599–618(1993);Cohen et al., *Meth. Enzymol.* 217:618–644(1993); Cline, *Pharmac. Ther.* 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, *Cell* 71:973–985 (1992); Rheinwald, *Meth. Cell Bio.* 21A:229 (1980); and Pittelkow and Scott, *Mayo Clinic Proc.* 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/ProphylacticAdministration and Composition-Antibodies.

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, *J. Biol. Chem.* 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, *Science* 249:1527–1533 (1990); Treat et al., in *Liposomes in the Therapy of Infectious Disease and Cancer*, Lopez-Berestein and Fidler, eds., Liss, N.Y. (1989), pp. 353–365; Lopez-Berestein, ibid., pp. 317–327; see generally ibid.)

In yet another embodiment, the compound or composition can be delivered in a controlled release system. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see *Medical Applications of Controlled Release*, Langer and Wise, eds., CRC Pres., Boca Raton, Fa. (1974); *Controlled Drug Bioavailability, Drug Product Design and Performance*, Smolen and Ball, eds., Wiley, NY (1984); Ranger and Peppas, *J., Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105(1989)). Inyetanother embodiment, a controlledrelease system can be placed in proximity of the therapeutic target, i.e., the brain, thus requiring only a fraction of the systemic dose (see, e.g., Goodson, *Medical Applications of Controlled Release*, supra, vol. 2 (1984), pp. 115–138).

Other controlled release systems are discussed in the review by Langer (*Science* 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al, *Proc. Natl. Acad. Sci. USA* 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the US Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, to gether with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed to gether in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages ofhuman antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging-Antibodies. Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., *J. Cell. Biol.* 101:976–985 (1985); Jalkanen, et al., *J. Cell. Biol.* 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments," in *Tumor Imaging: The Radiochemical Detection of Cancer*, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Antibody and Other Kits. The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be amonoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, MO).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

In order to facilitate understanding of the following examples certain frequently occurring methods and/or terms will be described. "Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but can vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which can be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation can be accomplished using known buffers and conditions with 10 units to T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

Having now generally described the invention, the same will be more readily understood through reference to the following example which is provided by way of illustration, and is not intended to be limiting of the present invention.

EXAMPLE 1

Bacterial Expression and Purification of MPIF-1

The DNA sequence encoding for MPIF-1, ATCC # 75676 is initially amplified using PCR oligonucleotide primers corresponding to the 5' and sequences of the processed MPIF-1 protein (minus the signal peptide sequence) and the vector sequences 3' to the MPIF-1 gene. Additional nucleotides corresponding to Bam HI and XbaI were added to the 5' and 3' sequences respectively. The 5' oligonucleotide primer has the sequence 5'-TCAGGATCCGTCACA AAAGATGCAGA-3' (SEQ ID NO:8) contains a BamHI restriction enzyme site followed by 18 nucleotides of MPIF-1 coding sequence starting from the presumed terminal amino acid of the processed protein codon. The 3' sequence 5'-CGCTCTAGAGTAAAACGACGGCCAGT-3' (SEQ ID NO:9) contains complementary sequences to an XbaI site.

The restriction enzyme sites correspond to the restriction enzyme sites on the bacterial expression vector pQE-9 (Qiagen, Inc. Chatsworth, Calif.). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with BamHI and XbaI. The amplified sequences are ligated into pQE-9 and are inserted in frame with the sequence encoding for the histidine tag and the RBS. The ligation mixture is then used to transform *E. coli* strain M15/rep4 available from Qiagen. M15/rep4 contains multiple copies of the plasmid pREP4, which expresses the lacI repressor and also confers kanamycin resistance (Kanehur). Transformants are identified by their ability to grow on LB plates and ampicillin/kanamycin resistant colonies are selected. Plasmid DNA is isolated and confirmed by restriction analysis overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the lacI repressor, clearing the P/O leading to increased gene expression. Cells are grown an extra 3 to 4 hours. Cells are then harvested by centrifugation. The cell pellet is solubilized in the chaotropic agent 6 M Guanidine HCl. After clarification, solubilized MPIF-1 is purified from this solution by chromatography on a Nickel-Chelate column under conditions that allow for tight binding by proteins containing the 6-His tag. Hochuli, E. et al., J. Chromatography 411:177–184 (1984). MPIF-1 (95% pure) is eluted from the column in 6 M guanidine HCl pH 5.0 and for the purpose of renaturation adjusted to 3 M guanidine HCl, 100 mM sodium phosphate, 10 mM glutathione (reduced) and 2 mM glutathione (oxidized). After incubation in this solution for 12 hours the protein is dialyzed to 10 mM sodium phosphate.

Alternatively, the following non-tagged primers were used to clone the gene into plasmid pQE70:

5' primer: 5' CCC GCA TGC GGG TCA CAA AAG ATG CAG 3' (SEQ ID NO:10)
SphI

3' primer: 5' AAA GGA TCC TCA ATT CTT CCT GGT CTT 3' (SEQ ID NO:11)
BamHI Stop

Construction of *E. coli* optimized MPIF-1

In order to increase expression levels of MPIF-1 in an *E. coli* expression system, the codons of the gene were optimized to highly used *E. coli* codons. For the synthesis of the optimized region of MPIF-1, a series of 4 oligonucleotides were made: mpif-1 oligo numbers 1–4 (set forth below). These overlapping oligos were used in a PCR reaction for seven rounds at the following conditions:

| Denaturation | 95 degrees | 20 seconds |
|---|---|---|
| Annealing | 58 degrees | 20 seconds |
| Extension | 72 degrees | 60 seconds |

Following the seven rounds of synthesis, a 5' primer to this region, (ACA TGC ATG CGU GUU ACC AAA GAC GCU GAA ACC GAA UUC AUG AUG UCC (SEQ ID NO:12)) and a 3' primer to this entire region, (GCC CAA GCTTTC AGT TTT TAC GGG TTT TGA TAC GGG (SEQ ID NO:13)), were added to a PCR reaction, containing 1 microliter from the initial reaction of the six oligonucleotides. This product was amplified for 30 rounds using the following conditions:

| Denaturation | 95 degrees | 20 seconds |
|---|---|---|
| Annealing | 55 degrees | 20 seconds |
| Extension | 72 degrees | 60 seconds |

The product produced by this final reaction was restricted with Sph I and HindIII, and cloned into pQE70, which was also cut with Sph I and HindIII. These clones were expressed and found to have superior expression levels that without the above mutations.

mpif oligo number 1:
  5' GCA TGC GUG UUA CCA AAG ACG CUG AAA CCG AAU UCA UGA UGU CCA AAC UGC CGC UGG AAA ACC CGG UUC UGC UGG ACC GUU UCC ACG C 3' (SEQ ID NO:14)

mpif-1 oligo number 2:
  5' GCU GGA AUC CUA CUU CGA AAC CAA CUC CGA AUG CUC CAA ACC GGG UGU UAU CUU CCU GAC CAA AAA AGG UCG UCG UUU CUG CGC UAA CCC GUC CGA CAA ACA GG 3' (SEQ ID NO:15)

mpif1 oligo number 3:
  5' AAG CTT TCA GTT TTT ACG GGT TTT GAT ACG GGT GTC CAG TTT CAG CAT ACG CAT ACA AAC CTG AAC CTG TTT GTC GGA CGG GTT AGC GC 3' (SEQ ID NO:16)

mpif-1 oligo number 4:
  5'GGT TTC GAA GTA GGA TTC CAG CAG GGA GCA CGG GAT GGA ACG CGG GGT GTA GGA GAT GCA GCA GTC AGC GGA GGT AGC GTG GAA ACGOGTC CAG C 3' (SEQ ID NO:17)

Construction of MPIF-1 Deletion Mutants

Deletion mutants were constructed from the 5' terminus of the MPIF-1 gene using the *E. coli* optimized MPIF-1 construct set forth above. The primers used to construct the 5' deletions are set forth below. The PCR amplification was performed as set forth above for the *E. coil* optimized MPIF-1 construct. The products for the Delta 17-A qe6, Delta 23, Delta 28 were restricted with NcoI for the 5' site and HindIII for the 3' site and cloned into plasmid pQE60 that was digested with NcoI and HindIII. All other products were restricted with SphI for the 5' site and HindIII for the 3' site and cloned into plasmid pQE70 that was digested with SphI and HindIII.

The 5' primers used are as follows:

Delta 17-A qe6 (pQE60)
  5' NcoI gc gca g ccatgg aa aac ccg gtt ctg ctg gac 3' (SEQ ID NO:18)

The resulting amino acid sequence of this deletion mutant: MENPVLLDRFHATSADCCISYTPRSIPC-

SLLESYFETNSECSKPGVIFLTK KGRRFCANPSD-
KQVQVCMRMLKLDTRIKTRKN (SEQ ID NO:19)

Delta 16-A qe7 (pQE70)

5' SphI gc cat g gcatgc tg gaa aac ccg gtt ctg ctg gac (SEQ ID NO:20)

The resulting amino acid sequence of this deletion mutant: MLENPVLLDRFHATSADCCISYTPR-SIPCSLLESYFETNSECSKPGVIFLT KKGRRFCANPSD-KQVQVCMRMLKLDTRIKTRKN (SEQ ID NO:21)

Delta 23 (pQE60)

5' NcoI gc gca g ccatgg ac cgt ttc cac gct acc tcc (SEQ ID NO:22)

The resulting amino acid sequence of this deletion mutant: MDRFHATSADCCISYTPRSIPCSLLESY-FETNSECSKPGVIFLTKKGRRF CANPSDKQVQVCM-RMLKLDTRIKTRKN (SEQ ID NO:23)

Delta 24 (pQE70)

5' SphI gcc atg gcatgc gtt tcc acg cta cct cc (SEQ ID NO:24)

The resulting amino acid sequence of this deletion mutant: MRFHATSADCCISYTPRSIPCSLLESY-FETNSECSKPGVIFLTKKGRRFC ANPSDKQVQVCM-RMLKLDTRIKTRKN (SEQ ID NO:4)

Delta 28 (pQE60)

5' NcoI gcg cag ccatgg cta cct ccg ctg act gct gc (SEQ ID NO:25)

The resulting amino acid sequence of this deletion mutant: MATSADCCISYTPRSIPCSLLESYFET-NSECSKPGVIFLTKKGRRFCANPS DKQVQVCMRM-LKLDTRIKTRKN (SEQ ID NO:26)

S70 to A mutant (Ser at position 70 was mutated to Ala) (pQE70)

antisense ttc gaa gta ggc ttc cag cag (SEQ ID NO:27)
sense ctg ctg gaa gcc tac ttc gaa (SEQ ID NO:28)
5' SphI full gcc atg gcatgc gtg tta cca aag acg ctg aaa cc (SEQ ID NO:29)

The resulting amino acid sequence of this deletion mutant: MRVTKDAETEFMMSKLPLENPVLLDRF-HATSADCCISYTPRSIPCSLLE aYFETNSECSKPGVI-FLTKKGRRFCANPSDKQVQVCMRMLKLDTRIKT RKN (SEQ ID NO:30)

The 3' primer used for all constructs:

3' Hind III gcc c aagctt tca gt ttt tca ggg ttt tga tac ggg (SEQ ID NO:31)

The "mature" MPIF-1 for *E. coli* expression (Mutant-1 in FIG. 19) MRVTKDAETEFMMSKLPLENPVLLDRF-HATSADCCISYTPRSIPCSLLE SYFETNSECSKPGVI-FLTKKGRRFCANPSDKQVQVCMRMLKLDTRIKT RKN (SEQ ID NO:3)

EXAMPLE 2

Most of the vectors used for the transient expression of the MPIF-1 gene sequence in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing.

Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human HeLa, 283, H9 and Jurkart cells, mouse NIH3T3 and C127 cells, Cos 1, Cos 7 and CV1, African green monkey cells, quail QC 1–3 cells, mouse L cells and Chinese hamster ovary cells. Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that cany several hundred or even several thousand copies of the gene of interest. Another useful selection marker is the enzyme glutamine synthase (GS) (Murphy et al., *Biochem J*. 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530(1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

A. Expression of Recombinant MPIF-1 in COS Cells

The expression of plasmid, CMV-MPIF-1 HA is derived from a vector pcDNAI/Amp (Invitrogen) containing: (1) SV40 origin of replication, (2) ampicillin resistance gene, (3) *E. coli* replication origin, (4) CMV promoter followed by a polylinker region, a SV40 intron and polyadenylation site. A DNA fragment encoding the entire MPIF-1 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (Wilson, H., et al., *Cell* 37:767(1991)). The infusion of HA tag to our target protein allows easy detection of the recombinant protein with an antibody that recognizes the HA epitope.

The plasmid construction strategy is described as follows:

The DNA sequence, ATCC # 75676, encoding for MPIF-1 is constructed by PCR on the original EST cloned using two primers: the 5' primer 5'-GGAAAGCTTATG AAGGTCTCCGTGGCT-3' (SEQ ID NO:32) contains a HindIII site followed by 18 nucleotides of MPIF-1 coding sequence starting from the initiation codon; the 3' sequence 5'-CGCTCTAGATCAAGCGTAGTCT -GGGACGTCGTATGGGTAATTCTTCCTGGTCTT GATCC-3' (SEQ ID NO:33) contains complementary sequences to Xba I site, translation stop codon, HA tag and the last 20 nucleotides of the MPIF-1 coding sequence (not including the stop codon). Therefore, the PCR product contains a HindIII site, MPIF-1 coding sequence followed by HA tag fused in frame, a translation termination stop codon next to the HA tag, and an XbaI site. The PCR amplified DNA fragment and the vector, pcDNAI/Amp, are digested with HindIII and XbaI restriction enzyme and ligated. The ligation mixture is transformed into *E. coli* strain SURE (available from Stratagene Cloning Systems, 11099 North Torrey Pines Road, La Jolla, Calif. 92037) the transformed culture is plated on ampicillin media plates and resistant colonies are selected. Plasmid DNA is isolated from transformants and examined by restriction analysis for the presence of the correct fragment. For expression of the recombinant MPIF-1, COS cells are transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the MPIF-1-HA protein is detected by radiolabelling and immunoprecipitation method. (E. Harlow, D. Lane, Antibodies: A Laboratory Manual, Cold Spring Harbor Laboratory Press, (1988)). Cells are labeled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). (Wilson, I. et al., Id. 37:767 (1984)). Both cell lysate and culture media are precipitated with a HA specific monoclonal antibody. Proteins precipitated are analyzed on 15% SDS-PAGE gels.

B. Cloning and Expression in CHO Cells

The vector pC1 is used for the expression of MPIF-1 protein. Plasmid pC1 is a derivative of the plasmid pSV2-dhfr (ATCC Accession No. 37146). Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985:438–4470) plus a fragment isolated from the enhancer of the immediate early gene of human cytomegalovirus (CMV) (Boshart et al., *Cell* 41:521–530, 1985). Downstream of the promoter are the following single restriction enzyme cleavage sites that allow the integration of the genes: BamHI, followed by the 3' intron and the polyadenylation site of the rat preproinsulin gene. Other high efficient promoters can also be used for the expression, e.g., the human β-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding MPIF-1, ATCC No. 75676, is amplified using PCR oligonucleotide primers corresponding to the 5' and 3' sequences of the gene:

The 5' primer has the sequence:

5' AAA <u>GGA TCC GCC ACC</u> ATG AAG GTC TCC GTG GTC 3'

BamHI KOZAK (SEQ ID NO:34) containing the underlined BamHI restriction enzyme site and a portion of the MPIF-1 protein coding sequence of FIG. 1 (SEQ ID NO:1). Inserted into an expression vector, as described below, the 5' end of the amplified fragment encoding human MPIF-1 provides an efficient signal peptide. An efficient signal for initiation of translation in eukaryotic cells, as described by Kozak, M., J. Mol. Biol. 196:947–950 (1987) is appropriately located in the vector portion of the construct.

The 3' primer has the sequence:

5' AAA <u>GGA TCC TCA</u> ATT CTT CCA GGT CTT 3'

BamHI Stop (SEQ ID NO:35) containing the Asp718 restriction site and a portion of nucleotides complementary to the MPIF-1 coding sequence set out in FIG. 1 (SEQ ID NO:1), including the stop codon.

The amplified fragments are isolated from a 1% agarose gel as described above and then digested with the endonucleases BamHI and Asp718 and then purified again on a 1% agarose gel.

The isolated fragment and the dephosphorylated vector are then ligated with T4 DNA ligase. *E. coli* HB101 cells are then transformed and bacteria identified that contained the plasmid pC1 inserted in the correct orientation using the restriction enzyme BamHI. The sequence of the inserted gene is confirmed by DNA sequencing.

Transfection of CHO-DHFR-cells

Chinese hamster ovary cells lacking an active DHFR enzyme are used for transfection. 5 μg of the expression plasmid C1 are cotransfected with 0.5 μg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 μM, 2 μM, 5 μM). The same procedure is repeated until clones grow at a concentration of 100 μM.

The expression of the desired gene product is analyzed by Western blot analysis and SDS-PAGE.

EXAMPLE 3

Expression Pattern of MPIF-1 in Human Tissue

Northern blot analysis was carried out to examine the levels of expression of MPIF-1 in human tissues. Total cellular RNA samples were isolated with RNAzol™ B system (Biotecx Laboratories, Inc. 6023 South Loop East, Houston, Tex. 77033). About 10 ug of total RNA isolated from each human tissue specified is separated on 1% agarose gel and blotted onto a nylon filter. (Sambrook, Fritsch, and Maniatis, Molecular Cloning, Cold Spring Harbor Press, (1989)). The labeling reaction is done according to the Stratagene Prime-It kit with 50 ng DNA fragment. The labeled DNA is purified with a Select-G-50 column. (5 Prime-3 Prime, Inc. 5603 Arapahoe Road, Boulder, Colo. 80303). The filter is then hybridized with radioactive labeled full length MPIF-1 gene at 1,000,000 cpm/ml in 0.5 M $NaPO_4$, pH 7.4 and 7% SDS overnight at 65° C. After wash twice at room temperature and twice at 60° C. with 0.5× SSC, 0.1% SDS, the filter is then exposed at −70° C. overnight with an intensifying screen.

EXAMPLE 4

Expression and Purification of Chemokine MPIF-1 Using a Baculovirus Expression System SF9 cells were infected with a recombinant baculovirus designed to express the MPIF-1 cDNA. Cells were infected at an MOI of 2 and cultured at 28° C. for 72–96 hours. Cellular debris from the infected culture was removed by low speed centrifugation. Protease inhibitor cocktail was added to the supernatant at a final concentration of 20 $\mu$g/ml Pefabloc SC, 1 $\mu$g/ml leupeptin, 1 $\mu$g/ml E-64 and 1 mM EDTA. The level of MPIF-1 in the supernatant was monitored by loading 20–30 $\mu$l of supernatant only 15% SDS-PAGE gels. MPIF-1 was detected as a visible 9 Kd band, corresponding to an expression level of several mg per liter. MPIF-1 was further purified through a three-step purification procedure: Heparin binding affinity chromatography. Supernatant of baculovirus culture was-mixed with ⅓ volume of buffer containing 100 mM HEPES/MES/NaOAc pH 6 and filtered through 0.22 $\mu$m membrane. The sample was then applied to a heparin binding column (HEl poros 20, Bi-Perceptive System Inc.). MPIF-1 was eluted at approximately 300 mM NaCl in a linear gradient of 50 to 500 mM NaCl in 50 mM HEPES/MES/NaOAc at pH 6; Cation exchange chromatography. The MPIF-1-enriched from heparin chromatography was subjected to a 5-fold dilution with a buffer containing 50 mM HEPES/MES/NaOAc pH 6. The resultant mixture was then applied to a cation exchange column (S/M poros 20, Bio-Perceptive System Inc.). MPIF-1 was eluted at 250 mM NaCl in a linear gradient of 25 to 300 mM NaCl in 50 mM HEPES/MES/NaOAc at pH 6; Size exclusion chromatography. Following the cation exchange chromatography, MPIF-1 was further purified by applying to a size exclusion column (HW50, TOSO HAAS, 1.4×45 cm). MPIF-1 fractionated at a position close to a 13.7 Kd molecular weight standard (RNase A), corresponding to the dimeric form of the protein.

Figure 3B:
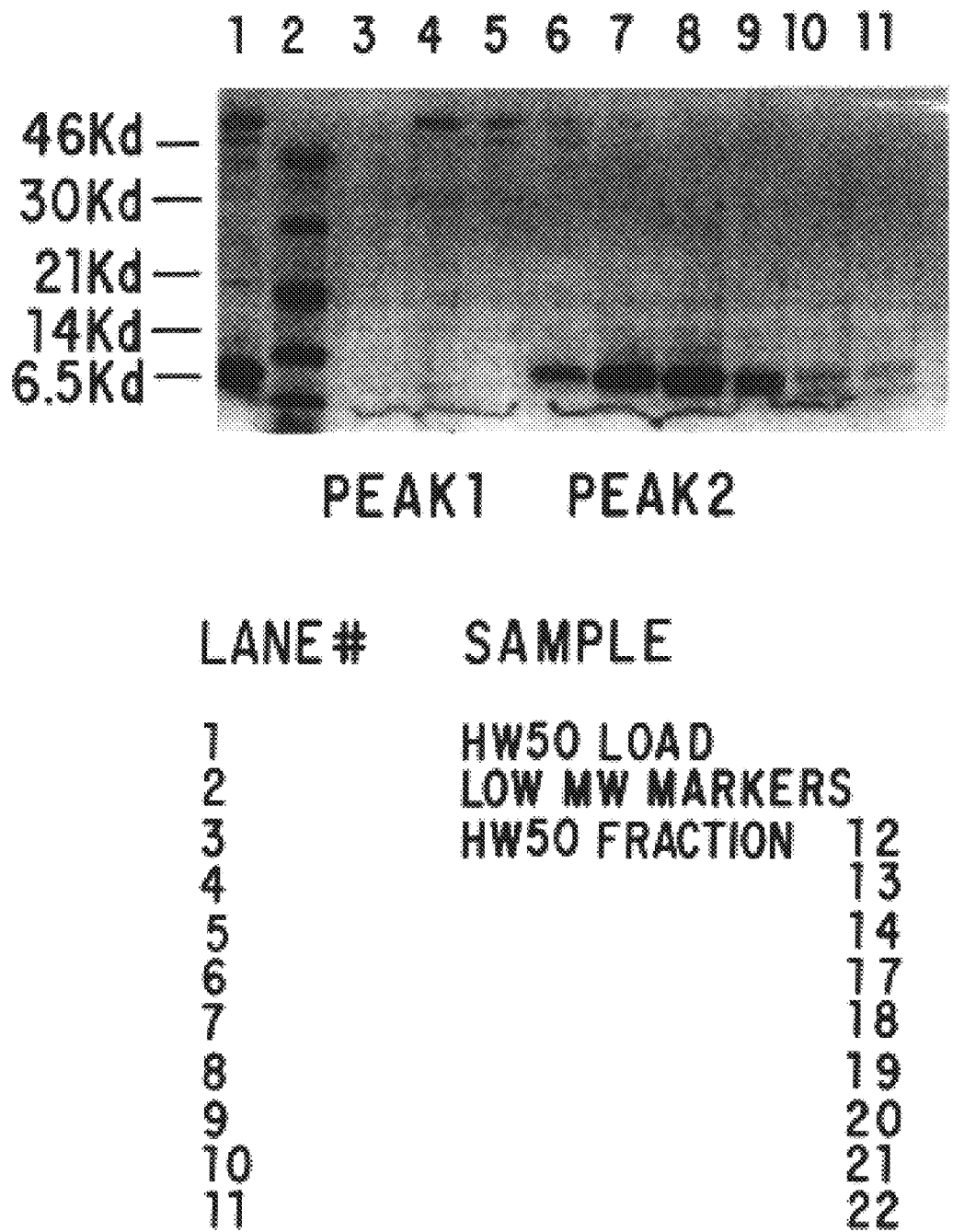

Following the three-step purification described above, the resultant MPIF-1 was judged to be greater than 90% pure as determined from commassie blue staining of an SDS-PAGE gel (FIGS. 3A–3B).

The purified MPIF-1 was also tested for endotoxin/LPS contamination. The LPS content was less than 0.1 ng/ml according to LAL assays (Bio Whittaker).

EXAMPLE 5

Effect of Baculovirus-expressed M-CIF and MPIF-1 on M-CSF and SCF-stimulated Colonyformation of Freshly Isolated Bone Marrow Cells A low density population of mouse bone marrow cells were incubated in a treated tissue culture dish for one hour at 37° C. to remove monocytes, macrophages, and other cells that adhere to the plastic surface. The non-adherent population of cells were then plated (10,000 cells/dish) in agar containing growth medium in the presence or absence of the factors shown in FIG. 8. Cultures were incubated for 10 days at 37° C. (88% $N_2$, 5% $CO_2$, and 7% $O_2$) and colonies were scored under an inverted microscope. Data is expressed as mean number of colonies and was obtained from assays performmned in triplicate.

EXAMPLE 6

Effect of MPIF-1 and M-CIF on IL-3 and SCF Stimulated Proliferation and Differentiation of Lin- Population of Bone Marrow Cells A population of mouse bone marrow cells enriched in primitive hematopoietic progenitors was obtained using a negative selection procedure, where the committed cells of most of the lineages were removed using a panel of monoclonal antibodies (anti cdllb, CD4, CD8, CD45R, and Gr-1 antigens) and magnetic beads. The resulting population of cells (lineage depleted cells) were plated ($5 \times 10^4$ cells/ml) in the presence or absence of the indicated chemokine (50 ng/ml) in a growth medium supplemented with IL-3 (5 ng/ml) plus stem cell factor (SCF) (100 ng/ml). After seven days of incubation at 37° C. in a humidified incubator (5% $CO_2$, 7% $O_2$, and 88% $N_2$ environment), cells were harvested and assayed for the HPP-CFC, and immature progenitors. In addition, cells were analyzed for the expression of certain differentiation antigens by FACScan. Colony data are expressed as mean number of colonies (+/− SD) and were obtained from assays performed in six dishes for each population of cells (FIG. 9).

EXAMPLE 7

MPIF-1 Inhibits Colony Formation in Response to IL-3, M-CSF, and GM-CSF

Mouse bone marrow cells were flushed from both the femur and tibia, separated on a ficoll density gradient and monocytes removed by plastic adherence. The resulting population of cells were incubated overnight in an MEM-based medium supplemented with IL-3 (5 ng/ml), GM-CSF (5 ng/ml), M-CSF (10 ng/ml) and G-CSF (10 ng/ml). These cells were plated at 1,000 cells/dish in agar-based colony formation assays in the presence of IL-3 (5 ng/ml), GM-CSF (5 ng/ml) or M-CSF (5 ng/ml) with or without at 50 ng/ml. The data is presented as colony formation as a percentage of the number of colonies formed with the specific factor alone. Two experiments are shown with the data depicted as the average of duplicate dishes with error bars indicating the standard deviation for each experiment (FIG. 11).

EXAMPLE 8

Expression via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted and the chunks of tissue remain fixed to the bottom of the flask and fresh media (e.g Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, *DNA* 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer having contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbeccol's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

EXAMPLE 9

In Vitro Myeloprotection

As demonstrated above, MPIF-1 is a potent inhibitor of the Low Proliferative Potential Colony-Forming Cell (LPP-CFC), a myeloid progenitor that gives rise to granulocyte and monocyte lineages. To demonstrate that MPIF-1 provides protection for LPP-CFC from the cytotoxicity of the cell cycle acting chemotherapeutic drug, lineage-depleted populations of cells (Lin-cells) were isolated from mouse bone marrow and incubated in the presence of multiple cytokines with or without MPIF-1. After 48 hours, one set of each culture received 5-Fu and the incubation was then continued for additional 24 hours, at which point the numbers of surviving LPP-CFC were determined by a clonogenic assay. As shown in FIG. 21A, ~40% of LPP-CFC were protected from the 5-Fu-induced cytotoxicity in the presence of MPIF-1, whereas little protection (<5%) of LPP-CFC was observed in the absence of MPIF-1 in the presence of an unrelated protein. High Proliferative Potential Colony-Forming Cells (HPP-CFC) were not protected by MPIF-1 under the same culture conditions, demonstrating specificity of the MPIF-1 protective effect.

Figure 15A:
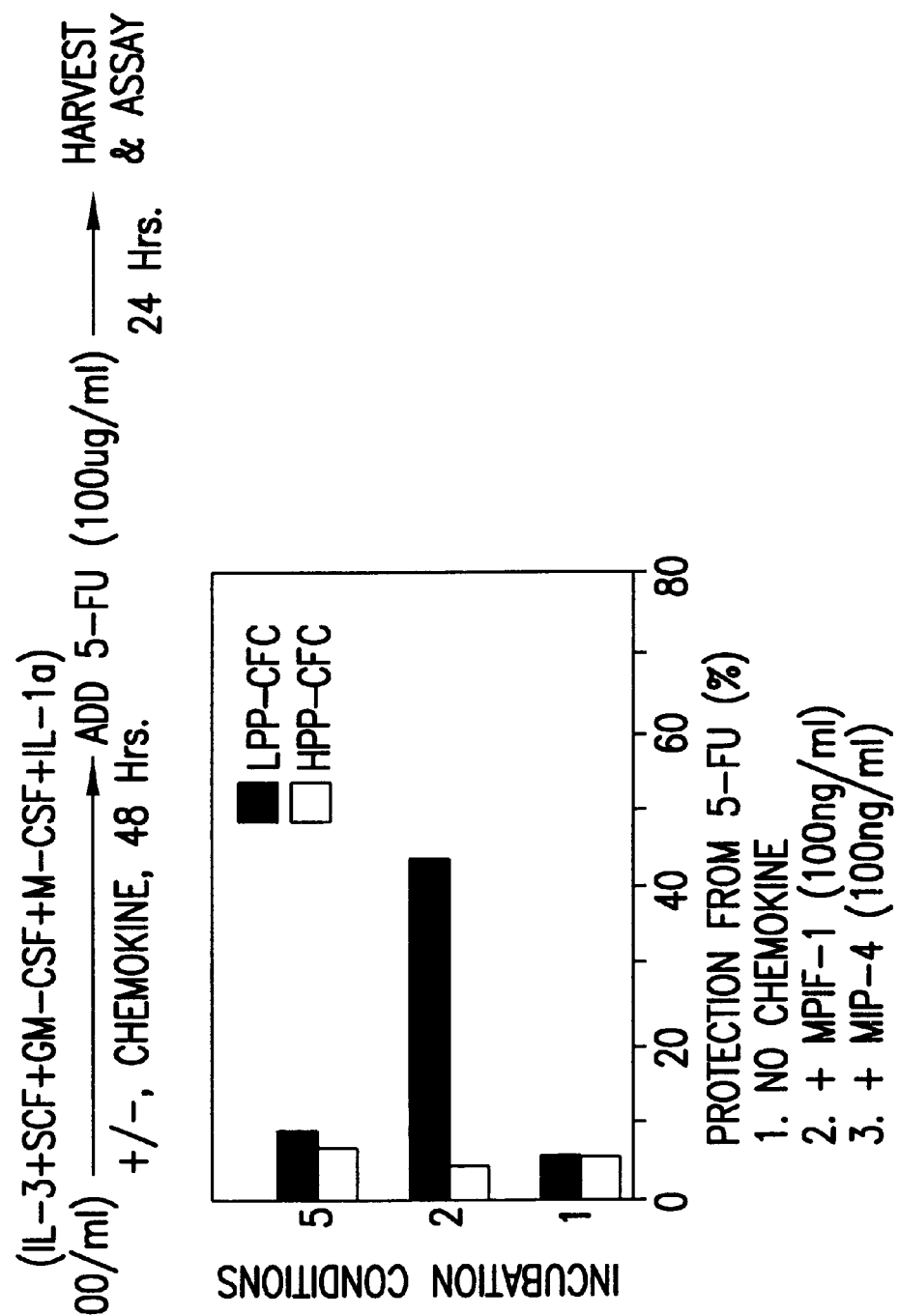
FIGS. 15A–15B. (A) shows the myeloprotective effect of MPIF-1 on the 5-Fu-induced killing of LPP-CFC cells. (B) shows the myeloprotective effect of MPIF-1 on the Ara-C induced killing of LPP-CFC cells.
Figure 15B:
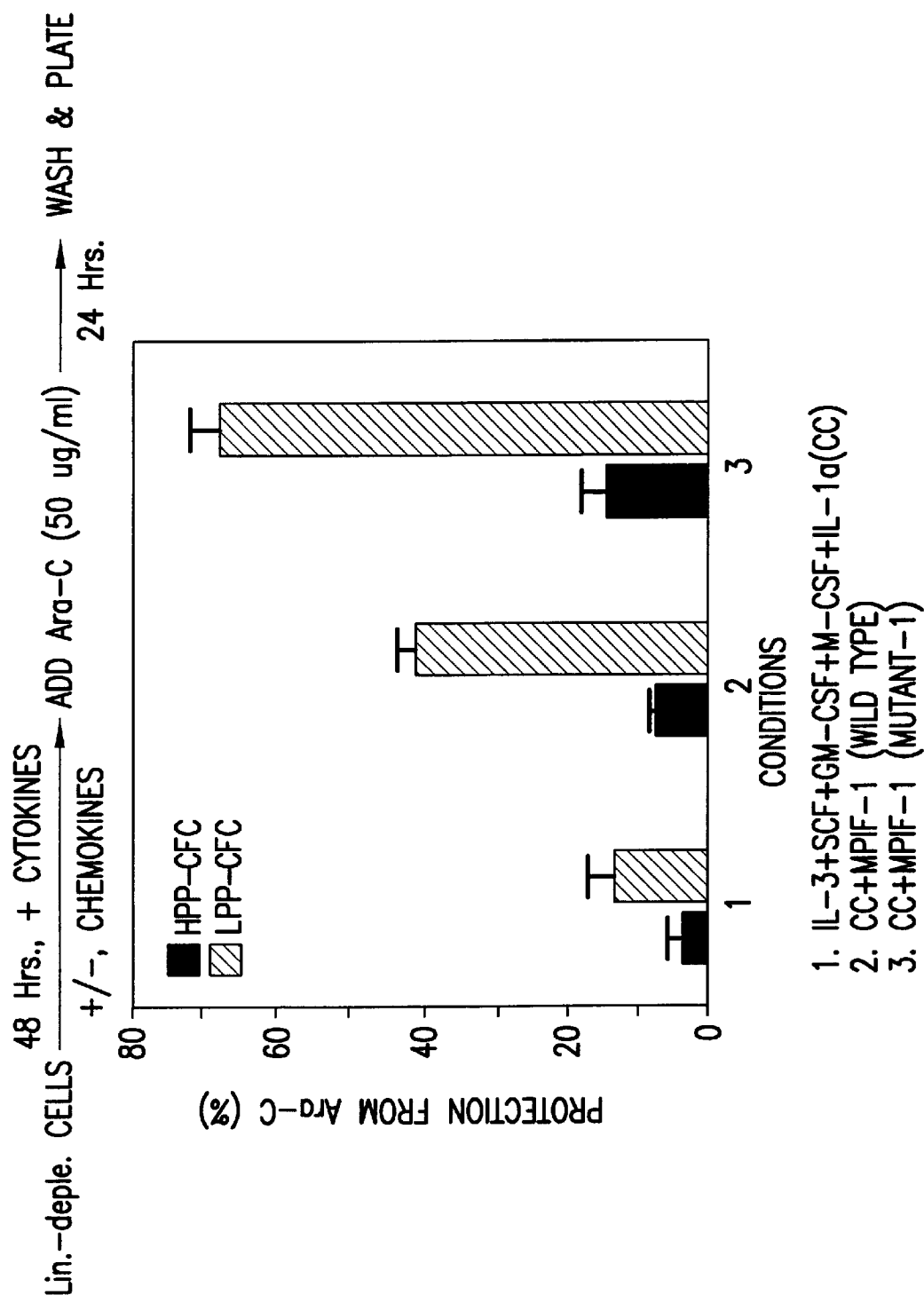

Similar experiments were performed using the chemotherapeutic agent, Ara-C instead of 5-Fu. As shown in FIG. 15B, dramatic protection of LPP-CFC by both from wild type MPIF-1 and a mutant MPIF-1 (i.e., mutant-1, see Example 11 below for description of this mutant). Thus, MPIF-1 is able to protect LPP-CFC from the cytotoxicity induced by both chemotherapeutic drugs, 5-Fu and Ara-C.

EXAMPLE 10

In Vivo Myeloprotection

The in vitro myeloprotection results suggest that myelotoxicity elicited by the cytotoxic drugs, a severe side effect observed in cancer patients undergoing chemotherapy, might be ameliorated if the critical cell types within the bone marrow could be protected by MPIF-1 during the period of action of the chemotherapeutic drugs. To demonstrate in vivo myeloprotection, two types of experiments were performed in mice. In one experiment, a group of mice (Group-4) were injected (I.P.) daily for three days, at 24 hour intervals, with 1.0 mg/Kg MPIF-1, and on the third day these mice were also injected (I.P.) with 5-Fu at 150 mg/Kg. Animals injected with either saline (Group-1), MPIF-1 alone (Group-2), or 5-Fu alone (Group-3) served as controls. Then, four animals from each of the groups were sacrificed at 3, 6, and 10 days post 5-Fu administration to determine White Blood Cell (WBC) counts in the peripheral blood. As shown in the FIG. 16, injection of MPIF-1 alone had little effect on the WBC counts. As expected, 5-Fu treatment resulted in a dramatic reduction in the circulating WBC counts on day 6 post 5-Fu. Significantly, animals treated with MPIF-1 prior to 5-Fu administration exhibited about two fold higher WBC counts in the blood compared to animals treated with 5-Fu alone. Thus, treatment of mice with MPIF-1 prior to 5-Fu results in the accelerated recovery from neutropenia.

Hematopoietic stem and multipotential progenitor cells in the bone marrow are responsible for restoring all the hematopoietic lineages following chemotherapy. In normal individuals, these cells divide less frequently, and are, therefore, spared from a single dose of the chemotherapeutic drug. However, these cells are killed if a second dose of the drug is administered within three days after the first dose because the critical progenitor cell types in the marrow are rapidly dividing during this period.

Figure 17:
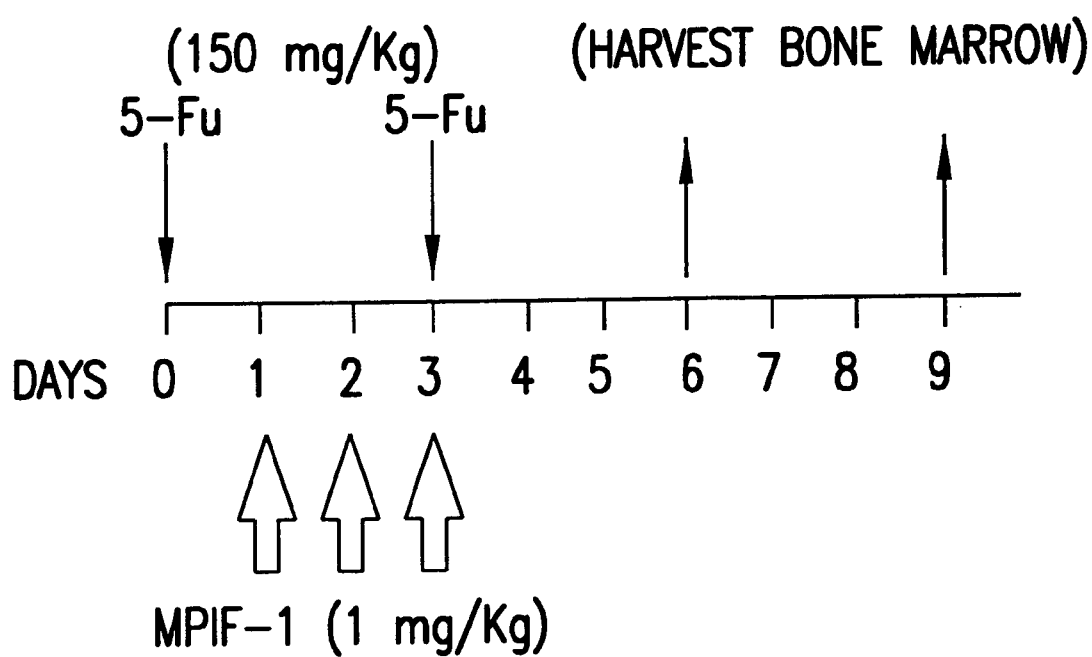
FIG. 17 shows the experimental design involving three groups of mice (6 animals per group) that were treated as follows: Group-1, injected with saline on days 1, 2, and 3; Group-2, injected with 5-Fu on days 0 and 3; and Group-3, injected with 5-Fu on days 0 and 3 and MPIF-1 on days 1, 2, and 3. Bone marrow was harvested on days 6 and 9 to determine HPP-CFC and LPP-CFC frequencies using a clonogenic assay.

To demonstrate that MPIF-1 is able to protect these cell types in the bone marrow, the following experiment was performed. The experimental was performed using three groups of mice (6 animals per group) that were treated as follows: Group-1, injected with saline on days 1,2, and 3; Group-2, injected with 5-Fu on days 0 and 3; and Group-3, injected with 5-Fu on days 0 and 3 and MPIF-1 on days 1, 2, and 3. (See FIG. 17.) Bone marrow was harvested on days 6 and 9 to determine HPP-CFC and LPP-CFC frequencies using a clonogenic assay well known to those of skill in the art. The results demonstrate that administration of MPIF-1 prior to the second dose of 5-Fu results in a rapid recovery of the HPP-CFC and LPP-CFC frequencies by day 9 compared to animals treated with 5-Fu alone. (See FIG. 18.)

EXAMPLE 11

Studies with the MPIF-1 Mutants

A number of MPIF-1 variants that are truncated from the N-terminus have been identified and characterized. The amino terminal sequences of these variants as determined by Edman degradation are presented in the FIG. 19. For example, Mutants-2, -3, -7, and -8 arose spontaneously during the purification of the mature form of MPIF-1 and this preparation is called Preparation K0871. Similarly, Mutants-2, -3, -4, and -5 were discovered in another batch of the purified MPIF-1 preparation (Preparation HG0300-B7). Since it was not possible to purify these variants from one another, Preparations K0871 and HG00300-B7 were used as is in the experiments described below. Mutant-6, which is identical to Mutant-3 with respect to the amino terminal sequence except for the N-terminal methionine, was generated by in vitro mutagenesis. Mutant-1, which is identical to the wild type except for the N-terminal methionine, was also generated by mutagenesis. In addition, an alternatively spliced form of MPIF-1 (Mutant-9), the cDNA clone of which encodes for a protein of 137 amino acids (FIG. 20A) was discovered (See FIG. 19). Comparison of the amino acid sequence for Mutant-9' s with that of MPIF-1 reveals an insertion of 18 amino acids between residues 45 and 46 in the MPIF-1 sequence and a loss of arginine 46 of MPIF-1 (FIG. 20B). The following summarizes the biological activities of these MPIF-1 mutant proteins.

Intracellular Calcium mobilization. In the foregoing Examples, MPIF-1 protein has been shown to mobilize calcium in monocytes. The wild type and mutant MPIF-1 proteins were tested for their ability to induce mobilization of intracellular calcium in human monocytes using human MIP-1 a as a positive control. The experiment was performed as follows: Human monocytes were isolated by elutriation and loaded with Indo-1/acetoxymethylester by incubating $1\times10^6$ cells in 1 ml of in HBSS containing 1 mM $CaCl_2$, 2 mM $MgSO_4$, 5 mM glucose and 10 mM HEPES, pH 7.4 plus 2.5 mM Indo-1/acetoxymethylester for 30 min at 37° C. Cells were then washed with HBSS and resuspended in the same buffer at $5\times10^5$ cells/ml and stimulated with various concentrations of the indicated proteins at 37° C. The fluorescent signal induced in response to changes in intracellular calcium $((Ca^{++})i)$ was measured on a Hatchi F-2000 fluorescence spectrophotometer by monitoring Indo-1 excitation at 330 nm and emission at 405 and 485 nm. The results are shown in FIG. 21.

The results demonstrate that preparations K0871, HG00300-B7, and Mutant-9 are ten-fold more active than the wild type, whereas Mutants-6 is indistinguishable from the wild type and Mutant-1 is about two-fold more active than the wild type. (See, FIG. 21). Since MIP-1α and MPIF-1 are 45% identical with respect to the primary amino acid sequence, it was of interest to determine whether they interacted with the same receptor. To explore this possibility, the ability of MPIF-1 to desensitize MIP-1α-induced calcium mobilization was studied. FIGS. 22A and 22B show that MIP-1α and the MPIF-1 wild type protein can desensitize each others ability to mobilize calcium in monocytes, but not MCP-4 (another beta-chemokine).

In similar experiments, preparations K087 1, HG00300-B7, and Mutants-1, -6, and -9 were able to block MIP-1α induced calcium mobilization. This experiment was performed as follows: Calcium mobilization response of human monocytes to the indicated proteins at 100 ng/ml was measured as indicated above for the experiment disclosed in FIG. 21. For desensitization studies, monocytes were first exposed to one factor and when the response to the first treatment returned to baseline a second factor was added to the same cells. No response to the second factor is indicated by the (−) sign and a stimulatory response to the first factor by a (+) sign. (See, FIG. 23).

Thus, MPIF-1 and its mutant variants appear to interact with or share a component of the cell surface receptor for MIP-1α. Recent demonstration that the MIP-1α receptor serves as a cofactor in facilitating the entry of HIV into human monocytes and T-lymphocytes raises an interesting possibility that MPIF-1 its variants might interfere with the process of HIV entry into the cells.

Chemotaxis. Chemotaxis of human peripheral blood mononuclear cell (PBMC) fraction (consisting mainly of lymphocytes and monocytes) was measured in response to various concentrations of MPIF-1 and its variants in a 96-well neuroprobe chemotaxis chambers. The experiment was performed as follows: cells were washed three times in HBSS with 0.1% BSA (HBSS/BSA) and resuspended at $2\times10^6$/ml for labeling. Calcein-AM (Molecular Probes) was added to a final concentration of 1 mM and the cells were incubated at 37° C. for 30 minutes. Following this incubation, the cells were washed three times in HBSS/BSA. Labeled cells were then resuspended to $8\times10^6$/ml and 25 ml of this suspension ($2\times10^5$ cells) dispensed into each upper chamber of a 96 well chemotaxis plate. The chemotactic agent was distributed at various concentrations in the bottom chamber of each well. The upper and the bottom chambers are separated by a polycarbonate filter (3–5 mm pore size; PVP free; NeuroProbe, Inc.). Cells were allowed to migrate for 45–90 minutes and then the number of migrated cells (both attached to the bottom surface of the filter as well as in the bottom chamber) were quantitated using a Cytofluor 11 fluorescence plate reader (PerSeptive Biosystems). Values represent concentrations at which peak activity was observed with the relative fold induction over background indicated in parentheses.

The results, shown in FIG. 24, demonstrate that preparations K0871 and HG00300-B7 are more potent inducers of chemotaxis than the wild type, whereas Mutants-1 and -6 were indistinguishable from the wild type.

Effects on colony formation by LPP-CFC.

To determine the impact of MPIF-1 variants on colony formation by LPP-CFC, a limiting number of mouse bone marrow cells were plated in soft agar containing medium supplemented with multiple cytokines with or without various concentrations of MPIF-1 variants. The experiment was performed as follows: a low density population of mouse bone marrow cells were plated (1,500 cells/3.5 cm diam. dish) in agar containing medium with or without the indicated MPIF-1 variants at various concentrations, but in the presence of the following recombinant murine cytokines IL-3 (5 ng/ml), SCF (100 ng/ml), IL-1 alpha (10 ng/ml), and M-CSF (5 ng/ml). Dishes were then incubated in a tissue culture incubator for 14 days at which point LPP-CFC colonies were scored under an inverted microscope. Data presented in FIG. 25 are pooled from several different experiments where each condition was assayed in duplicates.

The results demonstrate that the effective concentration required for 50% of maximal inhibition in the case of preparations K0871 and HG00300-B7 were 20- to 100-fold lower than that of the wild type and for Mutant-6 it was 2- to 10-fold lower. (See FIG. 25). Thus, deletion of the N-terminal amino acids of MPIF-1 protein results in an increased potency of the molecule.

EXAMPLE 12

In Vivo Stem Cell Mobilization Induced by MPIF-1

To demonstrate that MPIF-1 stimulates stem cell mobilization in vivo, the following experiment was performed. Six mice were used for each treatment group (C57Black 6/J, female, about 6 weeks old). The mice were injected (I.P.) with either saline (vehicle control) or MPIF-1 at 5 µg/mouse. After 30 minutes, mice were bled and analyzed for WBC by Coulter counter. Then, blood from all six animals of each group was pooled and analyzed for the Gr. 1+cells and CD34.Sca-1+double positive cells by FACScan. WBC counts are expressed as Mean±S.D. and FACScan data as % of total cells. Since CD34.Sca-1+double positive cells are thought to exhibit properties expected of the hematopoietic stem cells, the results shown in FIG. 26 illustrate that MPIF-1 can be used as stem cell mobilizer.

EXAMPLE 13

MPIF-1 Treatment During 5-Fu Treatment Results in Faster Recovery of Platelets and Granulocytes Two of the major complications resulting from chemotherapy are neutropenia (reduced blood neutrophil counts) and thrombocytopenia (reduced platelet counts). Granulocyte-Colony Simulating Factor (G-CSF) is currently used in the clinic to mitigate neutropenia. G-CSF is known to stimulate colony formation by the Colony Forming Unit-Granulocyte (CFU-G) in vitro and stimulate granulocyte production in animal models. Thrombopoietin (Tpo) is in clinical trials for the purpose of alleviating thrombocytopenia. Tpo is known to stimulate colony formation by Colony Forming Unit-Megakaryocyte (CFU-Meg) in vitro and stimulate platelet production in experimentally induced thrombocytopeniain animals. One of the major limitations of G-CSF in the clinic is that it is not effective in alleviating neutropenia in patients that are subjected to multiple cycles of chemotherapy. This is likely due to the depletion of CFU-G in the bone marrow, a target cell upon which G-CSF acts. Tpo might also suffer from the same fate as indicated by the initial clinical trial results. Any agent that can prevent the depletion of G-CSF and Tpo target cells during chemotherapy would be of great clinical value. The data shown below suggests that MPIF-1 could meet this clinical need.

In the previous Examples, MPIF-1 has been shown to inhibit colony formation by bipotential, granulocyte/monocyte myeloid progenitors in vitro. In particular, Examples 9 and 10 provide data demonstrating that MPIF-1 protects primitive, multipotential myeloid progenitors from 5-Fu induced cytotoxicity in vitro and in vivo. These multipotential progenitors are expected to give rise to more committed progenitors of all the myeloid lineages including CFU-G and CFU-Meg. The following experiment was performed to demonstrate that MPIF-1 treatment during two or three cycles of 5-Fu treatment results in faster recovery of platelets and granulocytes.

Materials and Methods: C57BL6 female mice (7–10 weeks old) with a mean body weight 19.4g (±1.1 S.D., n=150) were used. All mice were housed under standard diet and housing conditions of dark/light cycle and temperature throughout the course of the experiment. MPIF-1 preparation (HG00304-E6) was made in $E.$ $coli$ and represents the truncated form of MPIF-1 lacking 23 N-terminal amino acids of the mature protein (i.e., MPIF-1 Mutant-3 in FIG. 19 with an N-terminal Met added thereto). Clinical grade of G-CSF (Neupogen®) was purchased from the Shady Grove Pharmacy, Rockville, Md. 20850 (Neupogen® is manufactured by Amgen Inc., Amgen Center, Thousand Oaks, Calif. 91320). 5-Fluorouracil (5-Fu) was purchased from Sigma Chemicals and it was freshly prepared by dissolving in warm water just prior to use. MPIF-1 solution was freshly prepared by dilution in normal saline. Likewise, G-CSF was diluted in a buffer consisting of 10 mM sodium acetate, 5% (wt/v) mannitol, 0.004% (v/v) Tween 80, pH 4.0. Appropriate fluorochrome conjugated rat monoclonal antibodies against mouse CD41a, Gra.1, and Mac.1 antigens were purchased from Pharmingen.

Five groups of mice (30 mice per group) were treated as follows:

Group 1 was injected I.P. with 0.1 ml of normal saline on −2, −1, 0, 6, 7, and 8 days to serve as normal control.

Group 2 was injected with I.P. with 0.2 ml of 5-Fu solution (at 100 mg/kg body weight) on days 0 and 8.

Group 3 was injected with 5-Fu as in Group 2 and in addition 0.1 ml of MPIF-1 solution (at 1.0 mg/Kg body weight) was injected I.P. on −2, −1, 0, 6, 7, and 8 days.

Group 4 was injected with 5-Fu as in Group 2 and in addition 0.1 ml of G-CSF solution (at 0.5 mg/Kg body weight) was injected I.P. on 1, 2, 3, 9, 10, and 11 days.

Group 5 was injected with 5-Fu as in Group 2, MPIF-1 as in Group 3, and G-CSF as in Group 4.

Six animals from each of the groups were then analyzed on the indicated days for monitoring platelet and granulocyte recovery at the level of the peripheral blood and the bone marrow. It should be noted that the mice analyzed on 6 and 8 days post first 5-Fu did not receive second treatment with MPIF-1 5-Fu.

Peripheral blood was collected from the retroorbital sinus in EDTA-coated tubes and was immediately analyzed by FACS Vantage to determine platelet (CD41 a positive events) and granulocyte (Gra.1 and Mac.1 double positive cells) counts. It should be noted that the method of analysis and the species of animal employed here does not permit obtaining absolute counts. Instead, granulocytes are expressed as percentage of total white blood cells and platelets were estimated as CD4 1 a positive events per 15 seconds on the sorter. Mice were then sacrificed to obtain bone marrow cells using standard methods. Bone marrow cells were also analyzed by FACS to monitor percentage of Gra.1 and Mac.1 double positive populations of cells in the bone marrow. Since the stage at which these antigens begin to be expressed in the granulocyte lineage is not precisely known, Gra.1 and Mac.1 double positive cells in the bone marrow are expected to be heterogenous with regards to the stage of their development and maturation potential.

Bone marrow was also analyzed to determine the frequency of clonogenic progenitors using an in vitro clonogenic assay. Briefly, High Proliferative Potential Colony forming Cell (HPP-CFC) and Low Proliferative Potential Colony Forming Cell (LPP-CFC) assay was performed in a two-layered agar culture system. The bottom layer was prepared in 3.5 cm diameter dishes with 1 ml of MEM supplemented with 20% FBS, 0.5% Difco agar, 7.5 ng/ml mIL-3, 75 ng/ml mSCF, 7.5 ng/ml hM-CSF and 15 ng/ml mIL-1α. This layer was then overlayed with 0.5 ml of murine bone marrow cell suspension to have 2,000 cells/dish in MEM with 20% FBS and 0.3% agar. The to p agar was allowed to solidify at room temperature for about 15 minutes. The dishes were then incubated for 14 days in a tissue culture incubator (37° C., 88% $N_2$, 5% $CO_2$, and 7% $O_2$) and colonies were scored under an inverted microscope. In this experiment total colony counts are reported.

FACS data were generated by analyzing material obtained from three animals of each of the groups per time point, whereas the clonogenic assay was performed with cells obtained from six animals of each of the groups per time point. Finally, data points for the day 1 group of the experiment represents values obtained from the saline injected normal mice (Group 1).

Results: To monitor the recovery of platelets in the peripheral blood, the steady state levels of CD41a positive cells was determined by FACS Vantage. As shown in FIG. 27, MPIF-1 treatment prior to 5-Fu (Group 3) resulted in a much faster and stronger recovery of platelets than that observed in mice treated with 5-Fu+saline (Group 2). As expected the kinetics of platelet recovery in mice treated with G-CSF (Group 4) was indistinguishable from that observed in mice treated 5-Fu +saline. Also, administering G-CSF plus MPIF-1 to 5-Fu treated mice (Group 5) had little effect on the overall steady state levels of platelets when compared to that observed in mice treated with MPIF-1 alone (Group 3). Thus, MPIF pre-treatment of mice prior to the 5-Fu treatment resulted in a rapid recovery of platelets in the peripheral blood.

The recovery of granulocytes in the peripheral blood was monitored by quantitating the steady state levels of Gra.1 and Mac.1 double positive cells in the blood. As illustrated in the FIG. 28, 5-Fu treatment of mice resulted in a sharp decrease in the steady state levels of Gra.1 and Mac.1 double positive cells in the blood at six days after the first as well as the second 5-Fu treatments. MPIF-1 pre-treatment had two beneficial effects; the degree of neutropenia (the extent of depletion of Gra.1 and Mac.1 double positive cells) was much smaller and the rate of recovery was much faster compared to that observed in mice treated with 5-Fu+saline (Group 2). As expected, the administration of G-CSF after 5-Fu treatment (Group 4) resulted in a rapid recovery of Gra.1 and Mac.1 double positive cells in the blood. However, the extent of the recovery from neutropenia in the G-CSF treated mice was notably smaller than that observed in the MPIF-1 treated mice on day 8 (Group 3). The effect of administering MPIF-1 plus G-CSF (Group 5) on the granulocyte depletion and recovery was quite dramatic in that these mice displayed much higher steady state levels of Gra.1 and Mac.1 double positive cells in the blood than that observed in mice treated with either MPIF-1 G-CSF alone. Thus, as indicated in FIG. 28, it appears that MPIF-1 and G-CSF may exert additive effects when they are co-administered.

As indicated above, recovery at the level of the bone marrow was monitored by FACS Vantage method and clonogenic assay. Results obtained with FACS are illustrated in FIG. 29. As expected, the level of Gra.1 and Mac.1 double positive population of cells in the 5-Fu treated marrows (Group 2) remained remarkably depressed from days 6 through 14 and then recovered to normal level by day 16. This effect of 5-Fu mediated depletion of Gra.1 and Mac.1 double positive cells was completely abrogated when mice were treated with MPIF-1 prior to 5-Fu (Group 3). Surprisingly, G-CSF (Group 4) was able to prevent the depletion of the Gra.1 and Mac.1 double positive cells in response to the first 5-Fu dose, but not the second. This is likely due to the availability of G-CSF target cells and the timing of G-CSF administration. A similar response was evident in mice that were treated with MPIF-1 plus G-CSF (Group 5), although the extent of recovery on day 8 post first 5-Fu was much higher than that observed in mice treated with either MPIF-1 G-CSF alone.

Data from the clonogenic assay are presented in FIG. 30. The frequency of progenitors in the bone marrow remained depressed in response to 5-Fu throughout the fourteen days of the experiment period with a hint of recovery on day 16. This reduction in the frequency of the progenitors was abrogated in mice that were treated with MPIF-1 prior to 5-Fu. In contrast, G-CSF treatment of mice was not effective in sustaining the frequency of progenitors found either in normal or MPIF-1 treated marrows. The effect of administering G-CSF plus MPIF-1 on the progenitor frequency in the bone marrow appears to be complex.

Summary Preclinieal Pharmacology Tables

The following tables (Tables 2, 3, and 4) summarize the in vitro and in vivo primary and secondary pharmacology studies.

Table Key for Batches Referenced in Tables 2, 3, and 4. MPIF-1 batches are designated by a multi-component code which indicates the organism the protein was expressed in and the form of the expressed product (e.g., mature, full-length, or a variant). Letters after a hyphen at the end of the designation indicate either the organism the protein was expressed in or the vector used for expression (i.e., B=baculovirus, C=CHO cells, E=*E. coli*). The last three digits preceding the hyphen indicate the form or variant of the protein expressed (i.e., 300=full-length MPIF-1, 301=the MPIF-1 A 17 variant, 302=mature MPIF-1 with a methionine residue added to the amine terminus of the mature amino acid sequence,304=the MPIF-1Δ23 variant, 311=full-length MPIF-1). Thus, the batch designation indicates the form of the expressed MPIF-1 protein, whether the protein will be secreted from the host cell, and the form of the secreted protein, if any. For example, HG00300-B5 indicates that the full-length MPIF-1 protein was expressed using a baculovirus vector. Further, since MPIF-1 expressed using this system is processed by the insect host cells, the secreted form of this protein is mature MPIF-1.

One exception to the above noted nomenclature occurs with batch HG00300-B7. This batch contains a mixture of four different MPIF-1 polypeptides. The inventors believe that these polypeptides were produced as a result of proteolytic cleavage of MPIF-1 which occurred during the purification process. The MPIF-1 variants present in batch HG00300-B7 are discussed in Example 11.

TABLE 2

Primary Pharmacology-In Vitro

| Experimental Design | Cell Type | MPIF-1Δ23 Dose | Chemical Agent | Results |
| --- | --- | --- | --- | --- |
| Effect of MPIF-1 or MPIF-1Δ23 on colony formation using mouse bone marrow | HPP-CFC LPP-CFC | 0.01–100 ng/mL | NA | Both MPIF-1 and MPIF-1Δ23 caused a dose dependent reduction of the frequency of LPP-CFCs. MPIF-1Δ23 was significantly more effective than MPIF-1 at all concentrations tested. Neither isoform had a significant effect on the frequency of HPP-CFCs. |
| Effect of MPIF-1Δ23 on the proliferation of human hematopoietic progenitor cells | $CD34^+$, human cord blood | 1–1000 ng/mL | NA | MPIF-1Δ23 treatment resulted in 20% to 40% inhibition of cell survival. The results suggest that MPIF-1Δ23 is a myeloid progenitor inhibitory factor. |
| Determination of the specific progenitor cell types targeted by MPIF-1Δ23 | $CD34^+$, human | 50 ng/mL | NA | MPIF-1Δ23 inhibits (50% to 64%) the formation of CFU-GM and CFU-Mix. Formation of BFU-E, CFU-G, CFU-M, and CFU-Meg were not inhibited. The results define MPIF-1Δ23 as an inhibitor of human granulocyte/monocyte precursor cells. |
| Characterization of the inhibitory effects of MPIF-1Δ23 on mouse bone marrow | Mouse bone marrow | 50 ng/mL | NA | MPIF-1Δ23 reduced the frequency of myeloid CFU-GM colonies to 30% of control. The frequency of LPP-CFC colonies was reduced to 24% of control. MPIF-1Δ23 did not inhibit the formation of CFU-E, BFU-E and HPP-CFC colonies. |
| Determination of the ability of MPIF-1Δ23 to protect lineage-depleted populations of bone marrow cells from the cytotoxic effects of 5-FU | Mouse bone marrow | NA | 5-FU | MPIF-1Δ23 protects 40% to 50% of LPP-CFC from cytotoxicity induced by 5-FU. MPIF-1Δ23 did not protect HPP-CFC. |

TABLE 3

Primary Pharmacology - In Vivo

| Experimental Design | Species | MPIF-1 Batch | MPIF-1 Dose, Schedule, Route | Chemical Agent | Dose, Schedule, Route |
| --- | --- | --- | --- | --- | --- |
| In vivo effects of MPIF-1 or MPIF-1Δ23 on the frequency of HPP-CFC and LPP-CFC in peripheral blood and bone marrow | Mouse | HG00300-B5 HG00304-E2 | 0.5 mg/kg/ injection twice a day at 8 hour intervals for 2 days, i.p. | NA | NA |
| Determination of the optimal MPIF-1Δ23 dosing schedule for protection against the cytotoxic effects of 5-FU | Mouse | HG00304-E2 | 1 mg/kg, variable between Days −3 and 0, i.p. | 5-FU | 150 mg/kg, Day 0, i.p. |
| Determination of dose dependency of MPIF-1Δ23 on bone marrow recovery after 5-FU | Mouse | HG00304-E6 | 0.01 to 10 mg/kg, i.p. on Days −2, −1, 0 | 5-FU | 150 mg/kg, i.p. |
| Determination of the ability of MPIF-1Δ23 to protect myeloid progenitors in vivo from cytotoxic therapy | Mouse | HG00304-E6 | 1 mg/kg; Days −2, −1, 0, i.p. | 5-FU | 150 mg/kg, Day 0, i.p. |
| Determination of the protective effect of MPIF-1Δ23 against multiple cycles of chemotherapy | Mouse | HG00304-E6 | 1 mg/kg, Days −2, −1, 0, 6, 7, 8 | 5-FU | 100 mg/kg, Days 0 and 8, i.p. |
| Determination of the ability of MPIF-1Δ23 to accelerate recovery of bone marrow colonies, neutrophils and platelets after multiple cycles of chemotherapy Determination of the activity of MPIF-1Δ23 in combination with G-CSF | Mouse | HG00304-E6 | 1 mg/kg; Days −2, −1, 0, 6, 7, 8, i.p. | 5-FU G-CSF | 100 mg/kg, Days 0 and 8, i.p. 0.5 mg/kg, Days 1, 2, 3, 9, 10, and 11 |

| Experimental Design | Endpoint |
| --- | --- |
| In vivo effects of MPIF-1 or MPIF-1Δ23 on the frequency of HPP-CFC and LPP-CFC in peripheral blood and bone marrow | MPIF-1Δ23 significantly reduced the frequency of LPP-CFC in bone marrow. The effects of MPIF-1Δ23 on the frequency of LPP-CFC in blood were variable. MPIF-1Δ23 had no effect on the frequency of HPP-CFC. |

TABLE 3-continued

Primary Pharmacology - In Vivo

| | |
|---|---|
| Determination of the optimal MPIF-1Δ23 dosing schedule for protection against the cytotoxic effects of 5-FU | MPIF-1Δ23 given on Days −2, −1, and 0 was most effective in protecting bone marrow against the cytotoxic effects of 5-FU. |
| Determination of dose dependency of MPIF-1Δ23 on bone marrow recovery after 5-FU | A dose-dependent response was observed on Day 4, with the best recovery occurring at the lowest dose tested (0.01 mg/kg). No dose response was observed on Day 6. A bell shaped dose-response curve was obtained on Day 8, with optimal activity observed at 0.1 mg/kg. |
| Determination of the ability of MPIF-1Δ23 to protect myeloid progenitors in vivo from cytotoxic therapy | Colony formation from bone marrow of mice treated with MPIF-1Δ23 returned to normal 7 days after treatment with 5-FU. Bone marrow colony formation from mice treated with 5-FU alone showed no recovery at this time. |
| Determination of the protective effect of MPIF-1Δ23 against multiple cycles of chemotherapy | MPIF-1Δ23 protected progenitor cells after tow cycles of 5-FU. The most dramatic protection was seen after the second cycle of 5-FU. The chemoprotective effect of MPIF-1Δ23 was manifest in the periphery by increased numbers of hematopoietic-derived CD45$^+$ cells in blood. |
| Determination of the ability of MPIF-1Δ23 to accelerate recovery of bone marrow colonies, neutrophils and platelets after multiple cycles of chemotherapy Determination of the activity of MPIF-1Δ23 in combination with G-CSF | The degree of neutropenia as measured by the depletion of Gr-1 and Mac-1 double positive cells was significantly less and the rate of recovery more rapid in mice treated with MPIF-1 and 5-FU compared with that in mice treated with 5-FU alone. Treatment with G-CSF after 5-FU resulted in a rapid recovery of double positive cells in the blood. The extent of recovery in G-CSF treated mice was markedly less than that observed in MPIF-1 treated mice on Day 8. Mice treated with MPIF-1 and G-CSF had higher steady state levels of positive cell in the blood than those treated with either MPIF-1 or G-CSF alone. There was a marked decrease in colony formation from the bone marrow of mice treated with 5-FU. MPIF-1 treatment prior to 5-FU abrogated the effect of 5-FU on colony formation. There was a more rapid and stronger recovery of platelets in mice treated with MPIF-1 and 5-FU relative to that seen in mice treated with 5-FU alone. Addition of G-CSF had no further effect. |

TABLE 4

Secondary Pharmacology-In Vitro

| Experimental Design | Cell Type | MPIF-1 Batch | MPIF-1 Dose Range | Results |
|---|---|---|---|---|
| Determination of calcium mobilization by MPIF-1 or MPIF-1Δ23 | T cells, B cells, monocytes, neutrophils, basophils, dendritic cells, NK cells THP-1 cells | HG00300-B7 HG00302-E2 HG00302-E3 HG00304-E2 HG00304-E3 HG00304-E6 HG00304-E7 HG00301-C1 HG00311-C1 | 1 to 1000 ng/mL | Detectable responses were observed in monocytes and dendritic cells at 100 ng/mL. The monocytic cell line THP-1 responded to MPIF-1Δ23 with a maximal effect at 100 ng/mL. |
| Determination of the chemotactic activity of MPIF-1Δ23. | T cells, monocytes, neutrophils, lymphocytes, eosinophils, basophils, NK cells, platelets | HG00300-B5 HG00300-B7 HG00302-E1 HG00302-E2 HG00303-E1 HG00304-E2 HG00304-E6 HG00304-E7 | 0.1 to 1000 ng/mL | MPIF-1Δ23 stimulated chemotaxis in resting T cells with a maximal response at 10 ng/mL. MPIF-1Δ23 was chemotactic for freshly isolated monocytes with a maximal effect at 100 ng/mL. A weak chemotactic response was observed in neutrophils. There was no response in the other cells tested. |
| Effect of MPIF-1 or MPIF-1Δ23 on monocytes | Monocytes | HG00300-B7 HG00302-E1 HG00302-E2 HG00302-E3 HG00304-E3 HG00304-E6 HG00301-C1 HG00311-C1 | 0.5 to 1000 ng/mL | MPIF-1Δ23 induced a low but variable release of lysosomal N-acetyl-β-D-glucosidase from freshly isolated monocytes. MPIF-1Δ23 had no effect on the release of the lysosonal enzymes elastase, glucuromidase, and myleperoxidase. MPIF-1Δ23 does not induce monocytes to secrete IL-Iβ, TNF-α, IL-10, or IL-12. MPIF-1Δ23 had no effect on oxidative burst or cytotoxic activity of activated macrophages. |

TABLE 4-continued

Secondary Pharmacology-In Vitro

| Experimental Design | Cell Type | MPIF-1 Batch | MPIF-1 Dose Range | Results |
|---|---|---|---|---|
| Effect of MPIF-1 or MPIF-1Δ23 on histamine release | Basophils, human | HG00300-B5<br>HG00300-B7<br>HG00302-E2<br>HG00304-E6 | 1 to 1000 ng/mL | MPIF-1 and MPIF-1Δ23 did not induce histamine release from basophils. |
| Effect of MPIF-1 or MPIF-1Δ23 on NK cell-mediated killing | NK cells, human | HG00302-E1<br>HG00300-B7 | 1 to 1000 ng/mL | MPIF-1 and MPIF-1Δ23 had no effect on IL-2 stimulated NK cell-mediated killing of K562 cells. |
| Effect of MPIF-1 or MPIF-1Δ23 on platelet aggregation | Platelets, human | HG00302-E1<br>HG00300-B7 | 0.1 to 1000 ng/mL | MPIF-1Δ23 did not induce or modulate platelet aggregation. |
| Effect of MPIF-1Δ23 on the growth of non-transformed human cells | Fibroblasts, astrocytes, Schwann cells, smooth muscle cells, epithelial cells, vein and microvascular endothelial cells, bone marrow, B cells, T cells, monocytes, neutrophils, keratinocytes | HG00300-B7<br>HG00300-B5<br>HG00302-E1 | 0.1 to 1000 ng/mL | MPIF-1Δ23 did not induce, enhance, or inhibit the proliferation of the cells listed studied. |
| Effect of MPIF-1 or MPIF-1Δ23 on the release of IL-6 and prostaglandins | Human primary endothelial cells, lung fibroblasts, and aortic smooth muscle cells | HG00300-B5<br>HG00300-B7<br>HG00302-E1<br>HG00300-E2<br>HG00304-E2<br>HG00301-C1 | 0.1 to 1000 ng/mL | MPIF-1 and MPIF-1Δ23 had no effect on release of IL-6 or prostaglandins. |
| Effect of MPIF-1Δ23 on formation of capillaries | Primary microvascular endothelial cells | HG00304-E2 | 0.1 to 1000 ng/mL | MPIF-1Δ23 did not induce the formation of capillaries in vitro. |
| Effect of MPIF-1 on ability of tumor cells to infiltrate through a confluent monolayer of endothelial cells | Primary endothelial cells | HG00300-B7 | 0.1 to 1000 ng/mL | No effect. |
| Effect of MPIF-1 or MPIF-1Δ23 on adhesion of peripheral blood mononuclear cells or granulocytes to IL-1 activated endothelium | Primary endothelial cells | HG00300-B5<br>HG00300-B5<br>HG00304-E6<br>HG00304-E7<br>HG00301-C1 | 0.1 to 1000 ng/mL | No effect. |

EXAMPLE 14

Production, Recovery, and Purification of MPIF-1Δ23 Using the pHE4–5 Expression Vector MPIF-1 is a novel human β-chemokine. The mature form of MPIF-1 is secreted as a 99 amino acid peptide, with a molecular mass of 11.2 kDa. A truncated form (MPIF-1Δ23) 76 amino acids in length was also identified during initial expression studies of MPIF-1. In a baculovirus expression system, MPIF-1Δ23 was subsequently isolated and subcloned. Biological assays indicate that the truncated form is more active than the full length counterpart.

Cloning and Expression

The MPIF-1Δ23 gene originally isolated from an aortic endothelial complementary deoxyribonucleic acid library has been subcloned into the expression vector pHE4 at the single restriction enzyme cleavage sites NdeI and Asp 718 (FIG. 31) and has been transformed into the K12 derived *E. coli* strain SG 13009 (available from Susan Gottesman, National Institutes of Health, Bethesda, Md.). Additional strains of *E. coli* which may serve as suitable hosts for protein expression using pHE4 include strains DH5α and W3110 (ATCC Accession No. 27325). The pHE4 vector contains a strong synthetic promoter with two lac operators. Expression from this promoter is regulated by the presence of a lac repressor, and is induced using isopropyl β-D-thiogalactopyranoside (IPTG) or lactose. The plasmid also contains an efficient ribosomal binding site and a synthetic transcriptional terminator downstream of the MPIF-1Δ23 gene. The vector also contains the replication region of pUC plasmids and the neomycinphosphotransferase gene resulting in kanamycin resistance in transformed bacteria.

Method of Manufacture

Overview of Fermentation Process. The fermentation process for MPIF-1Δ23 is outlined in following stages and is illustrated in FIG. 32.

Master Seed Bank. A master cell bank (MCB) of *E. coli* transformed with the plasmid expressing MPIF-1Δ23 was prepared under current Good Manufacturing Practices. The bank was prepared in media containing glycerol as a cryopreservative, and frozen at −80° C. After preparation, the MCB was tested to assure the absence of phage or contamination with other micro-organisms.

First Seed Stage. First seed stage culture is prepared in a baffled shake flask containing inoculum preparation medium. The shake flask is inoculated at a 1:2000 dilution with thawed seed stock and is placed in a shaker maintained at 225 rpm and 37° C. for 12 hours.

Production Phase. Production Phase culture is prepared in a 100 liter Fed-Batch fermenter equipped with $DO_2$, pH, temperature and nutrient feed control. The production medium (37° C.) is inoculated with first seed stage culture to provide an optical density (OD) of 0.20 units per milliliter at 600 nm. When the culture reaches an OD of 10 plus or minus 2 units per milliliter at 600 nm, protein expression is induced with the addition of IPTG (final concentration 20 mM). Cells are harvested 4 hours after induction.

Cell Harvest Phase. Bacteria are recovered by centrifugation at 18,000 g using a continuous flow centrifuge. The resulting cell paste is stored at −80° C.

Recovery of MPIF-1Δ23

The recovery of MPIF-1Δ23 is outlined in FIG. 33.

Cell Lysis. The *E. coli* cell paste is thawed and resuspended in ten volumes of resuspension buffer. Cells are then disrupted following their passage (twice) through a homogenizer at 7000 psi.

Inclusion Body Wash. NaCl is added to the cell lysate to a final concentration of 0.5 M and then concentrated two-fold by tangential flow filtration using a 0.45-μm membrane. The remaining retentate is diafiltered against three volumes wash-2 buffer (100 mM Tris-HCl, 500 mM NaCl, and 25 mM EDTA-Na$_2$), followed by one volume wash-1 (100 mM Tris-HCl, 25 mM EDTA-Na$_2$). The retentate is diluted two-fold with wash-1 buffer, and the insoluble fraction is collected by continuous centrifugation. Alternatively, inclusion bodies can be washed by centrifugation.

Inclusion Body Solubilization. The resulting pellet obtained following centrifugation is suspended in an equivalent of nine packed inclusion body volumes of solubilization buffer (100 mM Tris-HCl, 1.75 M Guanidine-HCl, and 25 mM EDTA-Na$_2$). The suspension is stirred initially for 2 to 4 hours at room temperature, and then for 12 to 18 hours at 2° to 10° C.

Refold. The suspension is centrifuged, and the supernatant is collected and mixed with nine volumes of refold buffer (100 mM Sodium Acetate, 125 mM NaCl, and 2 mM EDTA-Na$_2$). The diluted material is kept for about two hours (2° to 10° C.) to allow the precipitate to settle. The material is filtered and then may be processed immediately or stored for up to 72 hours and then processed.

Purification

HS-50 Cation Exchange Chromatography. The purification of MPIF-1Δ23 is outlined in FIG. 34. The filtrate is loaded onto a POROS HS-50 column equilibrated with 50 mM NaOAc, 150 mM NaCl, pH 5.8 to 6.2. The protein is eluted in a stepwise manner with NaCl (300 to 1500 mM). Fractions are eluted with 500 mM NaCl are pooled and are diluted two-fold with water for injection.

HQ-50/CM-20 Anion/Cation Exchange Chromatography. Pooled fractions obtained following HS-50 chromatography are loaded onto a tandem set of columns (HQ-50 column followed by CM-20 column) equilibrated with CM-1 buffer. MPIF-1Δ23 is eluted from the CM-20 column with NaCl (100 to 900 mM). Eluted fractions are analyzed by sodium dodecyl sulfate-polyacrylamide gel electrophoresis (SDS-PAGE) and reverse-phase high-performance liquid chromatography (HPLC), those fractions containing MPIF-1 23 are pooled and concentrated by ultrafiltration or passage through an additional HS-50 column.

Size Exclusion Chromatography. The CM-20 eluate is loaded onto a Sephacryl-100 HR equilibrated with S-100 buffer. Fractions are collected and analyzed by SDS-PAGE and reverse-phase HPLC. Fractions containing MPIF-1Δ23 are pooled, sterile-filtered using a 0.2 pm filter and stored at 2° to 10° C.

Specifications for Bulk Substance

The following specifications, listed in Table 5, have been established for bulkMPIF-1Δ23.

TABLE 5

Tests and Tentative Specifications for Release of Bulk MPIF-1Δ23

| Description | Specification |
|---|---|
| Appearance | Clear, colorless solution |
| pH | 5.8 ± 0.2 |
| Protein concentration by BCA | 1–5 mg/mL |
| Purity* | |
| Reverse-phase HPLC | ≧90% |
| Size-exclusion HPLC | ≧90% |

TABLE 5-continued

Tests and Tentative Specifications for Release of Bulk MPIF-1Δ23

| Description | Specification |
|---|---|
| SDS-PAGE (Coomassie blue staning) | |
| Reducing conditions | ≧90% |
| Non-reducing conditions | ≧90% |
| Residual DNA | ≦100 pg per mg protein |
| Endotoxin Limulus amoebocyte lysate gel clot | ≦10 EU per mg protein |
| Bioassay (Assessed by Ca$^{2+}$ mobilization assay) | Report results |

*The purity of MPIF-1Δ23 preparations will be compared to a standard reference, the specifications for which are currently being defined.

Specifications for Drug Product

The finished drug product meets all of the specifications as described for the bulk substance in Table 5, and is also tested for sterility (21CRF610.12).

EXAMPLE 15

MPIF-1Δ23 Mediated Inhibition of Colony Formation Correlates With the Ability of MPIF-1 to Mobilize Intracellular Ca$^{2+}$ in Monocytes MPIF-1Δ23 inhibits LPP-CFC colony formation in in vitro soft agar assays and induces mobilization of intracellular calcium in monocytes including THP-1 cells (human myelomonocytic cell line). Both assays have been used to assess biological activity of MPIF-1Δ23 in purification and stability studies. In the LPP-CFC assay, freshly isolated murine bone marrow cells are plated in soft agar in the presence of multiple cytokines (5 ng/mL IL-3, 50 ng/mL SCF, 5 ng/mL M-CSF, and 10 ng/mL IL-1I ). Cultures are incubated for 14 days, after which time, colonies are scored using an inverted microscope.

Calcium mobilization assays use freshly isolated human monocytes or THP-1 cells loaded with Fura-2 (0.2 nM per million). When cells are stimulated with MPIF-1Δ23, Ca$^{2+}$ mobilization is assessed by a fluorimeter. The Ca$^{2+}$ mobilization assay provides a rapid indicator regarding the activity of the MPIF-1Δ23 preparation (Table 6).

TABLE 6

MPIF-1Δ23 Mediated Inhibition of Colony Formation Correlates With the Ability of MPIF-1 to Mobilize Intracellular Ca$^{2+}$ in Monocytes

| MPIF-1 Construct/Batch/Condition | Ca$^{2+}$ mobilization (ng/mL)* | LPP-CFC inhibition (ng/mL)† |
|---|---|---|
| MPIF-1/HG00300-B5 | 1000 | 20–40 |
| MPIF-1Δ23/HG00304-E2, stored at 4° C. for 3 months | 100 | 5–10 |
| MPIF-1Δ23/HG00304, stored for 1 week | 100 | 5–10 |
| MPIF-1Δ23/HG00304, stored for 4 weeks | 100 | 5–10 |
| MPIF-1/HG00302-E2, stored at 4° C. for 3 months | 1000 | >100 |
| MPIF-1Δ23/HG00304-E3, first peak from CM column | 100 | 5–10 |

TABLE 6-continued

MPIF-1Δ23 Mediated Inhibition of
Colony Formation Correlates With
the Ability of MPIF-1 to Mobilize
Intracellular $Ca^{2+}$ in Monocytes

| MPIF-1 Construct/Batch/Condition | $Ca^{2+}$ mobilization (ng/mL)* | LPP-CFC inhibition (ng/mL)† |
|---|---|---|
| MPIF-1Δ23/HG00304-E4, second peak from CM column | 100 | 5–10 |
| MPIF-1Δ23/HG00304-E3, third peak from CM column | >1000 | >1000 |

*Minimum concentration required to mobilize calcium in human monocytes and/or THP-1 cells.
†Concentration producing 50% inhibition of LPP-CFC colony formation compared to the control.

Formulation and Storage

Bulk MPIF-1Δ23 is manufactured aseptically, and the liquid formulation is a sterile, single-use, product. The protein is buffered in 50 mM sodium acetate, 125 mM NaCl, pH 5.8, filled into a 5-mL Wheaton Type 1 glass vials and stored at 2° to 8° C.

Stability

The stability study was performed using a protein concentration of 1.0 mg/mL buffered with sodium acetate at pH 5, 6, and 7 at temperatures of −80° C., 2° to 8° C., 20° to 25° C., and 2° to 8° C. MPIF-1Δ23 has been found to be stable for at least six months when stored at or below 2° to 80 C in a solution of 10 mM sodium acetate, 125 mM NaCl at pH 5 to 7. In currently ongoing studies, samples will be assayed for appearance, protein concentration, purity (SDS-PAGE (reduced and nonreduced); reverse-phase and size-exclusion HPLC), and activity ($Ca^{2+}$ mobilization bioassay) to meet the specifications previously outlined.

A stability study for the MPIF-1Δ23 batch (HG00304-E10) used in the preclinical to xicology studies was initiated. The MPIF-1Δ23 batch used in these studies was formulated at a protein concentration of 4.0 mg/mL in 50 mM NaOAc, 125 mM NaCl, pH 5.9. The storage conditions are −80° C., 2° to 8° C., 25° C., and 37° C., at a relative humidity of 60%, and at 45° C., at a relative humidity of 75%. The stability study duration is 12 months for temperatures up to 25° C., 6 months at 37° C., and 1 month at 45° C. The stability will be assayed for appearance, pH, protein concentration, purity (SDS-PAGE (reduced and non-reduced); reverse-phase and size-exclusion HPLC), and activity ($Ca^{2+}$ mobilization bioassay). Endotoxin assay and bioburden tests will be performed at selected time points.

EXAMPLE 16

MPIF-1 Protects the Gastrointestinal Tract From Taxol-Induced Cytotoxicity

Simultaneous administration of 0.3 mg/kg MPIF-1Δ23 (subcutaneous) on days 0, 1 and 2 with 10.5 mg/kg Taxol (intraperitoneal) protected rats from weight lose associated with gut toxicity. Rats treated with 0.3 mg/kg MPIF-1Δ23, maintained weight on days 0, 5 and actually gained in weight by day 9. Rats that received 0.1 mg/kg MPIF-1Δ23 or no MPIF-1Δ23 lost approximately 45 grams of weight between days 0 and 5.

Paclitaxol (Taxol®) and MPIF-1Δ23 were both administered on days 0, 1 and 2, as above. The individual weights of rats in all groups on day −2 (i.e., two days prior to the first administration of paclitaxol and MPIF-1) was approximately 185 g. By day 5, individuals in two test groups (those receiving paclitaxol and either no MPIF Δ23 or 0.1 mg/kg MPIF Δ23) weighed approximately 155 g. In contrast, individuals that received 0.3 mg/kg MPIF Δ23 weighed approximately 175 g. Individuals in the control group (rats receiving neither paclitaxol nor MPIFΔ23) had attained weights of approximately 195 g by day 5. The ability of MPIF-1 to protect animals from acute toxicity effects of paclitaxol demonstrates its ability to protect many cell types such as cells of the gastrointestinal tract, in addition to hematopoietic stem cells, from cytoxic agents.

EXAMPLE 17

Sublethal Model of Gastrointestinal Protection

C57B1/6 female mice (12 weeks old) were exposed to a total of 9 Gy $^{137}$Cesium sublethal irradiation (dose rate: 25.54 cGy/min) delivered in two equal doses of 4.5 Gy 4 hours apart on day 0. A group of mice designated "MPIF-1 (Pre)" was given MPIF-1 (1 mg/kg/BID i.p.) for four consecutive days (day −2 to day +1). A group designated "MPIF-1 (Post)" was given MPIF-1 (1 mg/kg/BID i.p) for seven consecutive days beginning one day post irradiation (day 1). A control group received only diluent (HBSS +0.1% normal mouse serum). All mice were put on acidified water seven days prior to irradiation. Three days before irradiation, Amoxicillin was added to the acidified water (0.5 mg/ml) and continued daily until day 7 post-irradiation. Mice were monitored for survival, condition and weight change. Data is shown as the percent change in weight for each group based on each individual mouse's weight on the day indicated as a percentage of the weight at the start of the experiment. (See FIGS. 37–38.) The ability of MPIF-1 to protect animals from acute toxicity effects of radiation demonstrates its ability to protect many cell types such as cells of the gastrointestinal tract, in addition to hematopoietic stem cells, from cytoxic agents.

EXAMPLE 18

Lethal Model of Gastrointestinal Protection

C57B1/6 female mice (12 weeks old) were exposed to a total of 11 Gy $^{137}$Cesium lethal irradiation (dose rate: 25.54 cGy/min) delivered in two equal doses of 5.5 Gy 4 hours apart on day 0. A group of mice designated "MPIF-1 (Pre)" was given MPIF-1 (1 mg/kg/BID i.p.) for four consecutive days (day −2 to day +1). A group designated "MPIF-1 (Post)" was given MPIF-1 (1 mg/kg/BID i.p.) for seven consecutive days beginning one day post irradiation (day 1). A control group received only diluent (HBSS +0.1% normal mouse serum). All mice were put on acidified water seven days prior to irradiation. Three days before irradiation, Amoxicillin was added to the acidified water (0.5 mg/ml) and continued daily until day 7 post-irradiation. Mice were monitored for survival, condition and weight change. Data is shown as the percent change in weight for each group based on each individual mouse's weight on the day indicated as a percentage of the weight at the start of the experiment. (See FIGS. 39–40.)

All of the control group (receiving no MPIF-1) died by day 20 post-irradiation. In contrast, 25% of the MPIF-1 (Post) group, and 57% of the MPIF-1 (Pre) group had survived at day 38 post-irradiation. The ability of MPIF-1 to protect animals from lethal radiation demonstrates its ability to protect many cell types such as cells of the gastrointestinal tract from cytotoxic agents.

EXAMPLE 19

Methods to Determine Cytoprotection

One method for determining the relative protective ability of MPIF-1 with a particular cytotoxic agent is to assess the Dose-Reduction Factor or Dose-Modifying Factor (DMF). (Weiss, Environ. Health Perspectives 105:1473–1478 (1997).; Brown et al., Pharmacol. Ther. 39:157–168 (1988); Yuhas et al., Int. J. Radiat. Biol. 15:233–237 (1973); Weiss et al., in Radiation and the Intestinal Tract, Dubois et al., eds., Boca Raton, Fla., CRC Press, pp. 183–199 (1995))

For example, mice are irradiated at a range of doses with and without MPIF-1. Protection of the gastrointestinal tract by MPIF-1 is measured by the DMF for 6–7 day survival after whole-body irradiation at comparatively high doses. The DMF for 30 day survival measures protection by MPIF-1 of the hematopoeitic system.

EXAMPLE 20

Construction of N-Terminal and/or C-Terminal Deletion Mutants

The following general approach may be used to clone a N-terminal or C-terminal MPIF-1 deletion mutant. Generally, two oligonucleotide primers of about 15–25 nucleotides are derived from the desired 5' and 3' positions of a polynucleotide of SEQ ID NO:1 or 6. The 5' and 3' positions of the primers are determined based on the desired MPIF-1 polynucleotide fragment. An initiation and stop codon are added to the 5' and 3' primers respectively, if necessary, to express the MPIF-1 polypeptide fragment encoded by the polynucleotide fragment. Preferred MPIF-1 polynucleotide fragments are those encoding the N-terminal and C-terminal deletion mutants disclosed above in the "MPIF-1 Polypeptides" section of the specification.

Additional nucleotides containing restriction sites to facilitate cloning of the MPIF-1 polynucleotide fragment in a desired vector may also be added to the 5' and 3' primer sequences. The MPIF-1 polynucleotide fragment is amplified from genomic DNA or from the deposited cDNA clone using the appropriate PCR oligonucleotide primers and conditions discussed herein or known in the art. The MPIF-1 polypeptide fragments encoded by the MPIF-1 polynucleotide fragments of the present invention may be expressed and purified in the same general manner as the full length polypeptides, although routine modifications may be necessary due to the differences in chemical and physical properties between a particular fragment and full length polypeptide.

As a means of exemplifying but not limiting the present invention, the polynucleotide encoding the MPIF-1 polypeptide fragment R-46 to N-120 is amplified and cloned as follows: A 5' primer is generated comprising a restriction enzyme site followed by an initiation codon in frame with the polynucleotide sequence encoding the N-terminal portion of the polypeptide fragment beginning with R-46. A complementary 3' primer is generated comprising a restriction enzyme site followed by a stop codon in frame with the polynucleotide sequence encoding C-terminal portion of the MPIF-1 polypeptide fragment ending with N-120.

The amplified polynucleotide fragment and the expression vector are digested with restriction enzymes which recognize the sites in the primers. The digested polynucleotides are then ligated together. The MPIF-1 polynucleotide fragment is inserted into the restricted expression vector, preferably in a manner which places the MPIF-1 polypeptide fragment coding region downstream from the promoter. The ligation mixture is transformed into competent E. coli cells using standard procedures and as described in the Examples herein. Plasmid DNA is isolated from resistant colonies and the identity of the cloned DNA confirmed by restriction analysis, PCR and DNA sequencing.

EXAMPLE 21

Protein Fusions of MPIF-1

MPIF-1 polypeptides are preferably fused to other proteins. These fusion proteins can be used for a variety of applications. For example, fusion of MPIF-1 polypeptides to His-tag, HA-tag, protein A, IgG domains, and maltose binding protein facilitates purification. (See Example 5; see also EP A 394,827; Traunecker, et al., Nature 331:84–86 (1988).) Similarly, fusion to IgG-1, IgG-3, and albumin increases the half-life in vivo. Nuclear localization signals fused to MPIF-1 polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in Example 2.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and MPIF-1 polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:
GGGATCCGGAGCCCAAATCTTCTGACAAAACT CACACATGCCCACCGTGCCCAGCACCTGAATT CGAGGGTGCACCGTCAGTCTTCCTCTTCCCC CCAAAACCCAAGGACACCCTCATGATCTCCCGG ACTCCTGAGGTCACATGCGTGGTGGTGGACGT AAGCCACGAAGACCCTGAGGTCAAGTTCAACTGG TACGTGGACGGCGTGGAGGTGCATAATGCCAAGAC AAAGCCGCGGGAGGAGCAGTACAACAGCACG TACCGTGTGGTCAGCGTCCTCACCGTCCTGCAC CAGGACTGGCTGAATGGCAAGGAGTACAAGTGCA AGGTCTCCAACAAAGCCCTCCCAACCCCCATC GAGAAACCATCTCCAAAGCCAAAGGGCAGCC CCGAGAACCACAGGTGTACACCCTGCCCCCATCC CGGGATGAGCTGACCAAGAACCAGGTCAGCCT GACCTGCCTGGTCAAAGGCTTCTATCCAAGCGACA TCGCCGTGGAGTGGGAGAGCAATGGGCAGCCGG AGAACAACTACAAGACCACGCCTCCCGTGCTGGA CTCCGACGGCTCCTTCTTCCTCTACAGCAAGCTCA CCGTGGACAAGAGCAGGTGGCAGCAGGGGA ACGTCTTCTCATGCTCCGTGATGCATGAGGCTC TGCACAACCACTACACGCAGAAGAGCCTCTCCCT GTCTCCGGGTAAATGAGTGCGACGGCCGCGACT CTAG AGGAT (SEQ ID NO:42)

Additionally, one or more components, motifs, sections, parts, domains, fragments, etc., of MPIF-1 may be recombined with one or more components, motifs, sections, parts, domains, fragments, etc. of one or more heterologous molecules. In preferred embodiments, the heterologous molecules are chemokine family members. In further preferred embodiments, the heterologous molecule is a growth factor such as, for example, platelet-derived growth factor (PDGF), insulin-like growth factor (IGFI), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

EXAMPLE 22

Production of an Antibody
Hybridoma Technology

The antibodies of the present invention can be prepared by a variety of methods. (See, Current Protocols, Chapter 2.) As one example of such methods, cells expressing MPIF-1 is administered to an animal to induce the production of sera containing polyclonal antibodies. In a preferred method, a preparation of MPIF-1 protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., *Nature* 256:495 (1975); Köhler et al., *Eur. J. Immunol.* 6:511 (1976); Köhler et al., *Eur. J. Immunol.* 6:292 (1976); Hammerling et al., in: *Monoclonal Antibodies and T-Cell Hybridomas*, Elsevier, N.Y., pp. 563–681 (1981).) In general, such procedures involve immunizing an animal (preferably a mouse) with MPIF-1 polypeptide or, more preferably, with a secreted MPIF-1 polypeptide-expressing cell. Such cells may be cultured in any suitable tissue culture medium; however, it is preferable to culture cells in Earle's modified Eagle's medium supplemented with 10% fetal bovine serum (inactivated at about 56 degree C), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (*Gastroenterology* 80:225–232 (1981).) The hybridoma cells obtained through such a selection are then assayed to identify clones which secrete antibodies capable of binding the MPIF-1 polypeptide.

Alternatively, additional antibodies capable of binding to MPIF-1 polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the MPIF-1 protein-specific antibody can be blocked by MPIF-1. Such antibodies comprise anti-idiotypic antibodies to the MPIF-1 protein-specific antibody and can be used to immunize an animal to induce formation of further MPIF-1 protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce $F(ab')_2$ fragments). Alternatively, secreted MPIF-1 protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, *Science* 229:1202 (1985); Oi et al., *Bio-Techniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).)

Isolation of Antibody Fragments Directed Against MPIF-1 From a Library of scFvs.

Naturally occuring V-genes isolated from human PBLs are constructed into a large library of antibody fragments which contain reactivities against MPIF-1 to which the donor may or may not have been exposed (see e.g., U.S. Pat. No. 5,885,793 incorporated herein in its entirety by reference).

Rescue of the Library. A library of scFvs is constructed from the RNA of human PBLs as described in WO92/01047. To rescue phage displaying antibody fragments, approximately $10^9$ *E. coli* harbouring the phagemid are used to inoculate 50 ml of 2×TY containing 1% glucose and 100 ug/ml of ampicillin (2×TY-AMP-GLU) and grown to an O.D. of 0.8 with shaking. Five ml of this culture is used to innoculate 50 ml of 2×TY-AMP-GLU, $2×10^8$ TU of delta gene 3 helper (M13 delta gene III, see WO92/01047) are added and the culture incubated at 37 degree C for 45 minutes without shaking and then at 37 degree C for 45 minutes with shaking. The culture is centrifuged at 4000 r.p.m. for 10 min. and the pellet resuspended in 2 liters of of 2×TY containing 100 ug/ml ampicillin and 50 ug/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harbouring a pUC19 derivative supplying the wild type gene III protein during phage morphogenesis. The culture is incubated for 1 hour at 37 degree C without shaking and then for a further hour at 37 degree C with shaking. Cells are spun down (IEC-Centra 8, 4000 revs/min for 10 min), resuspended in 300 ml 2×TY broth containing 100 ug ampicillin/ml and 25 ug kanamycin/ml (2×TY-AMP-KAN) and grown overnight, shaking at 37(C. Phage particles are purified and concentrated from the culture medium by two PEG-precipitations (Sambrook et al., 1990), resuspended in 2 ml PBS and passed through a 0.45 um filter (Minisart NML; Sartorius) to give a final concentration of approximately $10^{13}$ transducing units/ml (ampicillin-resistant clones).

Panning of the Library. Immunotubes (Nunc) are coated overnight in PBS with 4 ml of either 100 ug/ml or 10 ug/ml of a polypeptide of the present invention. Tubes are blocked with 2% Marvel-PBS for 2 hours at 37 degree C and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0 M Tris-HCl, pH 7.4. Phage are then used to infect 10 ml of mid-log E. coli TG1 by incubating eluted phage with bacteria for 30 minutes at 37 degree C. The E. coli are then plated on TYE plates containing 1% glucose and 100 ug/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see e.g., WO 92/01047) and then by sequencing.

EXAMPLE 23

Method of Treating Decreased Levels of MPIF-1

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of MPIF-1 in an individual can be treated by administering MPIF-1, preferably in the secreted form. Thus, the invention also provides a method of treatment of an individual in need of an increased level of MPIF-1 polypeptide comprising administering to such an individual a therapeutic comprising an amount of MPIF-1 to increase the activity level of MPIF-1 in such an individual.

For example, a patient with decreased levels of MPIF-1 polypeptide receives a daily dose 0.1–100 ug/kg of the polypeptide for six consecutive days. Preferably, the polypeptide is in the secreted form. The exact details of the dosing scheme, based on administration and formulation, are provided in the "Pharmaceutical Compositions" section herein.

EXAMPLE 24

Method of Treating Increased Levels of MPIF-1

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of MPIF-1. This technology is one example of a method of decreasing levels of MPIF-1 polypeptide, preferably a secreted form, due to a variety of etiologies.

For example, a patient diagnosed with abnormally increased levels of MPIF-1 is administered intravenously antisense polynucleotides at 0.5, 1.0, 1.5, 2.0 and 3.0 mg/kg day for 21 days. This treatment is repeated after a 7-day rest period if the treatment was well to lerated. The formulation of the antisense polynucleotide is provided in the "Pharmaceutical Compositions" section herein.

EXAMPLE 25

Method of Treatment Using Gene Therapy—Ex Vivo

One method of gene therapy transplants fibroblasts, which are capable of expressing MPIF-1 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding MPIF-1 can be amplified using PCR primers which correspond to the 5' and 3' end sequences respectively as set forth in Example 1. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector contains properly inserted MPIF-1.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the MPIF-1 gene is then added to the media and the packaging cells transduced with the vector. The packaging cells now produce infectious viral particles containing the MPIF-1 gene(the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether MPIF-1 protein is produced.

The engineered fibroblasts are then transplanted onto the host, either alone or after having been grown to confluence on cytodex 3 microcarrier beads.

EXAMPLE 26

Gene Therapy Using Endogenous MPIF-1 Gene

Another method of gene therapy according to the present invention involves operably associating the endogenous MPIF-1 sequence with a promoter via homologous recombination as described, for example, in U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:89328935 (1989); and Zijlstra et al., *Nature* 342:435438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous MPIF-1, flanking the promoter. The targeting sequence will be sufficiently near the 5' end of MPIF-1 so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous MPIF-1 sequence. This results in the expression of MPIF-1 in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the MPIF-1 locus, plasmid pUC18 (MBI Fermentas, Amherst, N.Y.) is digested with HindIII. The CMV promoter is amplified by PCR with an XbaI site on the 5' end and a BamHI site on the 3' end.

Two MPIF-1 non-coding sequences are amplified via PCR: one MPIF-1 non-coding sequence (MPIF-1 fragment 1) is amplified with a HindIII site at the 5' end and an Xba site at the 3'end; the other MPIF-1 non-coding sequence (MPIF-1 fragment 2) is amplified with a BamHI site at the 5'end and a HindIII site at the 3'end. The CMV promoter and MPIF-1 fragments (1 and 2) are digested with the appropriate enzymes (CMV promoter—XbaI and BamHI; MPIF-1 fragment 1-XbaI; MPIF-1 fragment 2-BamHI) and ligated together. The resulting ligation product is digested with HindIII, and ligated with the HindIII-digested pUC 18 plasmid.

Plasmid DNA is added to a sterile cuvette with a 0.4 cm electrode gap (BioRad). The final DNA concentration is generally at least 120 µg/ml. 0.5 ml of the cell suspension (containing approximately $1.5 \times 10^6$ cells) is then added to the cuvette, and the cell suspension and DNA solutions are gently mixed.

Electroporation is performed with a GenePulser apparatus (BioRad). Capacitance and voltage are set at 960 µF and 250–300 V, respectively. As voltage increases, cell survival decreases, but the percentage of surviving cells that stably incorporate 30 the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

EXAMPLE 27

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) MPIF-1 sequences into an animal to increase or decrease the expression of the MPIF-1 polypeptide. The MPIF-1 polynucleotide may be operatively linked to a promoter or any other genetic elements necessary for the expression of the MPIF-1 polypeptide by the target tissue. Such gene therapy and delivery techniques and methods are known in the art, see, for example, WO90/11092, WO98/11779; U.S. Pat. NO. 5,693,622, 5,705,151, 5,580,859; Tabata H. et al. *Cardiovasc. Res.* 35(3):470–479 (1997), Chao J. et al. *Pharmacol. Res.* 35(6):517–522 (1997), Wolff J. A., *Neuromuscul. Disord.* 7(5):314–318 (1997), Schwartz B. et al. *Gene Ther.* 3(5):405–411 (1996), Tsurumi Y. et al. *Circulation* 94(12):3281–3290 (1996) (incorporated herein by reference).

The MPIF-1 polynucleotide constructs may be delivered by any method that delivers injectable materials to the cells of an animal, such as, injection into the interstitial space of tissues (heart, muscle, skin, lung, liver, intestine and the like). The MPIF-1 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the MPIF-1 polynucleotides may also be delivered in liposome formulations (such as those taught in Felgner P. L. et al. *Ann. NY Acad. Sci.* 772:126–139 (1995) and Abdallah B. et al. *Biol. Cell* 85(1):1-7 (1995)) which can be prepared by methods well known to those skilled in the art.

The MPIF-1 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The MPIF-1 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked MPIF-1 polynucleotide injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked MPIF-1 polynucleotide constructs can be delivered to arteries during angioplasty by the catheter used in the procedure.

The dose response effects of injected MPIF-1 polynucleotide in muscle in vivo is determined as follows. Suitable MPIF-1 template DNA for production of mRNA coding for MPIF-1 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The MPIF-1 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for MPIF-1 protein expression. A time course for MPIF-1 protein expression may be done in a similar fashion except that quadriceps from different mice are harvested at different times. Persistence of MPIF-1 DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using MPIF-1 naked DNA.

EXAMPLE 28

MPIF-1 Transgenic Animals

The MPIF-1 polypeptides can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., *Appl. Microbiol. Biotechnol.* 40:691–698 (1994); Carver et al., *Biotechnology* (NY) 11:1263–1270 (1993); Wright et al., *Biotechnology* (NY) 9:830–834(1991); and Hoppe et al., U.S. Pat. No. 4,873,191 (1989)); retrovirus mediated gene transfer into germ lines (Van der Putten et al., *Proc. Natl. Acad. Sci., USA* 82:6148–6152 (1985)), blastocysts or embryos; gene targeting in embryonic stem cells (Thompson et al., *Cell* 56:313–321 (1989)); electroporation of cells or embryos (Lo, *Mol Cell. Biol.* 3:1803–1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717–723 (1989); etc. For a review of such techniques, see Gordon, "Transgenic Animals," *Intl. Rev. Cytol.* 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64–66 (1996); Wilmut et al., *Nature* 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., *Proc. Natl. Acad. Sci. USA* 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred.

Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., *Science* 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Similarly, the DNA encoding the full length MPIF-1 protein can also be inserted into a vector for tissue specific expression using the following primers.

In addition to expressing the polypeptide of the present invention in a ubiquitous or tissue specific manner in transgenic animals, it would also be routine for one skilled in the art to generate constructs which regulate expression of the polypeptide by a variety of other means (for example, developmentally or chemically regulated expression).

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to : outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of MPIF-1 polypeptides, studying conditions and/or disorders associated with aberrant MPIF-1 expression, and in screening for compounds effective in ameliorating such conditions and/or disorders.

EXAMPLE 29

MPIF-1 Knock-Out Animals

Endogenous MPIF-1 gene expression can also be reduced by inactivating or "knocking out" the MPIF-1 gene and/or its promoter using targeted homologous recombination. (E.g., see Smithies et al., *Nature* 317:230–234 (1985); Thomas & Capecchi, *Cell* 51:503–512 (1987); Thompson et al, *Cell* 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the MPIF-1 polypeptides. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular enviromnent, does not allow the introduced cells to be recognized by the host immune system.

Knock-out animals of the invention have uses which include, but are not limited to, animal model systems useful in elaborating the biological function of MPIF-1 polypeptides, studying conditions and/or disorders associated with aberrant MPIF-1 expression, and in screening for compounds effective in ameliorating such conditions and/or disorders.

EXAMPLE 30

Production of an Antibody
Hybridoma Technology

The antibodies of the present invention can be prepared by a variety of methods. (See, Current Protocols, Chapter 2.) As one example of such methods, cells expressing polypeptide(s) of the invention are administered to an animal to induce the production of sera containing polyclonal antibodies. In a preferred method, a preparation of polypeptide(s) of the invention is prepared and purified to render it substantially free of natural contaminants. Such a preparation is then introduced into an animal in order to produce polyclonal antisera of greater specific activity.

Monoclonal antibodies specific for polypeptide(s) of the invention are prepared using hybridoma technology. (Kohler, et al., *Nature* 256:495 (1975); Kohler, et al., *Eur. J. Immunol.* 6:511 (1976); Kohler, et al., *Eur. J. Immunol.* 6:292 (1976); Hammerling, et al., in *Monoclonal Antibodies and T-Cell Hybridomas*, Elsevier, N.Y. (1981), pp. 563–681). In general, an animal (preferably a mouse) is immunized with polypeptide(s) of the invention or, more preferably, with a secreted polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands, et al. (*Gastroenterology* 80:225–232 (1981)). The hybridoma cells obtained through such a selection are then assayed to identify clones which secrete antibodies capable of binding the polypeptide(s) of the invention.

Alternatively, additional antibodies capable of binding to polypeptide(s) of the invention can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by polypeptide(s) of the invention. Such antibodies comprise anti-idiotypic antibodies to the protein-specific antibody and are used to immunize an animal to induce formation of further protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, *Science* 229:1202 (1985); Oi et al., *BioTechniques* 4:214 (1986); Cabilly et al., U.S. Pat. No. 4,816,567; Taniguchi et al, EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).)

Isolation Of Antibody Fragments Directed Against Polypeptide(s) From A Library Of scFvs Naturally occurring V-genes isolated from human PBLs are constructed into a library of antibody fragments which contain reactivities against polypeptide(s) of the invention to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 *E. coli* harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, 2×10$^8$ TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 μg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 μg/ml ampicillin and 25 μg/ml kanamycin(2×TY-AMP-KAN) and grown overnight, shaking at 37° C. Phage particles are purified and concentrated from the culture medium by two PEG-precipitations (Sambrook, et al., 1990), resuspended in 2 ml PBS and passed through a 0.45 μm filter (Minisart NML; Sartorius) to give a final concentration of approximately 10$^{13}$ transducing units/ml (ampicillin-resistant clones).

Panning of the Library. Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately 10$^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0 M Tris-HCl, pH 7.4. Phage are then used to infect 10 ml of mid-log *E. coli* TG1 by incubating eluted phage with bacteria for 30 minutes at 37° C. The *E. coli* are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect *E. coli* HB 2151 and soluble scFv is produced (Marks et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

EXAMPLE 31

Lethal Irradiation Model

A schematic of the experimental protocol in Example 18 is shown in FIG. 41. As shown in FIG. 42, MPIF-1 (Δ23) enhances the survival of lethally irradiated mice. The ability of MPIF to enhance survival varies with experimental conditions.

The study shown in this example tested the activity of MPIF-1 (Δ23). However, one skilled in the art could easily modify the exemplified studies to test the activity of full length MPIF-1, or fragments thereof, as well as polynucleotides (e.g., via gene therapy), agonists, and/or antagonists of MPIF-1.

EXAMPLE 32

In vivo Myeloprotection From Radiation

Experiments showing that MPIF-1 increases mouse survival after lethal irradiation (see Example 18), suggest that this chemokine acts as a radioprotecting agent. To further investigate this activity, changes in the levels of bone marrow progenitors were examined in sublethally irradiated mice to determine if MPIF-1 improves recovery of these progenitors after irradiation.

A schematic of the experimental protocol is shown in FIG. 43. This is a modification of the protocol in Example 17. The MPIF-1 used was MPIF-1 (Δ23) batch HG00304-E11. A negative control group (IRR) received only vehicle (HBSS+ 0.1% normal mouse serum i.p.) from day −3 to day +3, except that the mice were rested 24 hours before and after radiation. For comparison in the bone marrow analysis, a control group (Normal) of mice received no irradiation.

Analysis of bone marrow cells. Mice from each group were sacrificed on days 4, 14, 21, and 38, and bone marrow (BM) samples were taken. Colony-formation assays in soft agar were used to determine the numbers of myeloid progenitors (colony-forming unit (CFU)-c and CFU-granulocyte erythroid megakaryocyte macrophage (CFU-GEMM)) from bone marrow. See, for example, Grzegorzewski et al., Blood 183:377 (1994); and Metcalf, *The Hematopoietic Colony Stimulating Factors*, Amsterdam, The Netherlands, Elsevier (1984) at page 27. Cells were cultured using a single-layer agar-based assay system with recombinant human erythropoietin (rhEpo) (8 U/ml) and recombinant mouse interleukin-3 (rmIL-3) (100 U/ml). Multipotential colonies containing granulocyte, erythroid, megakaryocyte, and macrophage lineages were scored as CFU-GEMM, whereas single lineage colonies, which contain monocyte (CFU-M), granulocyte (CFU-G), erythrocyte (both CFU-E and burst-forming unit (BFU)-E) or granulocyte/monocyte (CFU-GM) precursor cells were designated as CFU-c. The CFU-GEMM assay provides information on the recovery of multipotential progenitor cells in the bone marrow, while the CFU-c assay provides information on the recovery of more committed progenitors of each myeloid lineage. As shown in FIGS. 44–45, MPIF-1 administration resulted in a significant increase in the levels of mature and immature bone marrow progenitors.

The studies described in this example test the activity of MPIF-1 (Δ23). However, one skilled in the art could easily modify the exemplified studies to test the activity of full length MPIF-1, or fragments thereof, as well as polynucleotides (e.g., via gene therapy), agonists, and/or antagonists of MPIF-1.

EXAMPLE 33

Physical, Chemical, and Pharmaceutical Properties of MPIF

Dosage Form, Pharmacologic Class and Administration. Myeloid Progenitor Inhibitory Factor is a truncated (8.85 kDa) recombinant human protein β-chemokine. MPIF has been expressed in *E. coli* and has been purified to homogeneity.

MPIF is provided as a sterile colorless solution intended for injection. MPIF is formulated as a sterile solution containing varying concentrations (2–8 mg/mL) of MPIF buffered to pH 6.0±0.2 with sodium acetate and sodium chloride. The solution is filled in Type 1 single-use glass vials. Retention of bioactivity has been demonstrated for at least 1 year at 2° to 8° C. MPIF will be administered intravenously.

The MPIF protein consists of 77 amino acids (Δ23 plus an N-terminal Met residue) and has a molecular mass of 8.85 kDa.

General Description of Manufacturing Specifications. MPIF is expressed in and purified from *Escherichia coli*. The MPIF protein is present within protein structures commonly referred to as inclusion bodies. The natural insolubility of these inclusion bodies allows a purification process that removes contaminating *E. coli* components prior to solubilization of the protein.

Chromatography and filtration methods are used to isolate and purify the MPIF protein. The isolation and purification steps are monitored as follows:

The resolution profiles of the intermediate products eluted from the chromatographic columns are monitored continuously by ultraviolet absorbance at 280 nm.

The MPIF protein purity and content at different stages of purification are determined by analytical RP-HPLC.

Analytical methods are used to determine the concentration of MPIF, purity, and identity, as well as to detect potential impurities such as DNA, endotoxin, and microbiological bioburden.

Quality Control MPIF drug product is a clear, colorless solution. A single band is observed in sodium dodecyl sulfate-polyacrylamide gel electrophoresis (SDS-PAGE) both under reducing and nonreducing conditions following Coomassie blue staining. A single peak elutes in size exclusion high-performance liquid chromatography (SE-HPLC). A major peak ($\geq 90\%$) with two minor peaks are observed by reversed phase high-performance liquid chromatography (RP-HPLC). Both minor peaks have the same molecular mass and the same N-terminus sequences (Edman degradation) as a major peak of MPIF. Peptide mapping by trypsin digest from various lots of MPIF consistently shows the same number of peptides that are in the process of being further characterized. The molecular mass of MPIF determined by mass spectrometer is 8.85 kDa.

Two bioassays are used to determine the activity of MPIF. A calcium mobilization assay in THP-1 human myeloid tumor cells measures the immediate consequence of MPIF binding to its only known receptor, CCR1. A chemoprotection assay provides a means to evaluate the ability of the compound to protect mouse marrow progenitors from the cytotoxic effects of 5-FU.

The studies described in this example test the activity of MPIF-1 (Δ23). However, one skilled in the art could easily modify the exemplified studies to test the activity of full length MPIF-1, or fragments thereof, as well as polynucleotides (e.g., via gene therapy), agonists, and/or antagonists of MPIF-1.

EXAMPLE 34

Nonclinical Studies

Introduction and Summary. Myelosuppression is one of the most common dose-limiting toxicities of cytotoxic chemotherapy. This suppression results from the loss of myeloid progenitors in the bone marrow and, when severe, increases the risk of hemorrhagic and infectious complications. Myeloid Progenitor Inhibitory Factor (MPIF) is being developed as a chemoprotective agent. MPIF has been characterized as a human β-chemokine. Chemokines (chemotactic cytokines) are soluble proteins secreted by a variety of cell types in response to injury, infection, or immune system activation. These proteins are structurally related by virtue of sequence homology and are functionally related by their ability to induce chemotactic responses among leukocyte populations.

The biological effects of MPIF on myeloid progenitor cells distinguish this chemokine from all known chemokines and cytokines (Premack, B. A. and Schall, U., *Nature Med.* 2(11):1174–1178 (1996); Rollins, B. J., *Blood* 90(3):909–928 (1997)). Nonclinical studies show that this novel chemokine limits progenitor cell proliferation and/or differentiation, thereby protecting these cells from the cytotoxic effects of chemotherapeutic agents (Patel et al., *J. Exp. Med.* 185:1163 (1997)). MPIF exhibits potent in vitro inhibition of low proliferative potential-colony-forming cells (LPP-CFC) from bone marrow. LPP-CFC are bipotential hematopoietic progenitors that give rise to the granulocyte and monocyte lineages. MPIF also reversibly inhibits colony formation by murine stem cell derived granulocyte and monocyte colony forming cells. Chemoprotection experiments in vitro have shown that MPIF protects these hematopoietic progenitors from the cytotoxic effects of antimetabolites (5-FU, ARA-C), antitumor antibiotics, topoisomerase I inhibitors, and taxanes.

MPIF protects myeloid progenitor cells in vivo when administered immediately before each cycle of chemotherapy. Treatment with MPIF also results in a more rapid recovery of both bone marrow progenitor cells and peripheral cell populations of neutrophils and platelets than the control in an in vivo chemotherapeutic model. Combined with results from in vitro studies, these results show a potential clinical application of MPIF as a protectant of hematopoietic progenitor cells from chemotherapy-induced myelosuppression.

Initiation of therapy with MPIF at the start of chemotherapy when the pool of precursors is greatest may result in preservation of progenitor pools during later cycles of chemotherapy. Once confirmed in the clinic, this result represents an advance over what can be achieved with growth factors such as granulocyte-colony stimulating factor (G-CSF) or granulocyte and monocyte-colony stimulating factor (GM-CSF) that have been unable to prevent progressive loss of progenitor cell reserves following repeated courses of chemotherapy. In addition, intervention with MPIF after multiple cycles of chemotherapy will be useful in assisting recovery from neutropenia and thrombocytopenia, even in patients with evidence of reduced progenitor cell reserve.

A phase I placebo-controlled, dose escalation study was conducted in healthy volunteers (n=25) receiving repeated doses (n=6). Dosing was initiated at a level calculated to be 2 logs below the optimal protective dose in the mouse and escalated to a dose of 100 µg/kg, which is more than one log below the highest dose which produced no detectable adverse effects in preclinical toxicology studies. Healthy volunteers were treated with 0.1, 1, 10, 30, and 100 ag/kg daily for 6 days. A cohort of 6 patients, 5 receiving MPIF and 1 receiving placebo, were entered at each dose level. No serious adverse events considered related to MPIF administration were observed. In general, the reported adverse events were mild and transient, and consisted primarily of mild headaches, myalgias and fatigue. Only one serious adverse event (possible TIA) of unknown relationship to the study agent was described in a 71 year old female, fifty-two hours after the final infusion. The symptoms in the patient resolved shortly after admission. No immune response such as development of antibodies was observed. Analysis of flow cytometry data showed a transient, dose-dependent decrease in CD 14-positive monocytes during the days of MPIF administration. However, no decrease in absolute monocyte or neutrophil counts was observed. No major changes in blood counts or evidence of inhibition of hematopoiesis was observed in these healthy volunteers with normal hematopoiesis. Pharmacokinetic studies revealed that the peak concentration ($C_{MAX}$) and area under the concentration time curve (AUC) initial were dose related, without evidence of drug accumulation after six days of treatment. (Example 34)

Pharmacologic Class and Rationale. MPIF, a recombinant human protein, is a truncated form of the human β-chemokine, Myeloid Progenitor Inhibitory Factor-1 (MPIF-1). One anticipated indication for MPIF is the protection of myeloid progenitor cells in patients receiving myelosuppressive chemotherapy.

Systemic therapy with cytotoxic drugs is the basis for most effective treatments of disseminated cancers. Additionally, adjuvant chemotherapy is often used following the treatment of localized disease with surgery or radiotherapy.

Since myelosuppression is one of the most common serious to xicities associated with chemotherapy, there is a significant clinical need for advances in the supportive care of patients undergoing myelosuppressive therapy. Nonclinical studies show that MPIF has significant potential as a protectant of hematopoietic precursor cells from the cytotoxic effects of chemotherapeutic agents.

Hematopoietic stem and multipotential progenitor cells are responsible for restoring all hematopoietic lineages. In normal individuals, these cells divide less frequently and are, therefore, relatively resistant to a single course of a chemotherapeutic drug. However, following multiple cycles of chemotherapy, myeloid progenitor cells respond with increased proliferation and become much more susceptible to the toxic effects from subsequent doses and courses of chemotherapeutic agents. Multiple courses of cytotoxic chemotherapy lead to the progressive loss of myeloid progenitor cells, which results in delayed recovery and worsening nadir counts for neutrophils and platelets.

The clinical value of such a protectant is the potential to decrease the incidence and/or duration of chemotherapy-induced cytopenias, thereby, reducing the likelihood of infection and bleeding following high dose or sequential cycles of chemotherapy. In addition, MPIF will provide a supportive measure for dose intensity, the timely administration of intensive chemotherapy.

Currently Available Therapies. Colony-stimulating factors (CSFs) have been used to support standard and intensified doses of chemotherapy for almost a decade. Nonclinical evidence is available that suggests that escalated doses of chemotherapy may substantially increase tumor cell destruction and improve survival in selected malignancies, but clinical confirmation of this concept is lacking. CSFs, which stimulate the production of granulocytes, macrophages, and platelets, are used after chemotherapy to shorten the duration of neutropenia or thrombocytopenia. In contrast, MPIF protects myeloid progenitor cells by transiently limiting their proliferation before and during exposure to chemotherapy. This different mode of action prevents the progressive loss of progenitor cell reserves that occurs following repeated doses of chemotherapy, even in conjunction with CSF administration. The use of MPIF therefore permits an increase in chemotherapy dose intensity.

NonclinicalStudies. MPIF functions as a chemoprotectant for committed myeloid progenitor cells. Compared with other chemoprotective agents which have shown efficacy in vitro and/or in animal models, MPIF displays a unique biological profile based on its ability to inhibit $CD34^+$ progenitor cell proliferation and colony formation by both colony-forming units-granulocyte and monocyte (CFU-GM) and colony-forming units-mixed (CFU-mix) cells. Among human progenitors MPIF displays similar inhibitory activities on CFU-GM and CFU-GEMM colony formation. Thus, MPIF inhibits $CD34^+$ multipotential progenitors, bipotential progenitors, and committed progenitors.

MPIF also functions as a potent, reversible inhibitor of murine Low Proliferate Potential-Colony Forming Cells (LPP-CFC) that include many of the committed myeloid progenitors that ultimately give rise to peripheral monocytes and granulocytes. MPIF was also found to inhibit more primitive High Proliferation Potential-Colony Forming Cells (HPP-CFC) that exhibit many of the properties of the pluripotential hematopoietic stem cells.

Tissue Expression of MPIF. The mRNA expression pattern of MPIF is complex with message originally detected in the lung, liver, bone marrow, activated monocytes and the myelomonocytic cell lines HL-60 and THP-1. More recently, distinct transcripts have been identified in pancreas, heart, skeletal muscle, and to a lesser extent bone marrow.

Nonclinical Pharmacology. The results from over 270 in vitro experiments indicate that MPIF has no detectable effect on tumor cell lines in the National Cancer Institute panel of tumors used for screening of anticancer agents nor on any of 52 additional tumor cell lines. Also, more than 75 cell-based assays were developed to study MPIF activity. Among normal cell types, the biological activity of MPIF is restricted to specific cells within the peripheral immune system and the hematopoietic progenitor cell compartment (Table 7). In particular, MPIF has been found to achieve the following:

Induce chemotactic responses in resting T-cells and monocytes.

Induce $Ca^{2+}$ mobilization in monocytes, monocyte-derived dendritic cells, and eosinophils.

Inhibit murine multipotential and committed progenitor colony formation at concentrations ranging from 0.1 to 100 ng/mL.

Inhibit human $CD34^+$ cell proliferation at concentrations ranging from 0.1 to 100 ng/mL.

TABLE 7

In vitro screening analyses of MPIF
75–80 Cell Based Assay Systems

| Endoderma Derived Cell | Mesoderma Derived Cell | Ectoderma Derived Cell | Tumor |
|---|---|---|---|
| Hepatocytes | Vascular endothelium | Neuronal cells | Proliferation |
| Lung epithelium | Osteoclasts/Osteoblasts | Astrocytes | Apoptosis |
| Gut epithelium | Chondrocytes | Cortical neurons | Differentiation |
| | Skin (fibroblasts) | GABAergic neurons | Migration |
| | Smooth muscle (aortic) | Schwann cells | |
| | Myocytes | Epidermal cells | NCI anti-cancer screening |
| | Immune system cells* | | |
| | Hematopoietic Stem Cells* | | |

*Biological activity found

Chemotactic Activity of MPIF

MPIF is a potent chemotactic factor for resting T-lymphocytes with maximal response noted at 110 ng/mL. MPIF did not stimulate chemotaxis in anti-CD3 activated T-cells over a broad range (0.1 to 1000 ng/mL). Freshly-isolated monocytes exhibited a chemotactic response to MPIF. Maximal migration was observed at 1100 ng/mL, a concentration 110-fold higher than that needed to elicit a comparable response among resting T-cells. A weak chemotactic response occurred in neutrophils. MPIF did not induce chemotaxis in B-lymphocytes, eosinophils, basophils, NK-cells, or platelets.

Effect of MPIF on Human Blood Cells. MPIF has the following in vitro effects on human blood cells Monocytes and Monocyte-derived Macrophages. The effect of MPIF on lysosomal enzyme release was determined in freshly isolated monocytes. A low but variable release of N-acetyl-β-D-glucosidase was observed over a range of 0.5 to 500 ng/mL. Although detectable, the release was significantly less than that induced by MIP-1β, MIP-1α, RANTES, or MCP-1. In other studies, MPIF (1 to 1000 ng/mL) had no effect on the release of the lysosomal enzymes elastase, glucouronidase, or myeloperoxidase. MPIF (0.1 to 100 ng/mL) did not induce monocytes to secrete IL-1β, tumor necrosis factor-α (TNF-α), IL-10, or IL-2. Moreover, no effect on oxidative burst or cytotoxic activity of activated macrophage was detected.

Basophils. Basophils purified from peripheral blood were incubated with MPIF (1 to 1000 ng/mL) for 10 minutes and the resultant supernatants were assayed for histamine release. MPIF did not induce histamine release.

NK Cells. Purified PBMC's were used as a source for the determination of the effect of MPIF on NK-mediated cell killing of K562 cells. MPIF (1 to 100 ng/mL) had no effect on IL-2 stimulated, NK-mediated killing of K562 cells.

Platelets. MPIF at concentrations of 0.1 to 100 ng/mL did not induce or modulate platelet activation or aggregation.

MPIF Inhibits Proliferation of Human CD34+ Progenitors

To assess the effect of MPIF on human hematopoietic progenitor cell proliferation, CD34+cells were isolated from cord blood, resuspended at $5 \times 10^4$ cells/mL, and cultured for 4 days in the presence of IL-3 and SCF. The resulting populations of myeloid progenitors were then washed and cultured under four conditions: medium alone; medium plus MPIF; medium plus cytokine cocktail of IL-3, GM-CSF, and erythropoietin (EPO); and medium plus cytokine cocktail and MPIF. After 6 additional days, the number of viable cells in each culture was determined. As shown in FIG. 46, myeloid progenitors do not survive when grown in media alone or medium plus MPIF. In contrast, the cytokine cocktail dramatically improved progenitor survival. Addition of MPIF (1–1000 ng/mL) resulted in significant (20–40%) inhibition of cell proliferation. (These results are representative of three independent experiments. Values are reported as the mean absorbance±SD of the triplicate wells.) (FIG. 46)

Inhibition of Human CFU-GM and CFU-Mix by MPIF

To determine if the inhibitory effect of MPIF targets a specific progenitor, CD34+derived precursor cells were cultured in medium (Methocult ™ semisolid medium containing IL-3, GM-CSF, SCF, EPO and TPO) that supports the development of BFU-E, CFU-G, CFU-M, CFU-GM, CFU-Meg, and CFU-Mix colonies. After 14 days in culture, the number and phenotype of colonies arising in the presence of MPIF were compared with those arising in medium alone or the control cytokines MIP-1α or Monocyte Chemoattractant Protein-4 (MCP-4).

The results of the two representative experiments indicate that MPIF inhibits (50–64%) the formation of both CFU-GM and CFU-Mix. MIP-1α and MCP-4 had no effect on colony formation of any progenitor population. These results confirm the inhibitory effects of MPIF on myeloid precursor development and define MPIF as an inhibitor of human granulocyte and monocyte precursor cells. (Table 8)

TABLE 8

Effect of MPIF on formation of human CD34+ progenitors

| Culture Conditions* | Colony Frequency (colonies per 1000 cells) | | | | | |
|---|---|---|---|---|---|---|
| | BFU-E | CFU-G | CFU-M | CFU-GM | CFU-Meg | CFU-Mix |
| Experiment Number 1 | | | | | | |
| Medium | 13 ± 2 | 15 ± 2 | 14 ± 3 | 16 ± 3 | 11 ± 3 | 11 ± 2 |
| MPIF-1 | 19 ± 2 | 18 ± 5 | 12 ± 2 | 8 ± 2 | 12 ± 2 | 5 ± 1 |
| MIP-1α | 17 ± 3 | 19 ± 5 | 14 ± 2 | 14 ± 4 | 12 ± 3 | 12 ± 2 |
| Experiment Number 2 | | | | | | |
| Medium | 14 ± 3 | 13 ± 3 | 13 ± 1 | 12 ± 3 | 13 ± 1 | 11 ± 2 |
| MPIF-1 | 14 ± 2 | 11 ± 1 | 12 ± 2 | 5 ± 1 | 12 ± 2 | 4 ± 1 |
| MPIF-1α | 12 ± 2 | 12 ± 3 | 13 ± 2 | 13 ± 2 | 14 ± 2 | 12 ± 1 |
| MCP-4 | 12 ± 1 | 14 ± 2 | 12 ± 1 | 12 ± 2 | 11 ± 1 | 12 ± 2 |

In Vitro Chemoprotection

To further assess the protective potential of MPIF, lineage-depleted cells (Lin⁻cells) were isolated from mouse bone marrow and incubated in the presence of a standard cytokine cocktail consisting of IL-3 (5 ng/mL), SCF (50 ng/mL) M-CSF (5 ng/mL), and IL-1α (10 ng/mL) with or without MPIF. After 60–70 hours, cultures were treated with a chemotherapy drug and the incubation was continued for an additional 3–24 hours, at which point the numbers of surviving LPP-CFC were determined by standard clonogenic assay. As shown in FIG. 47, the cytotoxic effects of the cell cycle specific agents 5-FU, Ara-C, paclitaxel and daunorubicin were significantly reduced by MPIF. In contrast, MPIF was unable to protect progenitors from the alkylating agents melphalan and thiotepa. These results support the role of MPIF as an inhibitor of multipotential myeloid progenitor cell proliferation and provide insight into the spectrum of chemotherapeutic agents against which this chemokine may be effective.

In another experiment, the protective effect of MPIF against 5-FU induced toxicity was measured using MPIF concentrations from 0.1 to 100 ng/ml, using two manufacturing lots of MPIF are shown, Lot #11 and Lot #19. The data indicate a dose response curve in terms of percent of colony protection with administration of MPIF. The data indicate that MPIF at 0.1 ng/ml confers approximately 30% chemoprotection, and MPIF at 1,000 ng/ml confers upwards of 80% chemoprotection. (Data not shown.)

Summary of In Vivo Studies

As shown in FIG. 48, the in vivo analyses of MPIF have been carried out primarily in mice with supportive studies of compound safety in rabbits and rats. The results from these studies indicate the following:

MPIF is a potent myeloprotectant for hematopoietic progenitor cells. The consequence of such protection is a more rapid recovery of bone marrow progenitors and peripheral cell populations following therapy as compared to controls.

MPIF can be administered daily (intravenously) for periods as long as 14 days with no significant to xicities.

MPIF has no effect on the cardiovascular system.

MPIF is not pyrogenic.

MPIF is rapidly cleared from the circulation.

In Vivo Protection of Myeloid Progenitors

Experiments were conducted to determine if MPIF protects myeloid progenitors in vivo against the effects of a chemotherapeutic agent. Mice were injected with MPIF (1.0 mg/kg i.p.) daily for 3 days at 24-hour intervals and then received a single injection of 5-FU (150 mg/kg i.p.) on the third day. Mice were sacrificed at various times after 5-FU treatment and the number of bone-marrow colonies were scored in standard HPP-CFC or LPP-CFC assays. The control groups included mice receiving saline only and 5-FU only. As shown in FIG. 49A, the number of bone-marrow colonies detected in MPIF treated mice returned to normal levels within 7 days of 5-FU administration. In contrast, bone-marrow colony formation from mice treated with 5-FU alone exhibited no recovery at this time. These results show that pretreatment with MPIF prior to chemotherapy allows a more rapid recovery of colony-forming cells, possibly through the ability of MPIF to protect myeloid progenitors.

A consequence of MPIF mediated protection of progenitors was manifested in the periphery where the total white blood cell (WBC) counts increased shortly after colony recovery was observed in the bone marrow. The data presented in FIG. 49B summarize eight independent experiments. The values indicated are expressed as mean WBC counts plus or minus standard error of the mean. The differences observed at Days 6 and 8 have associated p-values less than 0.001 and 0.0001, respectively.

Chemoprotective Effect of MPIF on Multiple Cycles of Therapy

Although the results shown thus far support the role of MPIF as a protectant of marrow precursors, protection through multiple cycles of therapy is the clinically relevant use for MPIF. The results of an experiment in which the chemoprotective effect of MPIF was determined during three cycles of therapy are presented in FIG. 50. Analysis of bone marrow colony formation using marrow obtained from normal mice, mice treated with 5-FU alone (100 mg/kg i.p.), or mice treated with 5-FU and MPIF (1.0 mg/kg i.p.) indicate that MPIF protected progenitors through all three cycles of 5-FU treatment (Grzegorzewski, K. J., et al., *Blood* (abstr:suppl) (accepted for publication)).

MPIF Dose Range and Dose Schedule

The nonclinical dose response of MPIF was broad, ranging from 0.0 1 to 10 mg/kg. This broad response was the rationale for selecting a 3-log range of doses for clinical testing.

The different nonclinical dosing schedules tested are presented in FIG. 51. The rationale for choosing a human dosing schedule of Days −2, −1, and 0 relative to chemotherapy administration was based on the observation that this treatment regimen provided the most consistent and reproducible protection of the many schedules tested in mice. In addition, given the relatively short in vivo serum half-life of MPIF and the long cell-cycling time of stem cell progenitors (McNiece et al., Int. *J. Cell Cloning* 8:146–160 (1990); Bertoncello et al., *Exp. Hematol.* 19:174–178 (1991)), it is theoretically beneficial to give patients multiple doses of MPIF in order to maximize progenitor cell exposure and, thus, the likelihood of protection.

Taken together, the in vivo and in vitro results show that MPIF is unique in its biological profile. The ability of this protein to function as a potent marrow protectant suggests that it will find application as a chemoprotection agent and will spare early myeloid progenitors from the effects of commonly used chemotherapeutic drugs. The clinical value of such an agent is evident in its potential to decrease the incidence and severity of chemotherapy-induced cytopenias, thereby reducing the likelihood of infection and bleeding.

Nonclinical Toxicology

Three nonclinical to xicology studies have been conducted under Good Laboratory Practice guidelines; a 7-day dose ranging study, a 14-day subchronic study, and a 25-day subchronic study. Doses up to 20 mg/kg produced no significant to xicities. A general summary of the multiple-dose studies (FIG. 52) and a summary of clinical observations for the nonclinical studies (FIG. 53) are presented. In addition, no autonomic or cardiovascular effects were observed with doses up to 10 mg/kg.

Nonclinical Absorption, Distribution, Metabolism, and Excretion

Pharmacokinetic studies of MPIF have been performed in BALBec female mice given a single intravenous or subcutaneous bolus of MPIF at a dose of 20 mg/kg. Three mice from each treatment group were sacrificed and bled at each time point, and the concentration of MPIF was determined by enzyme-linked immunosorbent assay. As shown in FIG. 54, intravenous administration of MPIF results in a rapid clearance with low, but detectable, levels persisting as late as 24 hours after injection. Subcutaneous administration yields a similar profile, with the major difference being a 30-minute delay in the appearance of peak serum levels. After this time, the clearance is indistinguishable from that observed among intravenously treated mice. The clearance of MPIF is consistent with that expected for small proteins.

A second pharmacokinetic study of MPIF was carried out in mice given a single intravenous bolus of 20 mg/kg. MPIF was cleared rapidly from the serum. MPIF could be detected 8 hours after administration at levels of 0.1% of the administered dose.

The studies described in this example test the activity of MPIF-1 ($\Delta 23$) in relation to use during chemotherapy. Many of these protocols are equally applicable to studies of MPIF-1 use during radiotherapy. Additionally, one skilled in the art could easily modify the exemplified studies to test the activity of full length MPIF-1, or fragments thereof, as well as polynucleotides (e.g., via gene therapy), agonists, and/or antagonists of MPIF-1.

EXAMPLE 35

Preclinical and Clinical Studies

Previous Human Experience

Clinical Study 00304-CRX-HV-01. A phase I study was conducted to evaluate the safety, pharmacokinetic (PK) and pharmacodynamic effects in healthy volunteers (Louie et al., *Blood* 90:1569A (abstr;suppl) (1997)). Thirty subjects (14M, 16F, median age 46, range: 21–73 yr) were randomized to receive 6 doses of MPIF or placebo administered over approximately one minute on six consecutive days in a blinded, placebo-controlled, sequential dose escalation (0.1, 1, 10, 30, 100 µg/kg) trial. Each dosing cohort consisted of 6 subjects randomized in a 5:1 active to placebo ratio. Adverse events (AE) were assessed for a four-week period. After two weeks, preliminary safety data were reviewed and a decision to start the next cohort was made. Blood samples were obtained for hematology, chemistry, PK, antigenicity and flow cytometry to evaluate peripheral blood cell populations.

This was a phase I safety study in healthy volunteers and, as such, establishing efficacy was not a primary objective. However, the evolution of the following laboratory parameters were evaluated:

White blood cell (WBC) count

Absolute neutrophil count (ANC)

Red blood cell (RBC) count

Platelet count

Peripheral blood cell composition by flow cytometry

There were no observed differences between active- and placebo-treated groups in terms of absolute neutrophil count as measured by absolute count or percentage change. These results are comparable to preclinical study results in normal animals. Likewise, no significant change from baseline was observed for white blood cells, red blood cells, or platelets.

Serial flow cytometry observations were obtained to further delineate the effects of MPIF on peripheral white blood cell sub-populations. The percentage of peripheral blood mononuclear cells (granulocytes, monocytes, T and B lymphocytes) as a function of dose and study day is presented graphically in FIGS. 55A–55D.

No significant change from baseline was observed for granulocytes, T lymphocytes, or B lymphocytes at any time during the study. The lack of effect on granulocyte count in healthy volunteers was consistent with lack of effect observed in healthy animals in preclinical studies.

A transient dose-dependent decrease in the proportion of CD 14-bearing peripheral monocytes was observed during the six days of MPIF administration in cohorts receiving 10–100 µg/kg/day.

A relative change from baseline analysis was conducted to assess the significance of monocyte CD14 inhibition during the treatment period. The relative percent change from baseline for gated CD14+ events was calculated. The baseline value was considered the control for each patient. The baseline levels were comparable between treatment arms, with the lowest pairwise comparison p-value=0.18 (comparisons between treatment and placebo).

The overall analysis of variance model was significant at all time points. The change from baseline was significantly different from 0 for the higher dose groups 10, 30, and 100 µg/Kg (p=0.000 1). There was also a significant difference between placebo and these three treatment arms. There was a significant difference between the 100 µg/Kg group and 30 µg/Kg group and 10 µg/Kg indicating a dose response.

To further examine the effects of the study drug on monocyte representation, the absolute monocyte count (AMC) was calculated. This was done in the same manner as absolute neutrophil counts are calculated, using the following formula:

AMC=WBC count×% monocytes (from the differential count)×1000

The results are presented in FIG. 56. The expected decrease in AMC was not observed during MPIF treatment when monocytes were quantitated by morphologic means. In fact, a slight increase was seen during the period of treatment, occurring at MPIF doses of 1 µg/kg and above, with a return to baseline counts within 2–3 days after the last dose.

The simplest interpretation of the monocyte data is that MPIF caused a dose-dependent change in monocyte chemotaxis, resulting in an influx of non-CD 14 bearing monocytes. This would account for the modest absolute monocyte count increase and the reduction in CD14 bearing monocytes observed by flow cytometry. By either method, there was clear evidence of transient and reversible biological activity.

Safety. One intended indication for MPIF is protection of myeloid precursor cells in patients receiving myelosuppressive chemotherapy. In dose-ranging, placebo-controlled clinical trials of this agent, the most frequently reported AE is anticipated to be myelosuppression and its infectious and hemorrhagic complications related to concomitant chemotherapy administration. In the preclinical and clinical studies, the effects of MPIF have been transient, reversible, and limited to cells of myeloid lineage. Although MPIF is expected to reduce the frequency, severity, and duration of chemotherapy-induced cytopenias, unexpectedly prolonged action could potentially worsen cytopenias.

In the phase 1 healthy volunteer study 00304-CRX-HV-01, eighteen subjects (14 active, 4 placebo) experienced a total of 32 adverse events (25 active, 7 placebo).

Adverse events were coded by the investigator as either "associated with study drug administration", "not associated with study drug administration", or "relationship to study drug administration unknown". In order to standardize adverse event reporting in terms of causality, those adverse events coded by the investigator as "relationship to study drug administration unknown", were considered by the sponsor to have possible causality and therefore have been reported under "related AE".

Based on these criteria, 11 of 25 MPIF-treated subjects experienced at least one adverse event considered associated with MPIF administration. Three of five subjects receiving placebo experienced at least one adverse event considered associated with drug administration. The incidence of adverse events among active- and placebo-treated subjects (44% vs. 60%, respectively) was comparable.

Twenty-nine of the 32 reported adverse events were of NCI CTC grade 1 or 2 severity. Two were of unknown severity. The most frequently reported adverse events were headache (5 subjects, 4 active/1 placebo), somnolence (3 subjects, 2 active/1 placebo), and leukopenia (3 subjects, 2 active/1 placebo). A summary of all reported AE for the phase I study is presented in Table 9.

TABLE 9

Summary of Adverse Events by Body System, COSTART and Treatment - Intention to Treat

| Body System (COSTART) | Placebo | | 0.1 μg/Kg | | 1.0 μg/Kg | | 10 μg/Kg | | 30 μg/Kg | | 100 μg/Kg | | All Active | |
|---|---|---|---|---|---|---|---|---|---|---|---|---|---|---|
| | N | % | N | % | N | % | N | % | N | % | N | % | N | % |
| Body as a Whole | 2 | 40 | 0 | 0 | 4 | 80 | 0 | 0 | 0 | 0 | 1 | 20 | 5 | 20 |
| Abdominal Pain | 1 | 20 | 0 | 0 | 0 | 0 | 0 | 0 | 0 | 0 | 0 | 0 | 0 | 0 |
| Asthenia | 0 | 0 | 0 | 0 | 1 | 20 | 0 | 0 | 0 | 0 | 0 | 0 | 1 | 4 |
| Back Pain | 0 | 0 | 0 | 0 | 1 | 20 | 0 | 0 | 0 | 0 | 0 | 0 | 1 | 4 |
| Headache | 1 | 20 | 0 | 0 | 4 | 80 | 0 | 0 | 0 | 0 | 0 | 0 | 4 | 16 |
| Injection Site Edema | 0 | 0 | 0 | 0 | 0 | 0 | 0 | 0 | 0 | 0 | 1 | 20 | 1 | 4 |
| Injection Site Pain | 0 | 0 | 0 | 0 | 0 | 0 | 0 | 0 | 0 | 0 | 1 | 20 | 1 | 4 |
| Digestion System | 1 | 20 | 0 | 0 | 1 | 20 | 0 | 0 | 0 | 0 | 0 | 0 | 1 | 4 |
| Diarrhea | 0 | 0 | 0 | 0 | 1 | 20 | 0 | 0 | 0 | 0 | 0 | 0 | 1 | 4 |
| Stomatitis | 1 | 20 | 0 | 0 | 0 | 0 | 0 | 0 | 0 | 0 | 0 | 0 | 0 | 0 |
| Hemic/Lymphatic System | 1 | 20 | 2 | 40 | 1 | 20 | 0 | 0 | 0 | 0 | 1 | 20 | 4 | 16 |
| Anemia | 0 | 0 | 0 | 0 | 1 | 20 | 0 | 0 | 0 | 0 | 0 | 0 | 1 | 4 |
| Ecchymosis | 0 | 0 | 1 | 20 | 0 | 0 | 0 | 0 | 0 | 0 | 0 | 0 | 1 | 4 |
| Leukocytosis | 0 | 0 | 0 | 0 | 0 | 0 | 0 | 0 | 0 | 0 | 1 | 20 | 1 | 4 |
| Leukopenia | 1 | 20 | 1 | 20 | 1 | 20 | 0 | 0 | 0 | 0 | 0 | 0 | 2 | 8 |
| Musculoskeletal System | 0 | 0 | 0 | 0 | 1 | 20 | 0 | 0 | 0 | 0 | 0 | 0 | 1 | 4 |
| Myalgia | 0 | 0 | 0 | 0 | 1 | 20 | 0 | 0 | 0 | 0 | 0 | 0 | 1 | 4 |
| Nervous System | 1 | 20 | 0 | 0 | 2 | 40 | 0 | 0 | 2 | 40 | 1 | 20 | 5 | 20 |
| Dizziness | 1 | 20 | 0 | 0 | 0 | 0 | 0 | 0 | 1 | 20 | 0 | 0 | 1 | 4 |
| Facial Paralysis | 0 | 0 | 0 | 0 | 0 | 0 | 0 | 0 | 0 | 0 | 1 | 20 | 1 | 4 |
| Somnolence | 1 | 20 | 0 | 0 | 2 | 40 | 0 | 0 | 0 | 0 | 0 | 0 | 2 | 8 |
| Vasodilatation | 1 | 20 | 0 | 0 | 1 | 20 | 0 | 0 | 0 | 0 | 0 | 0 | 1 | 4 |
| Vertigo | 0 | 0 | 0 | 0 | 0 | 0 | 0 | 0 | 1 | 20 | 0 | 0 | 1 | 4 |
| Respiratory System | 0 | 0 | 0 | 0 | 0 | 0 | 0 | 0 | 1 | 20 | 0 | 0 | 1 | 4 |
| Pharyngitis | 0 | 0 | 0 | 0 | 0 | 0 | 0 | 0 | 1 | 20 | 0 | 0 | 1 | 4 |
| Skin | 0 | 0 | 1 | 20 | 0 | 0 | 0 | 0 | 0 | 0 | 0 | 0 | 1 | 4 |
| Pruritus | 0 | 0 | 1 | 20 | 0 | 0 | 0 | 0 | 0 | 0 | 0 | 0 | 1 | 4 |
| Urogenital System | 0 | 0 | 0 | 0 | 0 | 0 | 1 | 20 | 0 | 0 | 1 | 20 | 2 | 8 |
| Metrorrhagia | 0 | 0 | 0 | 0 | 0 | 0 | 1 | 20 | 0 | 0 | 0 | 0 | 1 | 4 |
| Vaginitis | 0 | 0 | 0 | 0 | 0 | 0 | 0 | 0 | 0 | 0 | 1 | 20 | 1 | 4 |

One adverse event was reported as serious and severe. A 72-year-old white female experienced vertigo manifested by dizziness, nausea and vomiting, and gait instability approximately 56 hours after the final administration of MPIF (30 μg/kg). The subject was hospitalized overnight for observation and evaluation. Laboratory, head CT and carotid ultrasound exams were unrevealing. The subject had a similar episode in the distant past. The symptoms resolved quickly and the subject was discharged from the hospital the following morning without evidence of sequelae and completed the study. The relationship of this adverse event to study medication was reported by the Investigator as "unknown".

Pharmacokinetic Parameters. Pharmacokinetic parameters were evaluated in study 00304-CRX-HV-01. Plasma samples were obtained at baseline and following the initial administration at 5, 10, 15 and 30 minutes, 1,2,4 and 24 hours. Additional samples were obtained prior to and following the final administration to evaluate drug accumulation.

The data are summarized in FIG. 57. Circulating blood levels were readily detected in the 0.1 and 1.0 μg/kg cohorts for up to 30 minutes and 1 hour, respectively. Higher doses resulted in detectable levels for up to 24 hours post infusion. The AUC and $C_{MAX}$ were proportional to the administered dose. Among subjects receiving the highest dose levels (30 and 100 μg/kg), the $T_{1/2}$ was approximately 0.8 hours. Plasma levels prior to the final administration of study drug on day 6 indicated no evidence of drug accumulation.

These studies indicate that MPIF-1 does cause the side effects associated with G-CSF, such as skeletal pain, alopecia, diarrhea, neutropenic fever, mucositis, fever, fatigue, anorexia, etc.

The studies described in this example test the activity of MPIF-1 (Δ23). However, one skilled in the art could easily modify the exemplified studies to test the activity of full length MPIF-1, or fragments thereof, as well as polynucleotides (e.g., via gene therapy), agonists, and/or antagonists of MPIF-1.

EXAMPLE 36

Summary of Data and Guidance for the Investigator

Summary of Preclinical Data. In vivo studies show that MPIF is a potent protectant for hematopoietic progenitor cells. Inhibition of murine multipotential and committed progenitor colonies was observed at concentrations ranging from 0.1 to 100 ng/mL. In vitro experiments have shown that MPIF confers cytoprotection from the effects of antimetabolites, antitumor antibiotics, topoisomerase inhibitors, and taxanes. In in vivo studies, the consequence of such protection is a more rapid recovery of bone marrow progenitors and peripheral 5 cell populations following cytotoxic chemotherapy.

MPIF can be administered daily (intravenously) for periods as long as 14 days with no significant to xicities. No adverse effects were observed in animals up to the human equivalent dose of 1.67 mg/kg. No adverse effects were observed in animals in 28-day, repeated-dose to xicology studies at doses up to 20 mg/kg.

MPIF had no detectable growth-promoting effect in tumor cell lines in over 270 in vitro experiments.

Summary of Clinical Data. MPIF was safely administered and well tolerated in healthy volunteers (n=25) receiving repeated doses in a phase I placebo-controlled, dose escalation study (dose range: 0.1–100 µg/kg):

No serious adverse events considered related to MPIF administration were observed in healthy volunteers.

Transient, dose-dependent decreases in CD14 expression were observed in peripheral blood monocytes by flow cytometry analysis. Absolute monocyte and neutrophil counts as determined by differential count were unaffected.

MPIF was detectable up to 24 hours post-treatment.

MPIF was not immunogenic when administered to healthy volunteers.

Possible Risks and Side Effects. The effects of MPIF have been transient, reversible, and limited to cells of myeloid lineage in the preclinical and clinical studies. Although MPIF is expected to reduce the frequency, severity, and duration of chemotherapy-induced cytopenias, unexpectedly prolonged action could potentially worsen cytopenias.

Transient adverse events, with a frequency and severity comparable to placebo, were observed in the initial clinical study of healthy volunteers receiving multiple intravenous doses of up to 100 µg/kg of MPIF. No acute reactions considered related to the administration of MPIF were observed. MPIF was non-immunogenic in healthy volunteers.

Although few adverse events have been associated with MPIF administration, the introduction of an exogenous protein could potentially result in immunologically-mediated local or systemic reactions. Subjects could experience acute allergic reactions (such as fever, urticaria, hyper- or hypotension, and bronchospasm), or other reactions, such as vasculitis, or serum sickness. The possibility of renal dysfunction, hepatic dysfunction, immunosuppression, coagulopathy and neuropathy, although remote, cannot be excluded.

Subjects should be monitored closely during and after administration for any sign of acute adverse reaction. Emergency supplies (including epinephrine, corticosteroids, pressor agents, and cardiac defibrillation equipment) are to be readily available for use, should an acute reaction occur.

Contraindications. The safety of this product for use during pregnancy or in nursing mothers has not been demonstrated in clinical trials.
Precautions Information for Patients. MPIF, as with all investigational products, should only be used under the direction of a clinical trial physician or investigator who is familiar with this product.

The safety of this product for use during pregnancy or in nursing mothers has not been demonstrated in clinical trials. Experimental animal studies to assess the safety with respect to the development of the embryo or fetus, the course of gestation, and peri- and post-natal development have not been conducted. Any woman who has missed a menstrual period should be assumed pregnant until proven otherwise. Only imperative investigations should therefore be carried out during pregnancy when the likely benefit exceeds the risk incurred by the mother and fetus.

It is not known if MPIF is distributed in milk. Breast feeding should be interrupted if study drug administration is found necessary.

Laboratory Tests. Peripheral blood counts should be closely monitored in patients treated with MPIF. Laboratory tests should be carried out in accordance with the accompanying clinical protocol.

Product Interactions. MPIF is not anticipated to cause any serious interactions with other drugs.

Carcinogenesis, Mutagenesis, Impairment of Fertility. Animal studies to examine carcinogenic and mutagenic potential have not been conducted with MPIF. In vitro studies indicate that MPIF has no detectable effect on tumor cell lines.

Product Abuse and Dependence. The product abuse and dependence otential of MPIF has not been examined in nonclinical or clinical studies but is expected to be negligible.

Overdosage. There is no clinical experience with overdosage of MPIF. No toxicity has been observed in animals when a dose up to 20 mg/kg is given for 14 consecutive days. This is equivalent to a dose of 1.67 mg/kg in man.

Dosage and Administration. The optimal dose and dosing regimen for MPIF has not been determined. Initial studies evaluated the safety of daily dosing of 0.1 to 100 µg/kg of MPIF administered intravenously for up to 6 days. Phase 2A studies to determine biological activity and preliminary efficacy will evaluate a dose range of 1–100 µg/kg. Subsequent doses and dose regimens will be determined from the results of these early efficacy studies.

Supply and Storage. MPIF is supplied as sterile liquid formulation. This product must be stored between 2° and 8° C., in an area accessible only to authorized personnel. The diluted drug for patient administration has been shown to be stable for up to twelve hours at room temperature without degradation of the product.

The studies described in this example test the activity of MPIF-1 (Δ23). However, one skilled in the art could easily modify the exemplified studies to test the activity of full length MPIF-1, or fragments thereof, as well as polynucleotides (e.g., via gene therapy), agonists, and/or antagonists of MPIF-1.

EXAMPLE 37

Solution Structure and Dynamics of MPIF-1

Summary

Myeloid progenitor inhibitor factor-1 (MPIF-1) is an inhibitor of progenitor cells and an activator of monocytes. The solution structure of MPIF-1 has been determined by nuclear magnetic resonance (NMR) spectroscopy. Unlike many CC chemokines, MPIF-1 structure shows it to be a monomer. The structure is well defined except for the termini residues and adopts a characteristic chemokine fold of three β-strands and an overlying α-helix. In addition to the 4 cysteines that characterize most chemokines, MPIF-1 has two additional cysteines that form a disulfide bond. The backbone dynamics indicate that the functionally important N-terminal residues, residues of the N-terminal loop, and residues adjacent to the disulfide bonds show significant dynamics compared to the core of the protein. MPIF-1 is processed from a 99 amino acid proprotein at the N-terminus and the latter is also functional, though with reduced activity and is a monomer under a variety of solution conditions. MPIF-1 is therefore unique, as longer preproteins of all other chemokines associate. These studies are consistent with the idea that a monomer is sufficient for activating 7-TM receptors on leukocytes.

Introduction

Chemokines (chemotactic cytokines) mediate diverse biological processes, including leukocyte trafficking, hematopoiesis, and angiogenesis, and play a fundamental role in host defense against infection (Baggiolini, M., et al., Annu. Rev. Immunol. 15:675–705 (1997); Rollins, B. J., Blood 90:909–928 (1997); Luster, A. D., N. Engl. J. Med. 338:436–445 (1998)). About 40 chemokines have so far been identified; all are 70 to 100 amino acids in length, and are characterized by four conserved cysteines. Chemokines are broadly classified into CC and CXC families on the basis of whether the first two cysteines, are adjacent (CC) or separated by an amino acid (CXC). The CXC chemokines can be further divided into two subgroups, 'ELR' and 'non-ELR'. All ELR CXC chemokines activate neutrophils, whereas non-ELR CXC chemokines activate different subsets of lymphocytes. CC chemokines activate monocytes, macrophages, eosinophils, basophils, T-cells but not neutrophils. In addition, a single member of a C family, which contains only two cysteines, and a single member of a $CX_3C$ family have also been identified.

Myeloid Progenitor Inhibitory Factor-1 (MPIF-1) (also known as CKβ8), a member of the CC family, was initially identified in a large scale sequencing effort and is constitutively expressed in liver, lung pancreas, and bone marrow (Patel, V. P., et al., J. Exp. Med. 185:1163–1172(1997)). In addition to inhibition of colony formation of bone marrow cells that give rise to granulocyte and monocyte lineages, it is also chemotactic for monocytes and eosinophils (Patel, V. P., et al., J. Exp. Med. 185:1163–1172 (1997); Youn, B.-S., et al., Blood 91:3118–3126 (1998)). Alternative splicing results in two forms of the protein, named CKβ8 and CKPβ8-1, that are 99 and 116 amino acids in length, respectively (Youn, B.-S., et al., Blood 91:3118–3126 (1998)). Interestingly, atruncated form of the 99 amino acid protein (Δ24–99), henceforth referred to as MPIF-1, was observed to be substantially more active (Nardelli, B., et al., J. Immunol. 162:435–444 (1999); Berkhout, T. A., et al., Biochem. Pharmacol. 59:591–596 (2000)). Cross-desensitization experiments in monocytes and eosinophils indicate that MPIF-1 binds predominantly to the CCR1 receptor but incomplete desensitization in both cases also suggest that additional receptor(s) may be involved (Nardelli, B., et al., J. Immunol. 162:435–444 (1999)). MPIF-1 induces a rapid dose-dependent release of [$^3$H]-arachidonic acid from monocytes that is dependent on extracellular calcium and is blocked by phospholipase $A_2$ ($PLA_2$) inhibitors. Furthermore, $PLA_2$ activation is shown to be necessary for filamentous actin formation in monocytes.

Structures of several CXC and CC chemokines have been solved by NMR spectroscopy and X-ray crystallography (Clore, G. M., et al., Biochemistry 29:1689–1696 (1990); Fairbrother, W. J., et al., J. Mol. Biol. 242:252–270 (1994); Kim, K. S., et al., J. Biol. Chem. 269:32909–32915 (1994); Malkowski, M. G., et al., J. Biol. Chem. 270:7077(1995); Zhang, X., et al., Biochemistry, 33:8361–8366 (1994); Lodi, P. J., et al., Science 263:1762–1767 (1994); Skelton, N. J., et al., Biochemistry 34:5329–5342 (1995); Handel, T. M., and Domaille, P. J., Biochemistry 35:6569–6584 (1996); Kim, K. S., et al., FEBS Lett. 395:277–282 (1996); Crump, M. P., et al., J. Biol. Chem. 273:22471–22479 (1998); Sticht, H., et al., Biochemistry 38:5995–6002 (1999)). Most of the initially characterized chemokines were dimers and it was further observed that CXC and CC chemokines dimerize using different regions of the proteins. In CXC chemokines, the 1st β strand constitutes the dimer interface, whereas in the CC chemokines, the N-terminal residues constitute the dimer interface. These observations and the observation that the CXC chemokines activated only neutrophils and CC chemokines activated other leukocytes led to the belief that the dimer formation is essential for the leukocyte 7-TM receptor binding.

Subsequent discovery and characterization of chemokines such as SDF-1 (a CXC chemokine), MCP-3, eotaxin, HCC-2, and 1-309 (CC chemokines) has obviated these differences as these chemokines are predominantly monomers (Kim, K. S., et al., FEBS Lett. 395:277–282 (1996); Crump, M. P., et al., J. Biol. Chem. 273:22471–22479 (1998); Sticht, H., et al., Biochemistry 38:5995–6002 (1999); Crump, M. P., et al., EMBO J. 16:6996–7007 (1997)). Solution studies have also shown that the association is sensitive to ionic strength, buffer conditions and pH (Mayo, K. H., and Chen, M.-J., Biochemistry 28:9469–9478 (1989); Yang, Y., et al., J. Biol. Chem. 269:20110–20118 (1994); Lowman, H. B., et al., Protein Sci. 6:598–608 (1997)). Mutational studies (Czaplewski, L. G., et al., J. Biol. Chem. 274:16077–16084 (1999); Laurence, J. S., et al., Biochemistry 39:3401–3409 (2000); Paavola, C. D., et al., J. Biol. Chem. 273:33157–33165 (1998)) and trapping the chemokine in the monomer state (Rajarathnam, K., et al., Science 264:90–92 (1994); Rajarathnam, K., et al., J. Biol. Chem. 272:1725–1729(1997)) have shown that amonomer is sufficient for binding and activating the 7-TM receptors on leukocytes. Recent studies suggest that dimer formation could play arole in binding to proteoglycans and establishing a concentration gradient, a process that is essential for directed leukocyte trafficking (Hoogewerf, A. J., et al., Biochemistry 36:13570–13578 (1997); Koopmann, W., and Krangel, M. S., J. Biol. Chem. 272:10103–10109 (1997)).

In this study, the solution structure and the backbone dynamics of MPIF-1 were characterized by NMR spectroscopy. Further, the association propensities of MPIF-1 and the full length MPIF-1 proprotein were studied under a variety of solution conditions by sedimentation ultracentrifugation measurements. The implications of the structure and the dynamics, and the association properties are discussed in terms of its functions. The data from this study forms the structural basis for mutational studies and for structure-aided therapeutics for immune related diseases.

Experimental Procedures

Protein Expression and Purification. The MPIF-1 gene sequence was chemically synthesized with codons optimized for expression in E. coli. The gene was then subcloned into the expression vector pHE4 that contains a strong synthetic promoter with two lac operators, an efficient ribosomal binding site and a synthetic transcriptional terminator downstream of the inserted gene. The expression plasmid was transformed into the E. coli K 12 derived strain SG 13009. After induction with IPTG, MPIF-1 was produced as an insoluble protein and was extracted and refolded in 1.75 M Guanidine HCL in the presence of 5 mM cysteine. The expressed protein has an extra Met (the initiation codon) at the N-terminus and for simplicity is considered as the first residue of MPIF-1. The protein was purified to homogeneity by successive passages through a strong cation (poros HS-50), an anion (poros HQ-50) and a cation (poros CM-20) exchange column and finally through a size exclusion (Sephacryl S-100) column. The full-length 99 amino acid mature MPIF-1 was cloned, expressed and purified as outlined for the MPIF-1 protein.

TABLE 10

Sedimentation Equilibrium Ultracentrifugation Studies of MPIF-1 and Full Length MPIF-1

| Protein | Buffer | pH | Temperature (°) | Calc. MW[1] | State |
|---|---|---|---|---|---|
| MPIF-1 | 20 mM NaPi | 5.0 | 23 | 8.8 ± 0.6 | M |
| | 20 mM NaPi | 7.0 | 23 | 9.0 ± 0.8 | M |
| | 20 mM NaPi, 100 mM NaCl | 7.0 | 23 | 7.9 ± 1.2 | M |
| | 50 mM NaPi, 100 mM NaCl | 7.0 | 23 | 9.2 ± 0.5 | M |
| MPIF-1 (full length) | 20 mM Oac, 100 mM NaCl | 5.0 | 23 | 9.8 ± 0.6 | M |
| | 20 mM NaPi, 100 mM NaCl | 5.0 | 23 | 11.4 ± 0.7 | M |
| | 20 mM NaPi | 7.0 | 23 | 11.2 ± 0.6 | M |
| | 20 mM NaPi, 100 mM NaCl | 7.0 | 23 | 10.0 ± 1.0 | M |

[1]molecular weight calculated from fitting the data at three rotor speeds; 23,000, 28,000 and 40,000 rpm.

Sedimentation Equilibrium Analytical ultracentrifugation experiments were performed on a Beckman model XL-A ultracentrifuge at 20° C. at rotor speeds 23,000, 28,000 and 40,000 rpm. Experiments were carried out at two different starting concentrations in different buffers and ionic strength to study their effect on dimerization (Table 10). Absorbance was measured at 280 nm and the data was collected as an average of five successive radial scans using a 0.003 cm step size. The data was fitted to the following equation:

$$C_r = C_0 \exp(MH\delta) + C_0^2 K_u \exp(2 MH\delta) + E$$

where $\delta$ is $(r^2 - r_0^2)$, $H = (1 - \kappa\rho)(\omega^2/2RT)$, $C_r$ and $C_0$ are the concentrations at radius r and $r_0$ respectively, M is the molecular weight of the monomer, $\kappa$ is the partial specific volume, $\rho$ is the solvent density, $\omega$ is the angular velocity of the rotor, $K_\alpha$ is the association constant of the monomer-dimer equilibrium and E is the baseline offset. Partial specific volumes were calculated from the weight average of the partial specific volumes for individual amino acids. Data were fitted to the equation by nonlinear least squares using the Microcal Origin 4.1 software provided by Beckman for the XL-A. The quality of the fit was characterized by $\chi^2$, the sum of the squares of the residuals, and examination of the residuals for systematic deviation. The data were fitted to a single species or to a monomer-dimer model. The theoretical molecular weights of MPIF-1 and MPIF-1 (1–99) are 8854.6 and 11367.6 respectively and the data could be fitted to a monomer for both proteins under all solution conditions (Table 10).

NMR spectroscopy. All spectra were collected at 35° C. on a Varian Unity Plus 600 or a INOVA 500-MHz spectrometer, both equipped with field gradient accessories. The protein concentration was 2 mM in 20 mM sodium acetate, 1 mM sodium azide, pH 5.2 in 90% $H_2O$/10% $^2H_2O$ (v/v) or 99.99% $^2H_2O$. Chemical shifts are referenced to DSS using the method of Wishart et al., (Wishart, D. S., et al., *J. Biomol. NMR* 6:135–140 (1995)). Assignment of the main-chain NH, N, $C_\alpha$, and $C_\beta$ resonances were made based on HNCACB and CBCA(CO)NH experiments (Muhandiram, D. R., and Kay, L. E., *J. Magn. Reson.* 103:203–216 (1994)). The chemical shifts of the side-chain atoms were assigned from $^{15}$N-edited total correlation spectroscopy (TOCSY) (Zhang, O., et al., *J. Biomol. NMR* 4:845–858 (1994)) and HCCH-TOCSY (Kay, L. E., et al.,*J. Magn. Reson.* B 101:333 (1993)) experiments. High-resolution two-dimensional $^1H$-$^1H$ nuclear Overhauser enhancement spectroscopy (NOESY), TOCSY and DQF-COSY experiments were used to assign the aromatic protons. Inter-proton distances were derived from $^{15}$N-edited NOESY (mixing time 50 ms and 150 ms) and $^{15}$N/$^{13}$C-edited NOESY (mixing time 75 ms) experiments (Pascal, S. M., et al., *J. Magn. Reson.* B 103:197–201 (1994)). NOE cross-peak intensities were classified as strong, medium, weak, or very weak, corresponding to upper distance restraints of 2.8, 3.5,4.0, and 5.0 Å, respectively. Upper limits for non-stereo specifically assigned methyl and methylene protons were corrected appropriately with center averaging. In addition, 0.5 Å was added to the upper boundary to correct for higher intensity for distances involving methyl protons. $\phi$ restraints were obtained from an HNHA experiment (Kuboniwa, H., et al., *Nat. Struct. Biol.* 2:768 (1995)) and stereospecific assignment of the $\beta$ protons was obtained from $^3J$ coupling constants derived from an HACAHB experiment (Grzesiek, S., et al., *J. Am. Chem. Soc.* 117:5312–5315 (1995)), and the relative intensities of the NOEs from the NH and the C$\alpha$H to C$\beta$H protons in NOESY spectra. Stereospecific assignments of Leu 25 and 66 methyl protons were made on the basis of the relative NOE intensity of the $C_\alpha H$ to the $CH_3$ protons after establishing the $\chi 1$ angle.

Hydrogen-bond Restraints. The potential candidates for hydrogen-bonding were initially identified on the basis of observing slow exchanging amide protons from a series of 2D $^1H$-$^{15}N$ HSQC spectra recorded within 24 hours of dissolving the protein in $^2H_2O$. For each hydrogen bond, two distance restraints were used ($r_{NH-O}$, 1.8–2.3 Å and $r_{N-O}$, 2.4–3.3 Å). The hydrogen-bonding restraints were used only after an initial set of structures has been calculated. Only the amide protons which satisfied distance and angular restraints with hydrogen-bond acceptors were used in the structure calculations.

Data Processing and Structure Cakulations. All NMR spectra were processed using nmrPipe suite of programs (Delaglio, F., et al., *J. Biomol. NMR* 6:277–293 (1995)). Structures were calculated by the hybrid distance geometry-dynamical simulated annealing method using the program XPLOR (Brünger, A. T., XPLOR Version 3.1 Manual, Yale University, New Haven, Conn., (1993)). A total of 713 nonredundant NOE distance restraints (320 intra-residue, 178 sequential, 84 medium range and 132 long range NOEs) were used. In addition, 82 dihedral (53 $\phi$ and 29 $\chi_1$) and 36 hydrogen-bonding restraints (from 18 hydrogen-bonds) were used in the final structure calculations. The initial structures were generated with NOE restraints alone and in subsequent structure calculations, the dihedral and hydrogen-bond restraints were included. The simulated annealing calculations were carried out using the standard force-field parameter set and to pology file in XPLOR version 3.1. A total of 50 structures were generated and the best 30 structures were selected on the basis of the lowest energies and good stereochemical quality.

Dynamics. $^{15}$N-$T_1$, $T_2$ and [$^1$H]-$^{15}$N NOE experiments were recorded at 35° C. on a uniformly labeled $^{15}$N MPIF-1 using gradient version of the pulse sequences (Farrow, N. A., et al., *Biochemistry* 33:5984–6003 (1994)). All spectra were acquired with 544($t_2$) and 128 ($t_1$) real points and a recycle delay of 3 s was used for $T_2$ and 1.2s for the $T_1$ experiments. [$^1$H]-$^{15}$N NOEs were measured by recording HSQC spectra with and without proton saturation. The spectra without NOE were recorded with delays of 5 s and spectra with NOE with 2 s delay and 3 s of proton saturation to give the same delay of 5 s between transients. The spectra were processed using NMRPipe and the first two-dimensional $^{15}$N $T_1$ and $T_2$ spectra were manually assigned using the program PIPP. Subsequent spectra were automatically picked using the program CAPP. $T_1$ and $T_2$ values were obtained by nonlinear least-square fits of the cross peaks to a two-parameter exponential decay. Uncertainties in the $T_1$ and $T_2$ values were taken as the standard deviation of the fit. NOE values were obtained from the ratio of the peak intensities recorded with and without proton saturation. Uncertainties in the NOE values were estimated from the base line of the spectra as defined by Farrow et al., 1994 (Farrow, N. A., et al., *Biochemistry* 33:5984–6003 (1994)).

Results

Sedimentation equilibrium. Chemokine ability to associate is dependent on solution conditions such as pH and ionic strength. The association properties of the MPIF-1 and the full length MPIF-1 were studied using ultracentrifugation methods at different pH and ionic strengths. The summary of the results are shown in Table 10. The data indicate that both the proteins are monomeric under the experimental conditions and show no tendency to associate. The monomeric state of MPIF-1 is consistent with the NMR structure and also from the calculation of the correlation time from $^{15}N$ dynamics.

Figure 58D:
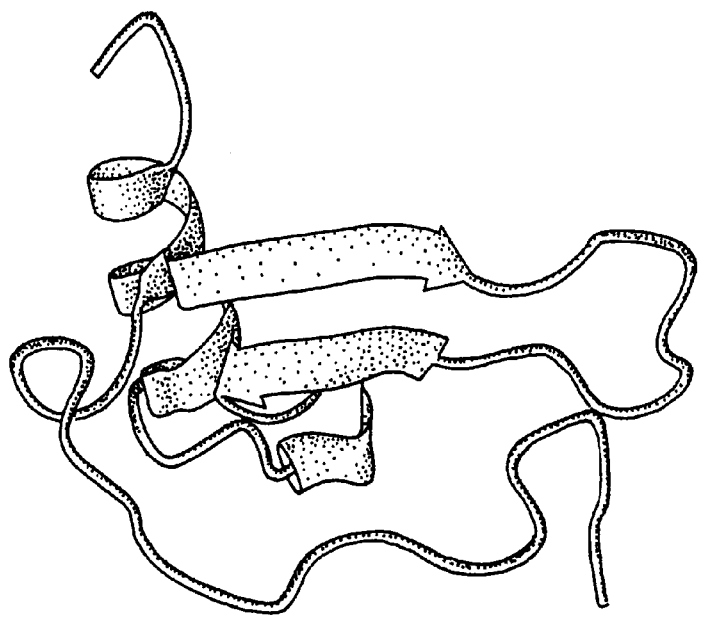
Figure 58A:
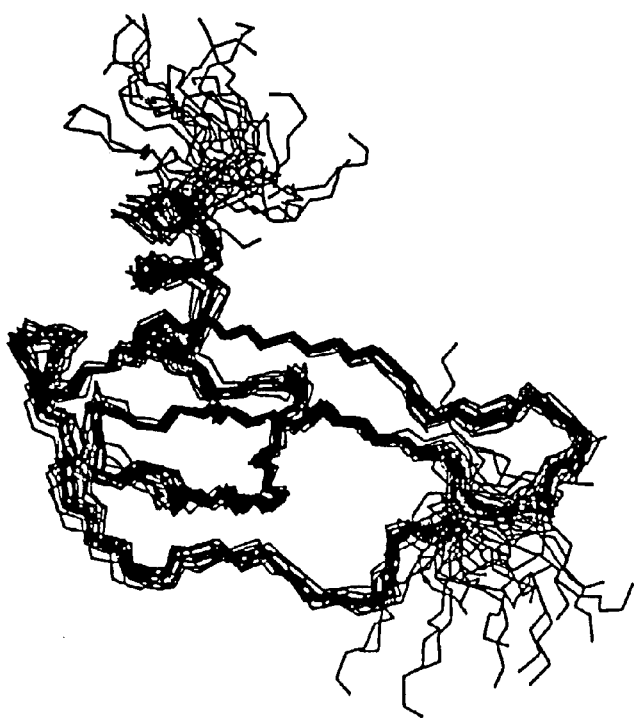
Figure 58E:
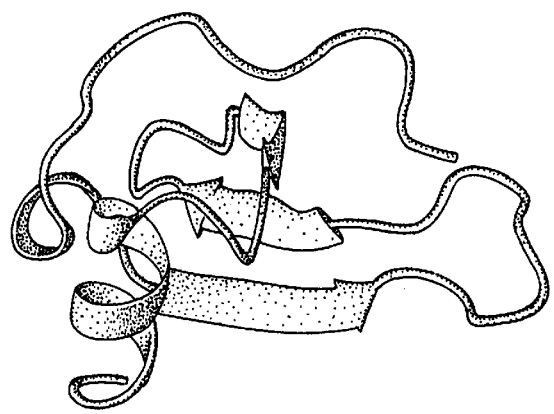
Figure 58C:
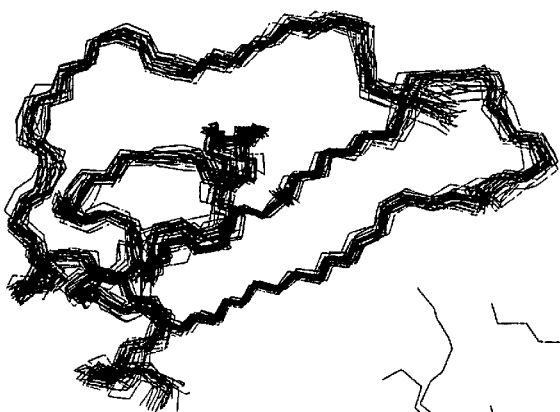

Structural Statistics of MPIF-1. The statistics of the 30 final simulated annealing (SA) structures are shown in Table 11, and the superimposition of the individual structures on the average structure is shown in FIG. 58A. The structure of the protein is well defined except for the terminal residues 1–10 and 67–77. The quality of the generated structures were tested using the programs PROCHECK (Laskowski, R. A., et al., *J. Appl. Crystallogr.* 26:283–291 (1993)) and VADAR (VADAR-structural analysis of protein structures. Available from http://www.pence.ualberta.ca) for various criteria such as the stereochemistry, hydrogen-bonds, the region of occupancy in the Ramachandran plot, van der Waals contacts, buried charged residues, number of buried residues and packing defects. All the 30 structures met the above criteria that are expected of a high resolution structure.

TABLE 11

Structural statistics and atomic r.m.s. differences for 30 calculated MPIF-1 structures

| Energies (kcal. mol$^{-1}$) | |
|---|---|
| NOE[a] | 3.21 ± 0.48 |
| Dihedral[a] | 0.01 ± 0.01 |
| bonds | 4.31 ± 0.09 |
| van der Waals | 1.54 ± 0.30 |
| Deviations from idealized geometry[b] | |
| Bonds (Å) | 0.0019 ± 0.0001 |
| Angles (°) | 0.536 ± 0.001 |
| Improper (°) | 0.305 ± 0.001 |
| Atomic r.m.s. difference (Å)[c] | |
| Backbone atoms (11–66) | 0.57 ± 0.08 |
| Heavy atoms (11–66) | 1.09 ± 0.08 |

[a]The values for NOE and torsion angles were calculated from a square well potential with a force constant of 50 kcal. mol$^{-1}$ Å$^2$ and 200 kcal mol$^{-1}$ rad$^{-2}$ respectively.
[b]The values for bonds, angles and impropers show the deviation from ideal values based on perfect stereochemistry.
[c]r.m.s. differences of the 30 final structures superimposed on the average structure.

Figure 59A:
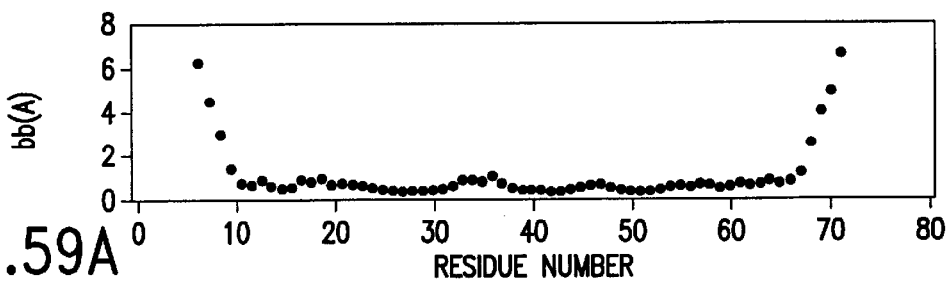
Figure 59B:
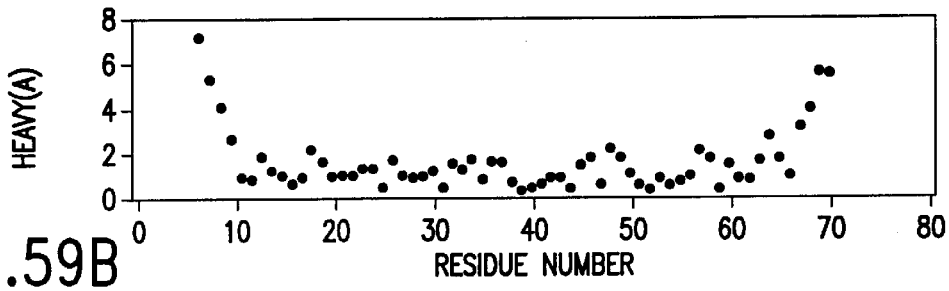
Figure 59C:
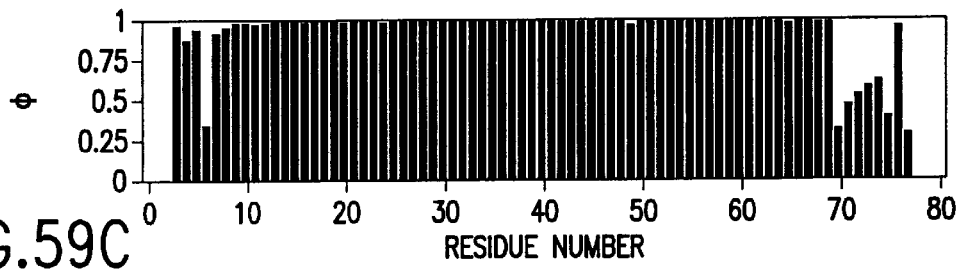
Figure 59D:
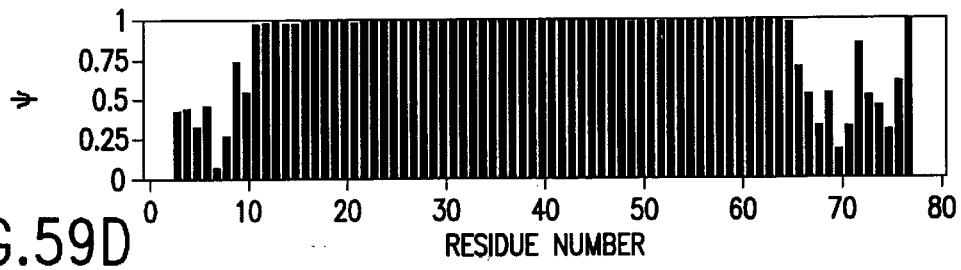
Figure 59E:
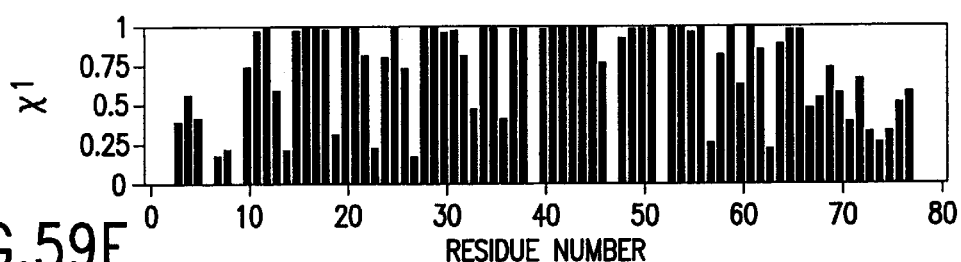
Figure 59F:
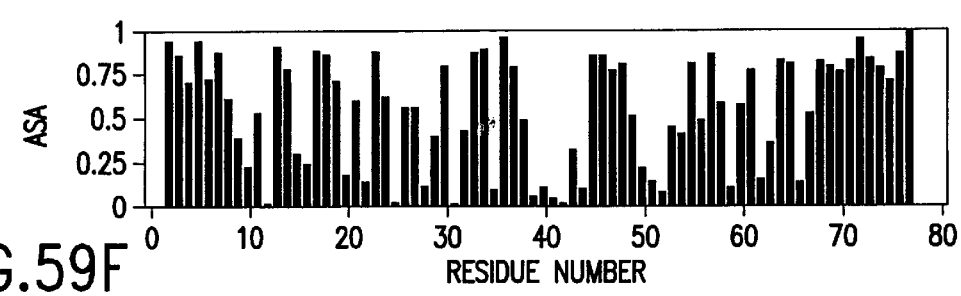
Figure 61A:
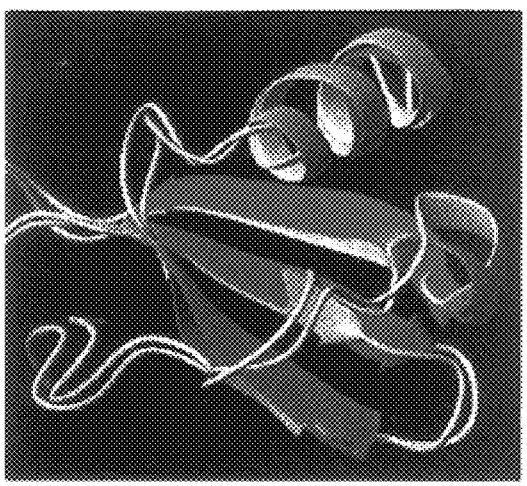
Figure 61B:
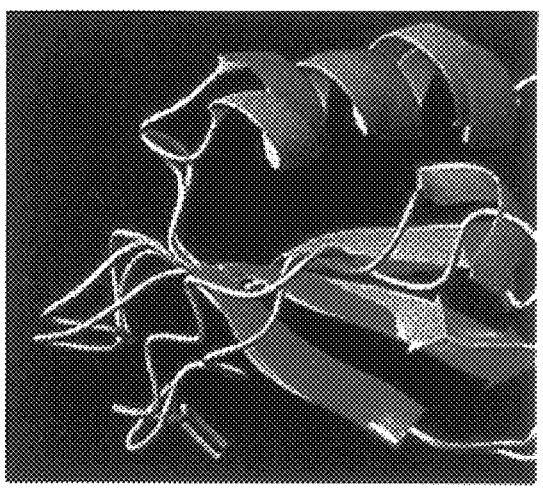
Figure 61C:
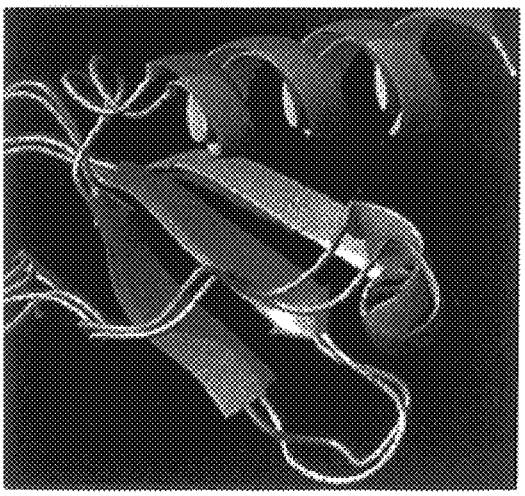
Figure 61D:
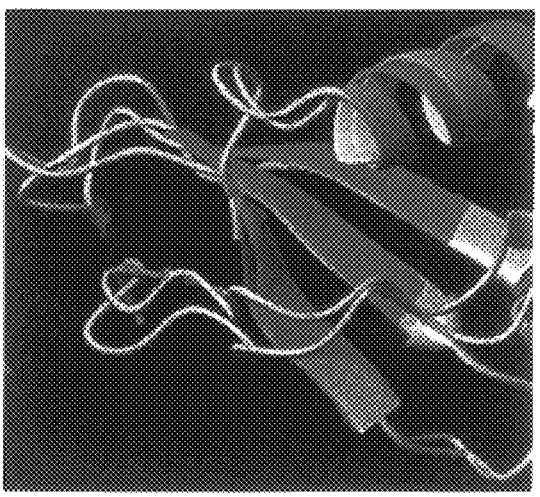
Figure 63A:
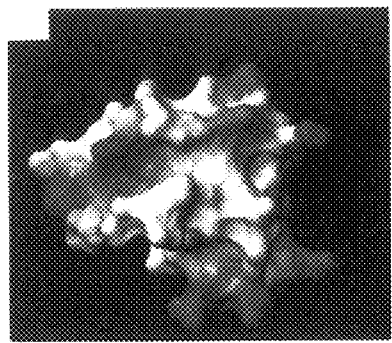
Figure 63B:
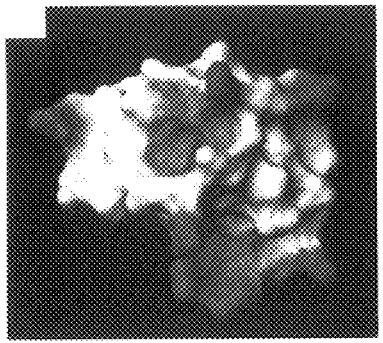
Figure 63C:
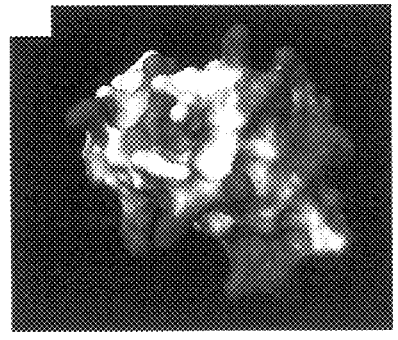
Figure 63D:
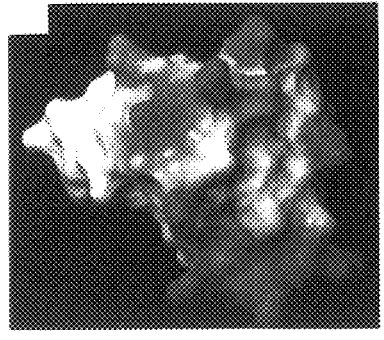

All the structures and the energy minimized average structure displayed good covalent geometry (Table 11) and minimal NMR constraint violations. None of the 30 SA structures had NOE violations greater than 0.2 Å and dihedral angle violations greater than 2°. The r.m.s. distribution for residues 11–66 between all 30 structures and the average structure is 0.57 Å for the backbone atoms and 1.09 Å for the heavy atoms (FIG. 59A, B). The precision of the torsion angles is assessed in terms of the order parameter S (Hyberts, S. G., et al., *Protein Sci.* 1:736–751 (1992)). The order parameter for the $\phi$ and $\psi$ torsion angles for the structured residues 11–66 is >0.95 indicating that the backbone of the structures is well defined (FIG. 59C, D). The order parameter for $\chi 1$ is shown in FIG. 59E. The FIG. 60F shows the solvent accessible area and a low value implies that the side chain is buried and inaccessible to the bulk solvent. These residues tend to be hydrophobic and in general are highly structured as evidenced by high order parameter for $\chi 1 > 0.9$ (FIG. 59E). One exception of a large hydrophobe that shows a low S is Ile-13. It is solvent exposed and is conserved in several CXC and CC chemokines and structure-function studies have shown an essential role for this residue in receptor binding. It is observed that all of the torsion angles in all 30 structures fall in the favored region of the Ramachandran plot. 72% of the residues fall in the core (most favored) region, 23% in the allowed region and 1% in the generous region.

Figure 58B:
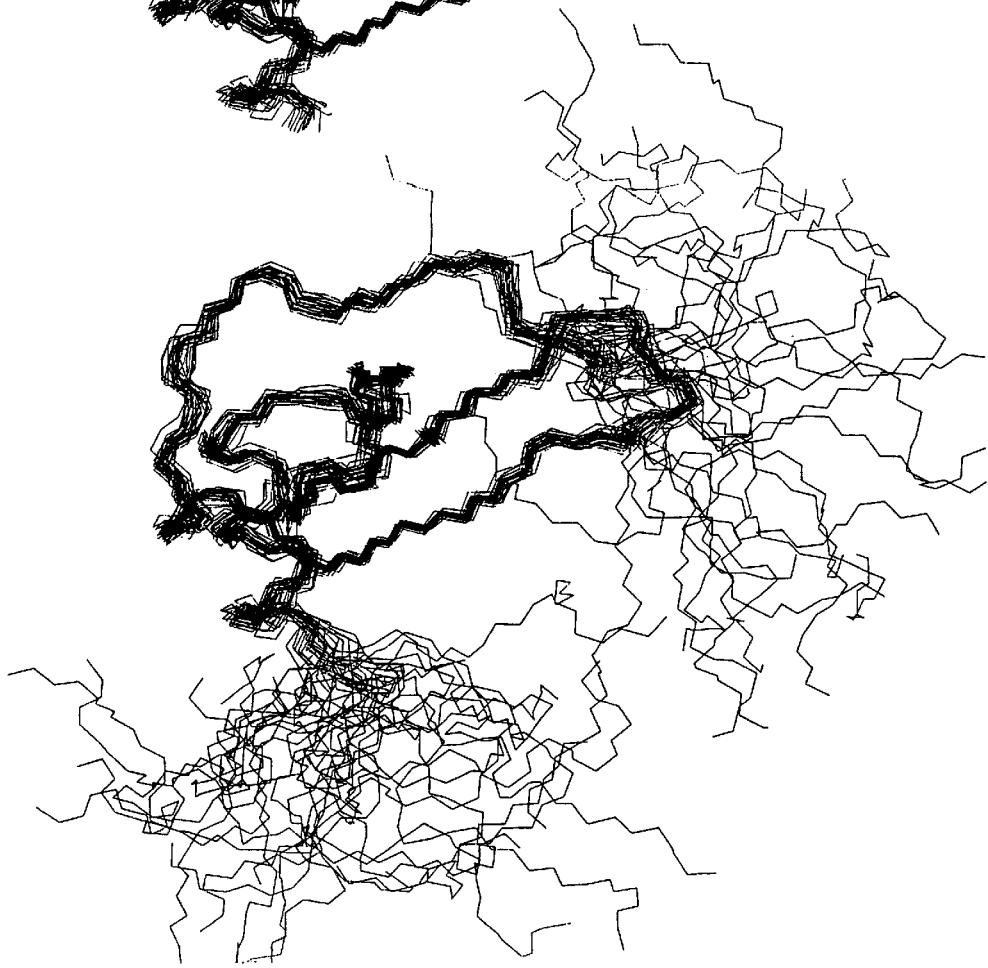

Solution Structure of MPIF-1. The structure of the MPIF-1 adopts a typical chemokine fold and consists of an extended loop at the N-terminus followed by three $\beta$ strands and a C-terminal $\alpha$ helix (FIG. 58B). The first ten residues preceding the CC motif show no or only sequential NOEs, have low order parameters for $\phi$ and $\psi$ and therefore lack defined structure. This is followed by an N-terminal loop that contains a series of turns (residues 13–20) that leads into a $3_{10}$ helix (residues 21–24). The first $\beta$ strand (residues 27–31) is connected by a type III turn to the second, strand (residues 39–44) which is connected by a type I turn to the third $\beta$ strand (residues 48–52). The third strand leads into the helix (residues 56–66) via a type III turn. Residues 67–77 are largely unstructured consistent with lack of long range NOEs, a few medium NOEs, and low order parameters. Hydroxyl protons of Thr-31 and Thr-44, located at the end of the 1st strand and the 2nd strand respectively, are H-bonded to the backbone carbonyls across the strand and therefore play a structural role. Of the six cysteines, four cysteines are characteristic of all CC chemokines: Cys-11 forms a disulfide with Cys-35, which is part of the turn linking first and second $\beta$ strands and Cys-12 forms adisulfide bond with Cys-51 in the third $\beta$ strand. MPIF-1 had two additional cysteines, Cys-22 in the $3_{10}$ helix and Cys-62 in the $\alpha$-helix. A data base of cysteine chemical shifts has been created and $C_\beta$ shifts were observed to be uniquely different in the free and the disulfide bonded form (unpublished results). The shifts of Cys-22 and Cys-62 indicate that they are involved in disulfide bond formation. The structure reveals that the cysteines are proximal to form a disulfide bond and this is also evident from the NMR properties such as the small coupling constant, slow exchanging amide proton and NOE pattern for Cys-62 that are characteristic of a helical residue. Cys-12-Cys-51 disulfide bond adopts a left handed twist in the majority of the structures whereas the other two disulfide bonds are unstructured. The core of the structure is well defined by a number of long-range hydrophobic contacts (Ile-20, Leu-25, Tyr-28, Phe-29, Val-40, Phe-42, Phe-50, Ala-52, Val-59, Met-63, and Leu-66) between residues of the $\alpha$ helix and the $\beta$-strands. Besides the disulfide bonds, long range NOEs between Thr-31, Gly-39, Tyr-15, Cys-11, Cys-12 and Cys-51 orient the N-terminal loop and the N-terminal residues with respect to the core structure which could be essential for their function.

Dynamics. The $^{15}$N $T_1$, $T_2$, and NOE relaxation data could be obtained for 60 out of 73 expected resonances (FIG. 60A–C). Data is not available for 4 prolines and could not be obtained for the remaining residues Met-1, Asp-2, His-5, Ala-6, Ser-8, Ile-13, Ser-19, Ser-33, Glu-34, Ser-36, Lys-46, Leu-66 and Lys-67, either due to chemical shift overlap or because signals were to o weak for reliable quantification of the intensities. The $^{15}$N $T_1$, $T_2$ and NOE relaxation data were analyzed to describe the internal dynamics of MPIF-1 using the model independent formalism of Lipari-Szabo (Lipari, G., and Szabo, A., *J. Am. Chem. Soc.* 104:4546–4559 (1982a); Lipari, G., and Szabo, A., *J. Am. Chem. Soc.* 104:4559–4570 (1982b)). Relaxation data for each residue were fitted to different models that include $S^2$-$\tau_c$ (model 1), $S^2$-$\tau_c$-$\tau_c$ (model 2), $S^2$-$\tau_c$-$R_{ex}$ (model 3), $S^2$-$\tau_c$-$\tau_c$-$R_{ex}$ (model 4) and a two-time scale model (model 5) that allows internal motions to occur at two distinct time scales (Clore, G., et al., *J. Am. Chem. Soc.* 112:4989–4991 (1990)). The appropriate model was chosen for each residue by evaluating the quality of the fit. The optimal $\tau_c$ was initially calculated on a per residue basis by minimizing the experimental and the calculated $T_1$, $T_2$, and NOE values using the isotropic spectral density function. Under conditions where the internal motions are slower than 100 ps and $T_2$ is not shortened significantly due to conformational exchange, $T_1/T_2$ ratio (FIG. 60D) is considered to be independent of the order parameters or internal motions and provides an estimate of the overall correlation time $\tau_c$. These residues were identified as those with $^{15}$N [$^1$H] NOE values <0.65 and for which the $T_1/T_2$ ratio was outside 1 SD from the mean. On this basis, 26 residues were excluded and $\tau_c$ was calculated to be 4.6±0.2 ns on the basis of the remaining 34 residues.

The generalized order parameters ($S^2$), chemical exchange ($R_{ex}$), and local correlation time ($\tau_e$) as a function of amino acid sequence are shown in FIGS. 60E–G. Generalized order parameters provide a measure of the amplitude of internal motion, where $S^2=1$ means that the given N—H bond vector is rigid while $S^2=0$ indicates that the motion is unrestricted. Residues 67–77 in the C-terminus and residues 1–10 preceding the first cysteine in the N-terminus exhibit low order parameters ($S^2<0.7$). Both termini are poorly defined in the NMR structures and the dynamics data confirm that these residues are intrinsically mobile and that the lack of structure is not due to lack of experimental restraints. Excluding the termini, the average $S^2$ values for residues 11–66 is 0.84±0.06. Other residues that exhibit low order parameters are Arg-18 and Ile-20 (0.7) that are part of the N-terminal loop. Relaxation data for residues Tyr-15, Cys-22, Thr-44, Cys-51, Ala-52, Asn-77 required an exchange term (model 3 and 4) (FIG. 60G) and for C-terminal residues 69–73 required the two time scale model. Residues Arg-3, Phe-4 and Thr-74 could not be fit to any model. All other residues could be fit to the simple model.

Discussion

MPIF-1 is a monomer in solution. NMR structure determination and the calculation of the rotational correlation time from $^{15}$N dynamics indicate that MPIF-1 exists as a monomer under the experimental conditions (50 mM acetate, pH 5.2). Ultracentrifugation studies under a variety of solution conditions also indicate that MPIF-1 exists as a monomer (Table 10).

Structural and solution studies have provided some insight into the association properties in chemokines but the molecular features that contribute to the specificity of the interactions remains elusive. CC chemokines show the greatest differences in their ability to associate and can exist from very high order polymers to monomers. RANTES (Skelton, N. J., et al., *Biochemistry* 34:5329–5342 (1995)), MIP-1α (Czaplewski, L. G., et al., *J. Biol. Chem.* 274:16077–16084 (1999)) MIP-1β (Lodi, P. J., et al., *Science* 263:1762–1767 (1994)) are highly associated at neutral pH (>100 kDa) but reversibly dissociate at lower pH to dimers whereas I-309, HCC-2 and MCP-3 are monomeric (Paolini, J. F., et al., *J. Immunol.* 153:2704–2717(1994); Sticht, H., et al., *Biochemistry* 38:5995–6002 (1999); Kim, K. S., et al., *FEBS Lett.* 395:277–282 (1996)).

CXC chemokines, on the other hand are more restricted in their association behavior and form only dimers and tetramers (Clark-Lewis, I., et al., *J. Leukocyte Biol.* 57:703–711 (1995)). Some of the residues that were thought to be critical for dimerization on the basis of the structures had little or no effect and conversely mutation of residues remote from the dimer interface resulted in monomers (Czaplewski, L. G., et al., *J. Biol. Chem.* 274:16077–16084 (1999); Laurence, J. S., et al., *Biochemistry* 39:3401–3409 (2000); Paavola, C. D., et al., *J. Biol. Chem.* 273:33157–33165 (1998)). Clearly a variety of stabilizing forces by residues that are far apart in the primary sequence play a role in promoting dimer and tetramer association.

However there is convincing data for both CXC and CC chemokines that a monomer is sufficient to bind and activate the 7-TM receptor on leukocytes. It has been shown previously by trapping 3 neutrophil activating chemokines (IL-8, NAP-2 and MGSA) in the monomeric state so that they cannot dimerize that the monomer is as active as the native protein in the in vitro functional assays (Rajarathnam, K., et al., *Science* 264:90–92 (1994); Rajarathnam, K., et al., *J. Biol. Chem.* 272:1725–1729 (1997)). Similarly, mutational studies in RANTES, MCP-1, MIP-1α, and MIP-1β have also shown that the monomer is the receptor binding species (Czaplewski, L. G., et al., *J. Biol. Chem.* 274:16077–16084 (1999); Laurence, J. S., et al., *Biochemistry* 39:3401–3409 (2000); Paavola, C. D., et al., *J. Biol. Chem.* 273:33157–33165 (1998)).

The question then arises what exactly is the role, if any, of dimer and higher order oligomers? Recent studies suggest that this role could be in binding to proteoglycans and establishing a concentration gradient, a process that is essential for trafficking leukocytes (Hoogewerf, A. J., et al., *Biochemistry* 36:13570–13578 (1997); Koopmann, W., and Krangel, M. S., *J. Biol. Chem.* 272:10103–10109 (1997)). Residues that are critical for proteoglycan binding are basic residues such as arginine, lysine and histidine in both CXC and CC chemokines and tend to be clustered and located away from the regions that are critical for binding to the 7-TM receptors. In this study, MPIF-1 did not show any propensity to form dimers in solution. Whether MPIF-1 and the other monomeric chemokines I-309 and HCC-2 dimerize in presence of cell surface proteoglycans is being investigated.

An intriguing property of chemokines is the presence of multiple species that have been differentially processed in either the N- or the C-terminus. Some chemokines, like MPIF-1, are secreted as large precursors that are proteolytically processed either at the N- or C-terminus to yield a functional protein. NAP-2, β-thromboglobulin (βTG), and connective tissue-activating protein-III (CTAP-III) are N-terminal products of platelet basic protein (PBP) and only NAP-2 is a potent activator of neutrophils whereas the others are considered to be inactive precursors. All four form dimers and tetramers (Yang, Y., et al., *J. Biol. Chem.*

269:20110–20118 (1994)); further, NAP-2 and CTAP-III, which are differentially processed at the C-terminus, have also been isolated from cell cultures (Ehlert, J. E., et al., *J. Immunol.* 161:4975–4982 (1998)).

The N-terminal region of functional chemokines consists of around 10 amino acids preceding the first conserved cysteine and mutational studies have shown an essential role for these residues for receptor binding and activation. Truncated CC chemokines display highly differential and unusual properties (Clark-Lewis, I., et al., *J. Leukocyte Biol.* 57:703–711(1995)). For example, in MCP-1, deletion of the first four residues results in a loss of activity whereas deletion of the first five residues results in a substantial recovery of activity. Further deletions result in loss of function but with a retained ability to bind the receptor and to function as an antagonist (Gong, J.-H., and Clark-Lewis, I.,*J. Exp. Med.* 181:631–640 (1995)). Successive deletion in the N-terminus of IL-8, a CXC chemokine, results in increased activity, loss of activity, and then conversion to an antagonist (Moser, B., et al., *J. Biol. Chem.* 268:7125–7128 (1993)). It has also been observed that truncation of N-terminal residues preceding the first cysteine in CC chemokines favors monomer formation and it has been suggested that the length of the N-terminal residues plays a role in dimerization.

Alternative splicing of the MPIF-1 gene results in two forms of the protein that are 99 and 116 amino acids respectively (termed CKβ8 and CKPβ8-1 respectively) (Youn, B.-S., et al., *Blood* 91:3118–3126 (1998)). This observation is exceptional among CC chemokines, as this difference in length lies in the N-terminal region (32 and 49 amino acids preceding the first cysteine respectively). Both forms of the protein were shown to have similar activity in myeloid progenitor inhibition and monocyte chemotaxis. Expression of the 99-amino acid protein in baculovirus resulted in three forms of the protein, full length and two truncated versions. The truncated versions were found to be more potent in both monocyte chemotaxis and myeloid progenitor inhibitory assays. The data for MPIF-1 and the full length MPIF-1 under a variety of solution conditions (Table 10) indicate that they are monomers and there is no correlation between the length of the N-terminal residues and the ability to form dimers. The differences in potency of the variants of MPIF-1, like other chemokines, plays a role in vivo, as the recruitment and activation of leukocytes is spatially and temporally regulated. One aspect of leukocyte activation is the release of peptidases and proteases that act on chemokines and thus modulate their activity and function.

Description of structure and comparison to other chemokines. MPIF-1 adopts atypical chemokine fold of three β-strands and an overlying α-helix. The core of the structure is well defined showing the lowest rmsd for the back bone and heavy atoms, high order parameters for φ, ψ, and $\chi_1$, most of the slow exchanging amides are those that form H-bonds between strands and those in the α-helix. Several CC chemokine structures including those of MIP-1β, RANTES, MCP-1, MCP-3, eotaxin, and HCC-1 have been elucidated (Lodi, P. J., et al., *Science* 263:1762–1767(1994); Skelton, N. J., et al., *Biochemistry* 34:5329–5342 (1995); Handel, T. M., and Domaille, P. J., *Biochemistry* 35:6569–6584 (1996); Kim, K. S., et al., *FEBS Lett.* 395:277–282 (1996); Crump, M. P., et al., *J. Biol. Chem.* 273:22471–22479 (1998); Sticht, H., et al., *Biochemistry* 38:5995–6002 (1999)). The secondary and tertiary structural elements of MPIF-1 are similar to that observed in the other CC chemokines (FIG. 61) though the sequence identity between MPIF-1 and other CC chemokines varies from ~25 to 60% (FIG. 62). Superposition of the backbone of the structured region (residues 11 to 66) of MPIF-1 and other CC chemokines show a rmsd from 1.5 to 2.0 Å. The lowest rmsd is observed for the structured regions (the strands and the helix) and higher rmsds are observed for the N-terminal residues, N-terminal loop and the 30s turn. The largest sequence difference is observed for these regions of protein and these are also the regions that are relatively less defined, are mobile and functionally important.

Besides the four cysteines (Cys-11, Cys-12, Cys-35, Cys-51), residues Ile-13, Tyr-15, Ile-20 (N-terminal loop), Leu-25, Tyr-28, Phe-29, Thr-31 (1st β strand), Val-40, Ile-41, Phe-42, Thr-44 (2nd β strand), Phe-50, Ala-52 (3rd β strand), Val-59, Met-63 and Leu-66 (α-helix) (numbering according to MPIF-1 sequence) are conserved or conservatively substituted (FIG. 62). Most are bulky hydrophobes located in either the strands or the helix and adopt the same side chain conformation in different structures and constitute the structural scaffold. Thr-3 1 and Thr-44 are polar residues that are completely buried and the structures reveal that the hydroxyl protons are H-bonded to the backbone carbonyls across the strand and therefore play a structural role.

The structures reveal that Cys12–Cys51 disulfide bond adopts predominantly a left handed spiral conformation. $^{15}$N dynamics data indicates that some of the cysteines and the residues in the vicinity of all the three disulfide bonds show conformational exchange showing that these regions of the protein are mobile and undergo conformational exchange. Cys11–Cys35 disulfide bond shows the largest segmental motion and it has been shown for example in IL-8, that subtle perturbations to the disulfide bond result in significant loss of function with no changes in structure (Rajarathnam, K., et al., *Biochemistry* 38:7653–7658 (1999)). It has been suggested that the dynamics of the N-terminal region, the disulfide bond and the 30s turn play an integral role in specific binding and activation (Clark-Lewis, I., et al., *J. Leukocyte Biol.* 5 7:703–711 (1995)). MPIF-1 shows highest sequence homology to HCC2, and the latter also has 6 cysteines, binds to CCR1, and is an inhibitor of stem cell proliferation. One difference between MPIF-1, HCC-2 and other CC chemokines is the Trp residue at position 58 in all CC chemokines besides MPIF-1, which has a Gln, and HCC-2, which has a Gly. MPIF-1 and HCC-2 structures reveal that the steric bulk of the indole side chain will be in the way of the disulfide bond.

In addition to the conserved hydrophobes, some of the charged residues are also conserved; Arg-18 of the N-terminal loop and Lys-45 and Arg-48 in the 40s turn are solvent exposed and have been implicated in binding to the negatively charged proteoglycans (Chakravarty, L., et al.,*J. Biol. Chem.* 273:29641–29647 (1998); Koopmann, W., et al.,*J. Immunol.* 163:2120–2127 (1999)). However, the location of the proteoglycan-binding domain, and the relative importance of the charged residues involved in binding varies from chemokine to chemokine. Charged residues in the C-terminal helix of IL-8 (Kuschert, G. S. V., et al., *Biochemistry* 37:11193 (1998)), PF-4 (Mayo, K. H., et al., *Biochem. J.* 312:357–365 (1995)), and MCP-1 (Chakravarty, L., et al., *J. Biol. Chem.* 273:29641–29647 (1998)), the residues of the 1st β-strand in SDF-1 (Amara, A., et al., *J Biol. Chem.* 274:23916–25 (1999)) and the residues of the 40s turn and the N-terminal loop in MIP-1α (Koopman, W. and Kvangel, M. S., *J. Biol. Chem.* 272:10103–10109 (1997)) and MIP-1β (Koopmann, W., et al.,*J. Immunol.* 63:2120–2127 (1999)) have been implicated in proteoglycan binding. MPIF-1 is a highly basic protein and has additional basic residues in the 40s loop (Lys-46) and in the α-helix (Lys-57, Arg-64, and Lys-67) showing that it binds proteoglycans more tightly (FIG. 63).

Structure-function

Activation of Monocytes: MPIF-1 binds to CCR1 with high affinity and has been shown to be a potent activator of monocytes (Nardelli, B., et al., *J. Immunol.* 162:435–444 (1999); Berkhout, T. A., et al., *Biochem. Pharmacol.* 59:591–596 (2000)). MCP-3, RANTES, MIP-1α and HCC-2 also bind and activate CCR1. Mutagenesis studies have indicated that the N-terminal residues preceding the first cysteine and residues of the N-terminal loop (between the second cysteine and preceding the $3_{10}$ helix) play important roles in receptor binding for both CXC and CC chemokines (Clark-Lewis, I., et al., *J. Leukocyte Biol.* 57:703–711 (1995); Gong, J.-H., and Clark-Lewis, I.,*J. Exp. Med.* 181:631–640 (1995); Moser, B., et al., *J. Biol Chem.* 268:7125–7128 (1993); Pakianathan, D. R., et al., *Biochemistry* 36:9642–9648 (1997)). It has been suggested that the N-terminal loop residues of the chemokine ligand interact with the N-terminal residues of the receptor constituting the initial docking site; this interaction optimally orients the ligand N-terminal residues for interacting with the receptor residues evoking a conformational change and a functional response (Crump, M. P., et al., *EMBO J.* 16:6996–7007 (1997); Clark-Lewis, I., et al.,*J. Leukocyte Biol.* 57:703–711 (1995)).

In MPIF-1 structure, the N-terminal loop residues are well defined (S for $\phi$, $\psi$, >0.95) and adopt a unique conformation. The $^{15}N$ dynamics data, on the other hand, indicate that this region of the protein is relatively mobile and shows fluctuations in the subnanosecond and conformational exchange in the slower millisecond time scale. A similar observation has been made in eotaxin (Crump, M. P., et al, *Protein Sci.* 8:2041–2054 (1999); Ye, J., et al., *J. Biomol. NMR* 15:115–124 (1999)), in vMIPII, a viral monomeric CC chemokine that binds multiple CXC and CC chemokine receptorss (LiWang, A. C., et al., *Biochemistry* 38:442–453 (1999)) and in fractalkine, a monomeric $CX_3C$ chemokine (Mizoue, L. S., et al., *Biochemistry* 38:1402–1414 (1999)). The N-terminal loop domain is adjacent and proximal to all the three disulfide bonds. Sequence analysis also reveals that residues corresponding to Ile-13, Tyr-15, Arg-18 and Ile-20 (numbering according to MPIF-1) are conserved or similarly substituted in other CC chemokines and mutagenesis of these residues results in reduced binding to their respective receptors. Ile-13, the first residue after the second cysteine, is solvent exposed in all CXC and CC chemokines and most likely plays a direct role in activation of receptors. In RANTES, the importance-of the N-terminal loop residues was observed to be receptor specific: Arg-17 was necessary for binding to CCR1, Phe-12 for binding to CCR3, Phe-12 and Ile-15 for binding to CCR5 (Pakianathan, D. R., et al., *Biochemistry* 36:9642–9648 (1997)). In most structures, Tyr-15 and Ile-20 are buried and adopt a similar conformation and are packed against other hydrophobic residues indicating a structural role. These observations show that in MPIF-1, Ile-13 and Arg-18 play a functional role and are directly involved in receptor binding and Tyr-15 and Ile-20 function as a part of the structural scaffold.

The NMR structure and the dynamics data of MPIF-1 indicate that the N-terminal residues preceding the first cysteine are unstructured. A similar observation has been made in all of the monomer NMR structures and dimeric CXC structures showing that the mobility of these residues is essential for optimal interaction with the receptor. All CXC chemokines that activate neutrophils have the characteristic 'ELR' sequence preceding the first cysteine that is essential for binding and activation (Clark-Lewis, I., et al., *J. Leukocyte Biol.* 57:703–711 (1995)). Such a signature sequence is absent for CC chemokines and sequence analysis does not provide any insight for receptor specificity. Further, CC chemokines show a complex ligand-receptor profile. Most CC chemokines that activate monocytes, macrophages, eosinophils and T-cells bind multiple receptors and most receptors bind multiple chemokines. On the other hand, an example of a ligand binding to only a single receptor is known (LARC and CCR6). The N-terminal residues of MPIF-1 show very little or no similarity with other CC chemokines that bind CCR1 (HCC-2, MCP-3, RANTES and MIP-1α). HCC-2 shows the highest overall sequence homology to MPIF-1 (~60%) but has none in the N-terminus. Recent structure-function studies in RANTES, which binds multiple receptors in addition to CCR1, showed receptor specific response on mutating certain N-terminal residues; Pro-2, Asp-6, and Thr-7 were essential for binding to CCR1; Pro-2 and Tyr-3 for binding to CCR3; and Tyr-3 and Asp-6 for binding to CCR5. None of the N-terminal residues are identical between MPIF-1 and RANTES and only one residue is conservatively substituted (Tyr-3 in RANTES and Phe-4 in MPIF-1). Tyr-3 is shown to play an essential role in RANTES for binding to CCR3 and whether MPIF-1 can bind to CCR3 remains to be tested. Interestingly, it has been shown recently that the length of the N-terminal residues and not the nature of the side chain is critical for MCP-1 binding to CCR2 (Jarnagin, et al., *Biochemistry* 38:16167–16177 (1999)).

Suppression of progenitor Cell Proliferation. All versions of MPIF-1 were shown to suppress progenitor cell proliferation and it was observed that the truncated versions were more potent in their inhibition than the proproteins. Remarkably CC and CXC chemokines such as MIP-1α, IL-8, GRO-β, PF-4, IP-10, and MCP-1 have been shown to suppress proliferation of progenitor cells whereas related chemokines such as GRO-α, NAP-2, MIP-1β and RANTES are non-suppressive. The chemokine profile shows that the ability to modulate progenitor cell proliferation is not related to activation of their cognate chemokine receptors. Additionally, a monomeric form of MIP-1α is significantly more potent than aggregated versions of the native protein (Czaplewski, L. G., et al., *J. Biol. Chem.* 274:16077–16084 (1999)) and MPIF-1 can act in monomeric form. These studies of the molecular basis of MPIF-1 function have clinically relevant implications for patients with various diseases, such as patients undergoing chemotherapy.

It will be clear that the invention may be practiced otherwise than as particularly described in the foregoing description and examples.

Numerous modifications and variations of the present invention are possible in light of the above teachings and, therefore, are within the scope of the appended claims.

The disclosures of all patents, patent applications, and publications referred to herein are hereby incorporated by reference. The disclosure of U.S. patent aplication Ser. No. 08/941,020, filed Sep. 30, 1997, is herein incorporated by reference in its entirety.

What is claimed is:

1. A method for inhibiting bone marrow stem cells, comprising:

(a) administering to a subject in need thereof a polypeptide comprising a fragment of the amino acid sequence of SEQ ID NO:2, wherein said fragment comprises the conserved Cys residues at positions 54 and 94 of SEQ ID NO:2 and inhibits bone marrow stem cells; and thereby (b) inhibiting bone marrow stem cells in said subject.

2. The method of claim 1, wherein said polypeptide comprises a heterologous polypeptide.

3. The method of claim 1, wherein said polypeptide is administered to protect hematopoietic stem cells during cancer chemotherapy.

4. The method of claim 1, wherein said polypeptide is administered in combination with a pharmaceutically acceptable carrier.

5. The method of claim 1, wherein said polypeptide comprises a Met residue at the N-terminus.

6. The method of claim 5, wherein said polypeptide comprises a heterologous polypeptide.

7. The method of claim 5, wherein said polypeptide is administered to protect hematopoietic stem cells during cancer chemotherapy.

8. The method of claim 5, wherein said polypeptide is administered in combination with a pharmaceutically acceptable carrier.

9. A method for inhibiting bone marrow stem cells, comprising:

(a) administering to a subject in need thereof a polypeptide comprising a fragment of human myeloid progenitor inhibitory factor-1 (MPIF-1) amino acid sequence encoded by the cDNA in ATCC Deposit No. 75676, wherein said fragment comprises the conserved Cys residues at posidbns 54 and 94 of SEQ ID NO:2 and inhibits bone marrow stem cells; and thereby (b) inhibiting bone marrow stem cells in said subject.

10. The method of claim 9, wherein said polypeptide comprises a heterologous polypeptide.

11. The method of claim 9, wherein said polypeptide is administered to protect hematopoietic stem cells during cancer chemotherapy.

12. The method of claim 9, wherein said polypeptide is administered in combination with a pharmaceutically acceptable carrier.

13. The method of claim 9, wherein said polypeptide comprises a Met residue at the N-terminus.

14. The method of claim 13, wherein said polypeptide comprises a heterologous polypeptide.

15. The method of claim 13, wherein said polypeptide is administered to protect hematopoietic stem cells during cancer chemotherapy.

16. The method of claim 13, wherein said polypeptide is administered in combination with a pharmaceutically acceptable carrier.

* * * * *

UNITED STATES PATENT AND TRADEMARK OFFICE
CERTIFICATE OF CORRECTION

PATENT NO.    : 6,495,129 B1
DATED         : December 17, 2002
INVENTOR(S)   : Li et al.

It is certified that error appears in the above-identified patent and that said Letters Patent is hereby corrected as shown below:

Title page,
Item [63], Related U.S. Application Data, "Continuation of application No. 09/571,013" should read -- Continuation-in-part of application No. 09/571,013 --; "said application No. 09/722,723" should read -- said application No. 08/722,723 --.

Column 256,
Line 35, please delete "posidbns" and insert therein -- positions --.

Signed and Sealed this

Thirteenth Day of December, 2005

JON W. DUDAS
*Director of the United States Patent and Trademark Office*

SEQUENCE LISTING

<160> NUMBER OF SEQ ID NOS: 42

<210> SEQ ID NO 1
<211> LENGTH: 363
<212> TYPE: DNA
<213> ORGANISM: Homo sapiens
<220> FEATURE:
<221> NAME/KEY: CDS
<222> LOCATION: (1)..(360)

<400> SEQUENCE: 1

```
atg aag gtc tcc gtg gct gcc ctc tcc tgc ctc atg ctt gtt act gcc        48
Met Lys Val Ser Val Ala Ala Leu Ser Cys Leu Met Leu Val Thr Ala
1               5                   10                  15 ctt gga tcc cag gcc cgg gtc aca aaa gat gca gag aca gag ttc atg        96
Leu Gly Ser Gln Ala Arg Val Thr Lys Asp Ala Glu Thr Glu Phe Met
            20                  25                  30 atg tca aag ctt cca ttg gaa aat cca gta ctt ctg gac aga ttc cat       144
Met Ser Lys Leu Pro Leu Glu Asn Pro Val Leu Leu Asp Arg Phe His
        35                  40                  45 gct act agt gct gac tgc tgc atc tcc tac acc cca cga agc atc ccg       192
Ala Thr Ser Ala Asp Cys Cys Ile Ser Tyr Thr Pro Arg Ser Ile Pro
    50                  55                  60 ggt tca ctc ctg gag agt tac ttt gaa acg aac agc gag tgc tcc aag       240
Gly Ser Leu Leu Glu Ser Tyr Phe Glu Thr Asn Ser Glu Cys Ser Lys
65                  70                  75                  80 ccg ggt gtc atc ttc ctc acc aag aag ggg cga cgt ttc tgt gcc aac       288
Pro Gly Val Ile Phe Leu Thr Lys Lys Gly Arg Arg Phe Cys Ala Asn
                85                  90                  95 ccc agt gat aag caa gtt cag gtt tgc atg aga atg ctg aag ctg gac       336
Pro Ser Asp Lys Gln Val Gln Val Cys Met Arg Met Leu Lys Leu Asp
            100                 105                 110 aca cgg atc aag acc agg aag aat tga                                    363
Thr Arg Ile Lys Thr Arg Lys Asn
        115                 120
```

<210> SEQ ID NO 2
<211> LENGTH: 120
<212> TYPE: PRT
<213> ORGANISM: Homo sapiens

<400> SEQUENCE: 2

```
Met Lys Val Ser Val Ala Ala Leu Ser Cys Leu Met Leu Val Thr Ala
1               5                   10                  15

Leu Gly Ser Gln Ala Arg Val Thr Lys Asp Ala Glu Thr Glu Phe Met
            20                  25                  30

Met Ser Lys Leu Pro Leu Glu Asn Pro Val Leu Leu Asp Arg Phe His
        35                  40                  45

Ala Thr Ser Ala Asp Cys Cys Ile Ser Tyr Thr Pro Arg Ser Ile Pro
    50                  55                  60

Gly Ser Leu Leu Glu Ser Tyr Phe Glu Thr Asn Ser Glu Cys Ser Lys
65                  70                  75                  80

Pro Gly Val Ile Phe Leu Thr Lys Lys Gly Arg Arg Phe Cys Ala Asn
                85                  90                  95

Pro Ser Asp Lys Gln Val Gln Val Cys Met Arg Met Leu Lys Leu Asp
            100                 105                 110

Thr Arg Ile Lys Thr Arg Lys Asn
        115                 120
```

```
<210> SEQ ID NO 3
<211> LENGTH: 100
<212> TYPE: PRT
<213> ORGANISM: Homo sapiens

<400> SEQUENCE: 3
```

Met Arg Val Thr Lys Asp Ala Glu Thr Glu Phe Met Met Ser Lys Leu
1               5                   10                  15

Pro Leu Glu Asn Pro Val Leu Leu Asp Arg Phe His Ala Thr Ser Ala
            20                  25                  30

Asp Cys Cys Ile Ser Tyr Thr Pro Arg Ser Ile Pro Cys Ser Leu Leu
        35                  40                  45

Glu Ser Tyr Phe Glu Thr Asn Ser Glu Cys Ser Lys Pro Gly Val Ile
    50                  55                  60

Phe Leu Thr Lys Lys Gly Arg Arg Phe Cys Ala Asn Pro Ser Asp Lys
65                  70                  75                  80

Gln Val Gln Val Cys Met Arg Met Leu Lys Leu Asp Thr Arg Ile Lys
                85                  90                  95

Thr Arg Lys Asn
            100

```
<210> SEQ ID NO 4
<211> LENGTH: 76
<212> TYPE: PRT
<213> ORGANISM: Homo sapiens

<400> SEQUENCE: 4
```

Met Arg Phe His Ala Thr Ser Ala Asp Cys Cys Ile Ser Tyr Thr Pro
1               5                   10                  15

Arg Ser Ile Pro Cys Ser Leu Leu Glu Ser Tyr Phe Glu Thr Asn Ser
            20                  25                  30

Glu Cys Ser Lys Pro Gly Val Ile Phe Leu Thr Lys Lys Gly Arg Arg
        35                  40                  45

Phe Cys Ala Asn Pro Ser Asp Lys Gln Val Gln Val Cys Met Arg Met
    50                  55                  60

Leu Lys Leu Asp Thr Arg Ile Lys Thr Arg Lys Asn
65                  70                  75

```
<210> SEQ ID NO 5
<211> LENGTH: 78
<212> TYPE: PRT
<213> ORGANISM: Homo sapiens

<400> SEQUENCE: 5
```

His Ala Ala Gly Phe His Ala Thr Ser Ala Asp Cys Cys Ile Ser Tyr
1               5                   10                  15

Thr Pro Arg Ser Ile Pro Cys Ser Leu Leu Glu Ser Tyr Phe Glu Thr
            20                  25                  30

Asn Ser Glu Cys Ser Lys Pro Gly Val Ile Phe Leu Thr Lys Lys Gly
        35                  40                  45

Arg Arg Phe Cys Ala Asn Pro Ser Asp Lys Gln Val Gln Val Cys Met
    50                  55                  60

Arg Met Leu Lys Leu Asp Thr Arg Ile Lys Thr Arg Lys Asn
65                  70                  75

```
<210> SEQ ID NO 6
<211> LENGTH: 599
<212> TYPE: DNA
```

```
<213> ORGANISM: Homo sapiens
<220> FEATURE:
<221> NAME/KEY: CDS
<222> LOCATION: (35)..(445)

<400> SEQUENCE: 6
gtcctccggc cagccctgcc tgcccaccag gagg atg aag gtc tcc gtg gct gcc      55
                                     Met Lys Val Ser Val Ala Ala
                                       1               5 ctc tcc tgc ctc atg ctt gtt act gcc ctt ggc tcc cag gcc cgg gtc      103
Leu Ser Cys Leu Met Leu Val Thr Ala Leu Gly Ser Gln Ala Arg Val
             10                  15                  20 aca aaa gat gca gag aca gag ttg acg atg tca aag ctt cca ttg gaa      151
Thr Lys Asp Ala Glu Thr Glu Leu Thr Met Ser Lys Leu Pro Leu Glu
         25                  30                  35 aat cca gta ctt ctg gac atg ctc tgg agg aga aag att ggt cct cag      199
Asn Pro Val Leu Leu Asp Met Leu Trp Arg Arg Lys Ile Gly Pro Gln
 40                  45                  50                  55 atg acc ctt tct cat gcc gca gga ttc cat gct act agt gct gac tgc      247
Met Thr Leu Ser His Ala Ala Gly Phe His Ala Thr Ser Ala Asp Cys
                 60                  65                  70 tgc atg tcc tac acc cca cga agc atc ccg tgt tca ctc ctg gag agt      295
Cys Met Ser Tyr Thr Pro Arg Ser Ile Pro Cys Ser Leu Leu Glu Ser
             75                  80                  85 tac ttt gaa acg aac agc gag tgc tcc aag ccg ggt gtc atc ttc ctc      343
Tyr Phe Glu Thr Asn Ser Glu Cys Ser Lys Pro Gly Val Ile Phe Leu
         90                  95                 100 acc aag aag ggg cga cgt ttc tgt gcc aac ccc agt gat aag caa gtt      391
Thr Lys Lys Gly Arg Arg Phe Cys Ala Asn Pro Ser Asp Lys Gln Val
    105                 110                 115 cag gtt tgc atg aga atg ctg aag ctg gac aca cgg atc aag acc agg      439
Gln Val Cys Met Arg Met Leu Lys Leu Asp Thr Arg Ile Lys Thr Arg
120                 125                 130                 135 aag aat tgaacttgtc aaggtgaagg ggacacaagt tgccagccac caactttctt      495
Lys Asn gcctcaacta acttcctgaa ttcttttttt aagaagcatt tattcttgtg ttctggattt      555
agagcaattc atcttttctc acctttaaaa aaaaaaaaa aaaa                       599

<210> SEQ ID NO 7
<211> LENGTH: 137
<212> TYPE: PRT
<213> ORGANISM: Homo sapiens

<400> SEQUENCE: 7

Met Lys Val Ser Val Ala Ala Leu Ser Cys Leu Met Leu Val Thr Ala
  1               5                  10                  15

Leu Gly Ser Gln Ala Arg Val Thr Lys Asp Ala Glu Thr Glu Leu Thr
             20                  25                  30

Met Ser Lys Leu Pro Leu Glu Asn Pro Val Leu Leu Asp Met Leu Trp
         35                  40                  45

Arg Arg Lys Ile Gly Pro Gln Met Thr Leu Ser His Ala Ala Gly Phe
     50                  55                  60

His Ala Thr Ser Ala Asp Cys Cys Met Ser Tyr Thr Pro Arg Ser Ile
 65                  70                  75                  80

Pro Cys Ser Leu Leu Glu Ser Tyr Phe Glu Thr Asn Ser Glu Cys Ser
                 85                  90                  95

Lys Pro Gly Val Ile Phe Leu Thr Lys Lys Gly Arg Arg Phe Cys Ala
            100                 105                 110
```

Asn Pro Ser Asp Lys Gln Val Gln Val Cys Met Arg Met Leu Lys Leu
        115                 120                 125

Asp Thr Arg Ile Lys Thr Arg Lys Asn
        130                 135

<210> SEQ ID NO 8
<211> LENGTH: 26
<212> TYPE: DNA
<213> ORGANISM: Primer

<400> SEQUENCE: 8
tcaggatccg tcacaaaaga tgcaga                                    26

<210> SEQ ID NO 9
<211> LENGTH: 26
<212> TYPE: DNA
<213> ORGANISM: Primer

<400> SEQUENCE: 9
cgctctagag taaaacgacg gccagt                                    26

<210> SEQ ID NO 10
<211> LENGTH: 27
<212> TYPE: DNA
<213> ORGANISM: Primer

<400> SEQUENCE: 10
cccgcatgcg ggtcacaaaa gatgcag                                   27

<210> SEQ ID NO 11
<211> LENGTH: 27
<212> TYPE: DNA
<213> ORGANISM: Primer

<400> SEQUENCE: 11
aaaggatcct caattcttcc tggtctt                                   27

<210> SEQ ID NO 12
<211> LENGTH: 48
<212> TYPE: DNA
<213> ORGANISM: Primer

<400> SEQUENCE: 12
acatgcatgc guguuaccaa agacgcugaa accgaauuca ugaugucc            48

<210> SEQ ID NO 13
<211> LENGTH: 36
<212> TYPE: DNA
<213> ORGANISM: Primer

<400> SEQUENCE: 13
gcccaagctt tcagtttta cgggttttga tacggg                          36

<210> SEQ ID NO 14
<211> LENGTH: 88
<212> TYPE: DNA
<213> ORGANISM: Primer

<400> SEQUENCE: 14
gcatgcgugu uaccaaagac gcugaaaccg aauucaugau guccaaacug ccgcuggaaa   60
acccgguucu gcuggaccgu uuccacgc                                     88

```
<210> SEQ ID NO 15
<211> LENGTH: 104
<212> TYPE: DNA
<213> ORGANISM: Primer

<400> SEQUENCE: 15
gcuggaaucc uacuucgaaa ccaacuccga augcuccaaa ccggguguua ucuuccugac      60 caaaaaggu cgucguuucu gcgcuaaccc guccgacaaa cagg                      104

<210> SEQ ID NO 16
<211> LENGTH: 89
<212> TYPE: DNA
<213> ORGANISM: Primer

<400> SEQUENCE: 16
aagctttcag tttttacggg tgggcagacg ggtgtccagt ttcagcatac gcatacaaac     60
ctgaacctgt ttgtcggacg gcttagcgc                                       89

<210> SEQ ID NO 17
<211> LENGTH: 94
<212> TYPE: DNA
<213> ORGANISM: Primer

<400> SEQUENCE: 17
ggtttcgaag taggattcca gcagggagca cgggatggaa cgcggggtgt aggagatgca     60
gcagtcagcg gaggtagcgt ggaaacggtc cagc                                 94

<210> SEQ ID NO 18
<211> LENGTH: 32
<212> TYPE: DNA
<213> ORGANISM: Primer

<400> SEQUENCE: 18
gcgcagccat ggaaaacccg gttctgctgg ac                                   32

<210> SEQ ID NO 19
<211> LENGTH: 83
<212> TYPE: PRT
<213> ORGANISM: Homo sapiens

<400> SEQUENCE: 19

Met Glu Asn Pro Val Leu Leu Asp Arg Phe His Ala Thr Ser Ala Asp
1               5                   10                  15

Cys Cys Ile Ser Tyr Thr Pro Arg Ser Ile Pro Cys Ser Leu Leu Glu
                20                  25                  30

Ser Tyr Phe Glu Thr Asn Ser Glu Cys Ser Lys Pro Gly Val Ile Phe
            35                  40                  45

Leu Thr Lys Lys Gly Arg Arg Phe Cys Ala Asn Pro Ser Asp Lys Gln
        50                  55                  60

Val Gln Val Cys Met Arg Met Leu Lys Leu Asp Thr Arg Ile Lys Thr
65                  70                  75                  80

Arg Lys Asn

<210> SEQ ID NO 20
<211> LENGTH: 35
<212> TYPE: DNA
<213> ORGANISM: Primer

<400> SEQUENCE: 20
gccatggcat gctggaaaac ccggttctgc tggac                                35
```

<210> SEQ ID NO 21
<211> LENGTH: 84
<212> TYPE: PRT
<213> ORGANISM: Homo sapiens

<400> SEQUENCE: 21

Met Leu Glu Asn Pro Val Leu Leu Asp Arg Phe His Ala Thr Ser Ala
1               5                   10                  15

Asp Cys Cys Ile Ser Tyr Thr Pro Arg Ser Ile Pro Cys Ser Leu Leu
            20                  25                  30

Glu Ser Tyr Phe Glu Thr Asn Ser Glu Cys Ser Lys Pro Gly Val Ile
        35                  40                  45

Phe Leu Thr Lys Lys Gly Arg Arg Phe Cys Ala Asn Pro Ser Asp Lys
    50                  55                  60

Gln Val Gln Val Cys Met Arg Met Leu Lys Leu Asp Thr Arg Ile Lys
65                  70                  75                  80

Thr Arg Lys Asn

<210> SEQ ID NO 22
<211> LENGTH: 32
<212> TYPE: DNA
<213> ORGANISM: Primer

<400> SEQUENCE: 22
gcgcagccat ggaccgtttc cacgctacct cc                                    32

<210> SEQ ID NO 23
<211> LENGTH: 77
<212> TYPE: PRT
<213> ORGANISM: Homo sapiens

<400> SEQUENCE: 23

Met Asp Arg Phe His Ala Thr Ser Ala Asp Cys Cys Ile Ser Tyr Thr
1               5                   10                  15

Pro Arg Ser Ile Pro Cys Ser Leu Leu Glu Ser Tyr Phe Glu Thr Asn
            20                  25                  30

Ser Glu Cys Ser Lys Pro Gly Val Ile Phe Leu Thr Lys Lys Gly Arg
        35                  40                  45

Arg Phe Cys Ala Asn Pro Ser Asp Lys Gln Val Gln Val Cys Met Arg
    50                  55                  60

Met Leu Lys Leu Asp Thr Arg Ile Lys Thr Arg Lys Asn
65                  70                  75

<210> SEQ ID NO 24
<211> LENGTH: 29
<212> TYPE: DNA
<213> ORGANISM: Primer

<400> SEQUENCE: 24
gccatggcat gcgtttccac gctacctcc                                        29

<210> SEQ ID NO 25
<211> LENGTH: 32
<212> TYPE: DNA
<213> ORGANISM: Primer

<400> SEQUENCE: 25
gcgcagccat ggctacctcc gctgactgct gc                                    32

<210> SEQ ID NO 26
<211> LENGTH: 73
<212> TYPE: PRT
<213> ORGANISM: Homo sapiens

<400> SEQUENCE: 26

Met Ala Thr Ser Ala Asp Cys Cys Ile Ser Tyr Thr Pro Arg Ser Ile
1               5                   10                  15

Pro Cys Ser Leu Leu Glu Ser Tyr Phe Glu Thr Asn Ser Glu Cys Ser
                20                  25                  30

Lys Pro Gly Val Ile Phe Leu Thr Lys Lys Gly Arg Arg Phe Cys Ala
            35                  40                  45

Asn Pro Ser Asp Lys Gln Val Gln Val Cys Met Arg Met Leu Lys Leu
        50                  55                  60

Asp Thr Arg Ile Lys Thr Arg Lys Asn
65                  70

<210> SEQ ID NO 27
<211> LENGTH: 21
<212> TYPE: DNA
<213> ORGANISM: Primer

<400> SEQUENCE: 27
ttcgaagtag gcttccagca g                                          21

<210> SEQ ID NO 28
<211> LENGTH: 21
<212> TYPE: DNA
<213> ORGANISM: Primer

<400> SEQUENCE: 28
ctgctggaag cctacttcga a                                          21

<210> SEQ ID NO 29
<211> LENGTH: 35
<212> TYPE: DNA
<213> ORGANISM: Primer

<400> SEQUENCE: 29
gccatggcat gcgtgttacc aaagacgctg aaacc                           35

<210> SEQ ID NO 30
<211> LENGTH: 100
<212> TYPE: PRT
<213> ORGANISM: Homo sapiens

<400> SEQUENCE: 30

Met Arg Val Thr Lys Asp Ala Glu Thr Glu Phe Met Met Ser Lys Leu
1               5                   10                  15

Pro Leu Glu Asn Pro Val Leu Leu Asp Arg Phe His Ala Thr Ser Ala
                20                  25                  30

Asp Cys Cys Ile Ser Tyr Thr Pro Arg Ser Ile Pro Cys Ser Leu Leu
            35                  40                  45

Glu Ala Tyr Phe Glu Thr Asn Ser Glu Cys Ser Lys Pro Gly Val Ile
        50                  55                  60

Phe Leu Thr Lys Lys Gly Arg Arg Phe Cys Ala Asn Pro Ser Asp Lys
65                  70                  75                  80

Gln Val Gln Val Cys Met Arg Met Leu Lys Leu Asp Thr Arg Ile Lys
                85                  90                  95

```
Thr Arg Lys Asn
        100
```

<210> SEQ ID NO 31
<211> LENGTH: 36
<212> TYPE: DNA
<213> ORGANISM: Primer

<400> SEQUENCE: 31
gcccaagctt tcagtttttta cgggttttga tacggg          36

<210> SEQ ID NO 32
<211> LENGTH: 27
<212> TYPE: DNA
<213> ORGANISM: Primer

<400> SEQUENCE: 32
ggaaagctta tgaaggtctc cgtggct          27

<210> SEQ ID NO 33
<211> LENGTH: 59
<212> TYPE: DNA
<213> ORGANISM: Primer

<400> SEQUENCE: 33
cgctctagat caagcgtagt ctgggacgtc gtatgggtaa ttcttcctgg tcttgatcc          59

<210> SEQ ID NO 34
<211> LENGTH: 33
<212> TYPE: DNA
<213> ORGANISM: Primer

<400> SEQUENCE: 34
aaaggatccg ccaccatgaa ggtctccgtg gtc          33

<210> SEQ ID NO 35
<211> LENGTH: 27
<212> TYPE: DNA
<213> ORGANISM: Primer

<400> SEQUENCE: 35
aaaggatcct caattcttcc aggtctt          27

<210> SEQ ID NO 36
<211> LENGTH: 92
<212> TYPE: PRT
<213> ORGANISM: Homo sapiens

<400> SEQUENCE: 36

```
Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90
```

<210> SEQ ID NO 37
<211> LENGTH: 4208
<212> TYPE: DNA
<213> ORGANISM: Homo sapiens

<400> SEQUENCE: 37

| | | | | | |
|---|---|---|---|---|---|
| aagcttaaaa | aactgcaaaa | aatagtttga | cttgtgagcg | gataacaatt | aagatgtacc | 60 |
| caattgtgag | cggataacaa | tttcacacat | taaagaggag | aaattacata | tggaccgttt | 120 |
| ccacgctacc | tccgctgact | gctgcatctc | ctacaccccg | cgttccatcc | cgtgctcgct | 180 |
| gctggaatcc | tacttcgaaa | ccaactccga | atgctccaaa | ccgggtgtta | tcttcctgac | 240 |
| caaaaaaggt | cgtcgtttct | cgctaaccc | gtccgacaaa | caggttcagg | tttgtatgcg | 300 |
| tatgctgaaa | ctggacaccc | gtatcaaaac | ccgtaaaaac | tgataaggta | cctaagtgag | 360 |
| tagggcgtcc | gatcgacgga | cgccttttt | ttgaattcgt | aatcatggtc | atagctgttt | 420 |
| cctgtgtgaa | attgttatcc | gctcacaatt | ccacacaaca | tacgagccgg | aagcataaag | 480 |
| tgtaaagcct | ggggtgccta | atgagtgagc | taactcacat | taattgcgtt | gcgctcactg | 540 |
| cccgctttcc | agtcgggaaa | cctgtcgtgc | cagctgcatt | aatgaatcgg | ccaacgcgcg | 600 |
| gggagaggcg | gtttgcgtat | tgggcgctct | tccgcttcct | cgctcactga | ctcgctgcgc | 660 |
| tcggtcgttc | ggctgcggcg | agcggtatca | gctcactcaa | aggcggtaat | acggttatcc | 720 |
| acagaatcag | gggataacgc | aggaaagaac | atgtgagcaa | aaggccagca | aaaggccagg | 780 |
| aaccgtaaaa | aggccgcgtt | gctggcgttt | ttccataggc | tccgcccccc | tgacgagcat | 840 |
| cacaaaaatc | gacgctcaag | tcagaggtgg | cgaaacccga | caggactata | aagataccag | 900 |
| gcgtttcccc | ctggaagctc | cctcgtgcgc | tctcctgttc | cgaccctgcc | gcttaccgga | 960 |
| tacctgtccg | cctttctccc | ttcgggaagc | gtggcgcttt | ctcatagctc | acgctgtagg | 1020 |
| tatctcagtt | cggtgtaggt | cgttcgctcc | aagctgggct | gtgtgcacga | accccccgtt | 1080 |
| cagcccgacc | gctgcgcctt | atccggtaac | tatcgtcttg | agtccaaccc | ggtaagacac | 1140 |
| gacttatcgc | cactggcagc | agccactggt | aacaggatta | gcagagcgag | gtatgtaggc | 1200 |
| ggtgctacag | agttcttgaa | gtggtggcct | aactacggct | acactagaag | aacagtattt | 1260 |
| ggtatctgcg | ctctgctgaa | gccagttacc | ttcggaaaaa | gagttggtag | ctcttgatcc | 1320 |
| ggcaaacaaa | ccaccgctgg | tagcggtggt | ttttttgttt | gcaagcagca | gattacgcgc | 1380 |
| agaaaaaaag | gatctcaaga | agatcctttg | atcttttcta | cggggtctga | cgctcagtgg | 1440 |
| aacgaaaact | cacgttaagg | gattttggtc | atgagattat | cgtcgacaat | tcgcgcgcga | 1500 |
| aggcgaagcg | gcatgcattt | acgttgacac | catcgaatgg | tgcaaaacct | ttcgcggtat | 1560 |
| ggcatgatag | cgcccggaag | agagtcaatt | cagggtggtg | aatgtgaaac | cagtaacgtt | 1620 |
| atacgatgtc | gcagagtatg | ccggtgtctc | ttatcagacc | gtttcccgcg | tggtgaacca | 1680 |
| ggccagccac | gtttctgcga | aaacgcggga | aaaagtggaa | gcggcgatgg | cggagctgaa | 1740 |
| ttacattccc | aaccgcgtgg | cacaacaact | ggcgggcaaa | cagtcgttgc | tgattggcgt | 1800 |
| tgccacctcc | agtctggccc | tgcacgcgcc | gtcgcaaatt | gtcgcggcga | ttaaatctcg | 1860 |
| cgccgatcaa | ctgggtgcca | gcgtggtggt | gtcgatggta | gaacgaagcg | gcgtcgaagc | 1920 |
| ctgtaaagcg | gcggtgcaca | atcttctcgc | gcaacgcgtc | agtgggctga | tcattaacta | 1980 |
| tccgctggat | gaccaggatg | ccattgctgt | ggaagctgcc | tgcactaatg | ttccggcgtt | 2040 |
| atttcttgat | gtctctgacc | agacacccat | caacagtatt | attttctccc | atgaagacgg | 2100 |
| tacgcgactg | ggcgtggagc | atctggtcgc | attgggtcac | cagcaaatcg | cgctgttagc | 2160 |

```
gggcccatta agttctgtct cggcgcgtct gcgtctggct ggctggcata aatatctcac    2220
tcgcaatcaa attcagccga tagcggaacg ggaaggcgac tggagtgcca tgtccggttt    2280
tcaacaaacc atgcaaatgc tgaatgaggg catcgttccc actgcgatgc tggttgccaa    2340
cgatcagatg cgcgctgggcg caatgcgcgc cattaccgag tccgggctgc gcgttggtgc    2400
ggatatctcg gtagtgggat acgacgatac cgaagacagc tcatgttata tcccgccgtt    2460
aaccaccatc aaacaggatt ttcgcctgct ggggcaaacc agcgtggacc gcttgctgca    2520
actctctcag ggccaggcgg tgaagggcaa tcagctgttg cccgtctcac tggtgaaaag    2580
aaaaaccacc ctggcgccca atacgcaaac cgcctctccc cgcgcgttgg ccgattcatt    2640
aatgcagctg gcacgacagg tttcccgact ggaaagcggg cagtgagcgc aacgcaatta    2700
atgtaagtta gcgcgaattg tcgaccaaag cggccatcgt gcctcccccac tcctgcagtt    2760 cgggggcatg gatgcgcgga tagccgctgc tggtttcctg gatgccgacg gatttgcact    2820
gccggtagaa ctccgcgagg tcgtccagcc tcaggcagca gctgaaccaa ctcgcgaggg    2880
gatcgagccc ggggtgggcg aagaactcca gcatgagatc cccgcgctgg aggatcatcc    2940
agccggcgtc ccggaaaacg attccgaagc ccaacctttc atagaaggcg gcggtggaat    3000
cgaaatctcg tgatggcagg ttgggcgtcg cttggtcggt catttcgaac cccagagtcc    3060
cgctcagaag aactcgtcaa gaaggcgata gaaggcgatg cgctgcgaat cgggagcggc    3120
gataccgtaa agcacgagga agcggtcagc ccattcgccg ccaagctctt cagcaatatc    3180
acgggtagcc aacgctatgt cctgatagcg gtccgccaca cccagccggc cacagtcgat    3240
gaatccagaa aagcggccat tttccaccat gatattcggc aagcaggcat cgccatgggt    3300
cacgacgaga tcctcgccgt cgggcatgcg cgccttgagc ctggcgaaca gttcggctgg    3360
cgcgagcccc tgatgctctt cgtccagatc atcctgatcg acaagaccgg cttccatccg    3420
agtacgtgct cgctcgatgc gatgtttcgc ttggtggtcg aatgggcagg tagccggatc    3480
aagcgtatgc agccgccgca ttgcatcagc catgatggat actttctcgg caggagcaag    3540
gtgagatgac aggagatcct gccccggcac ttcgcccaat agcagccagt cccttcccgc    3600
ttcagtgaca acgtcgagca cagctgcgca aggaacgccc gtcgtggcca gccacgatag    3660
ccgcgctgcc tcgtcctgca gttcattcag ggcaccggac aggtcggtct tgacaaaaag    3720
aaccgggcgc ccctgcgctg acagccggaa cacggcggca tcagagcagc cgattgtctg    3780
ttgtgcccag tcatagccga atagcctctc cacccaagcg gccggagaac ctgcgtgcaa    3840
tccatcttgt tcaatcatgc gaaacgatcc tcatcctgtc tcttgatcag atcttgatcc    3900
cctgcgccat cagatccttg gcggcaagaa agccatccag tttactttgc agggcttccc    3960
aaccttacca gagggcgccc cagctggcaa ttccggttcg cttgctgtcc ataaaaccgc    4020
ccagtctagc tatcgccatg taagcccact gcaagctacc tgctttctct ttgcgcttgc    4080
gttttccctt gtccagatag cccagtagct gacattcatc cggggtcagc accgtttctg    4140
cggactggct ttctacgtgt tccgcttcct ttagcagccc ttgcgccctg agtgcttgcg    4200
gcagcgtg                                                             4208
```

<210> SEQ ID NO 38
<211> LENGTH: 112
<212> TYPE: DNA
<213> ORGANISM: Homo sapiens

<400> SEQUENCE: 38

```
aagcttaaaa aactgcaaaa aatagtttga cttgtgagcg gataacaatt aagatgtacc      60
caattgtgag cggataacaa tttcacacat taaagaggag aaattacata tg             112
```

<210> SEQ ID NO 39
<211> LENGTH: 74
<212> TYPE: PRT
<213> ORGANISM: Homo sapiens

<400> SEQUENCE: 39

Met His Ala Thr Ser Ala Asp Cys Cys Ile Ser Tyr Thr Pro Arg Ser
1               5                   10                  15

Ile Pro Cys Ser Leu Leu Glu Ser Tyr Phe Glu Thr Asn Ser Glu Cys
                20                  25                  30

Ser Lys Pro Gly Val Ile Phe Leu Thr Lys Lys Gly Arg Arg Phe Cys
            35                  40                  45

Ala Asn Pro Ser Asp Lys Gln Val Gln Val Cys Met Arg Met Leu Lys
        50                  55                  60

Leu Asp Thr Arg Ile Lys Thr Arg Lys Asn
65                  70

<210> SEQ ID NO 40
<211> LENGTH: 79
<212> TYPE: PRT
<213> ORGANISM: Homo sapiens

<400> SEQUENCE: 40

Met His Ala Ala Gly Phe His Ala Thr Ser Ala Asp Cys Cys Met Ser
1               5                   10                  15

Tyr Thr Pro Arg Ser Ile Pro Cys Ser Leu Leu Glu Ser Tyr Phe Glu
                20                  25                  30

Thr Asn Ser Glu Cys Ser Lys Pro Gly Val Ile Phe Leu Thr Lys Lys
            35                  40                  45

Gly Arg Arg Phe Cys Ala Asn Pro Ser Asp Lys Gln Val Gln Val Cys
        50                  55                  60

Met Arg Met Leu Lys Leu Asp Thr Arg Ile Lys Thr Arg Lys Asn
65                  70                  75

<210> SEQ ID NO 41
<211> LENGTH: 85
<212> TYPE: PRT
<213> ORGANISM: Homo sapiens

<400> SEQUENCE: 41

Met Pro Gln Met Thr Leu Ser His Ala Ala Gly Phe His Ala Thr Ser
1               5                   10                  15

Ala Asp Cys Cys Met Ser Tyr Thr Pro Arg Ser Ile Pro Cys Ser Leu
                20                  25                  30

Leu Glu Ser Tyr Phe Glu Thr Asn Ser Glu Cys Ser Lys Pro Gly Val
            35                  40                  45

Ile Phe Leu Thr Lys Lys Gly Arg Arg Phe Cys Ala Asn Pro Ser Asp
        50                  55                  60

Lys Gln Val Gln Val Cys Met Arg Met Leu Lys Leu Asp Thr Arg Ile
65                  70                  75                  80

Lys Thr Arg Lys Asn
                85

<210> SEQ ID NO 42
<211> LENGTH: 733

-continued

```
<212> TYPE: DNA
<213> ORGANISM: Homo sapiens

<400> SEQUENCE: 42
gggatccgga gcccaaatct tctgacaaaa ctcacacatg cccaccgtgc ccagcacctg      60
aattcgaggg tgcaccgtca gtcttcctct tcccccaaa acccaaggac accctcatga     120
tctcccggac tcctgaggtc acatgcgtgg tggtggacgt aagccacgaa gaccctgagg    180
tcaagttcaa ctggtacgtg gacggcgtgg aggtgcataa tgccaagaca aagccgcggg    240
aggagcagta caacagcacg taccgtgtgg tcagcgtcct caccgtcctg caccaggact    300
ggctgaatgg caaggagtac aagtgcaagg tctccaacaa agccctccca accccatcg     360 agaaaaccat ctccaaagcc aaagggcagc ccgagaacc acaggtgtac accctgcccc     420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                      733
```